United States Patent
Desai et al.

(10) Patent No.: US 9,840,509 B2
(45) Date of Patent: Dec. 12, 2017

(54) HETEROCYCLIC COMPOUNDS

(71) Applicant: CADILA HEALTHCARE LIMITED, Ahmedabad, Gujarat (IN)

(72) Inventors: Ranjit C. Desai, Gujarat (IN); Rajesh Bahekar, Gujarat (IN); Dipam Patel, Gujarat (IN); Kiran Shah, Gujarat (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 0 days.

(21) Appl. No.: 15/112,536

(22) PCT Filed: Feb. 2, 2015

(86) PCT No.: PCT/IN2015/000063
§ 371 (c)(1),
(2) Date: Jul. 19, 2016

(87) PCT Pub. No.: WO2015/132799
PCT Pub. Date: Sep. 11, 2015

(65) Prior Publication Data
US 2016/0376277 A1   Dec. 29, 2016

(30) Foreign Application Priority Data

Feb. 3, 2014 (IN) ............................ 362/MUM/2014
Jul. 11, 2014 (IN) ......................... 2271/MUM/2014

(51) Int. Cl.
| | |
|---|---|
| *C07D 487/04* | (2006.01) |
| *C07D 473/34* | (2006.01) |
| *A61K 31/4985* | (2006.01) |
| *A61K 31/522* | (2006.01) |
| *A61K 31/5377* | (2006.01) |
| *A61K 31/55* | (2006.01) |
| *A61K 31/519* | (2006.01) |
| *A61K 45/06* | (2006.01) |

(52) U.S. Cl.
CPC ........ *C07D 487/04* (2013.01); *A61K 31/4985* (2013.01); *A61K 31/519* (2013.01); *A61K 31/522* (2013.01); *A61K 31/5377* (2013.01); *A61K 31/55* (2013.01); *A61K 45/06* (2013.01); *C07D 473/34* (2013.01)

(58) Field of Classification Search
CPC ............................ C07D 487/04; C07D 473/34; A61K 31/4985; A61K 31/522; A61K 31/5377; A61K 31/55
USPC ...................................... 544/263; 514/210.16
See application file for complete search history.

(56) References Cited

FOREIGN PATENT DOCUMENTS

| | | |
|---|---|---|
| WO | WO 95/03304 | 2/1995 |
| WO | WO 00/17203 | 3/2000 |
| WO | WO 01/19829 | 3/2001 |
| WO | WO 01/72751 | 10/2001 |
| WO | WO 02/080926 | 10/2002 |
| WO | WO 2005/037836 | 4/2005 |
| WO | WO 2008/121742 | 10/2008 |
| WO | WO 2010/009342 | 1/2010 |
| WO | WO 2011/046964 | 4/2011 |

OTHER PUBLICATIONS

International Search Report for PCT/IN2015/000063, dated Sep. 2, 2015, 8 pages.
Written Opinion of the International Preliminary Examining Authority, dated Mar. 23, 2016, 15 pages.
International Preliminary Report on Patentability, dated May 13, 2016, 7 pages.
Young et al., "Purine derivatives as competitive inhibitors of human erythrocyte membrane phosphatidylinositol 4-kinase", Journal of Medicinal Chemistry, vol. 33, No. 8, 1990, pp. 2073-2080.

*Primary Examiner* — Kahsay Habte
(74) *Attorney, Agent, or Firm* — Nixon & Vanderhye P.C.

(57) ABSTRACT

The present invention relates to heterocyclic compounds of the general formula (I) their pharmaceutically acceptable salts, pharmaceutically acceptable solvates, enantiomers, diastereomers, and polymorphs. The invention also relates to processes for the preparation of the compounds of invention, pharmaceutical compositions containing the compounds and their use as selective Bruton's Tyrosine Kinase (BTK) inhibitors.

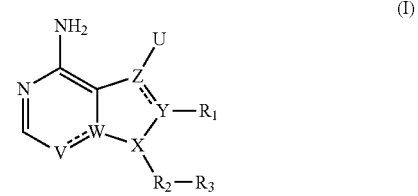

6 Claims, No Drawings

HETEROCYCLIC COMPOUNDS

This application is the U.S. national phase of International Application No. PCT/IN2015/000063 filed 2 Feb. 2015, which designated the U.S. and claims priority to IN Patent Application Nos. 362/MUM/2014 filed 3 Feb. 2014, and 2271/MUM/2014 filed 11 Jul. 2014, the entire contents of each of which are hereby incorporated by reference.

FIELD OF INVENTION

The present invention relates to novel heterocyclic compounds of the general formula (I) their pharmaceutically acceptable salts, pharmaceutically acceptable solvates, enantiomers, diastereomers, and polymorphs. The invention also relates to processes for the preparation of the compounds of invention, pharmaceutical compositions containing the compounds and their use as selective Bruton's Tyrosine Kinase (BTK) inhibitors.

BACKGROUND OF THE INVENTION

Bruton's Tyrosine Kinase (BTK) is a member of the Tec family kinases with a well-characterized role in B-cell receptor (BCR)-signaling and B-cell activation (Schwartzberg, P. L., Finkelstein, L. D and Readinger, J. A., Nat. Rev. Immunol., 2005, 5, 284-295). BTK is a key signaling enzyme expressed in all hematopoietic cells types, except T lymphocytes and natural killer cells. BTK is activated by the upstream Src-family kinases Blk, Lyn and Fyn and it lead to downstream activation of essential cell survival pathways such as NF-$_K$B and MAPK (Afar, D. E., Park, H., Howell, B. W., Rawlings, D. J., Cooper, J and Witte, O. N., Mol. Cell Biol., 1996, 16(7), 3465-3471). In turn, BTK phosphorylates and activates phospholipase-C☺ (PLC☺), leading to $Ca^{2+}$ mobilization and activation of NF-$_K$B and MAP kinase pathways (Bajpai, U. D., Zhang, K., Teutsch, M., Sen, R and Wortis, H. H., J. Exp. Med., 2000, 191, 1735-1744).

BTK is intimately involved in multiple signal-transduction pathways regulating survival, activation, proliferation and differentiation of B-lineage lymphoid cells. BTK is an upstream activator of multiple antiapoptotic signaling molecules and networks, including the signal transducer and activator of transcription 5 (STATS) protein, phosphatidylinositol (PI) 3-kinase/AKT/mammalian target of rapamycin (mTOR) pathway, and nuclear factor kappa B (NF-κB) (Mahajan, S., Vassilev, A., Sun, N., Ozer. Z., Mao, C and Uckun, F. M., J. Biol. Chem., 2001, 276, 31216-31228; Ortolano, S., Hwang, I. Y., Han, S. B and Kehrl, J. H., Eur. J. Immunol., 2006, 36, 1285-1295). This downstream signal transduction protein is a critical effector molecule that governs normal B-cell development, differentiation and functioning and has also been implicated in initiation, survival and progression of mature B-cell lymphoproliferative disorders (Kuppers, R., Nat. Rev. Cancer, 2005, 5(4), 251-262).

In B-cells, BTK is important for B-cell antigen receptor-, CD40- and Toll-like receptor 4-mediated activation and proliferation. Furthermore, BTK plays a role in B-cell antigen processing and presentation (Satterthwaite, A. B., Witte, O. N., Immunol. Rev., 2000, 175, 120-127). It is noteworthy that BTK is also essential in Fc☺ receptor-mediated inflammatory cytokine production [tumor necrosis factor ☺, interleukin (IL)-1☺ and IL-6] in monocytes/macrophages and therefore can contribute to immune complex-induced disease. BTK is abundantly expressed in malignant cells from patients with B-cell precursor (BCP)-acute lymphoblastic leukemia (ALL; the most common form of cancer in children and adolescents), chronic lymphocytic leukemia (CLL), and non-Hodgkin's lymphoma (NHL) (Khan, W. N., Immunol. Res., 2001, 23, 147-156). Consequently, BTK has emerged as a new molecular target for treatment of B-lineage leukemia's and lymphomas.

BTK mutations in human cause an inherited disease X-linked agammaglobulinemia, characterized by a lack of peripheral B-cells and low levels of serum Ig. Thus, BTK is a uniquely attractive kinase target for selective B-cell inhibition and small molecule based BTK inhibitors offers therapeutic benefit in the treatment of lymphoma and autoimmune diseases (Valiaho, J., Smith, C. I., Vihinen, M., Hum. Mutat., 2006, 27(12), 1209-1217).

BTK was recently identified in a siRNA screen as an essential kinase for survival in a subset of diffuse large-cell lymphomas driven by activated BCR, where an irreversible BTK inhibitor, PCI-32765 (Ibrutinib), was shown to promote apoptosis. A second study of Ibrutinib recently demonstrated in vivo clinical responses in dogs with aggressive B-cell lymphomas (Honigberg, L. A., Smith, A. M., Sirisawad, M., Verner, E., Loury, D., Chang, B., Li, S., Pan, Z., Thamm, D. H., Miller, R. A., Buggy, J. J., Proc. Natl. Acad. Sci., USA., 2010, 107(29), 13075-13080).

Thus BTKs are important in the regulation of many cellular processes including cell cycle regulation, proliferation, survival, apoptosis and motility and are significant components of the molecular mechanisms of diseases such as cancer, diabetes and immune inflammation (Buggy, J. J., Elias, L., Int. Rev. Immunol., 2012, 31(2), 119-132).

PRIOR ART

Published patent applications US2008/0076921, US2008/0108636, US2011/224235, US2012/100138/US2012/087915, US2012/183535, US2012/129873, US2012/129821, US2012/053189, WO2008/039218, WO2008/054827, WO2008/121742, WO2010/009342, WO2011/046964, WO2014/078578 and WO2011/153514, by Pharmacyclics Inc., discloses pyrazolo-pyrimidin-amine derivatives as BTK inhibitors for the treatment of autoimmune diseases or conditions, heteroimmune diseases or conditions, such as cancer, including lymphoma and inflammatory diseases or conditions. Hoffmann La Roche (WO2010/100070, US2010/222325, WO2010/122038, US2010/273768, WO2012/020008, US2012/040949, WO2010/000633, US2010/004231, WO2010/006947, US2010/016301, WO2014/064131, WO2014/076104, WO2014/083026, WO2014/090715), Biogen Idec Inc (WO2011/029046, US2012/157443, WO2011/029043, US2012/157442), CGI Pharmaceuticals Inc (WO2006/099075, US2006/229337, WO2009/137596, US2011/118233, WO2010/056875, US2011/301145, WO2010/068788), Avila Therapeutics Inc (US2012/0277832, WO2012/021444), BMS (WO2002/38797, US2003/040461), Boehringer (WO2014/025976), Principia (US2014/8673925), Ono Pharmaceuticals (US2013/0217880), Merck Sharp & Dohme (WO2013/010380, WO2014/093230) and Cellular Genomics Inc (WO2005/005429, US2005/101604) discloses diverse class of heterocyclic compounds as BTK inhibitors. BASF (WO2001/019829 and WO2002/080926) disclosed certain class of heterocyclic compounds as protein kinase inhibitors. Some of the recent patent application such as WO2014/187262, WO2014/188173, WO2014/161799, CN104086551, WO2014/135473, WO2014/116504, WO2014/113942, US2014/0206681, and WO2014/064131 discloses diverse class of heterocyclic compound as BTK inhibitors.

Since the ATP binding site of BTK shows a close homology to that of other Src-family kinases, such as lymphocyte-specific protein tyrosine kinase (LCK) and LYN, it is often difficult to find an ATP competitive inhibitor having sufficient selectivity. A lack of selectivity of an inhibitor for BTK over these kinases could potentially have negative consequences. BTK is a member of a group of eleven tyrosine kinases (the Tec family kinases, EGFR, Jak3, ErbB2, ErbB4, and BLK) that contain a conserved cysteine residue adjacent to the ATP-binding site. This cysteine (Cys481 in BTK) is a potential nucleophilic site which could form a covalent adduct with an electrophilic inhibitor. As the inhibitory activity of such an inhibitor is dependent on the covalent interaction, this cysteine residue provides a handle for achieving the desired degree of selectivity (Singh, J., Petter, R. C., Kluge, A. F., Curr. Opin. Chem. Biol., 2010, 14, 1-6; Cohen, M. S., Zhang, C., Shokat, K. M., Taunton, J., Science, 2005, 308, 1318-1321; Leproult, E., Barluenga, S., Moras, D., Wurtz, J. M., Winssinger, N., J. Med. Chem., 2011, 54, 1347-1355).

Reversible kinase inhibitors interact with the ATP-binding site. As the ATP-binding sites are highly conserved among kinases, it is difficult to develop a reversible inhibitor that selectively inhibits a desired kinase. Thus with reversible kinase inhibitors, it is difficult to achieve broad therapeutic window. Generating potent, selective, oral BTK inhibitors using covalent, irreversible and electrophilic compounds is feasible approach. However, the irreversible inhibitors exhibit toxicity due to covalent boding with off-target macromolecules. Thus to overcome undesirable off-target effects, it is essential to develop irreversible BTK inhibitors that covalently bind with BTK enzyme, without binding to off-target polypeptides.

Several BTK inhibitors are being developed as therapeutic agents for various indications. Among these, the covalent inhibitor Ibrutinib (Pharmacyclics) was developed as a selective and irreversible inhibitor of BTK, targeting the cysteine-481 residue in the active site. Ibrutinib is a potent nanomolar inhibitor of BTK and exhibited promising activity in preclinical models of BCR-driven B-lineage lymphoma and clinical testing in lymphoma patients (Pan, Z., Scheerens, H., Li, S. J., Schultz, B. E., Sprengeler, P. A., Burrill, L. C., Mendonca, R. V., Sweeney, M. D., Scott, K. C., Grothaus, P. G., Jeffery, D. A., Spoerke, J. M., Honigberg, L. A., Young, P. R., Dalrymple, S. A and Palmer, J. T., Chem. Med. Chem., 2007, 2, 58-61; Honigberg, L. A., Smith, A. M., Sirisawad, M., Verner, E., Loury, D., Chang, B., Li, S., Pan, Z., Thamm, D. H., Miller, R. A and Buggy, J. J., Proc. Natl. Acad. Sci. USA., 2010, 107, 13075-13080). Likewise, dianilinopyrimidine-based irreversible BTK inhibitors with micromolar activity were developed and two lead compounds, AVL-101 and AVL-291 (Avila Therapeutics) showed promising in vitro activity against lymphoma cells (Evans, E., Ponader, S., Karp, R., et al., Clin. Lymphoma Myeloma Leuk., 2011, 11 Suppl 2, S173-S174). Ibrutinib is a covalent BTK inhibitor, recently approved for the treatment of patients with various B-cell malignancies. Thus inhibition of BTK is emerging as a promising mechanism for targeting B-cell malignancies (Harrison, C., Nat. Rev. Drug Discov., 2012, 11(2), 96-97).

We herein disclose novel heterocyclic compounds of general formula (I) which are selective BTK inhibitors for the prevention and treatment of disease states mediated by BTK, including cancer and inflammation. More particularly, embodiments of the present invention describe irreversible kinase inhibitors including inhibition of BTK, that are useful as therapeutics in the treatment of a variety of pathological conditions including cancer, lymphoma, auto-immune diseases, heteroimmune diseases, inflammatory diseases and neurodegenerative diseases or conditions.

SUMMARY OF THE INVENTION

The present invention discloses heterocyclic compounds as defined by the general formula (I) that are selective BTK inhibitors for the prevention and treatment of disease states mediated by BTK. The compounds of the present invention are useful in the treatment of human or animal body, by inhibition of BTK. The compounds of this invention are therefore suitable for the prevention and treatment of disease states mediated by BTK.

EMBODIMENT(S) OF THE INVENTION

An embodiment of the present invention provides novel heterocyclic compounds represented by the general formula (I), their tautomeric forms, their enantiomers, their diastereoisomers, their stereoisomers, their pharmaceutically acceptable salts and pharmaceutical compositions containing them or their mixtures thereof.

In a further embodiment of the present invention is provided pharmaceutical compositions containing compounds of the general formula (I), their tautomeric forms, their enantiomers, their diastereoisomers, their stereoisomers, their pharmaceutically acceptable salts, or their mixtures in combination with suitable carriers, solvents, diluents and other media normally employed in preparing such compositions.

In a still further embodiment is provided the use of heterocyclic compounds of the present invention as selective BTK inhibitors, by administering a therapeutically effective and non-toxic amount of compounds of general formula (I) or their pharmaceutically acceptable compositions to the mammals.

In a still further embodiment is provided a process for preparing the novel compounds of the present invention.

DESCRIPTION OF THE INVENTION

Accordingly, the present invention relates to the compounds of the general formula (I) represented below and their pharmaceutically acceptable salts, enantiomers and their diastereomers;

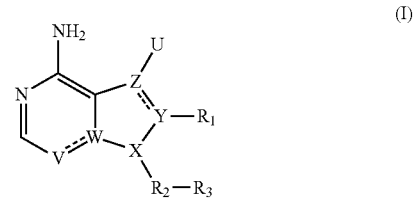

Wherein, V, W, X, Y & Z independently represents, 'C' or 'N'; $R_1$, represents groups selected from hydrogen, keto, halogen, unsubstituted or substituted groups selected from cyano, alkyl, haloalkyl, aryl, alkoxy, acyloxy, aryloxy, arylalkyl, heteroaryl, heterocyclyl, heterocycloalkyl, cycloalkyl, cycloalkylalkyl, aryloxyaryl, aryloxyalkyl, aryloxyheteroaryl groups;

$R_2$ represent the following ring system:

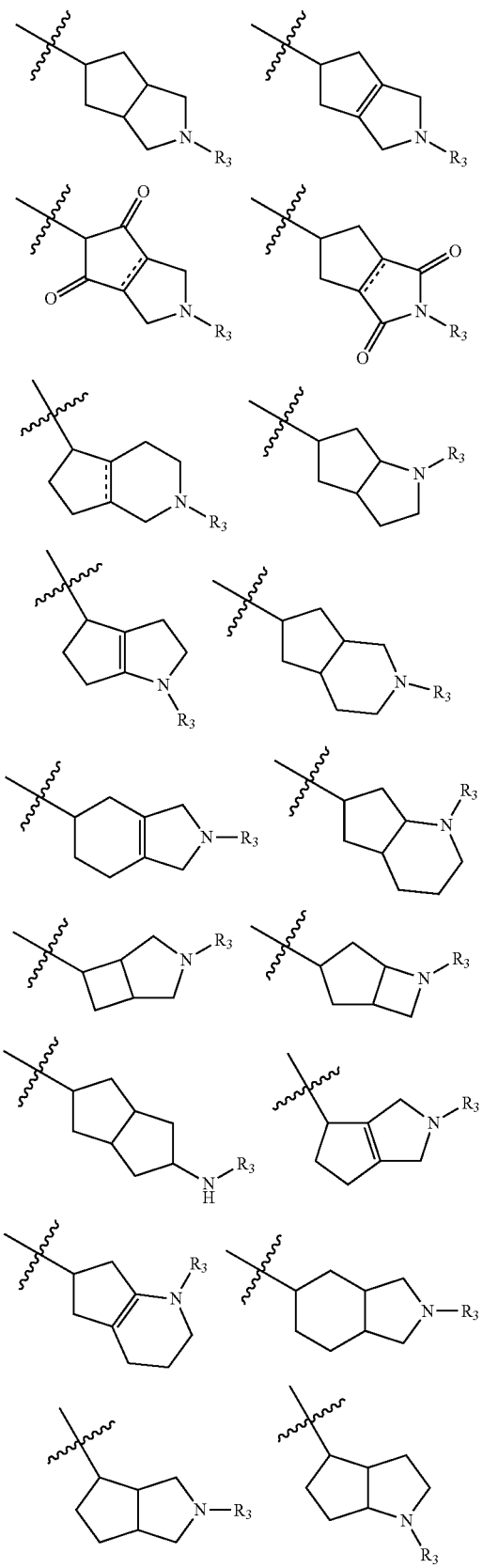

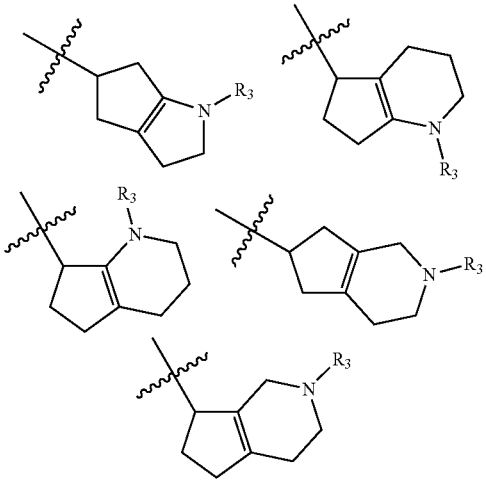

Wherein $R_3$ at each occurrence is independently selected from hydrogen, haloalkyl, $C_{1-7}$ alkyl, $C_{2-7}$ alkenyl, $C_{2-7}$ alkynyl, aryl, cycloalkyl, heterocycloalkyl, cycloalkyl($C_{1-7}$)alkyl, heterocycloalkyl($C_{1-7}$)alkyl, C(O)NH($C_{1-7}$)alkyl, C(O)—CH=CH$_2$, C(O)—CH=CH—$R_4$, C(O)—C(CN)=CH$_2$, C(O)—C(CN)=CH—$R_4$, SO$_2$—NH($C_{1-7}$)alkyl, SO$_2$—CH=CH$_2$, SO$_2$—CH=CH—$R_4$ groups;

$R_4$ is selected from —(CH$_2$)n-NR$_5$R$_6$; wherein, n=0-7 and each of $R_5$ and $R_6$ are independently selected from hydrogen, haloalkyl, $C_{1-7}$ alkyl, $C_{2-7}$ alkenyl, $C_{2-7}$ alkynyl, aryl, cycloalkyl, carbocycle, heterocycloalkyl, cycloalkyl($C_{1-7}$)alkyl, heterocycloalkyl($C_{1-7}$)alkyl; 'U' represent unsubstituted or substituted groups selected from alkyl, alkenyl, alkynyl, alkoxy, acyloxy, aryl, aryloxy, arylalkyl, cycloalkyl, cycloalkylalkyl, biaryl, heteroaryl, heterocycle, heterocycloalkyl, O-aryl, O-cycloalkyl, O-heteroaryl, O-heterocycle, O-heterocycloalkyl, aryloxyaryl, aryloxyalkyl, aryloxyheteroaryl, heteroaryloxyaryl, heteroaryloxyalkyl, heteroaryloxyheteroaryl, Ph-CO—N(R$_7$R$_8$), Ph-N(R$_9$)—CO—R$_{10}$, wherein, $R_7$, $R_8$ and $R_{10}$ are independently selected from hydrogen, halogen, alkyl, haloalkyl, alkoxy; aryl, cycloalkyl, heteroaryl, heterocycloalkyl; further substituted with halogen, alkyl, alkoxy, haloalkoxy groups and $R_9$ are independently selected from hydrogen, $C_{1-7}$ alkyl, $C_{2-7}$ alkenyl, $C_{2-7}$ alkynyl.

In a preferred embodiment, the groups, radicals described above may be selected from:

"Alkyl", as well as other groups having the prefix "alk", such as alkoxy and alkanoyl, means a carbon chain which may further be substituted with an oxygen atom as is well understood by a skilled artisan, which may further be either linear or branched, and combinations thereof, unless the carbon chain is defined otherwise. Examples of alkyl group include but are not limited to methyl, ethyl, propyl, isopropyl, butyl, sec-butyl, tert.-butyl, pentyl, hexyl etc. Where the specified number of carbon atoms permits e.g. from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Alkenyl" means carbon chains which contain at least one carbon-carbon double bond, and which may be linear or branched or combinations thereof, unless the carbon chain is defined otherwise. Examples of alkenyl include vinyl, allyl, isopropenyl, hexenyl, pentenyl, heptenyl, 1-propenyl, 2-butenyl, 2-methyl-2-butenyl etc. Where the specified number of carbon atoms permits, e. g., from $C_{5-10}$, the term alkenyl also includes cycloalkenyl groups and combinations of linear, branched and cyclic structures. When no number of carbon atoms is specified, $C_{(2-6)}$ is intended.

"Alkynyl" means carbon chains which contain at least one carbon-carbon triple bond, and which may be linear or branched or combinations thereof. Examples of alkynyl include ethynyl, propargyl, 3-methyl-1-pentynyl etc. When no number of carbon atoms is specified, $C_{(2-6)}$ is intended.

As used herein, "carbocycle" or "carbocyclic residue" is intended to mean any stable monocyclic or bicyclic or tricyclic ring, any of which may be saturated, partially unsaturated, or aromatic. Examples of such carbocycles includecyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). In a broader perspective, the term carbocycle is intended to include, wherever applicable, the groups representing cycloalkyl, phenyl and other saturated, partially saturated or aromatic residues;

"Cycloalkyl" is the subset of alkyl and means saturated carbocyclic ring having a specified number of carbon atoms, preferably 3-6 carbon atoms. Examples of cycloalkyl include cyclopropyl, cyclobutyl, cyclopentyl, cyclohexyl, cycloheptyl etc. A cycloalkyl group generally is monocyclic unless otherwise stated. Cycloalkyl groups are saturated unless and otherwise stated.

The "alkoxy" refers to the straight or branched chain alkoxides of the number of carbon atoms specified.

"Aryl" means a mono- or polycyclic aromatic ring system containing carbon ring atoms. The preferred aryls are monocyclic or bicyclic 6-10 membered aromatic ring systems. Phenyl and naphthyl are preferred aryls.

The terms "Heterocycle" or "heterocyclyl" refer to saturated or unsaturated non-aromatic rings or ring systems containing at least one heteroatom selected from O, S, N further optionally including the oxidized forms of sulfur, namely SO & $SO_2$. Examples of heterocycles include tetrahydrofuran (THF), dihydrofuran, 1,4-dioxane, morpholine, 1,4-dithiane, piperazine, piperidine, 1,3-dioxolane, imidazoline, imidazolidine, pyrrolidine, pyrroline, tetrahydropyran, dihydropyran, oxathiolane, dithiolane, 1,3-dioxane, 1,3-dithiane, oxathiane, thiomorpholine, etc. The term "heterocycloalkyl" refers to a heterocyclic group as defined above connected to an alkyl group as defined above;

"Heteroaryl" means an aromatic or partially aromatic heterocycle that contains at least one ring heteroatom selected from O, S and N. Heteroaryls thus include heteroaryls fused to the other kinds of rings, such as aryls, cycloalkyls, and heterocycles that are not aromatic. Examples of heteroaryl groups include; pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzthiazolyl, benzothiadiazolyl, dihydrobenzofuranyl, indolinyl, pyridazinyl, indazolyl, isoindolyl, dihydrobenzothienyl, indolinyl, pyridazinyl, indazolyl, isoindolyl, dihydrobenzothienyl, indolizinyl, cinnolinyl, phthalazinyl, quinazolinyl, napthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl etc. For heterocyclyl and heteroaryl groups, rings and ring systems containing from 3-15 carbon atoms are included, forming 1-3 rings.

An "aryloxy" group used either alone or in combination with other radicals, is selected from groups containing an aryl radical, as defined above, attached directly to an oxygen atom, more preferably groups selected from phenoxy, naphthyloxy, tetrahydronaphthyloxy, biphenyloxy, and the like;

"Cycloalkylalkyl" means an alkyl radical substituted with cycloalkyl group as defined herein. cycloalkylalkyl groups include cyclopropylmethyl, cyclobutylmethyl, cyclopentylmethyl, cyclohexylmethyl, and the like.

An "arylalkyl" group as used herein is an aromatic substituent that is linked to an alkyl group having from one to about six carbon atoms. examples of arylalkyl groups include benzyl group, phenethyl and the like.

The "acyloxy" group used either alone or in combination with other radicals, is selected from a suitable acyl group, directly attached to an oxygen atom; more preferably such groups are selected from acetyloxy, propionyloxy, butanoyloxy, iso-butanoyloxy, benzoyloxy and the like;

The term "Haloalkyl" means a alkyl structure in which at least one hydrogen is replaced with a halogen atom. In certain embodiments in which two or more hydrogen atoms are replaced with halogen atoms, the halogen atoms are all the same as one another.

In certain other embodiment in which two or more hydrogen atoms are replaced with halogen atoms, the halogen atoms are not all the same as one another.

"Aryloxyalkyl" means an alkyl radical substituted with aryloxy group as defined herein.

"Aryloxyaryl" means an aryl radical substituted with aryloxy group as defined herein.

"Aryloxyheteroaryl" means a heteroaryl radical substituted with aryloxy group as defined herein.

"Halo/Halogen" refers to fluorine, chlorine, bromine, iodine. Chlorine and fluorine are generally preferred.

Suitable groups and substituents on the groups may be selected from those described anywhere in the specification.

The term "substituted," as used herein, means that any one or more hydrogens on the designated atom is replaced with a selection from the indicated group, provided that the designated atom's normal valency is not exceeded, and that the substitution results in a stable compound. The term "substituted," as used herein, means that any one or more hydrogens on the designated atom is replaced with a selection from the indicated group, provided that the designated atom's normal valency is not exceeded, and that the substitution results in a stable compound.

"Pharmaceutically acceptable salts" refer to derivatives of the disclosed compounds wherein the parent compound is modified by making acid or base salts thereof. Examples of pharmaceutically acceptable salts include mineral or organic acid salts of the basic residues. Such conventional non-toxic salts include those derived from inorganic and organic acids selected from 1, 2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The term 'optional' or 'optionally' means that the subsequent described event or circumstance may or may not occur, and the description includes instances where the event or circumstance occur and instances in which it does not. For example, 'optionally substituted alkyl' means either 'alkyl' or 'substituted alkyl'. Further an optionally substituted group includes an unsubstituted group.

Unless otherwise stated in the specification, structures depicted herein are also meant to include compounds which differ only in the presence of one or more isotopically enriched atoms.

Particularly useful compounds may be selected from the following:

TABLE 1

| Compd | Structures | IUPAC Names |
|---|---|---|
| 1 | 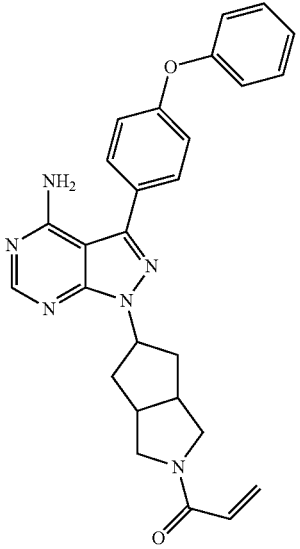 | 1-(5-(4-amino-3-(4-phenoxyphenyl)-1H-pyrazolo[3,4-d]pyrimidin-1-yl)hexahydrocyclopenta[c]pyrrol-2(1H)-yl)prop-2-en-1-one |
| 2 | 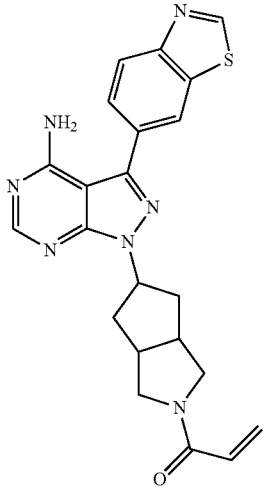 | 1-(5-(4-amino-3-(benzo[d]thiazol-6-yl)-1H-pyrazolo[3,4-d]pyrimidin-1-yl)hexahydrocyclopenta[c]pyrrol-2(1H)-yl)prop-2-en-1-one |

TABLE 1-continued

| Compd | Structures | IUPAC Names |
|---|---|---|
| 3 | 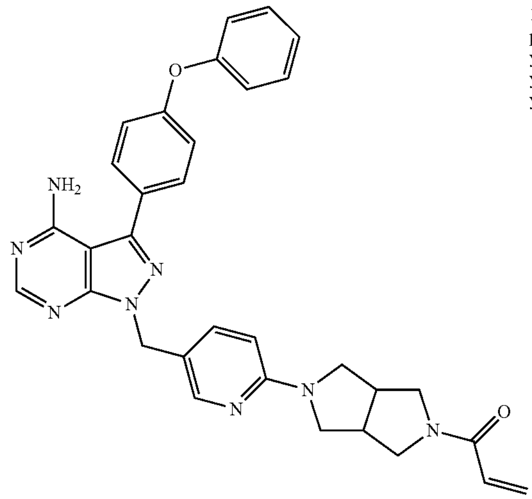 [SMILES: C=CC(=O)N1CC2CN(c3ccc(Cn4nc(-c5ccc(Oc6ccccc6)cc5)c5c(N)ncnc54)cn3)CC2C1] | 1-(5-(5-((4-amino-3-(4-phenoxyphenyl)-1H-pyrazolo[3,4-d]pyrimidin-1-yl)methyl)pyridin-2-yl)hexahydropyrrolo[3,4-c]pyrrol-2(1H)-yl)prop-2-en-1-one |
| 4 | 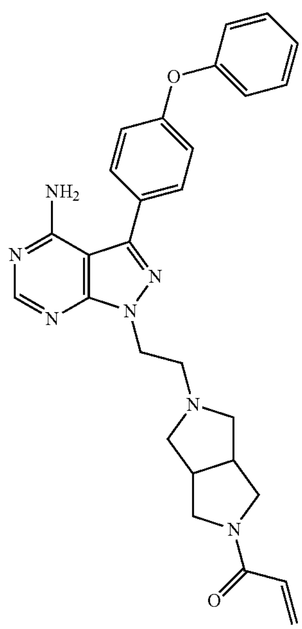 [SMILES: C=CC(=O)N1CC2CN(CCn3nc(-c4ccc(Oc5ccccc5)cc4)c4c(N)ncnc43)CC2C1] | 1-(5-(2-(4-amino-3-(4-phenoxyphenyl)-1H-pyrazolo[3,4-d]pyrimidin-1-yl)ethyl)hexahydropyrrolo[3,4-c]pyrrol-2(1H)-yl)prop-2-en-1-one |
| 5 | 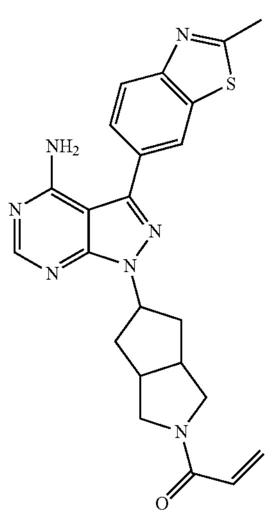 [SMILES: C=CC(=O)N1CC2CC(n3nc(-c4ccc5nc(C)sc5c4)c4c(N)ncnc43)CC2C1] | 1-(5-(4-amino-3-(2-methylbenzo[d]thiazol-6-yl)-1H-pyrazolo[3,4-d]pyrimidin-1-yl)hexahydrocyclopenta[c]pyrrol-2(1H)-yl)prop-2-en-1-one |

TABLE 1-continued
| Compd | Structures | IUPAC Names |
|---|---|---|
| 6 | 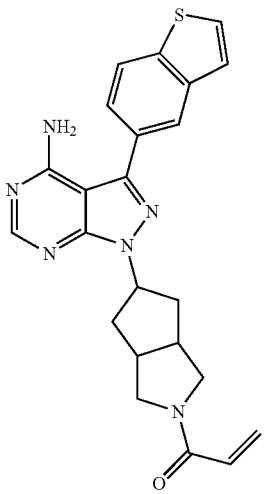 | 1-(5-(4-amino-3-(benzo[b]thiophen-5-yl)-1H-pyrazolo[3,4-d]pyrimidin-1-yl)hexahydrocyclopenta[c]pyrrol-2(1H)-yl)prop-2-en-1-one |
| 7 | 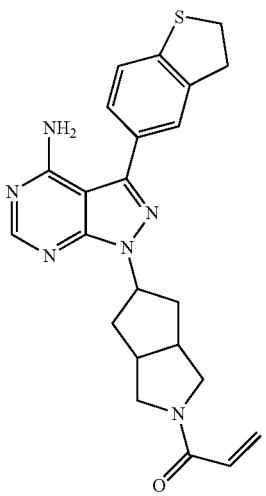 | 1-(5-(4-amino-3-(2,3-dihydrobenzo[b]thiophen-5-yl)-1H-pyrazolo[3,4-d]pyrimidin-1-yl)hexahydrocyclopenta[c]pyrrol-2(1H)-yl)prop-2-en-1-one |
| 8 | 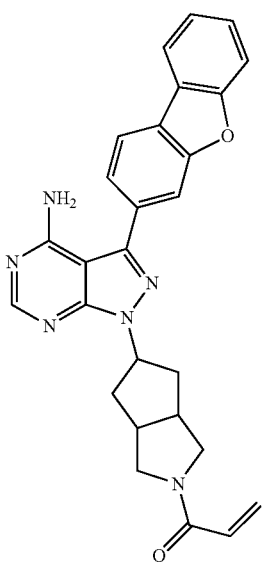 [SMILES: C=CC(=O)N1CC2CC(n3nc(-c4ccc5c(c4)oc4ccccc45)c4c(N)ncnc43)CC2C1] | 1-(5-(4-amino-3-(dibenzo[b,d]furan-3-yl)-1H-pyrazolo[3,4-d]pyrimidin-1-yl)hexahydrocyclopenta[c]pyrrol-2(1H)-yl)prop-2-en-1-one |

TABLE 1-continued
| Compd | Structures | IUPAC Names |
|---|---|---|
| 9 | 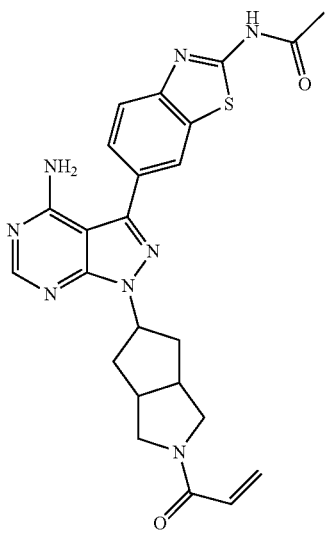 [SMILES: C=CC(=O)N1CC2CC(n3nc(-c4ccc5nc(NC(C)=O)sc5c4)c4c(N)ncnc43)CC2C1] | N-(6-(1-(2-acryloyloctahydrocyclopenta[c]pyrrol-5-yl)-4-amino-1H-pyrazolo[3,4-d]pyrimidin-3-yl)benzo[d]thiazol-2-yl)acetamide |
| 10 | 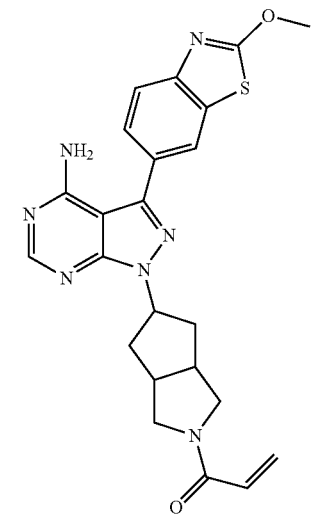 [SMILES: C=CC(=O)N1CC2CC(n3nc(-c4ccc5nc(OC)sc5c4)c4c(N)ncnc43)CC2C1] | 1-(5-(4-amino-3-(2-methoxybenzo[d]thiazol-6-yl)-1H-pyrazolo[3,4-d]pyrimidin-1-yl)hexahydrocyclopenta[c]pyrrol-2(1H)-yl)prop-2-en-1-one |

TABLE 1-continued
| Compd | Structures | IUPAC Names |
|---|---|---|
| 11 | 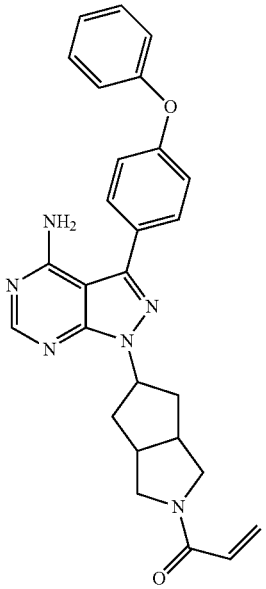 | 1-(5-(4-amino-3-(4-phenoxyphenyl)-1H-pyrazolo[3,4-d]pyrimidin-1-yl)hexahydrocyclopenta[c]pyrrol-2(1H)-yl)prop-2-yn-1-one |
| 12 | 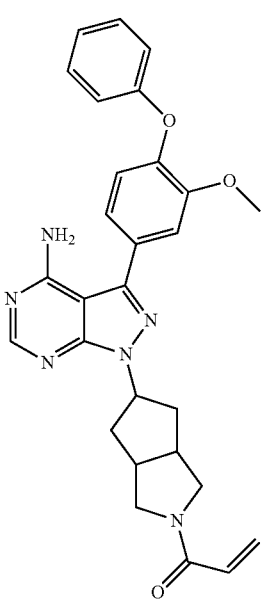 [SMILES: C=CC(=O)N1CC2CC(n3nc(-c4ccc(Oc5ccccc5)c(OC)c4)c4c(N)ncnc43)CC2C1] | 1-(5-(4-amino-3-(3-methoxy-4-phenoxyphenyl)-1H-pyrazolo[3,4-d]pyrimidin-1-yl)hexahydrocyclopenta[c]pyrrol-2(1H)-yl)prop-2-en-1-one |

TABLE 1-continued
| Compd | Structures | IUPAC Names |
|---|---|---|
| 13 | 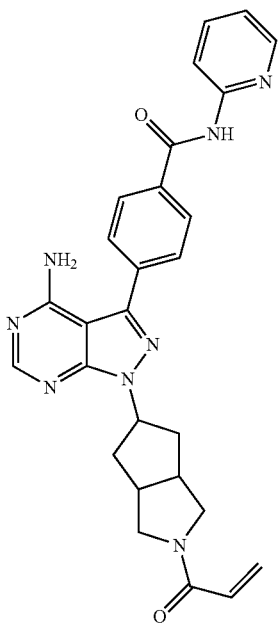 [SMILES: C=CC(=O)N1CC2CC(n3nc(-c4ccc(C(=O)Nc5ccccn5)cc4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-N-(pyridin-2-yl)benzamide |
| 14 | 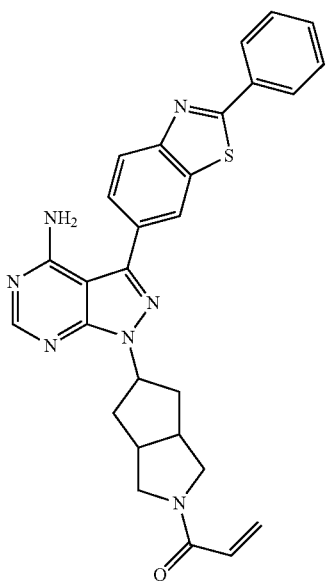 [SMILES: C=CC(=O)N1CC2CC(n3nc(-c4ccc5nc(-c6ccccc6)sc5c4)c4c(N)ncnc43)CC2C1] | 1-(5-(4-amino-3-(2-phenylbenzo[d]thiazol-6-yl)-1H-pyrazolo[3,4-d]pyrimidin-1-yl)hexahydrocyclopenta[c]pyrrol-2(1H)-yl)prop-2-en-1-one |

TABLE 1-continued
| Compd | Structures | IUPAC Names |
|---|---|---|
| 15 | 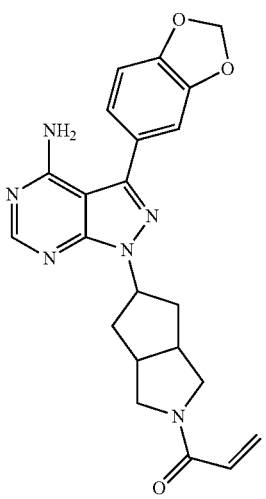 | 1-(5-(4-amino-3-(benzo[d][1,3]dioxol-5-yl)-1H-pyrazolo[3,4-d]pyrimidin-1-yl)hexahydrocyclopenta[c]pyrrol-2(1H)-yl)prop-2-en-1-one |
| 16 | 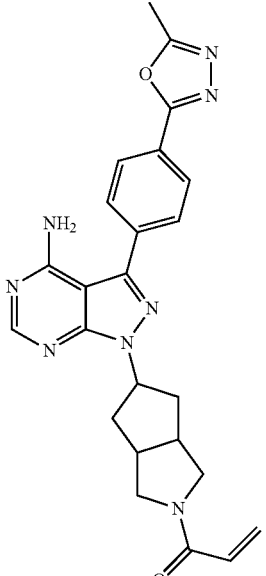 | 1-(5-(4-amino-3-(4-(5-methyl-1,3,4-oxadiazol-2-yl)phenyl)-1H-pyrazolo[3,4-d]pyrimidin-1-yl)hexahydrocyclopenta[c]pyrrol-2(1H)-yl)prop-2-en-1-one |
| 17 | 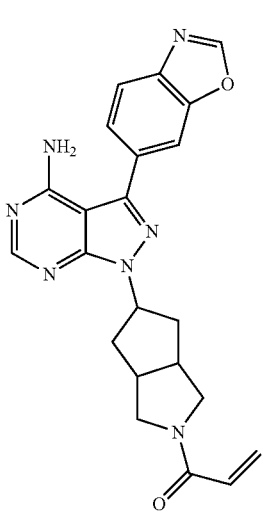 [SMILES: C=CC(=O)N1CC2CC(n3nc(-c4ccc5ncoc5c4)c4c(N)ncnc43)CC2C1] | 1-(5-(4-amino-3-(benzo[d]oxazol-6-yl)-1H-pyrazolo[3,4-d]pyrimidin-1-yl)hexahydrocyclopenta[c]pyrrol-2(1H)-yl)prop-2-en-1-one |

TABLE 1-continued
| Compd | Structures | IUPAC Names |
|---|---|---|
| 18 | 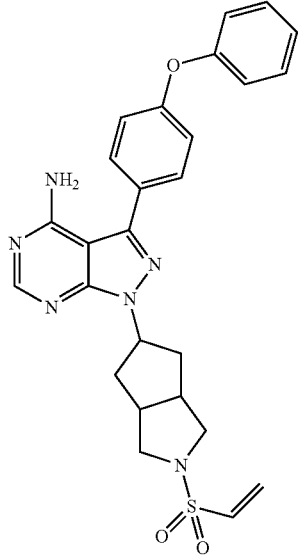 [SMILES: C=CS(=O)(=O)N1CC2CC(n3nc(-c4ccc(Oc5ccccc5)cc4)c4c(N)ncnc43)CC2C1] | 3-(4-phenoxyphenyl)-1-(2-(vinylsulfonyl)octahydrocyclopenta[c]pyrrol-5-yl)-1H-pyrazolo[3,4-d]pyrimidin-4-amine |
| 19 | 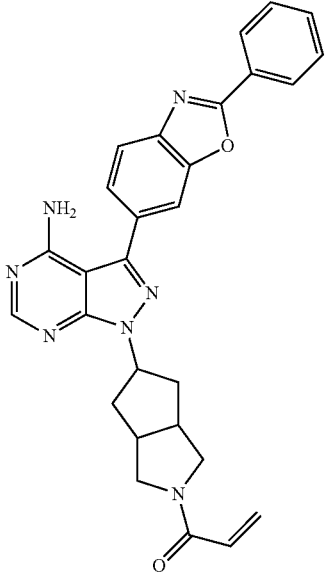 | 1-(5-(4-amino-3-(2-phenylbenzo[d]oxazol-6-yl)-1H-pyrazolo[3,4-d]pyrimidin-1-yl)hexahydrocyclopenta[c]pyrrol-2(1H)-yl)prop-2-en-1-one |

TABLE 1-continued
| Compd | Structures | IUPAC Names |
|---|---|---|
| 20 | 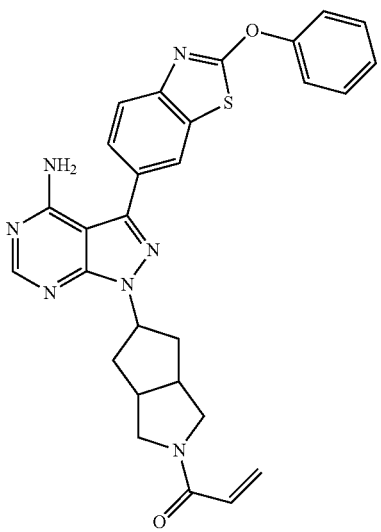 [SMILES: C=CC(=O)N1CC2CC(n3nc(-c4ccc5nc(Oc6ccccc6)sc5c4)c4c(N)ncnc43)CC2C1] | 1-(5-(4-amino-3-(2-phenoxybenzo[d]thiazol-6-yl)-1H-pyrazolo[3,4-d]pyrimidin-1-yl)hexahydrocyclopenta[c]pyrrol-2(1H)-yl)prop-2-en-1-one |
| 21 | 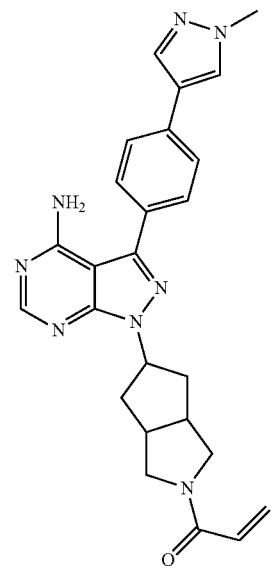 [SMILES: C=CC(=O)N1CC2CC(n3nc(-c4ccc(-c5cnn(C)c5)cc4)c4c(N)ncnc43)CC2C1] | 1-(5-(4-amino-3-(4-(1-methyl-1H-pyrazol-4-yl)phenyl)-1H-pyrazolo[3,4-d]pyrimidin-1-yl)hexahydrocyclopenta[c]pyrrol-2(1H)-yl)prop-2-en-1-one |
| 22 | 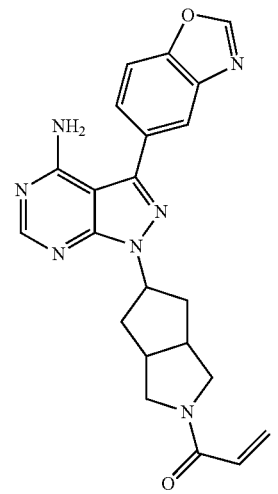 [SMILES: C=CC(=O)N1CC2CC(n3nc(-c4ccc5ocnc5c4)c4c(N)ncnc43)CC2C1] | 1-(5-(4-amino-3-(benzo[d]oxazol-5-yl)-1H-pyrazolo[3,4-d]pyrimidin-1-yl)hexahydrocyclopenta[c]pyrrol-2(1H)-yl)prop-2-en-1-one |

TABLE 1-continued
| Compd | Structures | IUPAC Names |
|---|---|---|
| 23 | 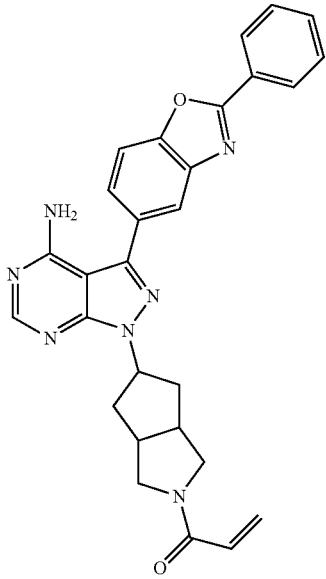 | 1-(5-(4-amino-3-(2-phenylbenzo[d]oxazol-5-yl)-1H-pyrazolo[3,4-d]pyrimidin-1-yl)hexahydrocyclopenta[c]pyrrol-2(1H)-yl)prop-2-en-1-one |
| 24 | 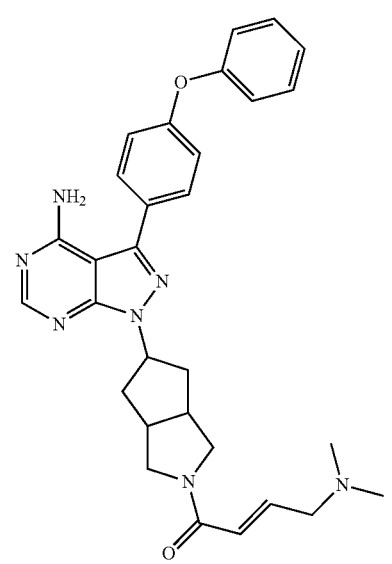 [SMILES: CN(C)C/C=C/C(=O)N1CC2CC(n3nc(-c4ccc(Oc5ccccc5)cc4)c4c(N)ncnc43)CC2C1] | (E)-1-(5-(4-amino-3-(4-phenoxyphenyl)-1H-pyrazolo[3,4-d]pyrimidin-1-yl)hexahydrocyclopenta[c]pyrrol-2(1H)-yl)-4-(dimethylamino)but-2-en-1-one |

TABLE 1-continued
| Compd | Structures | IUPAC Names |
|---|---|---|
| 25 | 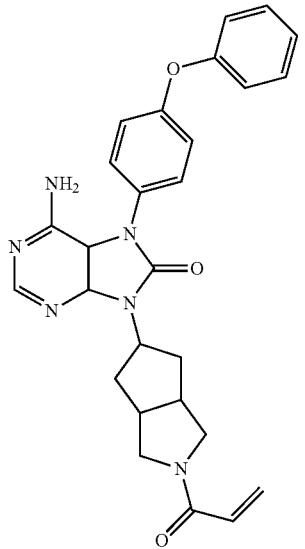 [SMILES: C=CC(=O)N1CC2CC(N3C(=O)N(c4ccc(Oc5ccccc5)cc4)C4C(N)=NC=NC43)CC2C1] | 9-(2-acryloyloctahydrocyclopenta[c]pyrrol-5-yl)-6-amino-7-(4-phenoxyphenyl)-5,7-dihydro-4H-purin-8(9H)-one |
| 26 | 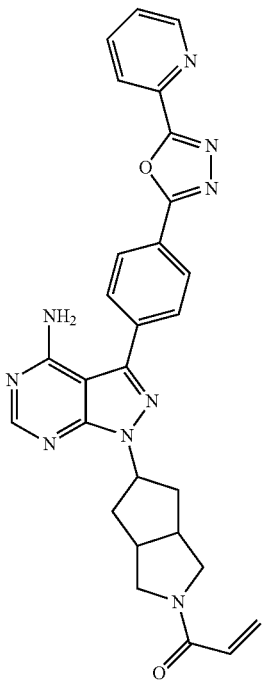 [SMILES: C=CC(=O)N1CC2CC(n3nc(-c4ccc(-c5nnc(-c6ccccn6)o5)cc4)c4c(N)ncnc43)CC2C1] | 1-(5-(4-amino-3-(4-(5-(pyridin-2-yl)-1,3,4-oxadiazol-2-yl)phenyl)-1H-pyrazolo[3,4-d]pyrimidin-1-yl)hexahydrocyclopenta[c]pyrrol-2(1H)-yl)prop-2-en-1-one |

TABLE 1-continued
| Compd | Structures | IUPAC Names |
|---|---|---|
| 27 | 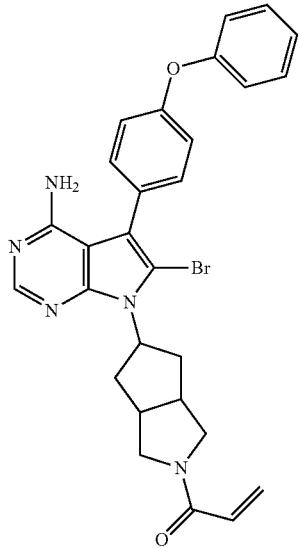 [SMILES: C=CC(=O)N1CC2CC(n3c(Br)c(-c4ccc(Oc5ccccc5)cc4)c4c(N)ncnc43)CC2C1] | 1-(5-(4-amino-6-bromo-5-(4-phenoxyphenyl)-7H-pyrrolo[2,3-]pyrimidin-7-yl)hexahydrocyclopenta[c]pyrrol-2(1H)-yl)prop-2-en-1-one |
| 28 | 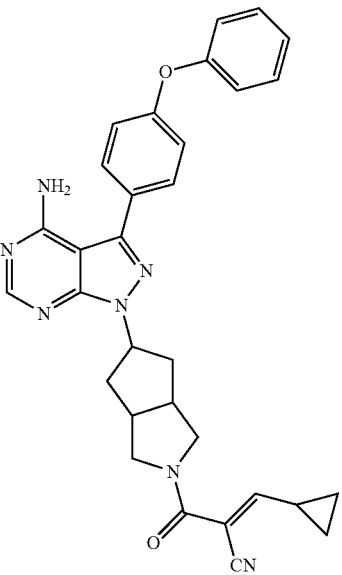 [SMILES: N#C/C(=C\C1CC1)C(=O)N1CC2CC(n3nc(-c4ccc(Oc5ccccc5)cc4)c4c(N)ncnc43)CC2C1] | (E)-2-(5-(4-amino-3-(4-phenoxyphenyl)-1H-pyrazolo[3,4-d]pyrimidin-1-yl)octahydrocyclopenta[c]pyrrole-2-carbonyl)-3-cyclopropylacrylonitrile |

TABLE 1-continued
| Compd | Structures | IUPAC Names |
|---|---|---|
| 29 | 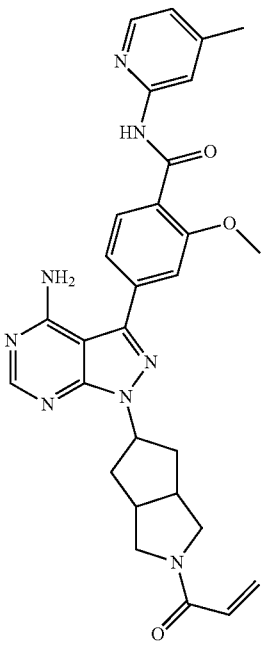 [SMILES: C=CC(=O)N1CC2CC(n3nc(-c4ccc(C(=O)Nc5cc(C)ccn5)c(OC)c4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-2-methoxy-N-(4-methylpyridin-2-yl)benzamide |
| 30 | 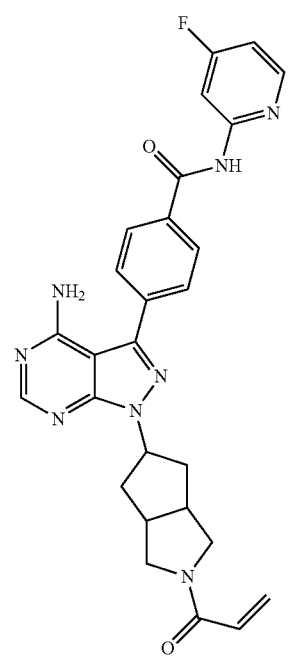 [SMILES: C=CC(=O)N1CC2CC(n3nc(-c4ccc(C(=O)Nc5cc(F)ccn5)cc4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-N-(4-methylpyridin-2-yl)benzamide |

TABLE 1-continued
| Compd | Structures | IUPAC Names |
|---|---|---|
| 31 | 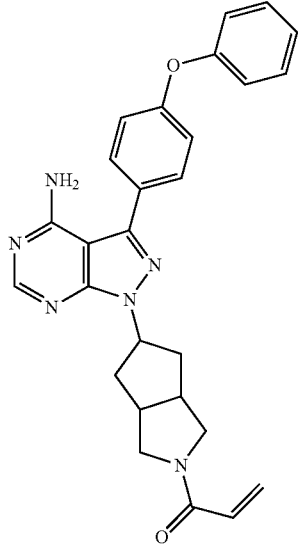 [SMILES: C=CC(=O)N1CC2CC(n3nc(-c4ccc(Oc5ccccc5)cc4)c4c(N)ncnc43)CC2C1] | 1-(5-(4-amino-5-(4-phenoxyphenyl)-7H-pyrrolo[2,3-d]pyrimidin-7-yl)hexahydrocyclopenta[c]pyrrol-2(1H)-yl)prop-2-en-1-one |
| 32 | 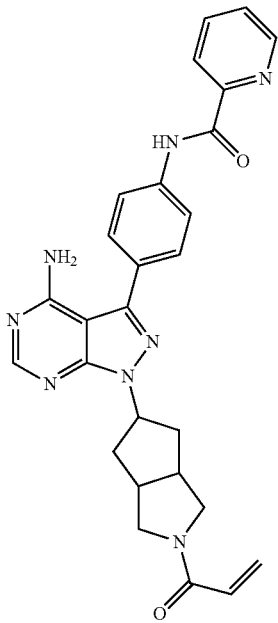 [SMILES: C=CC(=O)N1CC2CC(n3nc(-c4ccc(NC(=O)c5ccccn5)cc4)c4c(N)ncnc43)CC2C1] | N-(4-(1-(2-acryloyloctahydrocyclopenta[c]pyrrol-5-yl)-4-amino-1H-pyrazolo[3,4-d]pyrimidin-3-yl)phenyl)picolinamide |

TABLE 1-continued
| Compd | Structures | IUPAC Names |
|---|---|---|
| 33 | 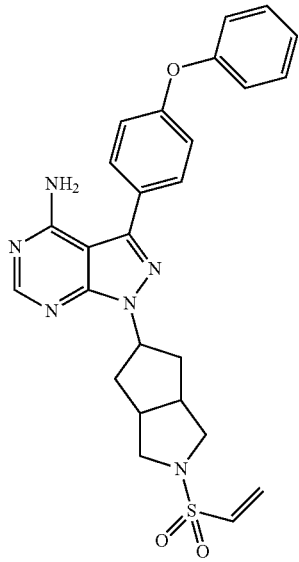 [SMILES: C=CS(=O)(=O)N1CC2CC(n3nc(-c4ccc(Oc5ccccc5)cc4)c4c(N)ncnc43)CC2C1] | 6-amino-7-(4-phenoxyphenyl)-9-(2-(vinylsulfonyl)octahydrocyclopenta[c]pyrrol-5-yl)-7H-purin-8(9H)-one |
| 34 | 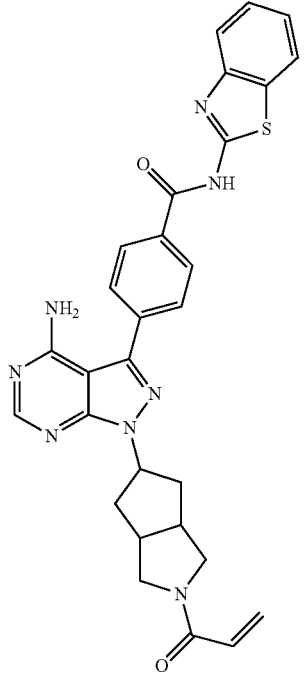 [SMILES: C=CC(=O)N1CC2CC(n3nc(-c4ccc(C(=O)Nc5nc6ccccc6s5)cc4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-N-(benzo[d]thiazol-2-yl)benzamide |

TABLE 1-continued
| Compd | Structures | IUPAC Names |
|---|---|---|
| 35 | 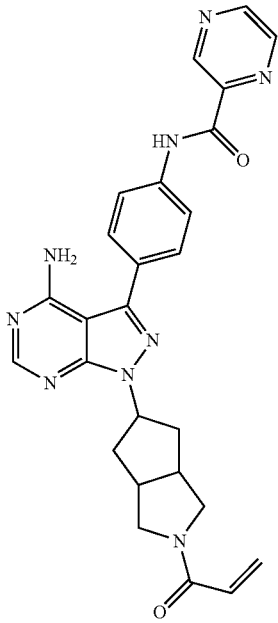 [SMILES: C=CC(=O)N1CC2CC(n3nc(-c4ccc(NC(=O)c5cnccn5)cc4)c4c(N)ncnc43)CC2C1] | N-(4-(1-(2-acryloyloctahydrocyclopenta[c]pyrrol-5-yl)-4-amino-1H-pyrazolo[3,4-d]pyrimidin-3-yl)phenyl)pyrazine-2-carboxamide |
| 36 | 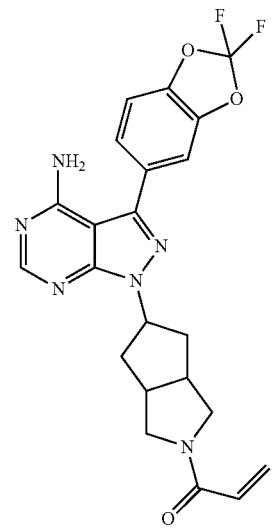 [SMILES: C=CC(=O)N1CC2CC(n3nc(-c4ccc5c(c4)OC(F)(F)O5)c4c(N)ncnc43)CC2C1] | 1-(5-(4-amino-3-(2,2-difluorobenzo[d][1,3]dioxol-5-yl)-1H-pyrazolo[3,4-d]pyrimidin-1-yl)hexahydrocyclopenta[c]pyrrol-2(1H)-yl)prop-2-en-1-one |

TABLE 1-continued
| Compd | Structures | IUPAC Names |
|---|---|---|
| 37 | 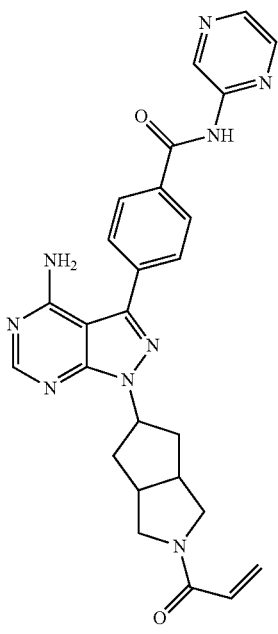 [SMILES: C=CC(=O)N1CC2CC(n3nc(-c4ccc(C(=O)Nc5cnccn5)cc4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-N-(pyrazin-2-yl)benzamide |
| 38 | 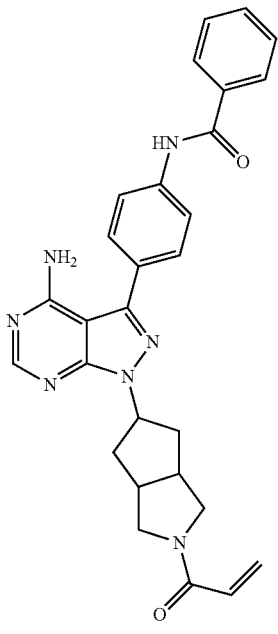 [SMILES: C=CC(=O)N1CC2CC(n3nc(-c4ccc(NC(=O)c5ccccc5)cc4)c4c(N)ncnc43)CC2C1] | N-(4-(1-(2-acryloyloctahydrocyclopenta[c]pyrrol-5-yl)-4-amino-1H-pyrazolo[3,4-d]pyrimidin-3-yl)phenyl)benzamide |

TABLE 1-continued
| Compd | Structures | IUPAC Names |
|---|---|---|
| 39 | 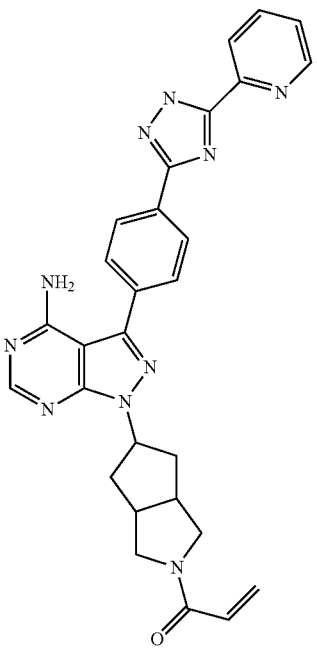 [SMILES: C=CC(=O)N1CC2CC(n3nc(-c4ccc(-c5n[nH]c(-c6ccccn6)n5)cc4)c4c(N)ncnc43)CC2C1] | 1-(5-(4-amino-3-(4-(5-(pyridin-2-yl)-1,3,4-thiadiazol-2-yl)phenyl)-1H-pyrazolo[3,4-d]pyrimidin-1-yl)hexahydrocyclopenta[c]pyrrol-2(1H)-yl)prop-2-en-1-one |
| 40 | 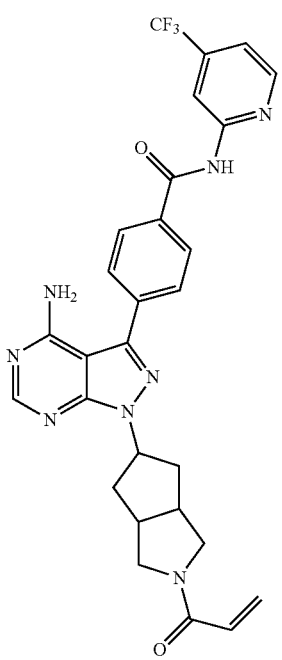 [SMILES: C=CC(=O)N1CC2CC(n3nc(-c4ccc(C(=O)Nc5cc(C(F)(F)F)ccn5)cc4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-N-(4-(trifluoromethyl)pyridin-2-yl)benzamide |

TABLE 1-continued

| Compd | Structures | IUPAC Names |
|---|---|---|
| 41 | 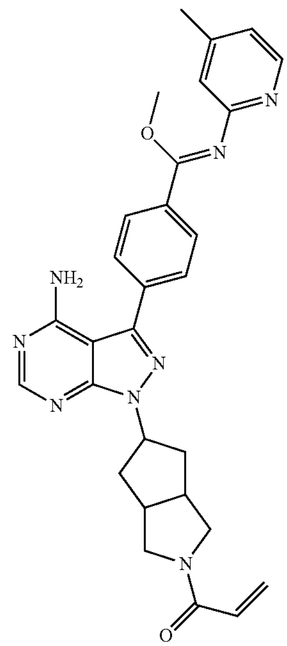 [SMILES: C=CC(=O)N1CC2CC(n3nc(-c4ccc(/C(=N/c5cc(C)ccn5)OC)cc4)c4c(N)ncnc43)CC2C1] | (Z)-methyl 4-(1-(2-acryloyloctahydrocyclopenta[c]pyrrol-5-yl)-4-amino-1H-pyrazolo[3,4-d]pyrimidin-3-yl)-N-(4-methylpyridin-2-yl)benzimidate |
| 42 | 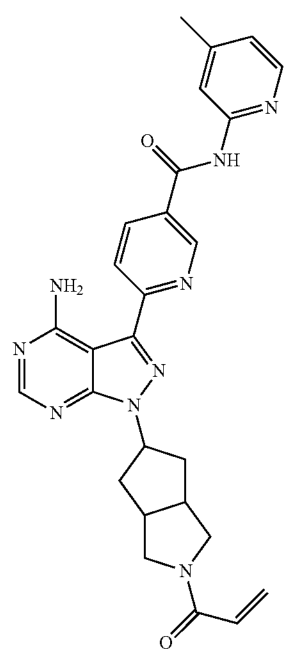 [SMILES: C=CC(=O)N1CC2CC(n3nc(-c4ccc(C(=O)Nc5cc(C)ccn5)cn4)c4c(N)ncnc43)CC2C1] | 6-(1-(2-acryloyloctahydrocyclopenta[c]pyrrol-5-yl)-4-amino-1H-pyrazolo[3,4-d]pyrimidin-3-yl)-N-(4-methylpyridin-2-yl)nicotinamide |

TABLE 1-continued
| Compd | Structures | IUPAC Names |
| --- | --- | --- |
| 43 | 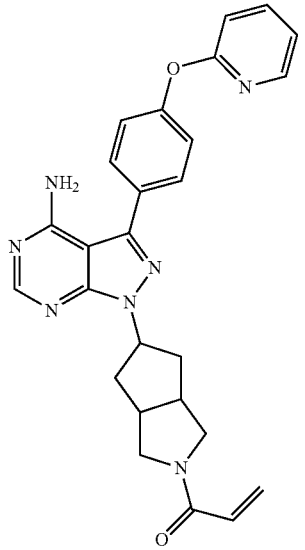 [SMILES: C=CC(=O)N1CC2CC(n3nc(-c4ccc(Oc5ccccn5)cc4)c4c(N)ncnc43)CC2C1] | 1-(5-(4-amino-3-(4-(pyridin-2-yloxy)phenyl)-1H-pyrazolo[3,4-d]pyrimidin-1-yl)hexahydrocyclopenta[c]pyrrol-2(1H)-yl)prop-2-en-1-one |
| 44 | 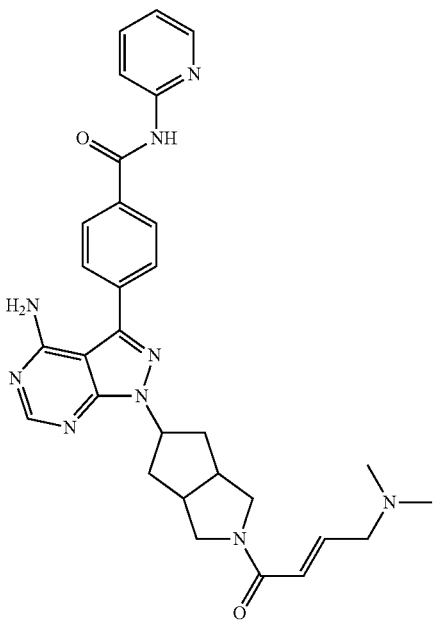 | (E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-(pyridin-2-yl)benzamide |

TABLE 1-continued
| Compd | Structures | IUPAC Names |
|---|---|---|
| 45 | 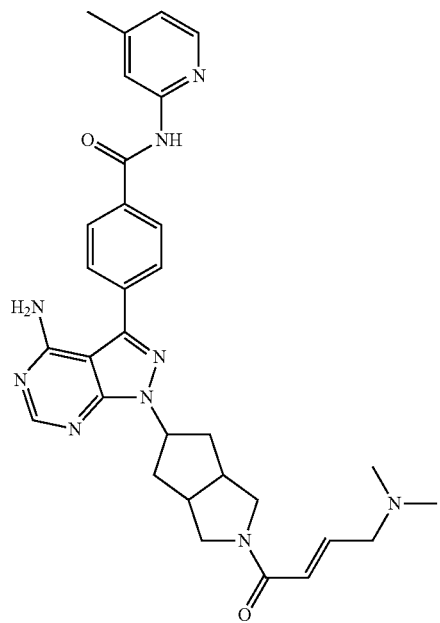 [SMILES: Cc1ccnc(NC(=O)c2ccc(-c3nn(C4CC5CN(C(=O)/C=C/CN(C)C)CC5C4)c4ncnc(N)c34)cc2)c1] | (E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-(4-methypyridin-2-yl)benzamide |
| 46 | 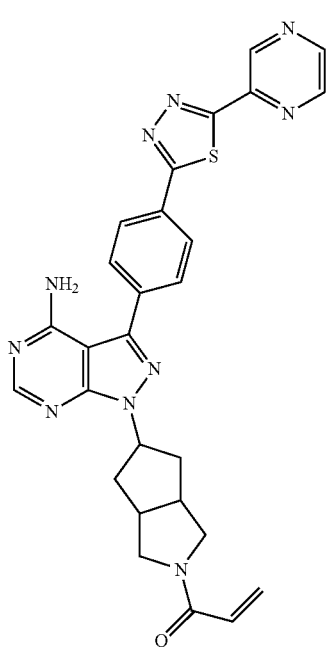 [SMILES: C=CC(=O)N1CC2CC(n3nc(-c4ccc(-c5nnc(-c6cnccn6)s5)cc4)c4c(N)ncnc43)CC2C1] | 1-(5-(4-amino-3-(4-(5-(pyrazin-2-yl)-1,3,4-thiadiazol-2-yl)phenyl)-1H-pyrazolo[3,4-d]pyrimidin-1-yl)hexahydrocyclopenta[c]pyrrol-2(1H)-yl)prop-2-en-1-one |

TABLE 1-continued
| Compd | Structures | IUPAC Names |
|---|---|---|
| 47 | 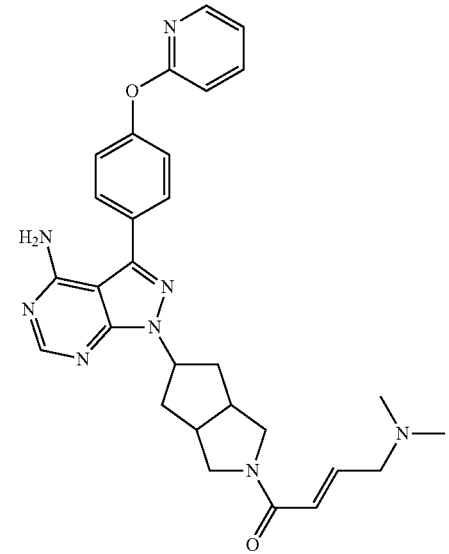 [SMILES: CN(C)C/C=C/C(=O)N1CC2CC(n3nc(-c4ccc(Oc5ccccn5)cc4)c4c(N)ncnc43)CC2C1] | (E)-1-(5-(4-amino-3-(4-(pyridin-2-yloxy)phenyl)-1H-pyrazolo[3,4-d]pyrimidin-1-yl)hexahydrocyclopenta[c]pyrrol-2(1H)-yl)-4-(dimethylamino)but-2-en-1-one |
| 48 | 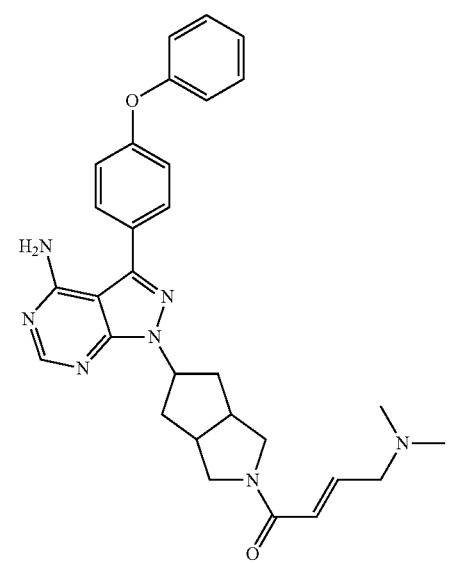 [SMILES: CN(C)C/C=C/C(=O)N1CC2CC(n3nc(-c4ccc(Oc5ccccc5)cc4)c4c(N)ncnc43)CC2C1] | (E)-1-(5-(4-amino-3-(4-phenoxyphenyl)-1H-pyrazolo[3,4-d]pyrimidin-1-yl)hexahydrocyclopenta[c]pyrrol-2(1H)-yl)-4-(dimethylamino)but-2-en-1-one |

TABLE 1-continued
| Compd | Structures | IUPAC Names |
|---|---|---|
| 49 | 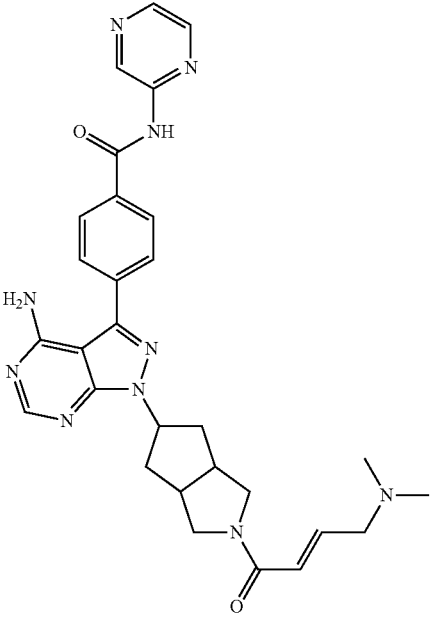 [SMILES: CN(C)C/C=C/C(=O)N1CC2CC(n3nc(-c4ccc(C(=O)Nc5cnccn5)cc4)c4c(N)ncnc43)CC2C1] | (E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-(pyrazin-2-yl)benzamide |
| 50 | 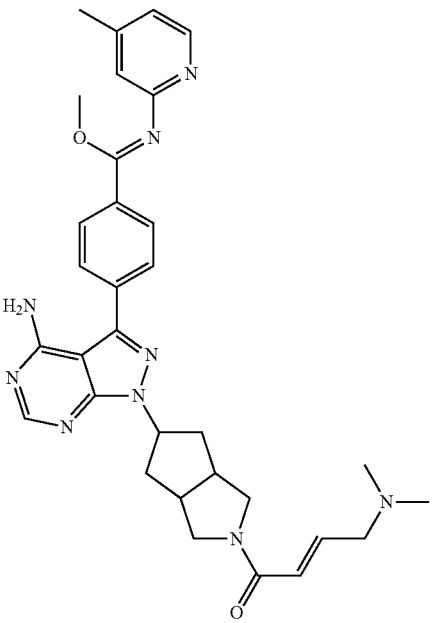 [SMILES: CO/C(=N\c1cc(C)ccn1)c1ccc(-c2nn(C3CC4CN(C(=O)/C=C/CN(C)C)CC4C3)c3ncnc(N)c23)cc1] | (Z)-methyl 4-(4-amino-1-(2-((E)-4-(dimethylamino)but-2-enoyl)octahydrocyclopenta[c]pyrrol-5-yl)-1H-pyrazolo[3,4-d]pyrimidin-3-yl)-N-(4-methylpyridin-2-yl)benzimidate |

TABLE 1-continued

| Compd | Structures | IUPAC Names |
|---|---|---|
| 51 | 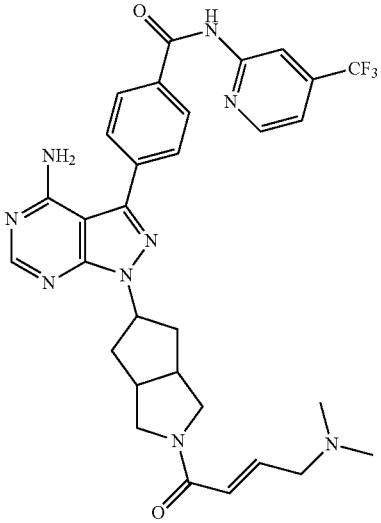 [SMILES: CN(C)C/C=C/C(=O)N1CC2CC(n3nc(-c4ccc(C(=O)Nc5cc(C(F)(F)F)ccn5)cc4)c4c(N)ncnc43)CC2C1] | (E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-(4-(trifluoromethyl)pyridin-2-yl)benzamide |
| 52 | 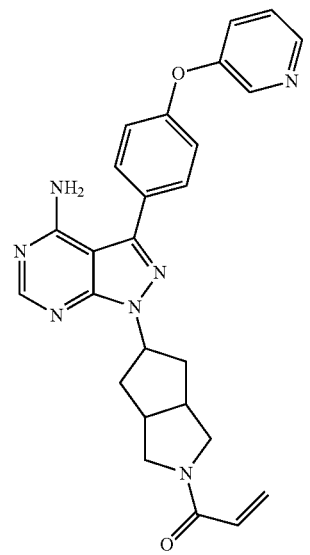 [SMILES: C=CC(=O)N1CC2CC(n3nc(-c4ccc(Oc5cccnc5)cc4)c4c(N)ncnc43)CC2C1] | 1-(5-(4-amino-3-(4-(pyridin-3-yloxy)phenyl)-1H-pyrazolo[3,4-d]pyrimidin-1-yl)hexahydrocyclopenta[c]pyrrol-2(1H)-yl)prop-2-en-1-one |
| 53 | 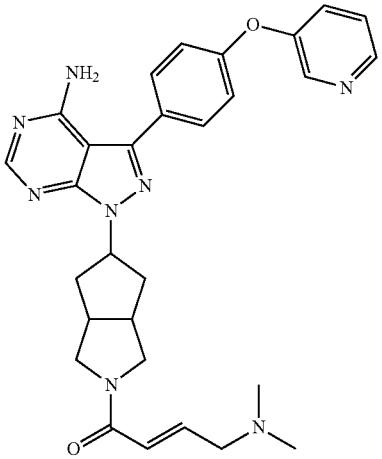 [SMILES: CN(C)C/C=C/C(=O)N1CC2CC(n3nc(-c4ccc(Oc5cccnc5)cc4)c4c(N)ncnc43)CC2C1] | (E)-1-(5-(4-amino-3-(4-(pyridin-3-yloxy)phenyl)-1H-pyrazolo[3,4-d]pyrimidin-1-yl)hexahydrocyclopenta[c]pyrrol-2(1H)-yl)-4-(dimethylamino)but-2-en-1-one |

TABLE 1-continued
| Compd | Structures | IUPAC Names |
|---|---|---|
| 54 | 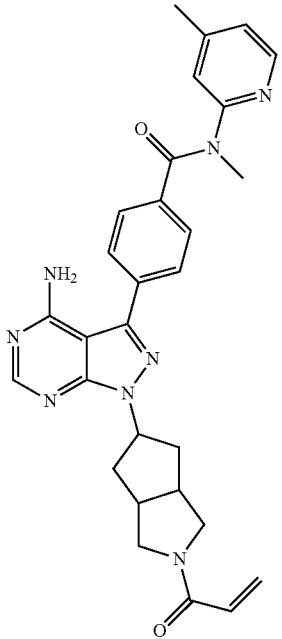 [SMILES: C=CC(=O)N1CC2CC(n3nc(-c4ccc(C(=O)N(C)c5cc(C)ccn5)cc4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-N-methyl-N-(4-methylpyridin-2-yl)benzamide |
| 55 | 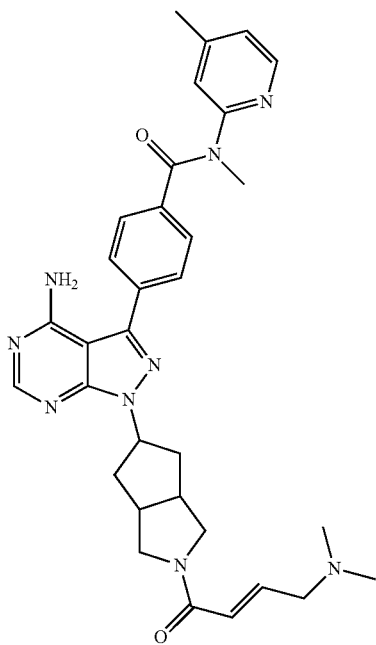 [SMILES: Cc1ccnc(N(C)C(=O)c2ccc(-c3nn(C4CC5CN(C(=O)/C=C/CN(C)C)CC5C4)c4ncnc(N)c34)cc2)c1] | (E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-methyl-N-(4-methylpyridin-2-yl)benzamide |

TABLE 1-continued

| Compd | Structures | IUPAC Names |
|---|---|---|
| 56 | 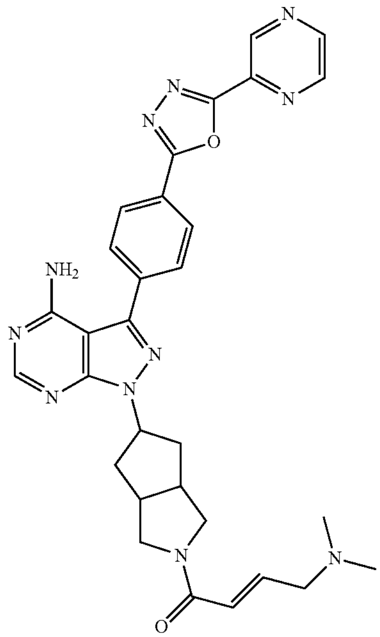 [SMILES: CN(C)C/C=C/C(=O)N1CC2CC(n3nc(-c4ccc(-c5nnc(-c6cnccn6)o5)cc4)c4c(N)ncnc43)CC2C1] | (E)-1-(5-(4-amino-3-(4-(5-(pyrazin-2-yl)-1,3,4-thiadiazol-2-yl)phenyl)-1H-pyrazolo[3,4-d]pyrimidin-1-yl)hexahydrocyclopenta[c]pyrrol-2(1H)-yl)-4-(dimethylamino)but-2-en-1-one |
| 57 | | (E)-1-(5-(4-amino-3-(4-(5-(pyridin-2-yl)-1,3,4-oxadiazol-2-yl)phenyl)-1H-pyrazolo[3,4-d]pyrimidin-1-yl)hexahydrocyclopenta[c]pyrrol-2(1H)-yl)-4-(dimethylamino)but-2-en-1-one | or pharmaceutically acceptable salts of any of the compounds above.

Following is a list of abbreviations used in the description of the preparation of the compounds of the present invention:
ALL: Acute lymphoblastic leukemia
ATP: Adenosine triphosphate
BTK: Bruton's Tyrosine Kinase
bs: broad singlet
CLL: Chronic lymphocytic leukemia
CDCl$_3$: Deuterated chloroform
CHCl$_3$: Chloroform
d: doublet
dd: doublet of doublet
dt: doublet of triplet
DCM: Dichloromethane
DMAC: N,N-(Dimethylacetamide)
DMAP: 4-(Dimethylamino) pyridine
DMF: N,N-Dimethyl formamide
DMSO: Dimethyl sulfoxide
EDTA: Ethylenediaminetetraacetic acid
EtOAc: Ethyl acetate
EtOH: Ethanol
HCl(g): Hydrogen chloride (gas)
K$_2$CO$_3$: Potassium carbonate
MeOH: Methanol
m: multiplet mmol: millimoles
µg: microgram
MS: Mass spectrum
NHL: Non-Hodgkin's lymphoma
Na$_2$CO$_3$: Sodium carbonate
ng: nanogram
NIS: N-iodosuccinimide
$^1$H NMR: Proton nuclear magnetic resonance
Pet ether: Petroleum ether, boiling range (60-80° C.)
POCl$_3$: Phosphorylchloride
s: singlet
t: Triplet
td: triplet of doublet
THF: Tetrahydrofuran
TLC: Thin layer chromatography The novel compounds of the present invention can be prepared using the reactions and techniques described below, together with conventional techniques known to those skilled in the art of organic synthesis, or variations thereon as appreciated by those skilled in the art.

The reactions can be performed in solvents appropriate to the reagents and materials employed and suitable for the transformations being affected. Preferred methods include those described below, where all symbols are as defined earlier unless and otherwise defined below.

The compounds of the formula (I) can be prepared as described in schemes below along with suitable modifications/variations which are well within the scope of a person skilled in the art.

Scheme I:

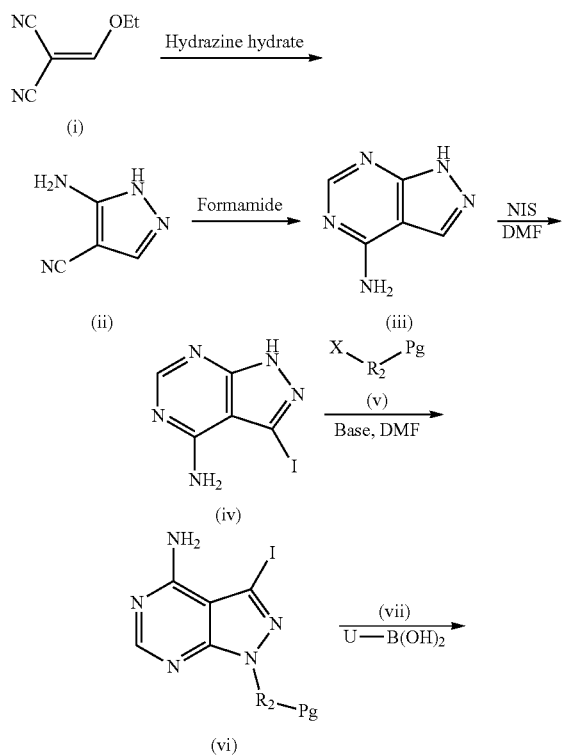

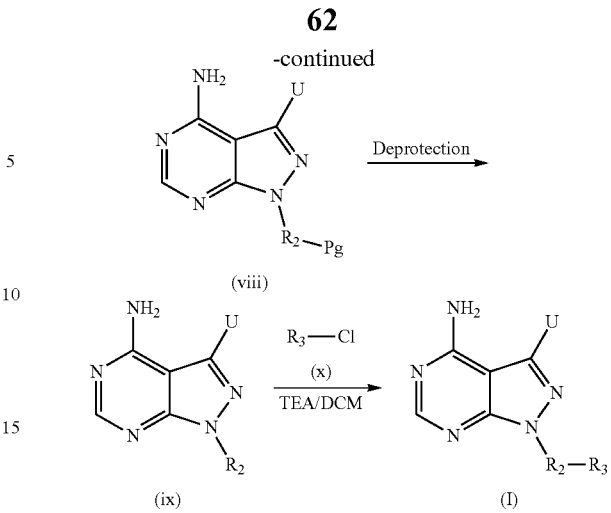

Wherein 'U', R$_2$ and R$_3$ are as defined earlier. Compound of formula (I) can be prepared by variety of methods familiar to those skilled in art. Compound of formula (i) was transformed into compound (ii) by reacted with hydrazine hydrate (Scheme-I). Compound of formula (ii) was cyclized using formamide to afford the compound of formula (iii). Compound (iii) was reacted with N-iodosuccinimide to get compound (iv). Compound (iv) reacted with compound (v) using different base to furnish the compound of formula (vi). Compound (vi) can subjected to Suzuki type of reaction, with compound (vii) using suitable catalysts, base and appropriate solvents to obtain compound of formula (viii). The deprotection of compound (viii) gives compound (ix). Compound (ix) is reacted with optionally substituted acid chlorides (x) to obtain compounds of formula (I).

The examples and preparations provided below further illustrate and exemplify the compounds of the present invention and methods of preparing such compounds. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

The compounds of formula (I) may also be synthesized as described in Scheme II. wherein 'U', R$_2$ and R$_3$ are as defined earlier. Compound (i) may be continently prepared by variety of methods familiar to those skilled in art. Compound (i) was transformed into compound (ii) by reacting with dibenzyl amine using different bases. Compound of formula (ii) was reacted with different protected cycloalkyl amines (iii) using suitable bases to furnish compound (iv). Compound (iv) was reduced to amine to afford the compound (v). Compound (v) was reacted with Triphosgene to get the compound (vi). Compound (vi) was deprotected to using Pd(OH)$_2$ to afford compound (vii). Compound (vii) was reacted with different Boronic acid to obtain compound (viii). Compound (viii) was deproted using suitable acid to get the compound (ix). Compound (ix) was reacted with optionally substituted acid chlorides using base to obtain compound of formula (I).

Scheme II

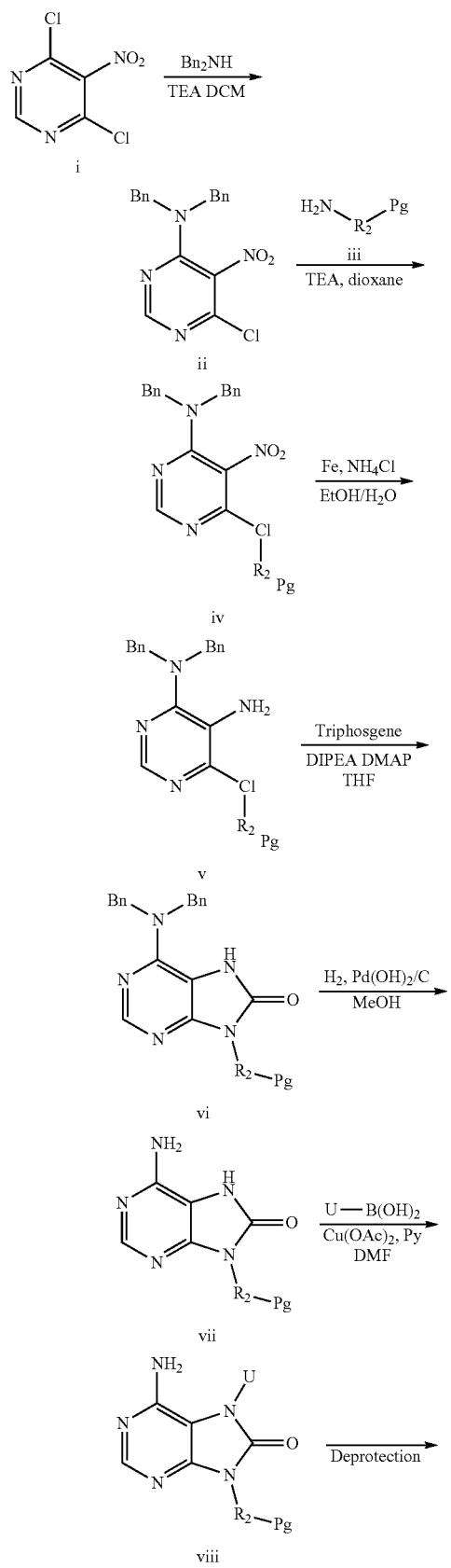

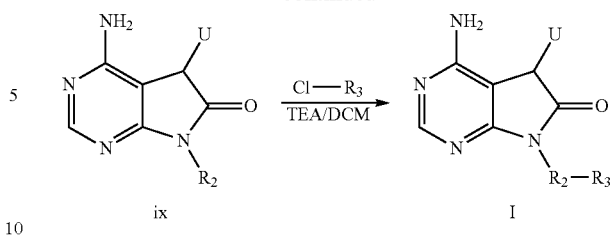

The compounds of formula (I) may also be synthesized as described in Scheme III. wherein 'U', $R_2$ and $R_3$ are as defined earlier. Compound (i) may be continently prepared by variety of methods familiar to those skilled in art. Compound (i) was transformed into compound (ii) using Ammonia. Compound (ii) reacted with compound (iii) using different base to furnish the compound of formula (iv). Compound (iv) can be subjected to Suzuki type of reaction, with compound (v) using suitable catalysts, base and appropriate solvents to obtain compound of formula (vi). Compound (vi) can be halogenated to afford compound (vii). The deprotection of compound (vii) gives compound (viii). Compound (viii) is reacted with optionally substituted acid chlorides to obtain compounds of formula (I).

Scheme III

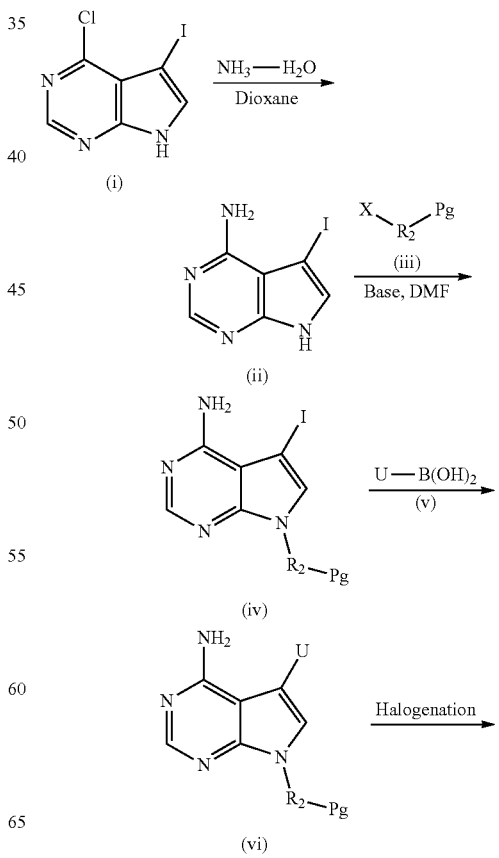

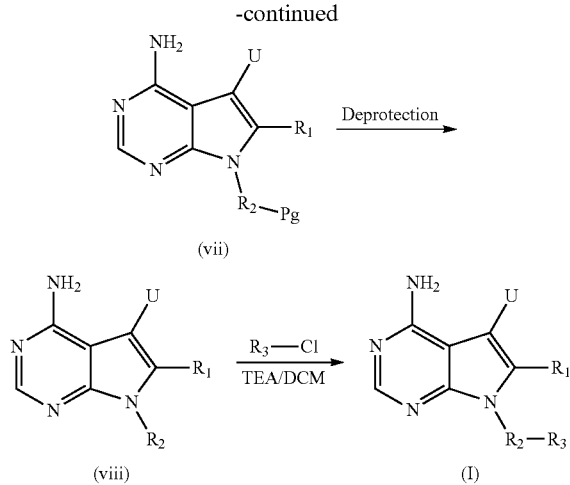

Compounds of the present invention can be isolated either as free amine form or as a salt corresponding to the acid used such as trifluoroacetic acid, hydrochloric acid, hydrobromic acid, oxalic acid, maleic acid, fumeric acid, succinic acid, p-toluene sulfonic acid or benzene sulfonic acid. The compounds can be purified where ever required, by recrystallization, trituration, precipitation, preparative thin layer chromatography, flash chromatography or by preparative HPLC method. The compounds of the present invention can be used either alone or in combination with one or more therapeutic agents or pharmaceutically acceptable salts thereof. Such use will depend on the condition of the patient being treated and is well within the scope of a skilled practitioner.

The invention is further illustrated by the following examples which describe the preferred way of carrying out the present invention. These are provided without limiting the scope of the present invention in any way.

$^1$H NMR spectral data given in the examples (vide infra) are recorded using a 400 MHz spectrometer (Bruker AVANCE-400) and reported in δ scale. Until and otherwise mentioned the solvent used for NMR is $CDCl_3$ using TMS as the internal standard.

Example: 1

Synthesis of 1-(5-(4-amino-3-(4-phenoxyphenyl)-1H-pyrazolo[3,4-d]pyrimidin-1-yl)hexahydrocyclopenta[c]pyrrol-2(1H)-yl)prop-2-en-1-one (compound No: 1)

Synthesis of titled compound was carried out, as described in Scheme-IV and step-wise procedure is described below.

Scheme-IV:

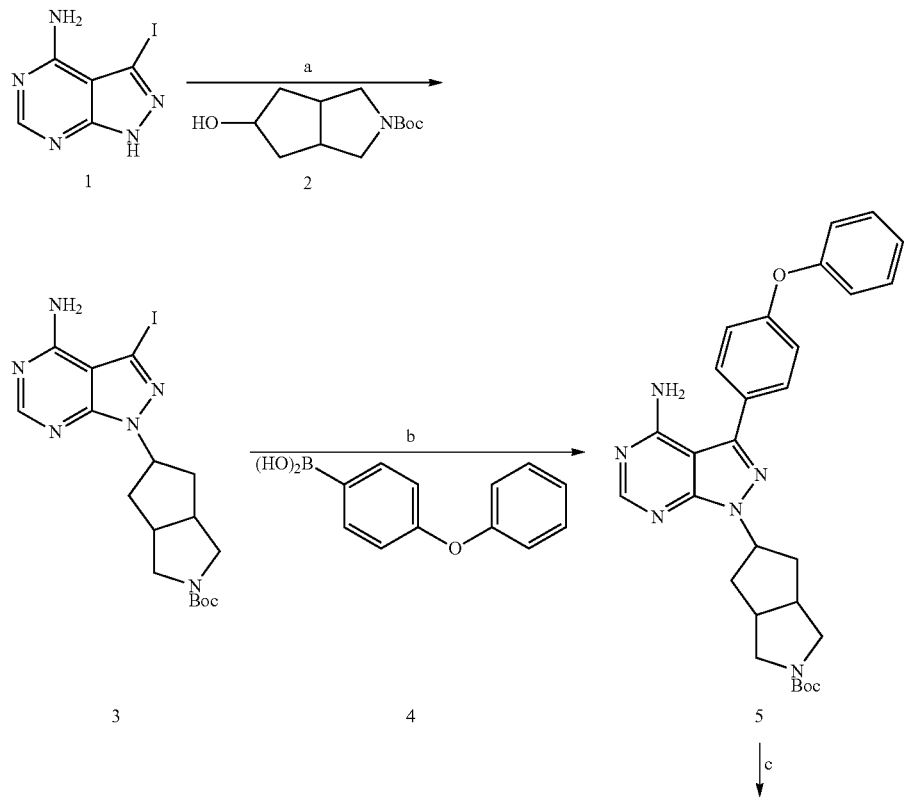

-continued

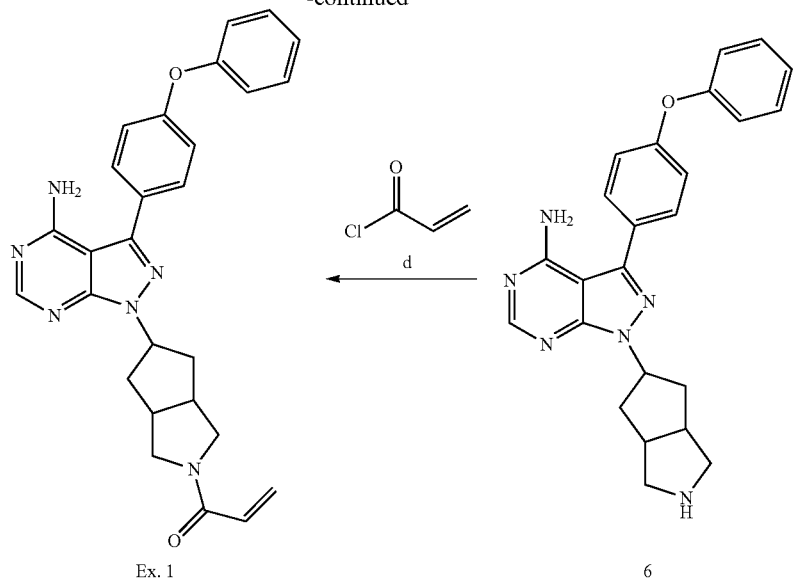

Ex. 1

Step-1: Synthesis of tert-butyl 5-(4-amino-3-iodo-1H-pyrazolo[3,4-d]pyrimidin-1-yl)hexahydrocyclopenta[c]pyrrole-2(1H)-carboxylate (3)

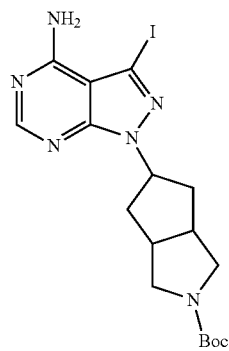 [SMILES: CC(C)(C)OC(=O)N1CC2CC(n3nc(I)c4c(N)ncnc43)CC2C1]

Intermediate 1 (2.0 g, 7.66 mmol), prepared as per general process disclosed in US 2012/0088912 and triphenylphosphine (6.53 g) were mixed together, in THF (20 mL). Tert-butyl 5-hydroxyhexahydrocyclopenta[c]pyrrole-2(1H)-carboxylate 2 (3.47 g, 15.32 mmol) was added to the mixture followed by the addition of diisopropyl diazodicarboxylate (2.26 mL, 11.49 mmol). The reaction mixture was stirred at room temperature overnight, filtered and concentrated. The residue obtained was purified by flash chromatography ($CH_2Cl_2$/MeOH=98/2) to get intermediate 3 as a white solid (2.75 g, 76% Yield). $^1$H NMR (DMSO-$d_6$, 400 MHz) δ ppm: 1.40 (s, 9H), 1.94-2.00 (m, 2H), 2.17-2.24 (m, 2H), 2.82-3.00 (m, 2H), 3.10-3.14 (m, 2H), 3.45-3.50 (m, 2H), 5.27-5.30 (m, 1H), 8.29 (s, 1H). MS (ESI-MS): m/z 471.10 $(M+H)^+$.

Step-2: Synthesis of tert-butyl 5-(4-amino-3-(4-phenoxyphenyl)-1H-pyrazolo[3,4-d]pyrimidin-1-yl)hexahydrocyclopenta[c]pyrrole-2(1H)-carboxylate (5)

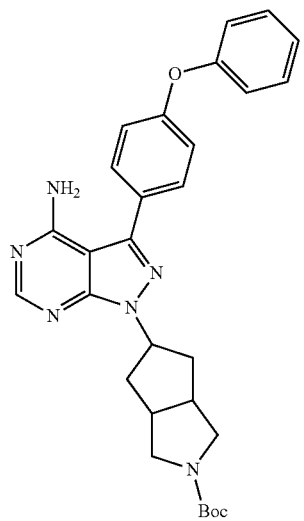 [SMILES: CC(C)(C)OC(=O)N1CC2CC(n3nc(-c4ccc(Oc5ccccc5)cc4)c4c(N)ncnc43)CC2C1]

To a stirred solution Intermediate 3 (2.7 g, 5.74 mmol), dissolved in dry DMF (27 mL), $PdCl_2(PPh_3)_2$ (0.4 g, 0.57 mmol), 4-phenoxyphenylboronicacid 4 (1.84 g, 8.61 mmol) and $KHCO_3$ (3.44 g, 34.46 mmol) was added. The reaction mixture was heated at 90° C. for 2 hrs, under $N_2$ atmosphere. Mixture was cooled to room temperature, diluted with water (50 mL) and extracted with EtOAc (3×50 mL). The combined organic layer was washed with water (2×25 mL) and brine solution (25 mL), dried over $Na_2SO_4$, and concentrated to dryness. The residue obtained was purified by column chromatography (using 0-5% methanol in DCM as a mobile phase) to obtain Intermediate 5 as an off white solid (2.2 g, 74% Yield). $^1$H NMR (DMSO-$d_6$, 400 MHz) δ ppm: 1.48 (s, 9H), 1.98-2.04 (m, 2H), 2.27-2.34 (m, 2H), 2.89 (s, 2H), 3.13-3.17 (m, 2H), 3.47 (q, 2H, J=8.0 Hz), 5.36 (q, 1H, J=8.0 Hz), 7.10-7.14 (m, 4H), 7.144-7.20 (m, 1H), 7.40-7.43 (m, 2H), 7.65-7.68 (m, 2H), 8.23 (s, 1H). ESI-MS (ESI-MS): m/z 535.23 (M+Na)+.

Step-3: Synthesis of 1-(octahydrocyclopenta[c]pyrrol-5-yl)-3-(4-phenoxyphenyl)-1H-pyrazolo[3,4-d]pyrimidin-4-amine (6)

Step-4: Synthesis of 1-(5-(4-amino-3-(4-phenoxyphenyl)-1H-pyrazolo[3,4-d]pyrimidin-1-yl)hexahydrocyclopenta[c]pyrrol-2(1H)-yl)prop-2-en-1-one, compound No: 1

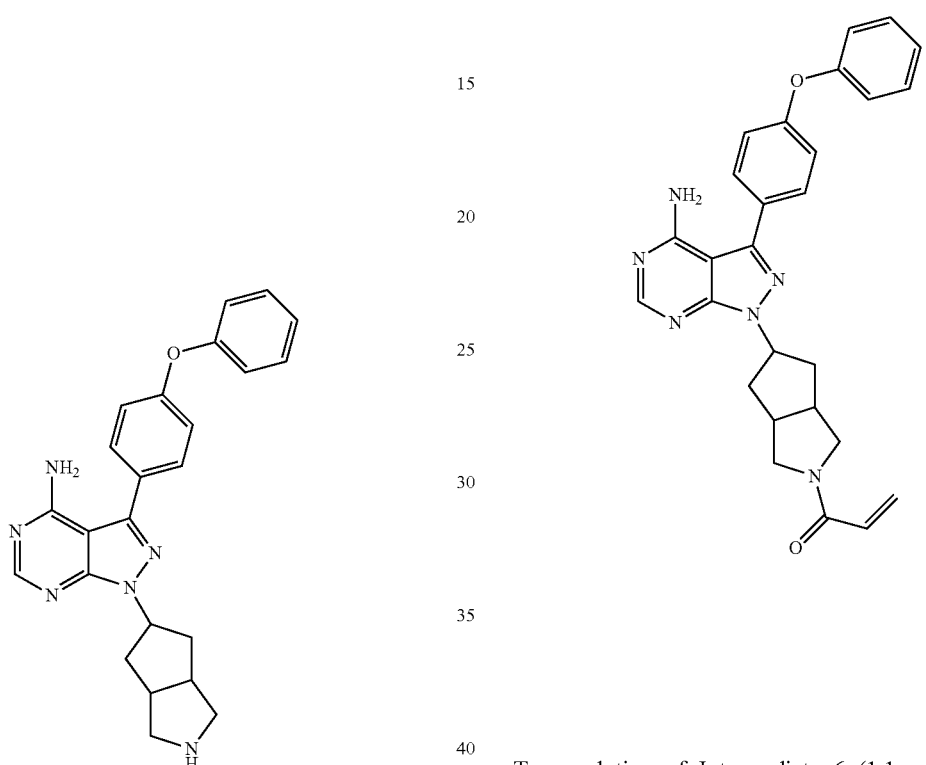

To a solution of Intermediate 5 (2.1 g, 4.09 mmol) in CH$_2$Cl$_2$ (40 mL) was added TFA (1.25 mL, 16.37 mmol). After stirring 2 hrs at room temperature, the solvent was removed and the residues were dissolved in a mixture of ethyl acetate (50 mL) and dilute aq. K$_2$CO$_3$. The organic layer was separated, dried over MgSO$_4$, filtered and concentrated to provide Intermediate 6 as a white solid (1.2 g, 71% Yield). $^1$H NMR (400 MHz) δ ppm: 1.92-1.96 (m, 2H), 2.31-2.39 (m, 2H), 2.74-2.78 (m, 2H), 2.89-2.30 (m, 2H), 3.12-3.20 (m, 2H), 5.43-5.37 (m, 1H), 7.11-7.20 (m, 5H), 7.41-7.45 (m, 2H), 7.64-7.66 (m, 2H), 8.24 (s, 1H); MS (ESI-MS): m/z 413.20 (M+H)+.

To a solution of Intermediate 6 (1.1 g, 2.66 mmol), dissolved in CH$_2$Cl$_2$ (30 mL), tri-ethyl amine (1.11 mL, 8.00 mmol) was added followed by addition of acryl chloride (0.2 mL, 2.53 mmol). The reaction was stopped after 2 hrs. The reaction mixture was washed with water and then with brine. The organic layer was separated, dried over MgSO$_4$, filtered and concentrated. Residue obtained was purified by flash chromatography (using CH$_2$Cl$_2$/MeOH=25/1, as a mobile phase) to get compound 1 as a white solid (0.75 g, 60% Yield). $^1$H NMR: (CDCL$_3$, 400 MHz): δ 8.36 (S, 1H), 7.66-7.62 (m, 2H), 7.37-7.41 (m, 2H), 7.13-7.20 (s, 3H), 7.07-7.09 (m, 2H), 6.36-6.50 (m, 2H), 5.68-5.71 (m, 1H), 5.53-5.59 (m, 3H), 3.82-3.87 (m, 2H), 3.45-3.53 (m, 2H), 3.10-3.21 (m, 2H), 2.50-2.58 (m, 2H), 2.11-2.17 (m, 2H); ESI-MS: (+ve mode) 467.20 (M+H)+ (100%); UPLC: 98.09%.

Example: 2

Synthesis of 4-(1-(2-acryloyloctahydrocyclopenta[c]pyrrol-5-yl)-4-amino-1H-pyrazolo[3,4-d]pyrimidin-3-yl)-N-(pyridin-2-yl)benzamide (compound No: 13)

Synthesis of titled compound was carried out, as described in Scheme-V and step-wise procedure is described below.

Scheme-V:
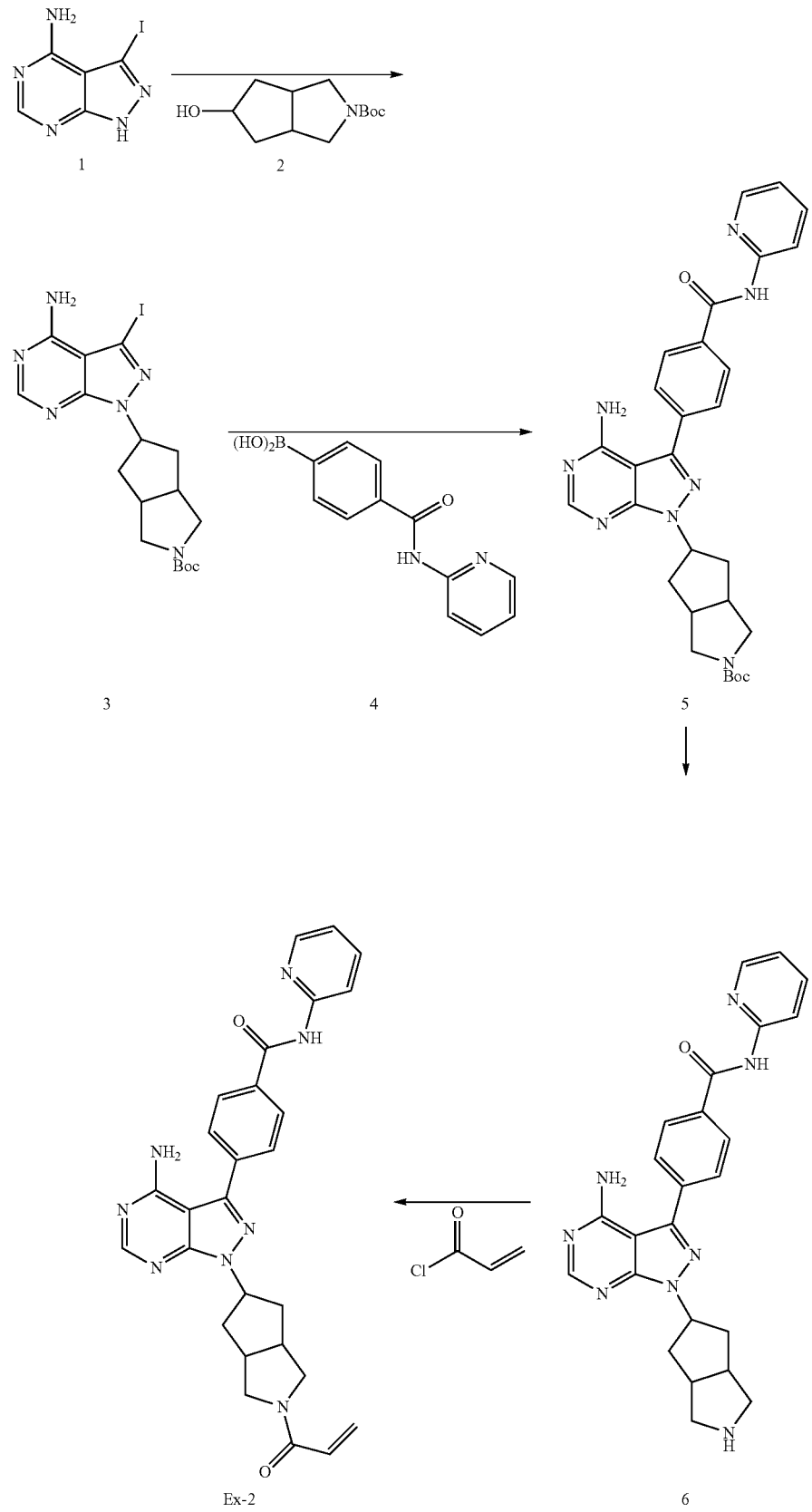

Step-1: Synthesis of tert-butyl 5-(4-amino-3-iodo-1H-pyrazolo[3,4-d]pyrimidin-1-yl)hexahydrocylcopenta[c]pyrrole-2(1H)-carboxylate (3)

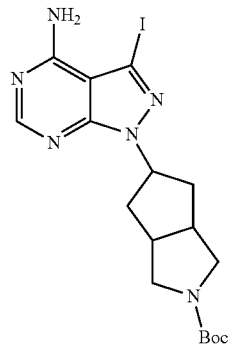 [SMILES: CC(C)(C)OC(=O)N1CC2CC(n3nc(I)c4c(N)ncnc43)CC2C1]

Intermediate 1 (0.22 g, 0.851 mmol) and triphenylphosphine (0.71 g) were mixed together in THF (10 mL). Tert-butyl 5-hydroxyhexahydrocyclopenta[c]pyrrole-2(1H)-carboxylate 2 (0.38 g, 1.7 mmol) was added to the reaction mixture followed by the addition of diisopropyl diazodicarboxylate (0.24 mL, 1.22 mmol). The reaction mixture was stirred at room temperature overnight, filtered and concentrated. The residue obtained was purified by flash chromatography (CH$_2$Cl$_2$/MeOH=98/2) to get intermediate 3 as a white solid (0.3 g, 76% Yield). $^1$H NMR (DMSO-d$_6$, 400 MHz) δ ppm: 1.40 (s, 9H), 1.94-2.00 (m, 2H), 2.17-2.24 (m, 2H), 2.82-3.00 (m, 2H), 3.10-3.14 (m, 2H), 3.45-3.50 (m, 2H), 5.27-5.30 (m, 1H), 8.29 (s, 1H). MS (ESI-MS): m/z 471.10 (M+H)$^+$.

Step-2: Synthesis of tert-butyl 5-(4-amino-3-(4-(pyridin-2-ylcarbamoyl)phenyl)-1H-pyrazolo[3,4-d]pyrimidin-1-yl)hexahydrocyclopenta[c]pyrrole-2(1H)-carboxylate (5)

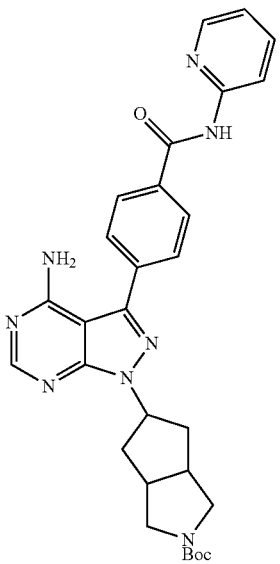 [SMILES: CC(C)(C)OC(=O)N1CC2CC(n3nc(-c4ccc(C(=O)Nc5ccccn5)cc4)c4c(N)ncnc43)CC2C1]

To a stirred solution of intermediate 3 (0.3 g, 0.638 mmol), dissolved in dry DMF (3 mL) were added PdCl$_2$(PPh$_3$)$_2$(0.089 g, 0.127 mmol), (4-(pyridin-2-ylcarbamoyl)phenyl)boronic acid 4 (0.31 g, 0.95 mmol) and KHCO$_3$ (0.340 g, 3.56 mmol). The reaction mixture was heated at 90° C. for 2 hrs, under N$_2$ atmosphere. Mixture was cooled to room temperature, diluted with water (50 mL) and extracted with EtOAc (3×50 mL). The combined organic layer was washed with water (2×25 mL) and brine solution (25 mL), dried over Na$_2$SO$_4$ and concentrated to dryness. The residue obtained was purified by column chromatography (silica gel, 0-5% methanol in DCM) to obtain intermediate 5 as an off white solid (0.25 g, 72.56% Yield). $^1$H NMR (DMSO-d$_6$, 400 MHz) δ ppm: 1.59 (s, 9H), 2.11-2.17 (m, 2H), 2.49-2.57 (m, 2H), 3.07-3.09 (m, 2H), 3.28 (bs, 2H), 3.64 (bs, 2H), 5.55 (q, 1H, J=8.0 Hz), 7.11 (q, 1H, J=8.0 Hz), 7.78-7.81 (m, 1H), 7.82 (m, 2H), 8.10 (d, 2H, J=8.0 Hz), 8.35 (m, 1H), 8.41-8.43 (m, 2H), 8.63 (s, 1H). ESI-MS (ESI-MS): m/z 541.41 (M+H)$^+$.

Step-3: Synthesis of 4-(4-amino-1-(octahydrocyclopenta[c]pyrrol-5-yl)-1H-pyrazolo[3,4-d]pyrimidin-3-yl)-N-(pyridin-2-yl)benzamide (6)

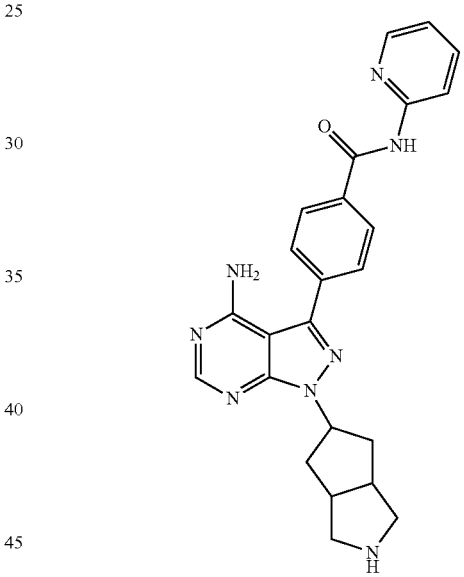

To a solution of Intermediate 5 (0.25 g, 0.462 mmol) in CH$_2$Cl$_2$ (10 mL), TFA (1.0 mL, 15.87 mmol) was added and the reaction mixture was stirred for 2 hrs at room temperature. The solvent was removed and the residue obtained was dissolved in a mixture of ethyl acetate (50 mL) and dilute aq. K$_2$CO$_3$. The organic layer was dried over MgSO$_4$, filtered and concentrated to get Intermediate 6 as a white solid (0.13 g, 63.85% Yield). $^1$H NMR (DMSO-d$_6$, 400 MHz) δ ppm: 1.15-1.23 (m, 2H), 2.32-2.37 (m, 2H), 2.54-2.58 (m, 2H), 2.93-2.97 (m, 2H), 3.24-3.29 (m, 2H), 5.33-5.37 (m, 1H), 7.16-7.19 (m, 1H), 7.77 (q, 2H, J=12.0 Hz), 7.84-7.88 (m, 1H), 8.18-8.20 (m, 2H), 8.22-8.24 (m, 1H), 8.25-8.30 (m, 1H), 8.40-8.41 (m, 1H), 10.83 (s, 1H); MS (ESI-MS): m/z 441.15 (M+H)$^+$.

Step-4: Synthesis of 4-(1-(2-acryloyloctahydrocyclopenta[c]pyrrol-5-yl)-4-amino-1H-pyrazolo[3,4-d]pyrimidin-3-yl)-N-(pyridin-2-yl)benzamide; compound No: 13

Example: 3

Compound 2: (1-(5-(4-amino-3-(benzo[d]thiazol-6-yl)-1H-pyrazolo[3,4-d]pyrimidin-1-yl)hexahydrocyclopenta[c]pyrrol-2(1H)-yl)prop-2-en-1-one

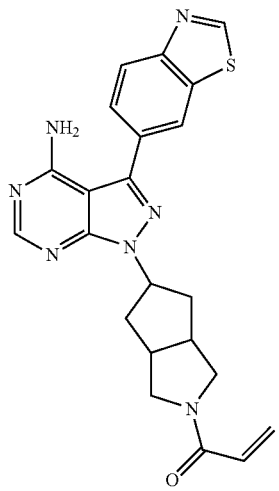

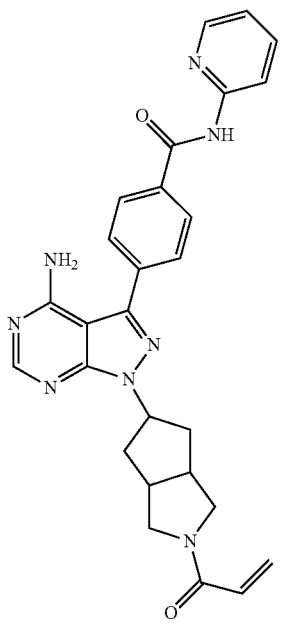 [SMILES: C=CC(=O)N1CC2CC(n3nc(-c4ccc(C(=O)Nc5ccccn5)cc4)c4c(N)ncnc43)CC2C1]

$^1$H NMR: (CDCl$_3$, 400 MHz): δ 9.11 (s, 1H), 8.41 (s, 1H), 8.34-8.30 (m, 2H), 7.87 (dd, 1H, J$_1$=1.6 Hz, J$_2$=8.4 Hz), 6.49 (dd, 1H, J$_1$=9.6 Hz, J$_2$=16.8 Hz), 6.42 (dd, 1H, J$_1$=2.8 Hz, J$_2$=16.8 Hz), 5.72 (dd, 1H, J$_1$=2.4 Hz, J$_2$=9.6 Hz), 5.64-5.57 (m, 1H), 5.50 (bs, 2H), 3.89-3.84 (m, 2H), 3.57-3.47 (m, 2H), 3.25-3.20 (m, 1H), 3.17-3.11 (m, 1H), 2.62-2.54 (m, 2H), 2.22-2.13 (m, 2H); ESI-MS: (+ve mode) 431.9 (M+H)$^+$ (100%); HPLC: 96.04%.

Example: 4

Compound 3: 1-(5-(5-((4-amino-3-(4-phenoxyphenyl)-1H-pyrazolo[3,4-d]pyrimidin-1-yl)methyl)pyridin-2-yl)hexahydropyrrolo[3,4-c]pyrrol-2(1H)-yl)prop-2-en-1-one

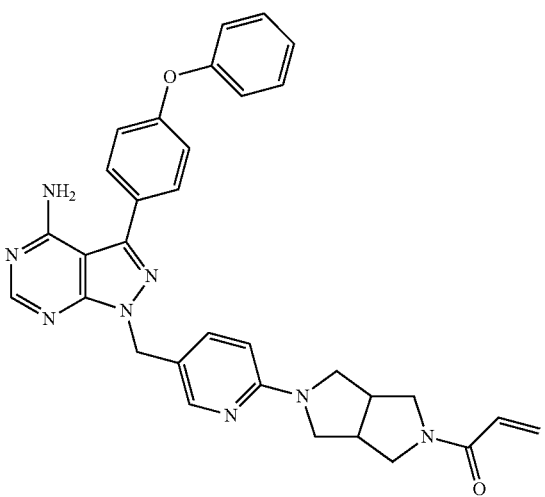 [SMILES: C=CC(=O)N1CC2CN(c3ccc(Cn4nc(-c5ccc(Oc6ccccc6)cc5)c5c(N)ncnc54)cn3)CC2C1]

To a solution of Intermediate 6 (0.13 g, 0.295 mmol), dissolved in CH$_2$Cl$_2$ (30 mL) and tri-ethyl amine (0.090 g, 0.886 mmol), acryl chloride (0.026 g, 0.295 mmol) was added and the reaction mixture was stirred for 2 hrs. The reaction mixture was washed with water and brine solution. The organic layer was dried over MgSO$_4$, filtered, concentrated and residue obtained was purified by flash chromatography, using CH$_2$Cl$_2$/MeOH (25/1) to get compound 13 as a white solid (0.03 g, 20.58% Yield). $^1$H NMR: (CDCl$_3$, 400 MHz): δ 8.72 (s, 1H), 8.43 (d, 1H, J=6.4 Hz), 8.39 (s, 1H), 8.35-8.34 (m, 1H), 8.13 (d, 2H, J=8.4 Hz), 7.88 (d, 2H, J=8.4 Hz), 7.83-7.79 (m, 1H), 7.14-7.11 (m, 1H), 6.49 (dd, 1H, J$_1$=10.0 Hz, J$_2$=16.8 Hz), 6.42 (dd, 1H, J$_1$=2.4 Hz, J$_2$=16.8 Hz), 5.72 (dd, 1H, J$_1$=2.8 Hz, J$_2$=10.0 Hz), 5.61-5.55 (m, 3H), 3.89-3.84 (m, 2H), 3.57-3.47 (m, 2H), 3.24-3.21 (m, 1H), 315-3.12 (m, 1H), 2.60-2.52 (m, 2H), 2.21-2.14 (m, 1H); ESI-MS: (+ve mode) 495.4 (M+H)$^+$ (100%); HPLC: 99.09.

$^1$H NMR: (DMSO-d$_6$, 400 MHz): δ 8.27 (S, 1H), 8.11-8.09 (m, 1H), 7.63-7.61 (m, 2H), 7.44-7.40 (m, 1H), 7.48-

7.44 (m, 2H), 7.19-7.17 (m, 1H), 7.13-7.09 (m, 5H), 6.56-6.49 (m, 1H), 6.44-6.41 (m, 1H), 6.11-6.06 (m, 1H), 5.64-5.61 (m, 1H), 5.39 (s, 2H), 4.41-4.39 (m, 2H), 3.81-3.80 (m, 1H), 3.64-3.57 (m, 2H), 3.46-3.45 (m, 2H), 3.19-3.16 (m, 2H); ESI-MS: (+ve mode) 559.35 (M+H)$^+$ (100%); HPLC: 95.82%.

Example: 5

Compound 4: 1-(5-(2-(4-amino-3-(4-phenoxyphenyl)-1H-pyrazolo[3,4-d]pyrimidin-1-yl)ethyl)hexahydropyrrolo[3,4-c]pyrrol-2(1H)-yl)prop-2-en-1-one

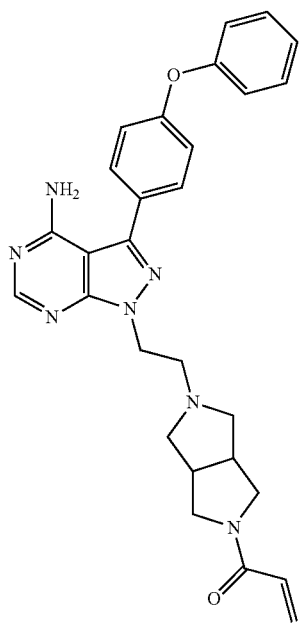 [SMILES: C=CC(=O)N1CC2CN(CCn3nc(-c4ccc(Oc5ccccc5)cc4)c4c(N)ncnc43)CC2C1]

$^1$H NMR: (CDCl$_3$, 400 MHz): δ 8.37 (s, 1H), 7.65 (dd, 2H, J$_1$=2.0 Hz, J$_2$=6.4 Hz), 7.40 (t, 2H, J=4.4 Hz), 7.18-7.13 (m, 3H), 7.09 (d, 2H, J=7.6 Hz), 6.37-6.27 (m, 2H), 5.61 (dd, 1H, J$_1$=3.6 Hz, J$_2$=9.2 Hz), 5.41 (bs, 2H), 3.79-3.68 (m, 2H), 3.35 (dd, 1H, J$_1$=4.8 Hz, J$_2$=12.8 Hz), 3.27 (dd, 1H, J$_1$=4.8 Hz, J$_2$=10.4 Hz), 3.08-3.05 (m, 1H), 2.96 (t, 1H, J=6.0 Hz), 2.89-2.86 (m, 1H), 2.77-2.75 (m, 1H), 2.70-2.57 (m, 4H); ESI-MS: (+ve mode) 496.15 (M+H)$^+$ (100%); HPLC: 96.62%.

Example: 6

Compound 5: 1-(5-(4-amino-3-(2-methylbenzo[d]thiazol-6-yl)-1H-pyrazolo[3,4-d]pyrimidin-1-yl)hexahydrocyclopenta[c]pyrrol-2(1H)-yl)prop-2-en-1-one

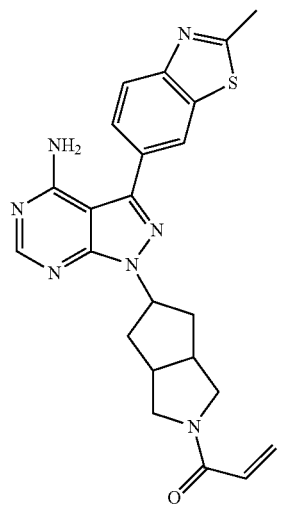 [SMILES: C=CC(=O)N1CC2CC(n3nc(-c4ccc5nc(C)sc5c4)c4c(N)ncnc43)CC2C1]

$^1$H NMR: (CDCl$_3$, 400 MHz): δ 8.40 (s, 1H), 8.19 (d, 1H, J=2.0 Hz), 8.12 (d, 1H, J=8.4 Hz), 7.77 (dd, 1H, J$_1$=2.0 Hz, J$_2$=8.4 Hz), 6.49 (dd, 1H, J$_1$=10.0 Hz, J$_2$=16.8 Hz), 6.42 (dd, 1H, J$_1$=2.8 Hz, J$_2$=16.8 Hz), 5.72 (dd, 1H, J$_1$=2.4 Hz, J$_2$=9.6 Hz), 5.61-5.57 (m, 1H), 5.31 (bs, 2H), 3.89-3.83 (m, 2H), 3.56-3.47 (m, 2H), 3.24-3.22 (m, 1H), 3.14-3.12 (m, 1H), 2.91 (s, 3H), 2.59-2.55 (m, 2H), 2.19-2.14 (m, 2H); ESI-MS: (+ve mode) 446.0 (M+H)$^+$ (100%); HPLC: 95.09%.

Example: 7

Compound 6: 1-(5-(4-amino-3-(benzo[b]thiophen-5-yl)-1H-pyrazolo[3,4-d]pyrimidin-1-yl)hexahydrocyclopenta[c]pyrrol-2(1H)-yl)prop-2-en-1-one

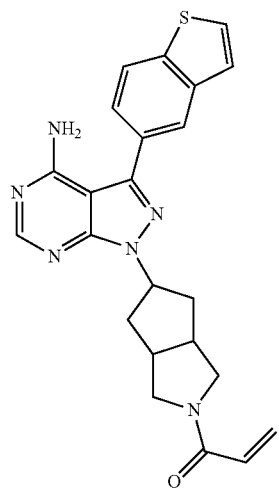 [SMILES: C=CC(=O)N1CC2CC(n3nc(-c4ccc5sccc5c4)c4c(N)ncnc43)CC2C1]

¹H NMR: (DMSO, 400 MHz): δ 8.24 (s, 1H), 8.16 (dd, 2H, J₁=6.0 Hz, J₂=4.4 Hz), 7.85 (d, 1H, J=5.6 Hz), 7.65 (dd, 1H, J=8.4 Hz, J₂=1.6 Hz), 7.56 (d, 1H, J=5.2 Hz), 7.62 (dd, 1H, J₁=10.4 Hz, J₂=16.8 Hz), 6.14 (dd, 1H, J₁=16.8 Hz, J₂=2.4 Hz), 5.67 (dd, 1H, J₁=10.0 Hz, J₂=2.4 Hz), 5.45-5.41 (m, 1H), 3.81-3.76 (m, 1H), 3.66-3.60 (m, 1H), 3.54-3.50 (m, 1H), 3.42-3.35 (m, 1H), 3.00-3.08 (m, 1H), 23.00-2.98 (m, 1H), 2.38-2.31 (m, 2H), 2.09-2.04 (m, 2H); ESI-MS: (+ve mode) 431.0 (M+H)⁺ (100%), 453.2 (M+Na)⁺ (25%); UPLC: 98.53%.

Example: 8

Compound 7: 1-(5-(4-amino-3-(2,3-dihydrobenzo[b]thiophen-5-yl)-1H-pyrazolo [3,4-d]pyrimidin-1-yl)hexahydrocyclopenta[c]pyrrol-2(1H)-yl)prop-2-en-1-one

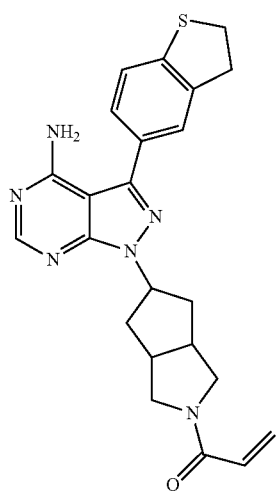 [SMILES: C=CC(=O)N1CC2CC(n3nc(-c4ccc5c(c4)CCS5)c4c(N)ncnc43)CC2C1]

¹H NMR (DMSO-d₆, 400 MHz) δ ppm: 8.22 (s, 1H), 7.55-7.51 (m, 2H), 7.42-7.38 (m, 2H), 6.65-6.58 (m, 1H), 6.16-6.11 (dd, 1H, J₁=2.8 Hz, J₂=17.2 Hz), 5.68-5.66 (m, 1H), 5.64-5.39 (m, 1H), 3.42-3.40 (m, 1H), 3.39-3.37 (m, 1H), 3.35-3.35 (m, 1H), 3.32-3.30 (m, 3H), 3.10-2.83 (m, 2H), 2.82-2.80 (m, 2H), 2.33-2.29 (m, 3H), 2.04-2.03 (m, 2H); (ESI-MS): (+ve mode) 433.05 (M+H)⁺. (100%), UPLC: 95.80%.

Example: 9

Compound 8: 1-(5-(4-amino-3-(dibenzo[b,d]furan-3-yl)-1H-pyrazolo[3,4-d]pyrimidin-1-yl)hexahydrocyclopenta[c]pyrrol-2(1H)-yl)prop-2-en-1-one

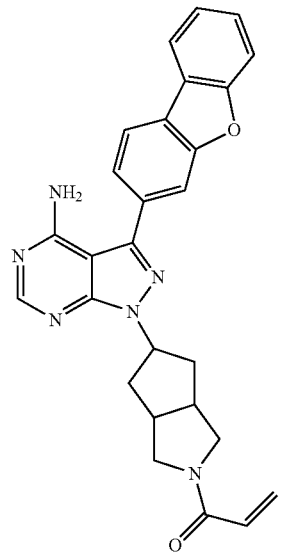 [SMILES: C=CC(=O)N1CC2CC(n3nc(-c4ccc5c(c4)oc4ccccc45)c4c(N)ncnc43)CC2C1]

¹H NMR: (DMSO, 400 MHz): δ 8.30-8.28 (m, 1H), 8.26 (s, 1H), 8.22-8.20 (m, 1H), 7.92 (d, 1H, J=0.8 Hz), 7.75-7.69 (m, 2H), 7.58-7.54 (m, 1H), 7.46-5.43 (m, 1H), 6.66-6.59 (m, 1H), 6.14 (dd, 1H, J₁=2.4 Hz, J₂=16.8 Hz), 5.67 (dd, 1H, J₁=2.4 Hz, J₂=10.4 Hz), 5.46-5.43 (m, 1H), 3.82-3.77 (m, 1H), 3.65-3.61 (m, 1H), 3.55-3.51 (m, 1H), 3.39-3.35 (m, 1H), 3.17-2.92 (m, 2H), 2.41-2.33 (m, 2H), 2.11-2.05 (m, 2H); ESI-MS: (+ve mode) 465.1 (M+H)⁺ (100%), 487.3 (M+Na)⁺ (10%); UPLC: 95.50.

Example: 10

Compound 9: N-(6-(1-(2-acryloyloctahydrocyclopenta[c]pyrrol-5-yl)-4-amino-1H-pyrazolo [3,4-d]pyrimidin-3-yl)benzo[d]thiazol-2-yl)acetamide

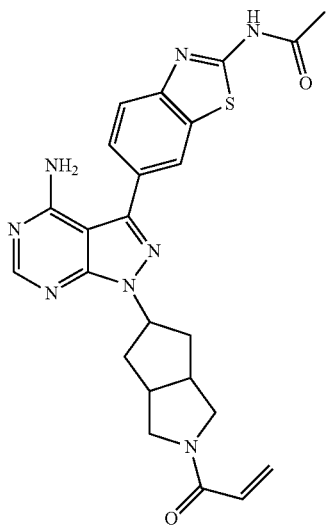 [SMILES: C=CC(=O)N1CC2CC(n3nc(-c4ccc5nc(NC(C)=O)sc5c4)c4c(N)ncnc43)CC2C1]

$^1$H NMR: (DMSO, 400 MHz): δ 12.41 (s, 1H), 8.24 (s, 2H), 8.87-8.85 (m, 1H), 7.69-7.67 (m, 1H), 6.65-6.58 (m, 1H), 6.14 (dd, 1H, $J_1$=2.4 Hz, $J_2$=14.4 Hz), 5.66 (dd, 1H, $J_1$=1.2 Hz, $J_2$=10.4 Hz), 5.44-5.41 (m, 1H), 3.81-3.38 (m, 3H), 3.40-3.33 (m, 1H), 3.11-2.99 (m, 2H), 2.50-2.37 (m, 2H), 2.20 (s, 3H), 2.12-1.90 (m, 2H); ESI-MS: (+ve mode) 489.3 (M+H)$^+$ (100%), 511.0 (M+Na)+(10%); UPLC: 95.29%.

Example: 11

Compound 10: 1-(5-(4-amino-3-(2-methoxybenzo[d]thiazol-6-yl)-1H-pyrazolo[3,4-d] pyrimidin-1-yl)hexahydrocyclopenta[c]pyrrol-2(1H)-yl)prop-2-en-1-one

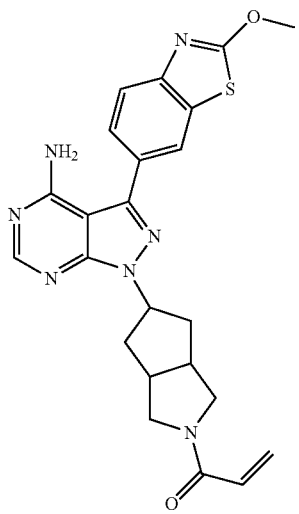 [SMILES: C=CC(=O)N1CC2CC(n3nc(-c4ccc5nc(OC)sc5c4)c4c(N)ncnc43)CC2C1]

$^1$H NMR (DMSO-d$_6$, 400 MHz) δ ppm: 8.23 (s, 1H), 8.17 (s, 1H), 7.79 (m, 1H, J=8.4 Hz), 7.67-7.65 (m, 1H), 6.64-6.58 (m, 1H), 6.30-6.11 (dd, 1H, $J_1$=2.4 Hz, $J_2$=16.8 Hz), 5.70-5.65 (dd, 1H, $J_1$=2.4 Hz, $J_2$=10.4 Hz), 5.45-5.42 (m, 1H), 4.19 (s, 3H), 3.80-3.76 (m, 1H), 3.62-3.53 (m, 1H), 3.40-3.38 (m, 1H), 3.10-2.83 (m, 1H), 2.82-2.80 (m, 2H), 2.36-2.32 (m, 2H), 2.06-2.05 (m, 2H); (ESI-MS): (+ve mode) 462.05 (M+H)$^+$. (100%), UPLC: 95.22%, Ret. time=3.09 min.

Example: 12

Compound 11: 1-(5-(4-amino-3-(4-phenoxyphenyl)-1H-pyrazolo[3,4-d]pyrimidin-1-yl)hexahydrocyclopenta[c]pyrrol-2(1H)-yl)prop-2-yn-1-one

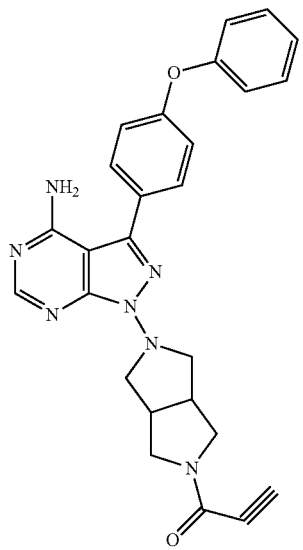 [SMILES: C#CC(=O)N1CC2CN(n3nc(-c4ccc(Oc5ccccc5)cc4)c4c(N)ncnc43)CC2C1]

$^1$H NMR: (DMSO-d$_6$, 400 MHz): δ 8.23 (s, 1H), 7.67-7.64 (m, 2H), 7.44-7.40 (m, 2H), 7.19-7.10 (m, 5H), 5.4 (s, 1H), 4.21-4.18 (m, 1H), 3.83-3.74 (m, 1H), 3.65-3.61 (m, 2H), 3.05-3.03 (m, 2H), 2.34-2.31 (m, 2H), 2.05-2.03 (m, 2H); ESI-MS: (+ve mode) 465.50 (M+H)$^+$ (100%); HPLC: 99.12%.

Example: 13

Compound 12: 1-(5-(4-amino-3-(3-methoxy-4-phenoxyphenyl)-1H-pyrazolo[3,4-d]pyrimidin-1-yl)hexahydrocyclopenta[c]pyrrol-2(1H)-yl)prop-2-en-1-one

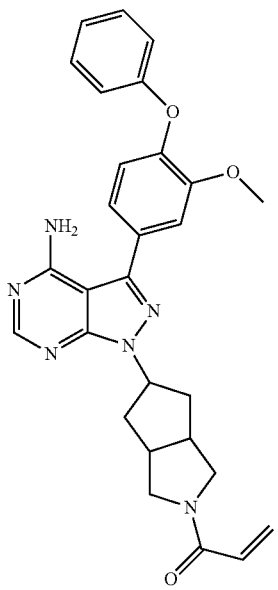 [SMILES: C=CC(=O)N1CC2CC(n3nc(-c4ccc(Oc5ccccc5)c(OC)c4)c4c(N)ncnc43)CC2C1]

$^1$H NMR: (CDCl$_3$, 400 MHz): δ 8.38 (s, 1H), 7.37-7.33 (m, 3H), 7.22 (dd, 1H, J$_1$=8.0 Hz, J$_2$=2.0 Hz), 7.14-7.08 (m, 2H), 7.03 (d, 2H, J=8.0 Hz), 6.51-6.37 (m, 2H), 5.70 (dd, 1H, J$_1$=10.0 Hz, J$_2$=2.4 Hz), 5.65 (bs, 2H), 5.60-5.53 (m, 1H), 3.95 (s, 3H), 3.89-3.84 (m, 2H), 3.55-3.51 (m, 2H), 3.24-3.21 (m, 1H) 3.15-3.11 (m, 1H), 2.63-2.54 (m, 2H), 2.21-2.12 (m, 2H); ESI-MS: (+ve mode) 497.1 (M+H)$^+$ (100%), 519.25 (M+Na)$^+$ (50%); UPLC: 95.90%.

Example: 14

Compound 14: 1-(5-(4-amino-3-(2-phenylbenzo[d]thiazol-6-yl)-1H-pyrazolo[3,4-d]pyrimidin-1-yl)hexahydrocyclopenta[c]pyrrol-2(1H)-yl)prop-2-en-1-one

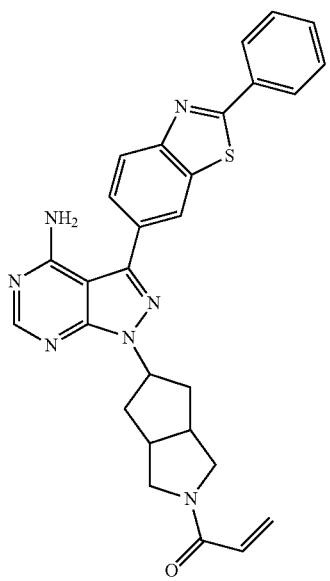 [SMILES: C=CC(=O)N1CC2CC(n3nc(-c4ccc5nc(-c6ccccc6)sc5c4)c4c(N)ncnc43)CC2C1]

$^1$H NMR: (CDCl$_3$, 400 MHz): δ 8.41 (s, 1H), 8.27 (d, 1H, J=1.6 Hz), 8.23 (d, 1H, J=8.0 Hz), 8.15-8.13 (m, 2H), 7.82 (dd, 1H, J$_1$=8.0 Hz, J$_2$=2.0 Hz), 7.56-7.53 (m, 3H), 6.52-6.38 (m, 2H), 5.70 (dd, 1H, J$_1$=10.0 Hz, J$_2$=2.0 Hz), 5.63-5.59 (m, 1H), 5.49 (bs, 2H), 3.90-3.84 (m, 2H), 3.57-3.48 (m, 2H), 3.25-3.22 (m, 1H), 3.17-3.14 (m, 1H), 2.63-2.55 (m, 2H), 2.22-2.13 (m, 2H); ESI-MS: (+ve mode) 507.6 (M+H)$^+$ (100%), 530.1 (M+Na)$^+$ (30%); UPLC: 97.51%.

85

Example: 15

Compound 15: 1-(5-(4-amino-3-(benzo[d] [1,3] dioxol-5-yl)-1H-pyrazolo[3,4-d]pyrimidin-1-yl) hexahydrocyclopenta[c]pyrrol-2(1H)-yl)prop-2-en-1-one

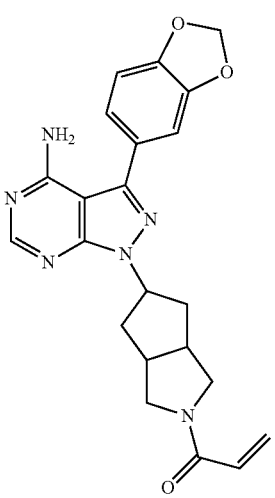

$^1$H NMR: (DMSO-$d_6$, 400 MHz): δ 8.21 (s, 1H), 7.15-7.13 (m, 1H), 7.12-7.10 (m, 1H), 7.09-7.07 (m, 1H), 6.65-6.58 (m, 1H), 6.16-6.12 (m, 1H), 6.11 (s, 2H), 5.68-5.64 (m, 1H), 5.42-5.35 (m, 1H), 3.83-3.81 (m, 1H), 3.80-3.75 (m, 1H), 3.65-3.60 (m, 1H), 3.50-3.49 (m, 1H), 3.08-3.06 (m, 1H), 2.99-2.96 (m, 1H), 2.36-2.82 (m, 2H), 2.07-2.04 (m, 2H); ESI-MS: (+ve mode) 419.58 (M+H)$^+$ (100%); HPLC: 96.33%.

86

Example: 16

Compound 16: 1-(5-(4-amino-3-(4-(5-methyl-1,3,4-oxadiazol-2-yl)phenyl)-1H-pyrazolo[3,4-d]pyrimidin-1-yl)hexahydrocyclopenta[c]pyrrol-2(1H)-yl) prop-2-en-1-one

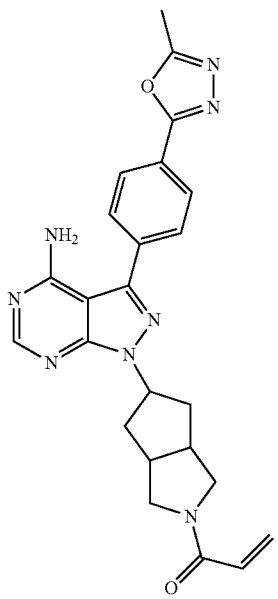 [SMILES: C=CC(=O)N1CC2CC(n3nc(-c4ccc(-c5nnc(C)o5)cc4)c4c(N)ncnc43)CC2C1]

$^1$H NMR: (DMSO-$d_6$, 400 MHz): δ 8.25 (s, 1H), 8.13-8.11 (d, 2H, J=8.0 Hz), 7.89-7.87 (d, 2H, J=8.0 Hz), 6.65-6.58 (m, 1H), 6.16-6.11 (dd, 1H, $J_1$=2.8 Hz, $J_2$=16.8 Hz), 5.68-6.65 (dd, 1H, $J_1$=2.4 Hz, $J_2$=20 Hz), 5.46-5.41 (m, 1H), 3.78-3.76 (m, 1H), 3.64-3.61 (m, 1H), 3.54-3.50 (m, 1H), 3.39-3.34 (m, 1H), 3.23-3.08 (m, 1H), 3.07-3.00 (m, 1H), 2.61 (s, 3H), 2.38-2.32 (m, 2H), 2.07-2.05 (m, 2H); ESI-MS: (+ve mode) 457.10 (M+H)$^+$ (100%); UPLC: 95.87%.

Example: 17

Compound 17: 1-(5-(4-amino-3-(benzo[d]oxazol-6-yl)-1H-pyrazolo[3,4-d]pyrimidin-1-yl)hexahydrocyclopenta[c]pyrrol-2(1H)-yl)prop-2-en-1-one

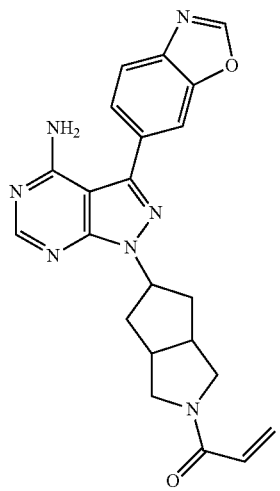 [SMILES: C=CC(=O)N1CC2CC(n3nc(-c4ccc5ncoc5c4)c4c(N)ncnc43)CC2C1]

$^1$H NMR: (CDCl$_3$, 400 MHz): δ 8.40 (s, 1H), 8.22 (s, 1H), 7.99-7.97 (m, 2H), 7.74-7.72 (m, 1H), 6.47-6.42 (m, 1H), 5.73-5.70 (m, 1H), 5.78-5.60 (m, 2H), 3.86-3.84 (m, 2H), 3.57-3.55 (m, 2H), 3.22-3.19 (m, 2H), 2.56-2.54 (m, 2H), 2.18-2.16 (m, 2H); ESI-MS: (+ve mode) 416.78 (M+H)$^+$ (100%); HPLC: 96.12%.

Example: 18

Compound 18: 3-(4-phenoxyphenyl)-1-(2-(vinylsulfonyl)octahydrocyclopenta[c]pyrrol-5-yl)-1H-pyrazolo[3,4-d]pyrimidin-4-amine

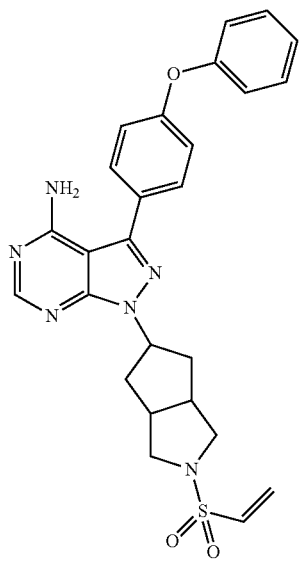 [SMILES: C=CS(=O)(=O)N1CC2CC(n3nc(-c4ccc(Oc5ccccc5)cc4)c4c(N)ncnc43)CC2C1]

$^1$H NMR: (DMSO, 400 MHz): δ 8.24 (s, 1H), 7.64 (dd, 2H, J$_1$=6.8 Hz, J$_2$=2.0 Hz), 7.44-7.40 (m, 2H), 7.19-7.10 (m, 5H), 6.94-6.87 (m, 1H), 6.21 (d, 1H, J=10.0 Hz), 6.15 (d, 1H, J=16.8 Hz), 5.41-65.30 (m, 1H), 3.29-3.24 (m, 2H), 3.04-3.01 (m, 4H), 2.34-2.32 (m, 2H), 2.10-1.90 (m, 2H); ESI-MS: (+ve mode) 503.15 (M+H)$^+$ (100%); UPLC: 95.16%.

Example: 19

Compound 19: 1-(5-(4-amino-3-(2-phenylbenzo[d]oxazol-6-yl)-1H-pyrazolo[3,4-d]pyrimidin-1-yl)hexahydrocyclopenta[c]pyrrol-2(1H)-yl)prop-2-en-1-one

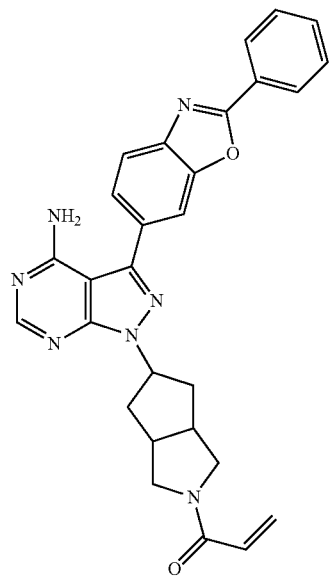 [SMILES: C=CC(=O)N1CC2CC(n3nc(-c4ccc5nc(-c6ccccc6)oc5c4)c4c(N)ncnc43)CC2C1]

$^1$H NMR: (CDCl$_3$, 400 MHz): δ 8.41 (s, 1H), 8.32-8.30 (m, 2H), 7.96-7.93 (m, 2H), 7.73-7.70 (m, 1H), 7.59-7.57 (m, 3H), 6.52-6.43 (m, 1H), 5.72-5.69 (m, 1H), 5.62-5.59 (m, 1H), 5.50-5.49 (m, 1H), 3.90-3.84 (m, 2H), 3.58-3.48 (m, 2H), 3.23-3.19 (m, 2H), 2.60-2.58 (m, 2H), 2.20-2.17 (m, 2H); ESI-MS: (+ve mode) 492.35 (M+H)$^+$ (100%); HPLC: 95.63%.

Example: 20

Compound 20: 1-(5-(4-amino-3-(2-phenoxybenzo[d]thiazol-6-yl)-1H-pyrazolo [3,4-d]pyrimidin-1-yl)hexahydrocyclopenta[c]pyrrol-2(1H)-yl)prop-2-en-1-one

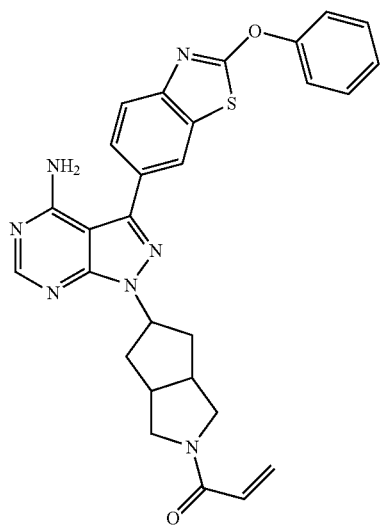 [SMILES: C=CC(=O)N1CC2CC(n3nc(-c4ccc5nc(Oc6ccccc6)sc5c4)c4c(N)ncnc43)CC2C1]

$^1$H NMR (DMSO-d$_6$, 400 MHz) δ ppm: 8.22 (s, 1H), 7.82 (d, 1H, J=8.4 Hz), 7.70-7.68 (m, 1H), 7.56-7.53 (m, 2H), 7.49-7.47 (m, 2H), 7.42-7.40 (m, 1H), 6.65-6.61 (m, 1H), 6.16 (dd, 1H, J$_1$=2.4 Hz, J$_2$=14.4 Hz), 5.68 (dd, 1H, J1=2.4 Hz, J$_2$=10.4 Hz), 5.64-5.40 (m, 1H), 3.58-3.50 (m, 1H), 3.38-3.36 (m, 1H), 3.35-3.33 (m, 1H), 3.25-2.84 (m, 2H), 2.82-2.80 (m, 2H), 2.36-2.32 (m, 2H), 2.08-2.00 (m, 2H); (ESI-MS): (+ve mode) 524.15 (M+H)$^+$. (100%), UPLC: 95.74%.

Example: 21

Compound 21: 1-(5-(4-amino-3-(4-(1-methyl-1H-pyrazol-4-yl)phenyl)-1H-pyrazolo [3,4-d]pyrimidin-1-yl)hexahydrocyclopenta[c]pyrrol-2(1H)-yl)prop-2-en-1-one

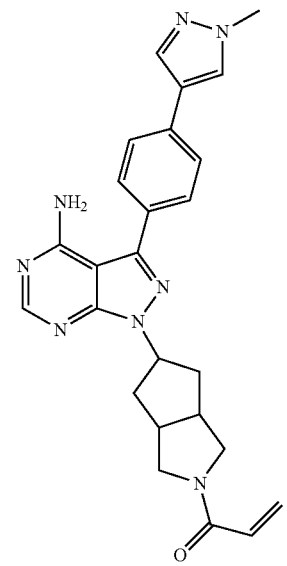 [SMILES: C=CC(=O)N1CC2CC(n3nc(-c4ccc(-c5cnn(C)c5)cc4)c4c(N)ncnc43)CC2C1]

$^1$H NMR (DMSO-d$_6$, 400 MHz) δ ppm: 8.38 (s, 1H), 7.86-7.83 (m, 1H), 7.71-7.70 (m, 3H), 7.69-7.63 (m, 2H), 6.51-6.37 (m, 2H), 5.72-5.69 (m, 1H), 5.59-5.44 (m, 2H), 3.99 (s, 1H), 3.50-3.46 (m, 2H), 3.23-3.14 (m, 2H), 2.57-2.55 (m, 2H), 2.18-2.14 (m, 2H), 1.68-1.59 (m, 2H); (ESI-MS): (+ve mode) 455.10 (M+H)$^+$. (100%), HPLC: 95.98%.

Example: 22

Compound 22: 1-(5-(4-amino-3-(benzo[d]oxazol-5-yl)-1H-pyrazolo[3,4-d]pyrimidin-1-yl)hexahydrocyclopenta[c]pyrrol-2(1H)-yl)prop-2-en-1-one

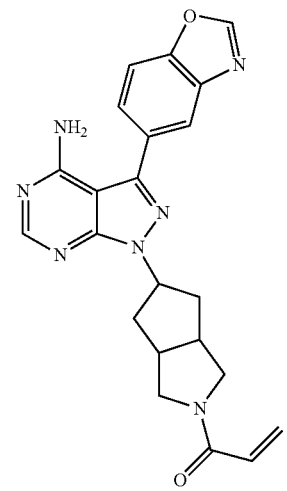

¹H NMR: (DMSO-d₆, 400 MHz): δ 8.84 (s, 1H), 8.24 (s, 1H), 8.01 (s, 1H), 7.93-7.91 (d, 1H, J=8.0 Hz), 7.73-7.71 (d, 1H, J=8.0 Hz), 6.65-6.58 (m, 1H), 6.16-6.11 (dd, 1H, $J_1$=2.8 Hz, $J_2$=16.8 Hz), 5.68-5.65 (dd, 1H, $J_1$=2.4 Hz, $J_2$=11.2 Hz), 5.44-5.41 (m, 1H), 3.78-3.66 (m, 2H), 3.63-3.60 (m, 2H), 3.53-3.50 (m, 1H), 3.40-3.38 (m, 1H), 3.15-2.85 (m, 2H), 2.07-2.05 (m, 2H); ESI-MS: (+ve mode) 416.10 (M+H)⁺ (100%); UPLC: 95.64%.

Example: 23

Compound 23: (5-(4-amino-3-(2-phenylbenzo[d]oxazol-5-yl)-1H-pyrazolo[3,4-d]pyrimidin-1-yl)hexahydrocyclopenta[c]pyrrol-2(1H)-yl)prop-2-en-1-one

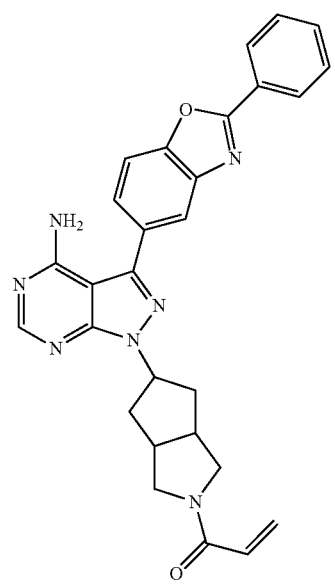 [SMILES: C=CC(=O)N1CC2CC(n3nc(-c4ccc5oc(-c6ccccc6)nc5c4)c4c(N)ncnc43)CC2C1]

¹H NMR: (DMSO-d₆, 400 MHz): δ 8.24-8.27 (m, 3H), 8.02-8.01 (d, 1H, J=4.0 Hz), 7.95-7.93 (d, 1H, J=8.0 Hz), 7.73-7.70 (m, 1H), 7.67-7.63 (m, 3H), 6.66-6.59 (m, 1H), 6.16-6.12 (m, 1H), 5.68-5.65 (m, 1H), 5.45-5.42 (m, 1H), 3.81-3.66 (m, 1H), 3.64-3.61 (m, 1H), 3.55-3.50 (m, 1H), 3.39-3.35 (m, 1H), 3.10-3.00 (m, 2H), 2.44-2.31 (m, 2H), 2.09-2.04 (m, 2H); ESI-MS: (+ve mode) 492.05 (M+H)⁺ (100%); UPLC: 97.40%.

Example: 24

Compound 24: (E)-1-(5-(4-amino-3-(4-phenoxyphenyl)-1H-pyrazolo[3,4-d]pyrimidin-1-yl)hexahydrocyclopenta[c]pyrrol-2(1H)-yl)-4-(dimethylamino)but-2-en-1-one

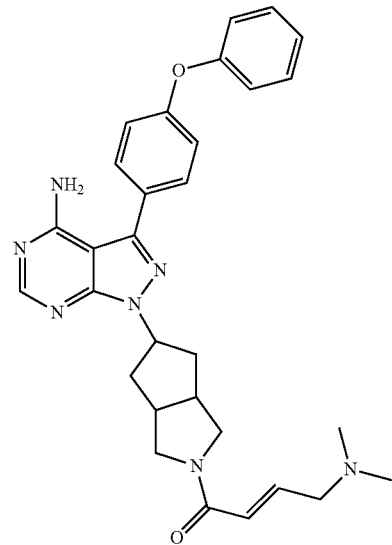 [SMILES: CN(C)C/C=C/C(=O)N1CC2CC(n3nc(-c4ccc(Oc5ccccc5)cc4)c4c(N)ncnc43)CC2C1]

¹H NMR: (D₂O, 400 MHz): δ 8.38 (s, 1H), 7.65 (d, 2H, J=6.8 Hz), 7.62-7.47 (m, 2H), 7.46-7.45 (m, 1H), 7.29-7.16 (m, 2H), 6.81-6.69 (m, 2H), 5.56-5.52 (m, 1H), 3.99-3.91 (m, 3H), 3.80 (dd, 1H, $J_1$=8.4 Hz, $J_2$=13.2 Hz), 3.63 (dd, 1H, $J_1$=4.4 Hz, $J_2$=11.2 Hz), 3.50 (dd, 1H, $J_1$=4.8 Hz, $J_2$=13.2 Hz), 3.20-3.11 (m, 2H), 2.93 (s, 6H), 2.47-2.41 (m, 2H), 2.23-2.16 (m, 2H); ESI-MS: (+ve mode) 525.7 (M+H)⁺ (100%); HPLC: 97.25%.

Example: 25

Compound 25: 9-(2-acryloyloctahydrocyclopenta[c]pyrrol-5-yl)-6-amino-7-(4-phenoxyphenyl)-5,7-dihydro-4H-purin-8(9H)-one $^1$H NMR (DMSO-d$_6$, 400 MHz) δ ppm: 8.12 (s, 1H), 7.45-7.41 (m, 4H), 7.20-7.17 (m, 1H), 7.15-7.11 (m, 1H), 6.63-6.56 (m, 1H), 6.15 (dd, 1H, J$_1$=4.0 Hz, J$_2$=16.0 Hz), 5.74-5.72 (m, 2H), 5.97-5.64 (m, 1H), 5.01-4.93 (m, 1H), 3.62-3.46 (m, 3H), 3.40-3.35 (m, 2H), 3.20-2.90 (m, 3H), 1.90-1.97 (m, 2H); (ESI-MS): (+ve mode) 483.10 (M+H)$^+$. (100%); HPLC: 98.02%.

Example: 26

Compound 26: 1-(5-(4-amino-3-(4-(5-(pyridin-2-yl)-1,3,4-oxadiazol-2-yl)phenyl)-1H-pyrazolo[3,4-d]pyrimidin-1-yl)hexahydrocyclopenta[c]pyrrol-2(1H)-yl)prop-2-en-1-one $^1$H NMR: (DMSO-d$_6$, 400 MHz): δ 8.84-8.83 (d, 1H, J=4.0 Hz), 8.31-8.26 (m, 4H), 8.12-8.08 (m, 1H), 7.95-7.93 (d, 2H, J=8.0 Hz), 7.69-7.66 (m, 1H), 6.65-6.59 (m, 1H), 6.16-6.12 (dd, 1H, J$_1$=2.4 Hz, J$_2$=16.8 Hz), 5.65-5.68 (dd, 1H, J$_1$=2.4 Hz, J$_2$=10.4 Hz), 5.47-5.44 (m, 1H), 3.81-3.77 (m, 1H), 3.65-3.61 (m, 1H), 3.55-3.50 (m, 1H), 3.39-3.33 (m, 1H), 3.12-2.90 (m, 2H), 2.42-2.31 (m, 2H), 2.09-2.07 (m, 2H); ESI-MS: (+ve mode) 520.20 (M+H)$^+$ (85%); UPLC: 95.96%.

Example: 27

Compound 27: 1-(5-(4-amino-6-bromo-5-(4-phenoxyphenyl)-7H-pyrrolo[2,3-d]pyrimidin-7-yl)hexahydrocyclopenta[c]pyrrol-2(1H)-yl)prop-2-en-1-one

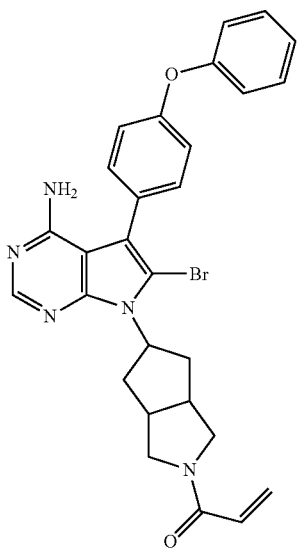 [SMILES: C=CC(=O)N1CC2CC(n3c(Br)c(-c4ccc(Oc5ccccc5)cc4)c4c(N)ncnc43)CC2C1]

¹H NMR (DMSO-d₆, 400 MHz) δ ppm: 8.13 (s, 1H), 7.46-7.41 (m, 4H), 7.21-7.19 (m, 1H), 7.15-7.13 (m, 2H), 7.11-7.09 (m, 2H), 6.65-6.54 (m, 1H), 6.16 (dd, 1H, $J_1$=2.4 Hz, $J_2$=16.8 Hz), 5.68 (dd, 1H, $J_1$=2.4 Hz, $J_2$=10.4 Hz), 5.35-5.33 (m, 1H), 3.52-3.50 (m, 1H), 3.38-3.34 (m, 1H), 3.33-3.31 (m, 1H), 3.12-2.83 (m, 1H), 2.81-2.80 (m, 1H), 2.67-2.65 (m, 2H), 2.37-2.35 (m, 1H), 2.33-2.00 (m, 2H); (ESI-MS): (+ve mode) 546.15 (M+H)⁺. (100%); UPLC: 95.60%.

Example: 28

Compound 28: 2-(5-(4-amino-3-(4-phenoxyphenyl)-1H-pyrazolo[3,4-d]pyrimidin-1-yl)octahydrocyclopenta[c]pyrrole-2-carbonyl)-3-cyclopropylacrylonitrile

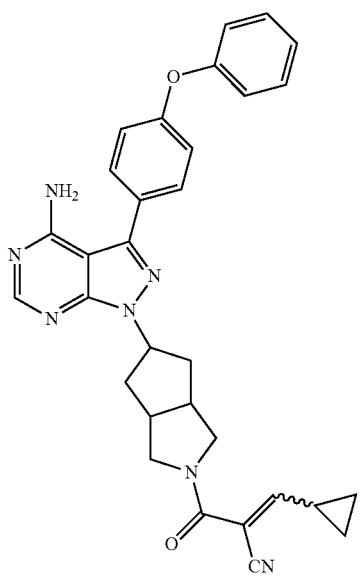 [SMILES: N#CC(=CC1CC1)C(=O)N1CC2CC(n3nc(-c4ccc(Oc5ccccc5)cc4)c4c(N)ncnc43)CC2C1]

¹H NMR: (CDCl₃-d₁, 400 MHz): δ 8.38 (s, 1H), 7.67-7.65 (m, 2H), 7.42-7.32 (m, 2H), 7.19-7.15 (m, 3H), 7.11-7.09 (m, 2H), 6.87-6.84 (d, 1H, J=11.6 Hz), 5.59-5.53 (m, 1H), 5.41 (s, 2H), 4/05-3.88 (m, 2H), 3.68-3.54 (m, 2H), 3.23-3.12 (m, 2H), 2.62-2.52 (m, 2H), 2.17-2.08 (m, 2H), 1.44-1.26 (m, 2H), 0.98-0.93 (m, 2H), 0.89-0.87 (m, 1H); ESI-MS: (+ve mode) 532.25 (M+H)⁺ (100%); UPLC: 95.05%.

97

Example: 29

Compound 29: 4-(1-(2-acryloyloctahydrocyclopenta[c]pyrrol-5-yl)-4-amino-1H-pyrazolo[3,4-d]pyrimidin-3-yl)-2-methoxy-N-(4-methylpyridin-2-yl)benzamide

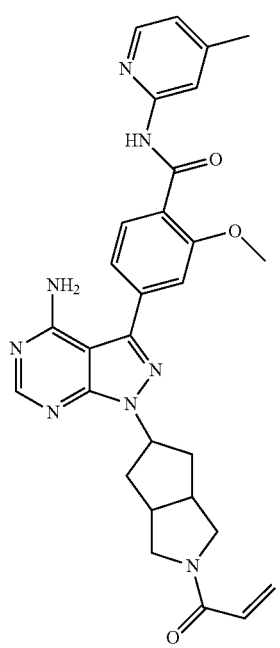 [SMILES: C=CC(=O)N1CC2CC(n3nc(-c4ccc(C(=O)Nc5cc(C)ccn5)c(OC)c4)c4c(N)ncnc43)CC2C1]

$^1$H NMR: (DMSO, 400 MHz): δ 10.42 (s, 1H), 8.26 (s, 1H), 8.23-8.21 (m, 1H), 8.16-8.10 (m, 1H), 8.07 (d, 1H, J=8.0 Hz), 7.45-7.42 (m, 2H), 7.03-7.02 (m, 1H), 6.66-6.59 (m, 1H), 6.15 (dd, 1H, $J_1$=2.4 Hz, $J_2$=16.4 Hz), 5.67 (dd, 1H, $J_1$=2.8 Hz, $J_2$=10.4 Hz), 5.46-5.42 (m, 1H), 4.08 (s, 3H), 3.85-3.75 (m, 1H), 3.70-3.57 (m, 1H), 3.56-3.45 (m, 2H), 3.15-2.90 (m, 2H), 2.45-2.38 (m, 5H), 2.18-2.06 (m, 2H); ESI-MS: (+ve mode) 539.2 (M+H)$^+$ (100%); UPLC: 96.93%.

98

Example: 30

Compound 30: 4-(1-(2-acryloyloctahydrocyclopenta[c]pyrrol-5-yl)-4-amino-1H-pyrazolo[3,4-d]pyrimidin-3-yl)-N-(4-methylpyridin-2-yl)benzamide

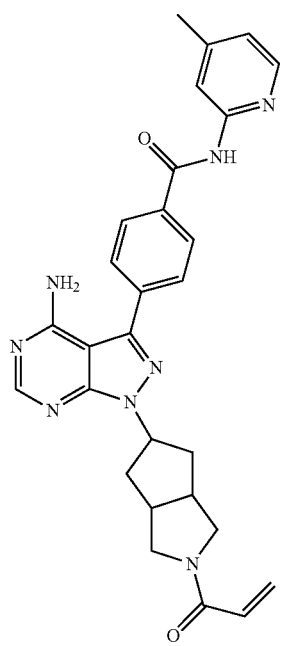 [SMILES: C=CC(=O)N1CC2CC(n3nc(-c4ccc(C(=O)Nc5cc(C)ccn5)cc4)c4c(N)ncnc43)CC2C1]

$^1$H NMR: (CDCl$_3$, 400 MHz): δ 8.59 (bs, 1H), 8.39 (s, 1H), 8.26 (s, 2H), 8.19 (d, 1H, J=5.2 Hz), 8.11 (d, 2H, J=8.0 Hz), 7.87 (d, 2H, J=8.0 Hz), 6.95 (d, 1H, J=5.2 Hz), 6.48 (dd, 1H, $J_1$=10.0 Hz, $J_2$=16.8 Hz), 6.40 (dd, 1H, $J_1$=2.4 Hz, $J_2$=16.8 Hz), 5.70 (dd, 1H, $J_1$=2.4 Hz, $J_2$=12.4 Hz), 5.60-5356 (m, 1H), 5.44 (bs, 2H), 3.88-3.83 (m, 2H), 3.56-3.46 (m, 2H), 3.23-3.21 (m, 1H), 3.14-3.12 (m, 1H), 2.59-2.54 (m, 2H), 2.43 (s, 3H), 2.20-2.09 (m, 2H); ESI-MS: (+ve mode) 509.1 (M+H)$^+$ (100%); HPLC: 96.67%.

Example: 31

Compound 31: 1-(5-(4-amino-5-(4-phenoxyphenyl)-7H-pyrrolo[2,3-d]pyrimidin-7-yl)hexahydrocyclopenta[c]pyrrol-2(1H)-yl)prop-2-en-1-one

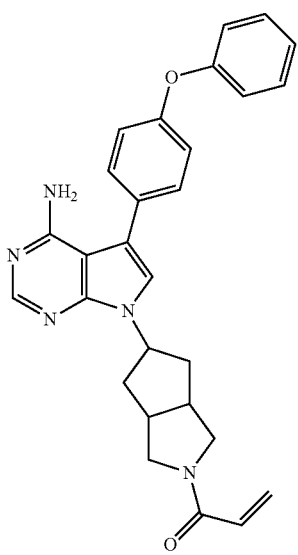 [SMILES: C=CC(=O)N1CC2CC(n3cc(-c4ccc(Oc5ccccc5)cc4)c4c(N)ncnc43)CC2C1]

$^1$H NMR (DMSO-d$_6$, 400 MHz) δ ppm: 8.16 (s, 1H), 7.45-7.41 (m, 3H), 7.15-7.13 (m, 2H), 6.70-6.66 (m, 5H), 6.86-6.59 (m, 1H), 6.16 (dd, 1H, J$_1$=2.8 Hz, J$_2$=10.4 Hz), 5.68 (dd, 1H, J$_1$=2.4 Hz, J$_2$=10.4 Hz), 5.30-5.24 (m, 1H), 3.80-3.78 (m, 1H), 3.66-3.51 (m, 2H), 3.51-3.35 (m, 1H), 3.10-2.95 (m, 1H), 2.37-2.34 (m, 1H), 2.32-2.25 (m, 3H), 2.07-2.05 (m, 2H); (ESI-MS): (+ve mode) 466.05 (M+H)$^+$. (100%); UPLC: 97.65%.

Example: 32

Compound 32: N-(4-(1-(2-acryloyloctahydrocyclopenta[c]pyrrol-5-yl)-4-amino-1H-pyrazolo[3,4-d]pyrimidin-3-yl)phenyl)picolinamide

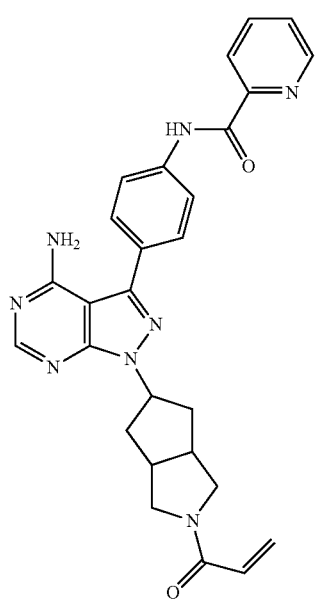 [SMILES: C=CC(=O)N1CC2CC(n3nc(-c4ccc(NC(=O)c5ccccn5)cc4)c4c(N)ncnc43)CC2C1]

$^1$H NMR: (DMSO-d$_6$, 400 MHz): δ10.82 (s, 1H), 8.77-8.76 (m, 1H), 8.23 (s, 1H), 8.18-8.12 (m, 1H), 8.11-8.09 (m, 3H), 7.71-7.65 (m, 3H), 6.65-6.59 (m, 1H), 6.16-6.11 (m, 1H), 5.68-5.65 (m, 1H), 5.43-5.41 (m, 1H), 3.82-3.79 (m, 1H), 3.76-3.73 (m, 1H0, 3.50-3.48 (m, 1H), 3.37-3.35 (m, 1H), 3.23-3.19 (m, 2H), 2.35-2.32 (m, 2H), 2.08-2.04 (m, 2H); ESI-MS: (+ve mode) 495.15 (M+H)$^+$ (100%); HPLC: 98.31%.

Example: 33

Compound 33: 6-amino-7-(4-phenoxyphenyl)-9-(2-(vinylsulfonyl)octahydrocyclopenta[c]pyrrol-5-yl)-7H-purin-8(9H)-one

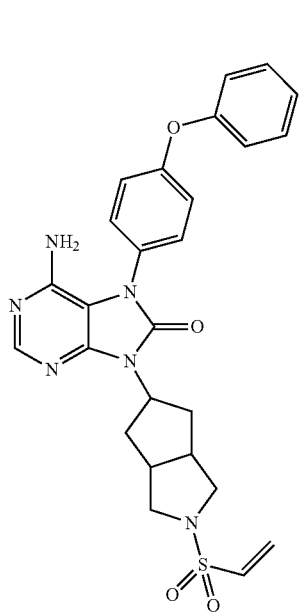 [SMILES: C=CS(=O)(=O)N1CC2CC(n3c(=O)n(-c4ccc(Oc5ccccc5)cc4)c4c(N)ncnc43)CC2C1]

¹H NMR: (DMSO, 400 MHz): δ 8.12 (s, 1H), 7.45-7.40 (m, 4H), 7.21-7.19 (m, 1H), 7.17-7.13 (m, 4H), 6.94-6.87 (m, 1H), 6.21-6.12 (m, 2H), 5.71 (m, 1H), 4.97 (m, 1H), 3.34-3.33 (m, 1H), 3.00-2.96 (m, 4H), 2.61-2.59 (m, 2H), 1.86-1.81 (m, 2H); ESI-MS: (+ve mode) 519.15 (M+H)⁺ (100%); 541.35 (M+Na)⁺ (10%); UPLC: 95.21%.

Example: 34

Compound 34: 4-(1-(2-acryloyloctahydrocyclopenta[c]pyrrol-5-yl)-4-amino-1H-pyrazolo[3,4-d]pyrimidin-3-yl)-N-(benzo[d]thiazol-2-yl)benzamide

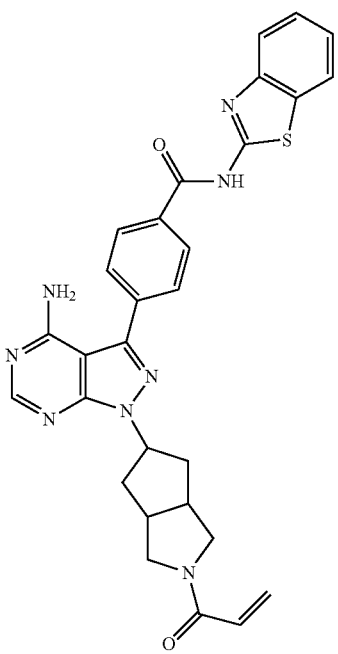 [SMILES: C=CC(=O)N1CC2CC(n3nc(-c4ccc(C(=O)Nc5nc6ccccc6s5)cc4)c4c(N)ncnc43)CC2C1]

¹H NMR: (DMSO-d₆, 400 MHz): δ 13.0 (s, 1H), 8.32-8.30 (m, 2H), 8.26 (s, 1H), 8.19-8.17 (m, 1H), 7.86-7.84 (m, 2H), 7.82-7.80 (m, 1H), 7.49-7.47 (m, 1H), 7.36-7.34 (m, 1H), 6.66-6.59 (m, 1H), 6.17-6.12 (m, 1H), 5.68-5.65 (m, 1H), 5.49-5.47 (m, 1H), 3.83-3.81 (m, 1H), 3.76-3.73 (m, 1H), 3.09-3.06 (m, 1H), 2.45-2.44 (m, 2H), 2.37-2.35 (m, 2H); ESI-MS: (+ve mode) 551.78 (M+H)⁺ (100%); HPLC: 97.74%.

Example: 35

Compound 35: N-(4-(1-(2-acryloyloctahydrocyclopenta[c]pyrrol-5-yl)-4-amino-1H-pyrazolo[3,4-d]pyrimidin-3-yl)phenyl)pyrazine-2-carboxamide

Example: 36

Compound 36: 1-(5-(4-amino-3-(2,2-difluorobenzo[d][1,3]dioxol-5-yl)-1H-pyrazolo[3,4-d]pyrimidin-1-yl)hexahydrocyclopenta[c]pyrrol-2(1H)-yl)prop-2-en-1-one

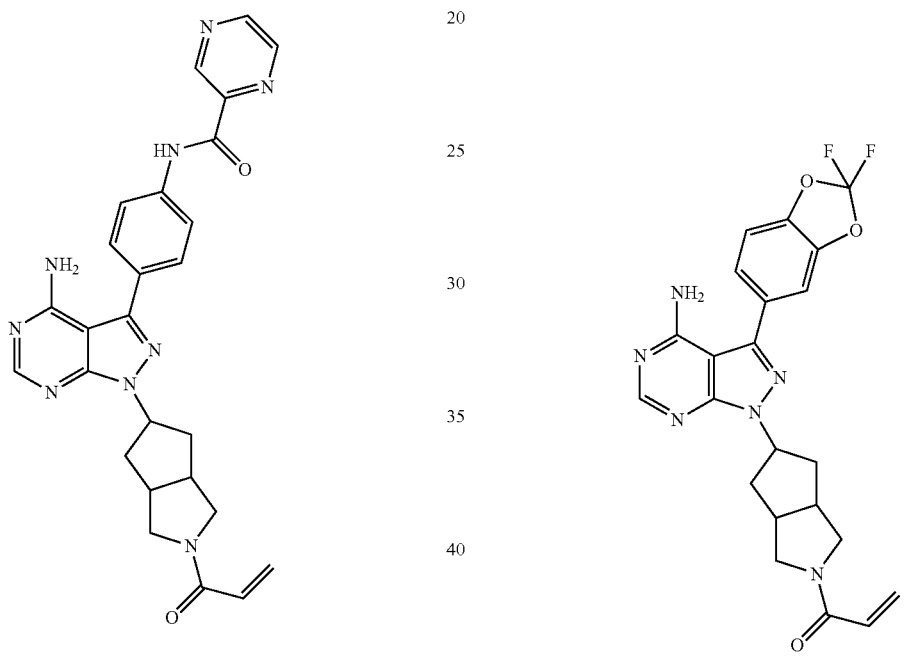

$^1$H NMR: (DMSO-d$_6$, 400 MHz): δ 10.92 (s, 1H), 9.32 (s, 1H), 8.95 (s, 1H), 8.84-8.83 (m, 1H), 8.23 (s, 1H), 8.11-8.09 (d, 2H, J=8.0 Hz), 7.69-7.67 (d, 2H, J=8.0 Hz), 6.65-6.59 (m, 1H), 6.16-6.11 (dd, 1H, J$_1$=2.8 Hz, J$_2$ 16.8 Hz), 5.68-5.43 (dd, 1H, J$_1$=2.4 Hz, J$_2$=10.4 Hz), 5.43-5.40 (m, 1H), 3.81-3.76 (m, 1H), 3.66-3.61 (m, 1H), 3.54-3.50 (m, 1H), 3.38-3.34 (m, 1H), 3.10-3.08 (m, 1H), 3.00-2.98 (m, 1H), 2.37-2.32 (m, 2H), 2.08-2.03 (m, 2H); ESI-MS: (+ve mode) 496.15 (M+H)$^+$ (100%); UPLC: 95.55%.

$^1$H NMR: (DMSO-d$_6$, 400 MHz): δ 8.19 (s, 1H), 7.21-7.19 (m, 1H), 7.17-7.14 (m, 1H), 7.07-7.05 (m, 1H), 6.59-6.55 (m, 1H), 6.15-6.12 (m, 1H), 5.67-5.64 (m, 1H), 5.40-5.32 (m, 1H), 3.81-3.79 (m, 1H), 3.78-3.75 (m, 1H), 3.59-3.57 (m, 1H), 3.51-3.48 (m, 1H), 3.03-3.00 (m, 1H), 2.97-2.93 (m, 1H), 2.36-2.82 (m, 2H), 2.02-2.00 (m, 2H); ESI-MS: (+ve mode) 455.78 (M+H)$^+$ (100%); HPLC: 96.22%.

Example: 37

Compound 37: 4-(1-(2-acryloyloctahydrocyclopenta[c]pyrrol-5-yl)-4-amino-1H-pyrazolo[3,4-d]pyrimidin-3-yl)-N-(pyrazin-2-yl)benzamide

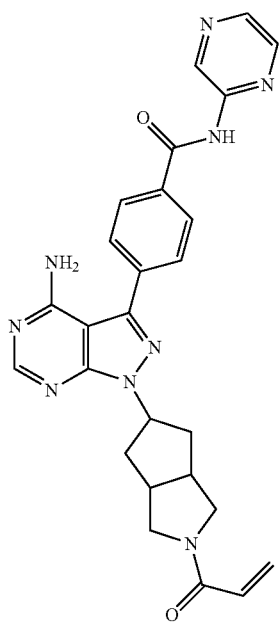 [SMILES: C=CC(=O)N1CC2CC(n3nc(-c4ccc(C(=O)Nc5cnccn5)cc4)c4c(N)ncnc43)CC2C1]

$^1$H NMR: (DMSO-d$_6$, 400 MHz): δ 11.22 (s, 1H), 9.45 (s, 1H), 8.50-8.49 (m, 1H), 8.44-8.43 (m, 1H), 8.23-8.22 (m, 2H), 7.83-7.81 (m, 2H), 6.66-6.59 (m, 1H), 6.16-6.12 (m, 1H), 5.68-5.65 (m, 1H), 5.47-5.44 (m, 1H), 3.81-3.80 (m, 1H), 3.79-3.76 (m, 1H), 3.54-3.53 (m, 1H), 3.39-3.38 (m, 2H), 3.08-3.01 (m, 2H), 2.39-2.31 (m, 2H), 2.09-2.06 (m, 2H); ESI-MS: (+ve mode) 496.25 (M+H)$^+$ (100%); HPLC: 96.38%.

Example: 38

Compound 38: N-(4-(1-(2-acryloyloctahydrocyclopenta[c]pyrrol-5-yl)-4-amino-1H-pyrazolo[3,4-d]pyrimidin-3-yl)phenyl)benzamide

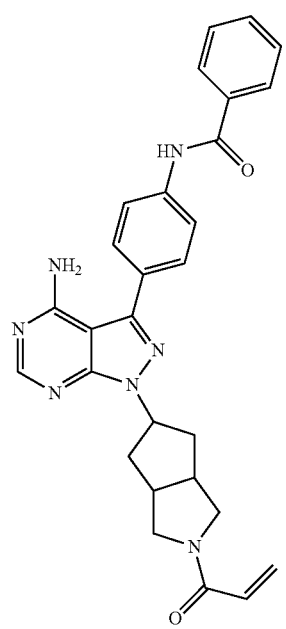 [SMILES: C=CC(=O)N1CC2CC(n3nc(-c4ccc(NC(=O)c5ccccc5)cc4)c4c(N)ncnc43)CC2C1]

$^1$H NMR: (DMSO-d$_6$, 400 MHz): δ 10.44 (s, 1H), 8.24 (s, 1H), 7.98 (d, 4H, J=8.0 Hz), 7.65 (d, 2H, J=8.4 Hz), 7.60-7.53 (m, 3H), 6.62 (dd, 1H, J$_1$=16.8 Hz, J$_2$=10.2 Hz), 6.14 (dd, 1H, J$_1$=16.8 Hz, J$_2$=2.4 Hz), 5.67 (dd, 1H, J$_1$=10.2 Hz, J$_2$=2.4 Hz), 5.42-5.38 (m, 1H), 3.78-3.75 (m, 1H), 3.66-3.60 (m, 1H), 3.55-3.50 (m, 1H), 3.37-3.33 (m, 1H), 3.10-3.06 (m, 1H), 3.01-2.98 (m, 1H), 2.37-2.32 (m, 2H), 2.08-2.05 (m, 2H); ESI-MS: (+ve mode) 494.1 (M+H)$^+$ (100%); UPLC: 96.83%.

Example: 39

Compound 39: 1-(5-(4-amino-3-(4-(5-(pyridin-2-yl)-1,3,4-thiadiazol-2-yl)phenyl)-1H-pyrazolo [3,4-d]pyrimidin-1-yl)hexahydrocyclopenta[c]pyrrol-2(1H)-yl)prop-2-en-1-one

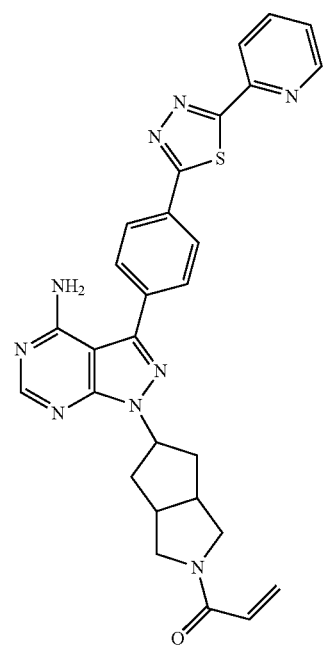 [SMILES: C=CC(=O)N1CC2CC(n3nc(-c4ccc(-c5nnc(-c6ccccn6)s5)cc4)c4c(N)ncnc43)CC2C1]

$^1$H NMR: (DMSO-d$_6$, 400 MHz): δ 8.74-8.76 (m, 1H), 8.33-8.35 (m, 1H), 8.22-8.26 (m, 3H), 8.08-8.15 (m, 1H), 7.87-7.89 (m, 2H), 7.62-7.64 (m, 1H), 6.59-6.66 (m, 1H), 6.12-6.17 (dd, 1H, J$_1$=2.4 Hz, J$_2$=16.8 Hz), 5.65-5.68 (m, 1H), 5.41-5.48 (m, 1H), 3.75-3.90 (m, 1H), 3.58-3.68 (m, 1H), 3.55-3.58 (m, 1H), 3.35-3.37 (m, 1H), 2.90-3.10 (m, 2H), 2.35-2.37 (m, 2H), 2.07-2.08 (m, 2H); ESI-MS: (+ve mode) 536.05 (M+H)$^+$ (100%); UPLC: 97.81%.

Example: 40

Compound 40: 4-(1-(2-acryloyloctahydrocyclopenta[c]pyrrol-5-yl)-4-amino-1H-pyrazolo[3,4-d]pyrimidin-3-yl)-N-(4-(trifluoromethyl)pyridin-2-yl)benzamide

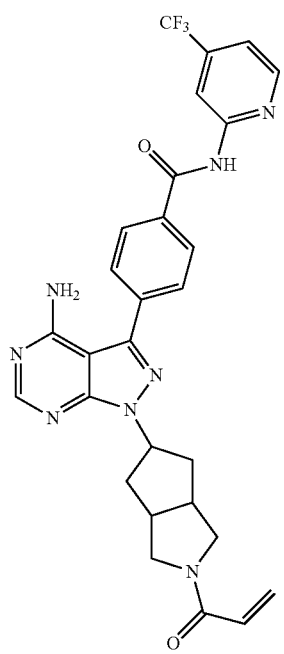 [SMILES: C=CC(=O)N1CC2CC(n3nc(-c4ccc(C(=O)Nc5cc(C(F)(F)F)ccn5)cc4)c4c(N)ncnc43)CC2C1]

$^1$H NMR: (CDCl$_3$, 400 MHz): δ 9.02 (bs, 1H), 8.73 (s, 1H), 8.51 (d, 1H, J=5.2 Hz), 8.39 (s, 1H), 8.14 (d, 2H, J=8.4 Hz), 7.89 (d, 2H, J=8.4 Hz), 7.33 (dd, 1H, J$_1$=0.8 Hz, J$_2$=5.2 Hz), 6.48 (dd, 1H, J$_1$=10.0 Hz, J$_2$=16.8 Hz), 6.40 (dd, 1H, J$_1$=2.4 Hz, J$_2$=16.8 Hz), 5.69 (dd, 1H, J$_1$=2.4 Hz, J$_2$=9.6 Hz), 5.60-5.56 (m, 3H), 3.87-3.83 (m, 2H), 3.56-3.47 (m, 2H), 3.25-3.20 (m, 1H), 3.18-3.09 (m, 1H), 2.57-2.53 (m, 2H), 2.18-2.15 (m, 2H); ESI-MS: (+ve mode) 563.3 (M+H)$^+$ (100%); HPLC: 99.55%.

Example: 41

Compound 41: (1-(5-(4-amino-3-(benzo[d]thiazol-6-yl)-1H-pyrazolo[3,4-d]pyrimidin-1-yl)hexahydrocyclopenta[c]pyrrol-2(1H)-yl)prop-2-en-1-one

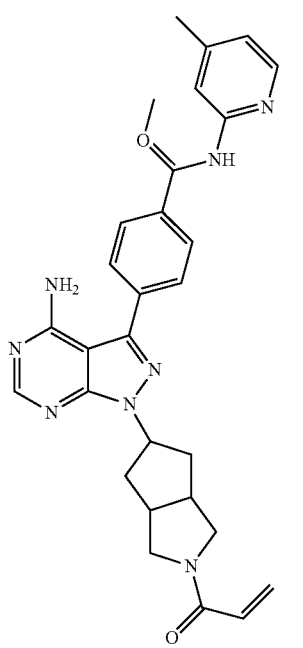

$^1$H NMR: (CDCl$_3$, 400 MHz): δ 8.47 (d, 2H, J=8.4 Hz), 8.32 (s, 2H), 7.75 (d, 2H, J=8.4 Hz), 7.53 (d, 1H, J=6.4 Hz), 6.52-6.45 (m, 2H), 6.42 (dd, 1H, J$_1$=2.4 Hz, J$_2$=16.8 Hz), 5.72 (dd, 1H, J$_1$=2.8 Hz, J$_2$=10.0 Hz), 5.59-5.55 (m, 1H), 3.91 (s, 3H), 3.87-3.83 (m, 2H), 3.56-3.47 (m, 2H), 3.26-3.21 (m, 1H), 3.16-3.11 (m, 1H), 2.58-2.53 (m, 2H), 2.36 (s, 3H), 2.19-2.15 (m, 2H); ESI-MS: (+ve mode) 523.2 (M+H)$^+$ (100%); HPLC: 98.58%.

Example: 42

Compound 42: 6-(1-(2-acryloyloctahydrocyclopenta[c]pyrrol-5-yl)-4-amino-1H-pyrazolo[3,4-d]pyrimidin-3-yl)-N-(4-methylpyridin-2-yl)nicotinamide

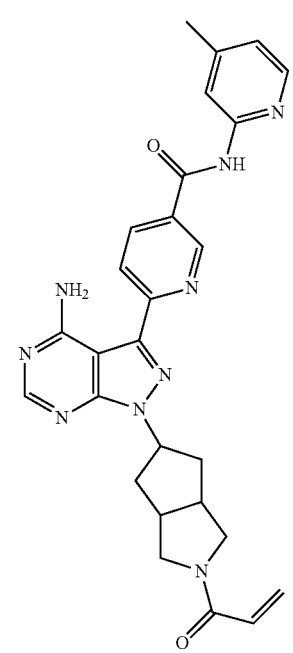 [SMILES: C=CC(=O)N1CC2CC(n3nc(-c4ccc(C(=O)Nc5cc(C)ccn5)cn4)c4c(N)ncnc43)CC2C1]

$^1$H NMR: (DMSO-d$_6$, 400 MHz): δ 10.77 (s, 1H), 8.26-8.25 (m, 2H), 8.19-8.17 (m, 2H), 8.08 (m, 1H), 7.80-7.78 (m, 2H), 7.03-7.02 (m, 1H), 6.66-6.59 (m, 1H), 6.16-6.12 (m, 1H), 5.68-5.65 (m, 1H), 5.48-5.43 (m, 1H), 3.81-3.79 (m, 1H), 3.77-3.74 (m, 1H), 3.61-3.58 (m, 1H), 3.22-3.18 (m, 2H), 3.13-3.07 (m, 2H), 2.35 (s, 3H), 2.08-2.06 (m, 2H); ESI-MS: (+ve mode) 509.35 (M)$^+$ (100%); HPLC: 97.99%.

Example: 43

Compound 43: 1-(5-(4-amino-3-(4-(pyridin-2-yloxy)phenyl)-1H-pyrazolo[3,4-d]pyrimidin-1-yl) hexahydrocyclopenta[c]pyrrol-2(1H)-yl)prop-2-en-1-one Example: 44

Compound 44: (E)-4-(4-amino-1-(2-(4-(dimethylamino)but-2-enoyl) octahydrocyclopenta [c]pyrrol-5-yl)-1H-pyrazolo[3,4-d]pyrimidin-3-yl)-N-(pyridin-2-yl) benzamide

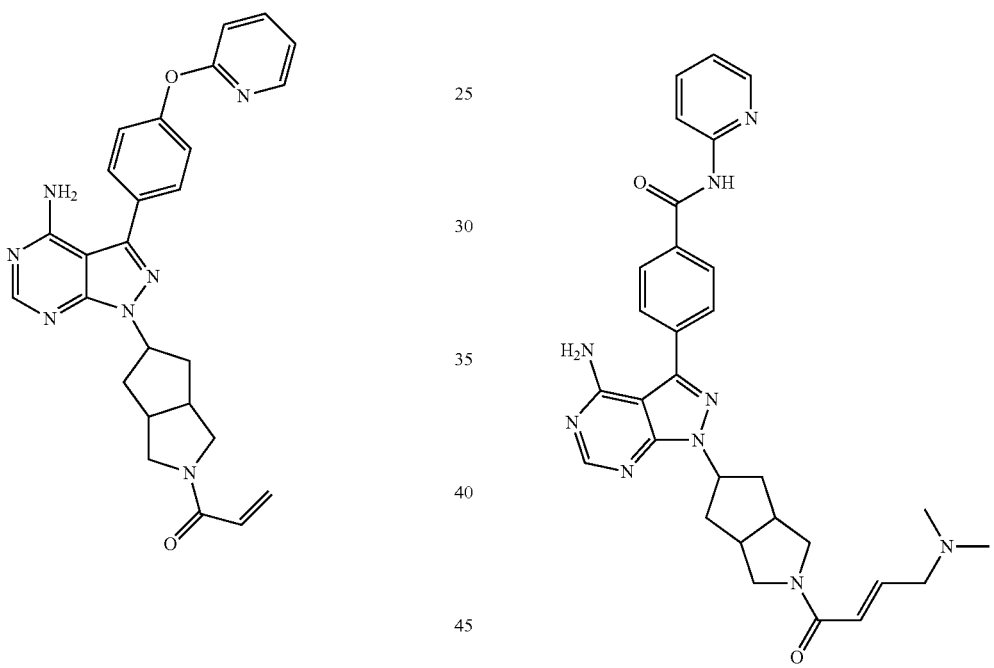

$^1$H NMR: (DMSO-$d_6$, 400 MHz): δ 8.24 (s, 1H), 8.20-8.18 (dd, 1H, $J_1$=8.0 Hz, $J_2$=8.0 Hz), 7.90-7.86 (m, 1H), 7.71-7.69 (d, 2H, J=8.0 Hz), 7.29-7.27 (d, 2H, J=16 Hz), 7.18-7.15 (m, 1H), 7.11-7.09 (d, 1H, J=8.0 Hz), 6.65-6.58 (m, 1H), 6.16-6.11 (dd, 1H, $J_1$=4.0 Hz, $J_2$=8.0 Hz), 5.68-5.65 (dd, 1H, $J_1$=2.4 Hz, $J_2$=10 Hz), 5.44-5.40 (m, 1H), 3.80-3.76 (m, 1H), 3.65-3.50 (m, 3H), 3.08-3.07 (m, 1H), 3.00-2.97 (m, 1H), 2.38-2.32 (m, 2H), 2.08-2.03 (m, 2H); ESI-MS: (+ve mode) 468.00 (M+H)$^+$ (100%); UPLC: 95.99%.

$^1$H NMR (DMSO-$d_6$, 400 MHz) δ ppm: 10.89 (s, 1H), 9.83-9.81 (m, 1H), 8.35-8.29 (m, 1H), 8.28-8.23 (m, 1H), 8.22-8.20 (m, 3H), 7.89-7.81 (m, 1H), 7.80-7.78 (m, 1H), 6.72-6.70 (m, 1H), 6.66-6.64 (m, 1H), 5.53-5.50 (m, 1H), 3.91-3.89 (m, 2H), 2.79 (d, 6H, J=4.4 Hz); (ESI-MS): (+ve mode) 552.40 (M+H)$^+$. (100%); UPLC: 98.02%.

Example: 45

Compound 45: (E)-4-(4-amino-1-(2-(4-(dimethyl-amino)but-2-enoyl)octahydrocyclopenta[c]pyrrol-5-yl)-1H-pyrazolo[3,4-d]pyrimidin-3-yl)-N-(4-methyl-pyridin-2-yl) benzamide Example: 46

Compound 46: 1-(5-(4-amino-3-(4-(5-(pyrazin-2-yl)-1,3,4-thiadiazol-2-yl)phenyl)-1H-pyrazolo[3,4-d]pyrimidin-1-yl)hexahydrocyclopenta[c]pyrrol-2(1H)-yl)prop-2-en-1-one

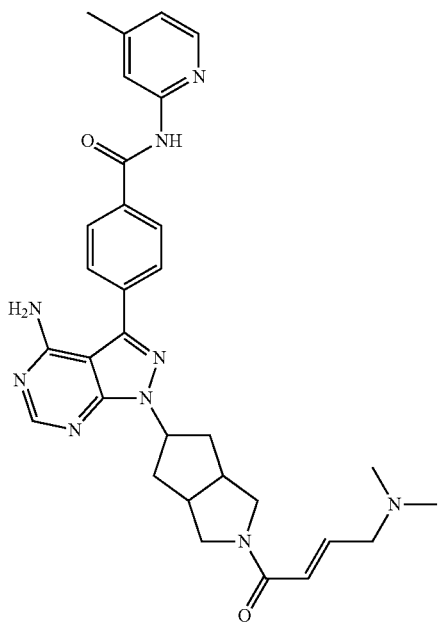

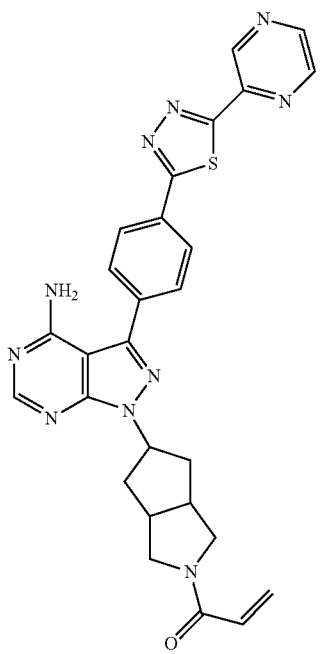 [SMILES: C=CC(=O)N1CC2CC(n3nc(-c4ccc(-c5nnc(-c6cnccn6)s5)cc4)c4c(N)ncnc43)CC2C1]

$^1$H NMR: (D$_2$O, 400 MHz): δ 8.47 (s, 1H), 8.34 (d, 1H, J=6.4 Hz), 8.23 (d, 2H, J=8.4 Hz), 7.96 (d, 2H, J=8.4 Hz), 7.59-7.56 (m, 2H), 6.83-6.70 (m, 2H), 5.64-5.51 (m, 1H), 4.01-3.95 (m, 3H), 3.83 (dd, 1H, J$_1$=8.4 Hz, J$_2$=13.2 Hz), 3.67 (dd, 1H, J$_1$=4.8 Hz, J$_2$=11.2 Hz), 3.55 (dd, 1H, J$_1$=4.8 Hz, J$_2$=13.2 Hz), 3.27-3.23 (m, 1H), 3.21-3.18 (m, 1H), 2.91 (s, 6H), 2.65 (s, 3H), 2.54-2.47 (m, 2H), 2.30-2.24 (m, 2H); ESI-MS: (+ve mode) 566.3 (M+H)$^+$ (100%); HPLC: 96.24%.

$^1$H NMR: (DMSO-d$_6$, 400 MHz): δ 9.53 (s, 1H), 8.87-8.85 (m, 2H), 8.27-8.25 (m, 3H), 7.90-7.88 (d, 2H, J=8.0 Hz), 6.66-6.59 (m, 1H), 6.17-6.12 (m, 1H), 5.68-5.65 (m, 1H), 5.47-5.42 (m, 1H), 3.80-3.78 (m, 1H), 3.56-3.52 (m, 1H), 3.37-3.33 (m, 1H), 3.10-2.90 (m, 3H), 2.39-2.32 (m, 2H), 2.10-2.07 (m, 2H); ESI-MS: (+ve mode) 537.20 (M+H)$^+$ (100%); HPLC: 97.71%.

Example: 47

Compound 47: (E)-1-(5-(4-amino-3-(4-(pyridin-2-yloxy)phenyl)-1H-pyrazolo[3,4-d]pyrimidin-1-yl)hexahydrocyclopenta[c]pyrrol-2(1H)-yl)-4-(dimethylamino)but-2-en-1-one $^1$H NMR: (DMSO-d$_6$, 400 MHz): δ 8.24 (s, 1H), 8.21-8.19 (m, 1H), 7.90-7.86 (m, 1H), 7.71-7.69 (m, 2H), 7.30-7.28 (m, 2H), 7.19-7.15 (m, 1H), 7.12-7.10 (d, 1H, J=8.0 Hz), 6.66-6.60 (m, 1H), 6.42-6.38 (d, 1H, J=16 Hz), 5.44-5.41 (m, 1H), 3.77-3.74 (m, 1H), 3.62-3.59 (m, 1H), 3.52-3.48 (m, 1H), 3.37-3.36 (m, 1H), 3.09-2.99 (m, 4H), 2.36-2.31 (m, 2H), 2.15 (s, 6H), 2.08-2.04 (m, 2H); ESI-MS: (+ve mode) 525.45 (M+H)$^+$ (100%); HPLC: 96.91%.

Example: 48

Compound 48: (E)-1-(5-(4-amino-3-(4-phenoxyphenyl)-1H-pyrazolo[3,4-d]pyrimidin-1-yl)hexahydrocyclopenta[c]pyrrol-2(1H)-yl)-4-(dimethylamino)but-2-en-1-one $^1$H NMR: (CD$_3$OD, 400 MHz): δ 8.43 (s, 1H), 8.09 (d, 2H, J=6.4 Hz), 7.45-7.41 (m, 2H), 7.22-7.16 (m, 3H), 7.13-7.11 (m, 2H), 6.87 (d, 1H, J=15.2 Hz), 6.77 (dd, 1H, J$_1$=6.8 Hz, J$_2$=14.0 Hz), 5.69-5.64 (m, 1H), 3.98 (d, 2H, J=6.8 Hz), 3.97-3.92 (m, 1H), 3.83-3.78 (m, 1H), 3.67-3.64 (m, 4H), 3.54 (dd, 1H, J$_1$=4.8 Hz, J$_2$=13.2 Hz), 3.32-3.28 (m, 1H), 3.21-3.17 (m, 1H), 2.93 (s, 6H), 2.55-2.50 (m, 2H), 2.24-2.19 (m, 2H); ESI-MS: (+ve mode) 524.3 (M+H)$^+$ (100%); HPLC: 97.39%.

117
Example: 49

Compound 49: (E)-4-(4-amino-1-(2-(4-(dimethyl-amino)but-2-enoyl) octahydrocyclopenta [c] pyrrol-5-yl)-1H-pyrazolo[3,4-d]pyrimidin-3-yl)-N-(pyrazin-2-yl)benzamide

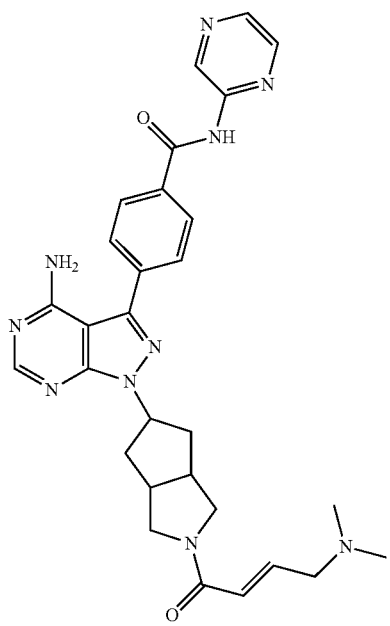 [SMILES: CN(C)C/C=C/C(=O)N1CC2CC(n3nc(-c4ccc(C(=O)Nc5cnccn5)cc4)c4c(N)ncnc43)CC2C1]

$^1$H NMR: (DMSO-$d_6$, 400 MHz): δ 11.25 (s, 1H), 9.45 (s, 1H), 8.51-8.50 (m, 1H), 8.44 (m, 1H), 8.26 (s, 1H), 8.23-8.21 (m, 2H), 7.83-7.81 (m, 2H), 6.64-6.61 (m, 1H), 6.43-6.39 (m, 1H), 5.48-5.45 (m, 1H), 3.81-3.78 (m, 1H), 3.76-3.72 (m, 1H), 3.68-3.62 (m, 1H), 3.20-3.18 (m, 1H), 3.04-3.02 (m, 3H), 2.99-2.97 (m, 1H), 2.37-2.15 (m, 2H), 2.15 (m, 6H), 2.08 (m, 2H); ESI-MS: (+ve mode) 553.45 (M+H)$^+$ (100%); HPLC: 95.44%.

118
Example: 50

Compound 50: (Z)-methyl 4-(4-amino-1-(2-((E)-4-(dimethylamino)but-2-enoyl)octahydrocyclopenta[c]pyrrol-5-yl)-1H-pyrazolo[3,4-d]pyrimidin-3-yl)-N-(4-methyl pyridin-2-yl) benzimidate

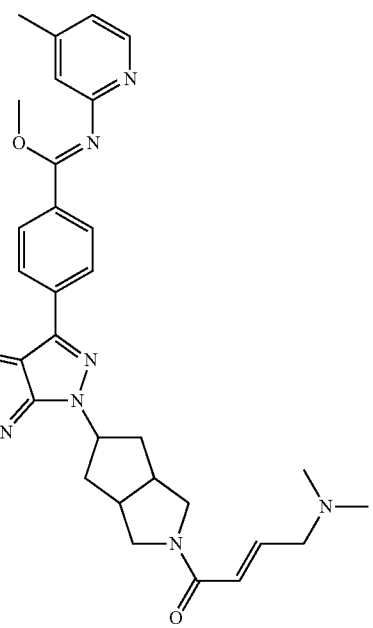

$^1$H NMR: (CD$_3$OD, 400 MHz): δ 8.73 (d, 1H, J=6.4 Hz), 8.47 (s, 1H), 8.31 (d, 2H, J=8.4 Hz), 8.13 (s, 1H), 7.98 (d, 2H, J=8.4 Hz), 7.77-7.76 (m, 1H), 6.87 (d, 1H, J=15.2 Hz), 6.78 (dd, 1H, J$_1$=6.8 Hz, J$_2$=13.6), 5.72-5.68 (m, 1H), 4.31 (s, 3H), 3.98 (d, 2H, J=7.2 Hz), 3.96-3.93 (m, 1H), 3.81 (dd, 1H, J$_1$=8.0 Hz, J$_2$=12.8 Hz), 3.68 (dd, 1H, J$_1$=4.8 Hz, J$_2$=11.2 Hz), 3.53 (dd, 1H, J$_1$=4.8 Hz, J$_2$=13.2 Hz), 3.31-3.26 (m, 2H), 2.70 (s, 3H), 2.57-2.52 (m, 2H), 2.26-2.24 (m, 2H); ESI-MS: (+ve mode) 580.5 (M+H)$^+$ (100%); HPLC: 96.62%.

Example: 51

Compound 51: (E)-4-(4-amino-1-(2-(4-(dimethyl-amino)but-2-enoyl)octahydrocyclopenta [c] pyrrol-5-yl)-1H-pyrazolo[3,4-d]pyrimidin-3-yl)-N-(4-(trifluoromethyl) pyridine-2-yl)benzamide

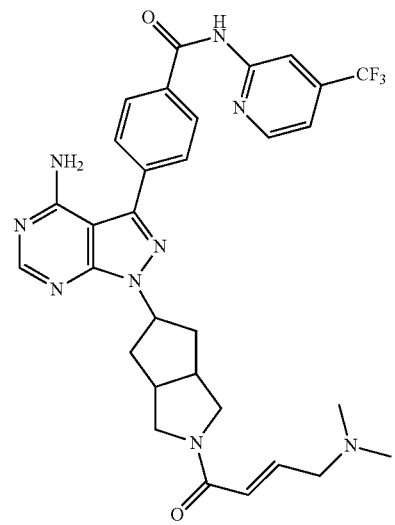 [SMILES: CN(C)C/C=C/C(=O)N1CC2CC(n3nc(-c4ccc(C(=O)Nc5cc(C(F)(F)F)ccn5)cc4)c4c(N)ncnc43)CC2C1]

$^1$H NMR: (CD$_3$OD, 400 MHz): δ 8.68 (d, 1H, J=5.6 Hz), 8.55 (s, 1H), 8.48 (s, 1H), 8.30 (d, 2H, J=8.4 Hz), 7.94 (d, 2H, J=8.4 Hz), 7.65 (dd, 1H, J$_1$=1.2 Hz, J$_2$=5.6 Hz), 6.9 (d, 1H, J=15.2 Hz), 6.80-6.75 (m, 1H), 5.69-5.66 (m, 1H), 4.09 (d, 2H, J=7.2 Hz), 4.00-3.94 (m, 1H), 3.81 (dd, 1H, J$_1$=8.0 Hz, J$_2$=12.8 Hz), 3.69 (dd, 1H, J$_1$=4.4 Hz, J$_2$=11.2 Hz), 3.53 (dd, 1H, J$_1$=4.4 Hz, J$_2$=13.2 Hz), 3.32-3.27 (m, 2H), 2.93 (s, 6H), 2.57-2.52 (m, 2H), 2.28-2.23 (m, 2H); ESI-MS: (+ve mode) 620.4 (M+H)$^+$ (100%); HPLC: 97.87%.

Example: 52

Compound 52: 1-(5-(4-amino-3-(4-(pyridin-3-yloxy)phenyl)-1H-pyrazolo[3,4-d]pyrimidin-1-yl)hexahydrocyclopenta[c]pyrrol-2(1H)-yl)prop-2-en-1-one

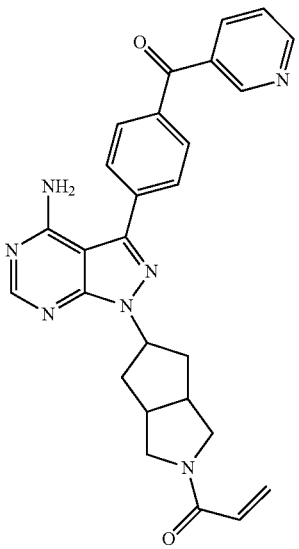 [SMILES: C=CC(=O)N1CC2CC(n3nc(-c4ccc(C(=O)c5cccnc5)cc4)c4c(N)ncnc43)CC2C1]

$^1$H NMR: (CDCl$_3$-di, 400 MHz): δ 8.50-8.46 (m, 2H), 8.35 (s, 1H), 7.70-7.68 (d, 2H, J=8.0 Hz), 7.43-7. 7.34 (m, 2H), 7.21-7.19 (d, 2H, J=8.0 Hz), 6.47-6.39 (m, 2H), 5.73-5.70 (m, 1H), 5.59-5.55 (m, 1H), 3.88-3.83 (m, 2H), 3.61-3.47 (m, 4H), 3.23-3.13 (m, 2H), 2.57-2.52 (m, 2H), 2.18-2.16 (m, 2H); ESI-MS: (+ve mode) 468.15 (M+H)$^+$ (100%); HPLC: 95.64%.

121

Example: 53

Compound 53: (E)-1-(5-(4-amino-3-(4-(pyridin-3-yloxy)phenyl)-1H-pyrazolo[3,4-d]pyrimidin-1-yl)hexahydrocyclopenta[c]pyrrol-2(1H)-yl)-4-(dimethylamino)but-2-en-1-one

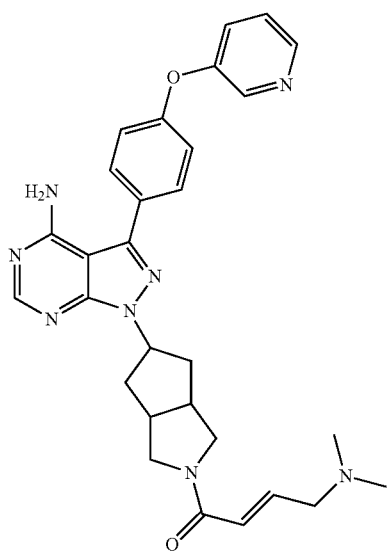 [SMILES: CN(C)C/C=C/C(=O)N1CC2CC(n3nc(-c4ccc(Oc5cccnc5)cc4)c4c(N)ncnc43)CC2C1]

¹H NMR: (DMSO-d$_6$, 400 MHz): δ 8.47-8.48 (m, 1H), 8.41-8.39 (m, 1H), 8.23 (s, 1H), 7.70-7.67 (m, 2H), 7.58-7.55 (m, 1H), 7.48-7.45 (m, 1H), 7.23-7.21 (m, 2H), 6.64-6.59 (m, 1H), 6.42-6.38 (m, 1H), 5.43-5.40 (m, 1H), 3.77-3.74 (m, 1H), 3.64-3.61 (m, 1H), 3.52-3.49 (m, 1H), 3.09-2.96 (m, 5H), 2.35-2.30 (m, 2H), 2.15 (s, 6H), 2.06-2.04 (m, 2H); ESI-MS: (+ve mode) 525.45 (M+H)⁺ (100%); HPLC: 95.44%.

122

Example: 54

Compound 54: 4-(1-(2-acryloyloctahydrocyclopenta[c]pyrrol-5-yl)-4-amino-1H-pyrazolo[3,4-d]pyrimidin-3-yl)-N-methyl-N-(4-methylpyridin-2-yl)benzamide

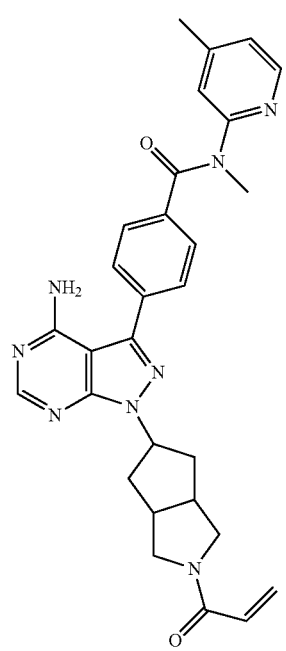 [SMILES: C=CC(=O)N1CC2CC(n3nc(-c4ccc(C(=O)N(C)c5cc(C)ccn5)cc4)c4c(N)ncnc43)CC2C1]

¹H NMR: (DMSO-d$_6$, 400 MHz): δ 8.23 (s, 1H), 8.21-8.20 (m, 1H), 7.58 (d, 1H, J=8.4 Hz), 7.12-7.10 (m, 1H), 7.04-7.02 (m, 1H), 6.65-6.58 (m, 1H), 6.16-6.11 (m, 1H), 5.40-5.38 (m, 1H), 3.77-3.75 (m, 1H), 3.62-3.59 (m, 1H), 3.53-3.49 (m, 1H), 3.43 (s, 3H), 3.11-3.08 (m, 1H), 2.98-2.96 (m, 1H), 2.34-2.29 (m, 3H), 2.21 (s, 3H), 2.06-2.03 (m, 2H); ESI-MS: (+ve mode) 523.35 (M+H)⁺ (100%); HPLC: 98.29%.

Example: 55

Compound 55: (E)-4-(4-amino-1-(2-(4-(dimethylamino)but-2-enoyl) octahydrocyclopenta [c] pyrrol-5-yl)-1H-pyrazolo[3,4-d]pyrimidin-3-yl)-N-methyl-N-(4-methyl pyridin-2-yl)benzamide

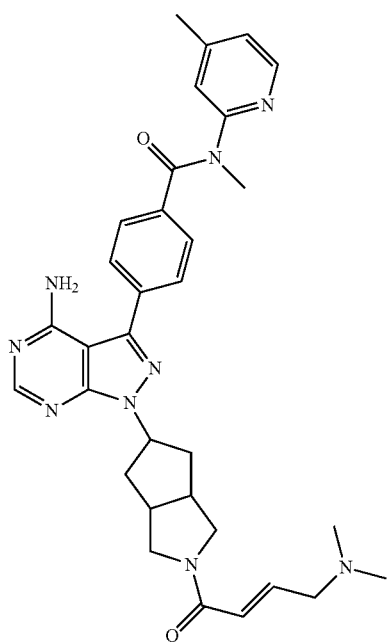 [SMILES: Cc1ccnc(N(C)C(=O)c2ccc(-c3nn(C4CC5CN(C(=O)/C=C/CN(C)C)CC5C4)c4ncnc(N)c34)cc2)c1]

¹H NMR: (DMSO-d₆, 400 MHz): δ 8.22 (s, 1H), 8.20 (d, 1H, J=8.4 Hz), 7.57-7.55 (m, 2H), 7.43-7.41 (m, 2H), 7.11-7.09 (m, 1H), 7.03-7.02 (m, 1H), 6.63-6.59 (m, 1H), 6.41 (m, 1H), 5.39 (m, 1H), 3.79-3.72 (m, 1H), 3.59-3.57 (m, 2H), 3.43-3.42 (m, 2H), 3.08 (s, 3H), 3.05-3.03 (m, 2H), 2.32-2.30 (m, 2H), 2.16-2.09 (m, 3H), 2.09-2.06 (m, 3H), 2.04-2.02 (m, 6H); ESI-MS: (+ve mode) 580.55 (M+H)⁺ (100%); HPLC: 96.27%.

Example: 56

Compound 56: (E)-1-(5-(4-amino-3-(4-(5-(pyrazin-2-yl)-1,3,4-thiadiazol-2-yl) phenyl)-1H-pyrazolo[3,4-d]pyrimidin-1-yl)hexahydrocyclopenta[c]pyrrol-2(1H)-yl)-4-(dimethylamino)but-2-en-1-one

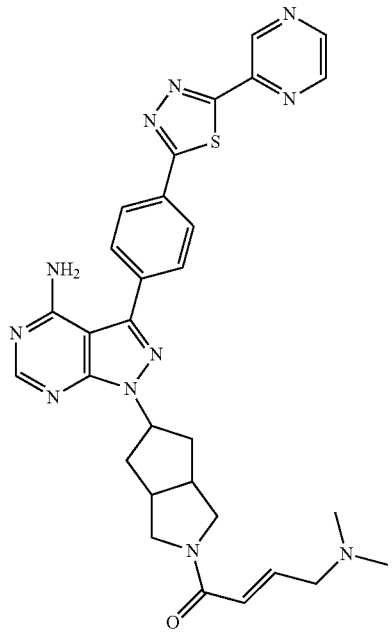 [SMILES: CN(C)C/C=C/C(=O)N1CC2CC(n3nc(-c4ccc(-c5nnc(-c6cnccn6)s5)cc4)c4c(N)ncnc43)CC2C1]

¹H NMR: (DMSO-d₆, 400 MHz): δ 9.54 (S, 1H), 8.88-8.86 (m, 2H), 8.27-8.25 (m, 3H), 7.90-7.88 (d, 2H, J=8.0 Hz), 6.66-6.59 (m, 1H), 6.43-6.39 (d, 2H, J=16 Hz), 5.47-5.43 (m, 1H), 3.80-3.75 (m, 1H), 3.65-3.60 (m, 1H), 3.53-3.51 (m, 1H), 3.83-3.33 (m, 1H), 3.09-3.00 (m, 4H), 2.40-2.32 (m, 2H), 2.15 (s, 6H), 2.09-2.07 (m, 2H); ESI-MS: (+ve mode) 594.40 (M+H)⁺ (100%); HPLC: 97.57%.

Example: 57

Compound 57: (E)-1-(5-(4-amino-3-(4-(5-(pyridin-2-yl)-1,3,4-oxadiazol-2-yl)phenyl)-1H-pyrazolo[3,4-d]pyrimidin-1-yl)hexahydrocyclopenta[c]pyrrol-2(1H)-yl)-4-(dimethylamino)but-2-en-1-one

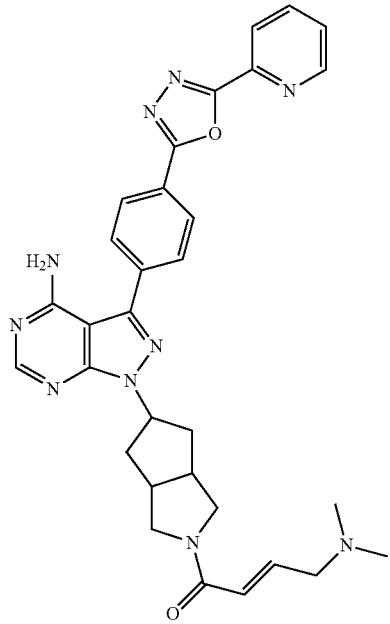 [SMILES: CN(C)C/C=C/C(=O)N1CC2CC(n3nc(-c4ccc(-c5nnc(-c6ccccn6)o5)cc4)c4c(N)ncnc43)CC2C1]

¹H NMR: (DMSO-d₆, 400 MHz): δ 8.85-8.84 (m, 1H), 8.32-8.27 (m, 4H), 8.13-8.09 (m, 1H), 7.95-7.93 (m, 2H), 7.69-7.67 (m, 1H), 6.50-6.61 (m, 1H), 6.43-6.39 (m, 1H), 5.47-5.44 (m, 1H), 3.77-3.75 (m, 1H), 3.62-3.60 (m, 1H), 3.52-3.50 (m, 1H), 3.17-3.03 (m, 5H), 2.37-2.32 (m, 2H), 2.15 (s, 6H), 2.12-2.08 (m, 2H); ESI-MS: (+ve mode) 577.55 (M+H)⁺ (100%); HPLC: 99.24%.

Using the above procedures, following compounds (Table-2) can be prepared, using different boronic acids and finally reacting with optionally substituted acid chlorides.

TABLE 2

| Compd | Structures | IUPAC Names |
|---|---|---|
| 58 | 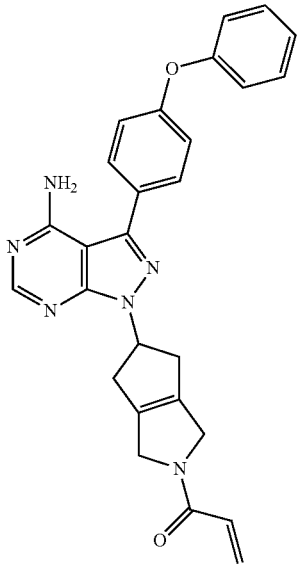 [SMILES: C=CC(=O)N1CC2=C(CC(n3nc(-c4ccc(Oc5ccccc5)cc4)c4c(N)ncnc43)C2)C1] | 1-(5-(4-amino-3-(4-phenoxyphenyl)-1H-pyrazolo[3,4-d]pyrimidin-1-yl)-5,6-dihydrocyclopenta[c]pyrrol-2(1H,3H,4H)-yl)prop-2-en-1-one |
| 59 | 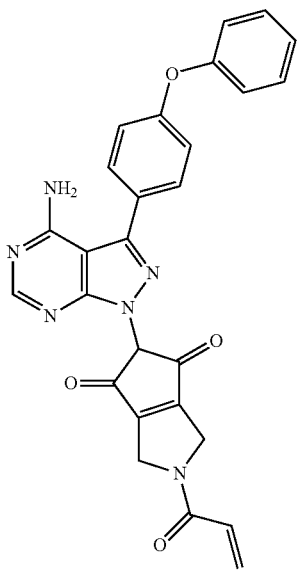 [SMILES: C=CC(=O)N1CC2=C(C1)C(=O)C(n1nc(-c3ccc(Oc4ccccc4)cc3)c3c(N)ncnc31)C2=O] | 2-acryloyl-5-(4-amino-3-(4-phenoxyphenyl)-1H-pyrazolo[3,4-d]pyrimidin-1-yl)-2,3-dihydrocyclopenta[c]pyrrole-4,6(1H,5H)-dione |

| Compd | Structures | IUPAC Names |
|---|---|---|
| 60 | 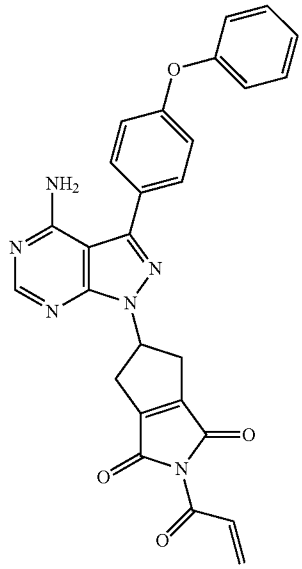 [SMILES: C=CC(=O)N1C(=O)C2=C(CC(n3nc(-c4ccc(Oc5ccccc5)cc4)c4c(N)ncnc43)C2)C1=O] | 2-acryloyl-5-(4-amino-3-(4-phenoxyphenyl)-1H-pyrazolo[3,4-d]pyrimidin-1-yl)-5,6-dihydrocyclopenta[c]pyrrole-1,3(2H,4H)-dione |
| 61 | 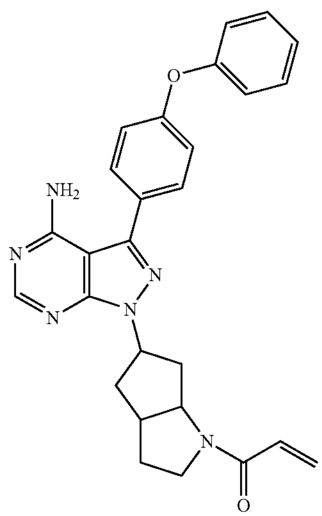 [SMILES: C=CC(=O)N1CCC2CC(n3nc(-c4ccc(Oc5ccccc5)cc4)c4c(N)ncnc43)CC21] | 1-(5-(4-amino-3-(4-phenoxyphenyl)-1H-pyrazolo[3,4-d]pyrimidin-1-yl)hexahydrocyclopenta[b]pyrrol-1(2H)-yl)prop-2-en-1-one |
| 62 | 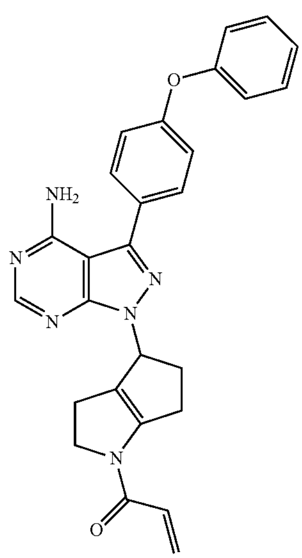 [SMILES: C=CC(=O)N1CCC2=C1CCC2n1nc(-c2ccc(Oc3ccccc3)cc2)c2c(N)ncnc21] | 1-(4-(4-amino-3-(4-phenoxyphenyl)-1H-pyrazolo[3,4-d]pyrimidin-1-yl)-2,3,5,6-tetrahydrocyclopenta[b]pyrrol-1(4H)-yl)prop-2-en-1-one |

TABLE 2-continued
| Compd | Structures | IUPAC Names |
|---|---|---|
| 63 | 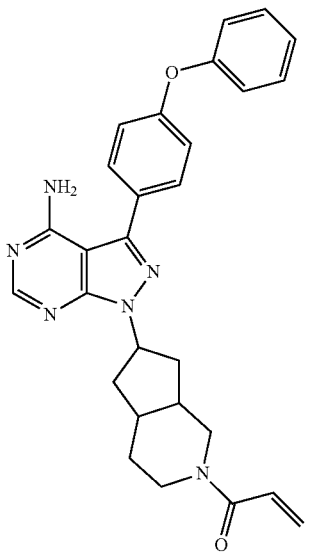 [SMILES: C=CC(=O)N1CCC2CC(n3nc(-c4ccc(Oc5ccccc5)cc4)c4c(N)ncnc43)CC2C1] | 1-(6-(4-amino-3-(4-phenoxyphenyl)-1H-pyrazolo[3,4-d]pyrimidin-1-yl)hexahydro-1H-cyclopenta[c]pyridin-2(3H)-yl)prop-2-en-1-one |
| 64 | 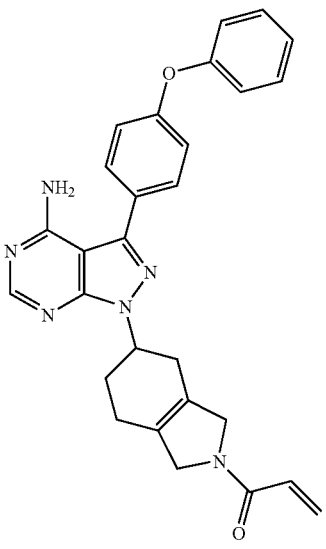 [SMILES: C=CC(=O)N1CC2=C(CC(n3nc(-c4ccc(Oc5ccccc5)cc4)c4c(N)ncnc43)CC2)C1] | 1-(5-(4-amino-3-(4-phenoxyphenyl)-1H-pyrazolo[3,4-d]pyrimidin-1-yl)-4,5,6,7-tetrahydro-1H-isoindol-2(3H)-yl)prop-2-en-1-one |
| 65 | 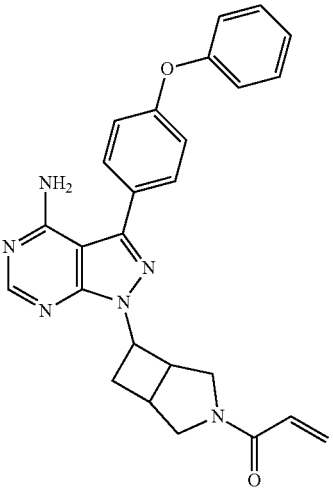 [SMILES: C=CC(=O)N1CC2CC(n3nc(-c4ccc(Oc5ccccc5)cc4)c4c(N)ncnc43)C2C1] | 1-(6-(4-amino-3-(4-phenoxyphenyl)-1H-pyrazolo[3,4-d]pyrimidin-1-yl)-3-azabicyclo[3.2.0]heptan-3-yl)prop-2-en-1-one |

TABLE 2-continued

| Compd | Structures | IUPAC Names |
|---|---|---|
| 66 | 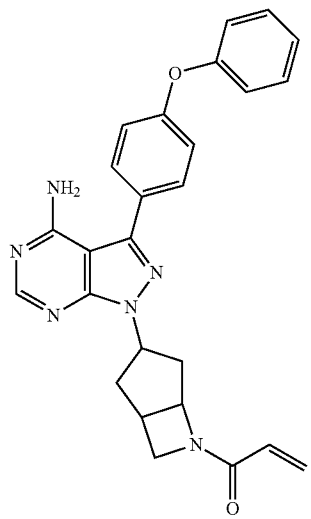 [SMILES: C=CC(=O)N1CC2CC(n3nc(-c4ccc(Oc5ccccc5)cc4)c4c(N)ncnc43)CC21] | 1-(3-(4-amino-3-(4-phenoxyphenyl)-1H-pyrazolo[3,4-d]pyrimidin-1-yl)-6-azabicyclo[3.2.0]heptan-6-yl)prop-2-en-1-one |
| 67 | 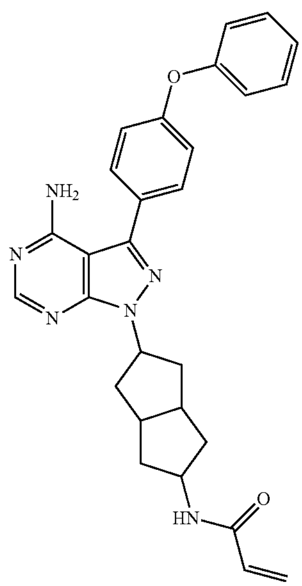 [SMILES: C=CC(=O)NC1CC2CC(n3nc(-c4ccc(Oc5ccccc5)cc4)c4c(N)ncnc43)CC2C1] | N-(5-(4-amino-3-(4-phenoxyphenyl)-1H-pyrazolo[3,4-d]pyrimidin-1-yl)octahydropentalen-2-yl)acrylamide |
| 68 | 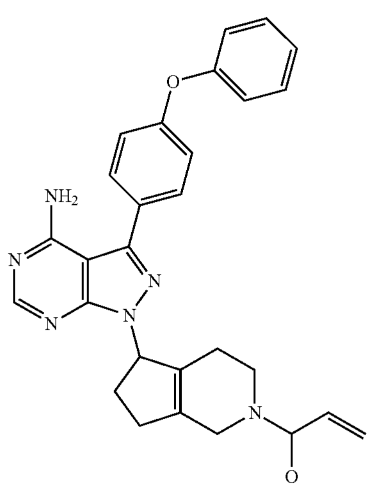 [SMILES: C=CC(O)N1CCC2=C(CCC2n2nc(-c3ccc(Oc4ccccc4)cc3)c3c(N)ncnc32)C1] | 1-(5-(4-amino-3-(4-phenoxyphenyl)-1H-pyrazolo[3,4-d]pyrimidin-1-yl)-3,4,6,7-tetrahydro-1H-cylcopenta[c]pyridin-2(5H)-yl)prop-2-en-1-one |

TABLE 2-continued
| Compd | Structures | IUPAC Names |
|---|---|---|
| 69 | 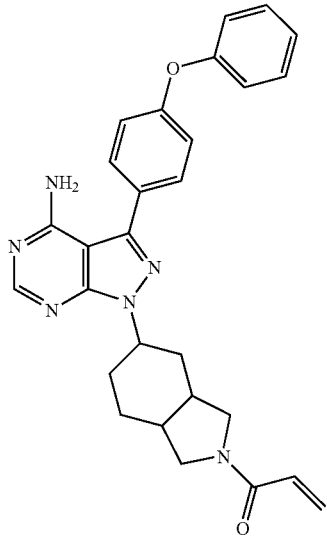 [SMILES: C=CC(=O)N1CC2CCC(n3nc(-c4ccc(Oc5ccccc5)cc4)c4c(N)ncnc43)CC2C1] | 1-(5-(4-amino-3-(4-phenoxyphenyl)-1H-pyrazolo[3,4-d]pyrimidin-1-yl)hexahydro-1H-isoindol-2(3H)-yl)prop-2-en-1-one |
| 70 | 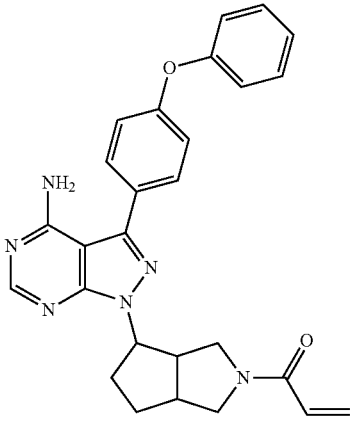 [SMILES: C=CC(=O)N1CC2CCC(n3nc(-c4ccc(Oc5ccccc5)cc4)c4c(N)ncnc43)C2C1] | 1-(4-(4-amino-3-(4-phenoxyphenyl)-1H-pyrazolo[3,4-d]pyrimidin-1-yl)hexahydrocyclopenta[c]pyrrol-2(1H)-yl)prop-2-en-1-one |
| 71 | 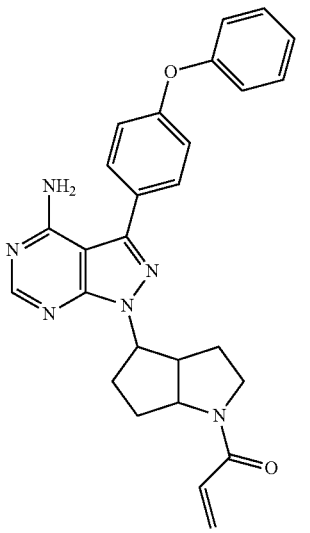 [SMILES: C=CC(=O)N1CCC2C1CCC2n1nc(-c2ccc(Oc3ccccc3)cc2)c2c(N)ncnc21] | 1-(4-(4-amino-3-(4-phenoxyphenyl)-1H-pyrazolo[3,4-d]pyrimidin-1-yl)hexahydrocyclopenta[b]pyrrol-1(2H)-yl)prop-2-en-1-one |

TABLE 2-continued
| Compd | Structures | IUPAC Names |
|---|---|---|
| 72 | 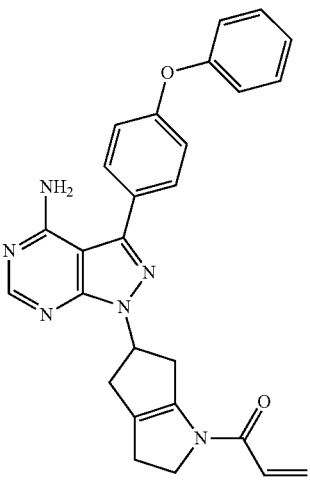 [SMILES: C=CC(=O)N1CCC2=C1CC(n1nc(-c3ccc(Oc4ccccc4)cc3)c3c(N)ncnc31)C2] | 1-(5-(4-amino-3-(4-phenoxyphenyl)-1H-pyrazolo[3,4-d]pyrimidin-1-yl)-2,3,5,6-tetrahydrocyclopenta[b]pyrrol-1(4H)-yl)prop-2-en-1-one |
| 73 | 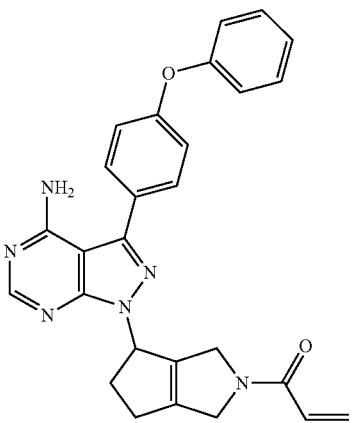 [SMILES: C=CC(=O)N1CC2=C(C1)C(n1nc(-c3ccc(Oc4ccccc4)cc3)c3c(N)ncnc31)CC2] | 1-(4-(4-amino-3-(4-phenoxyphenyl)-1H-pyrazolo[3,4-d]pyrimidin-1-yl)-5,6-dihydrocyclopenta[c]pyrrol-2(1H,3H,4H)-yl)prop-2-en-1-one |
| 74 | 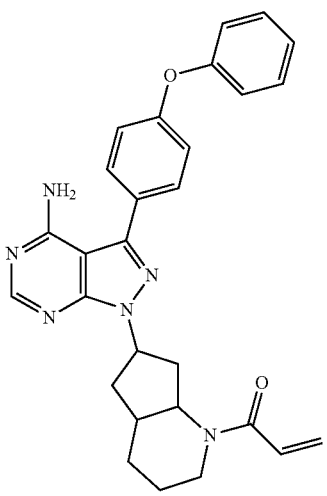 [SMILES: C=CC(=O)N1CCCC2CC(n3nc(-c4ccc(Oc5ccccc5)cc4)c4c(N)ncnc43)CC21] | 1-(6-(4-amino-3-(4-phenoxyphenyl)-1H-pyrazolo[3,4-d]pyrimidin-1-yl)octahydro-1H-cyclopenta[b]pyridin-1-yl)prop-2-en-1-one |

TABLE 2-continued
| Compd | Structures | IUPAC Names |
|---|---|---|
| 75 | 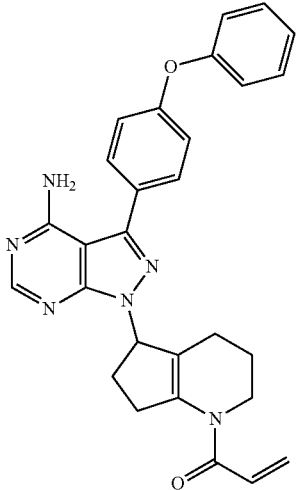 [SMILES: C=CC(=O)N1CCCC2=C1CCC2n1nc(-c2ccc(Oc3ccccc3)cc2)c2c(N)ncnc21] | 1-(5-(4-amino-3-(4-phenoxyphenyl)-1H-pyrazolo[3,4-d]pyrimidin-1-yl)-2,3,4,5,6,7-hexahydro-1H-cyclopenta[b]pyridin-1-yl)prop-2-en-1-one |
| 76 | 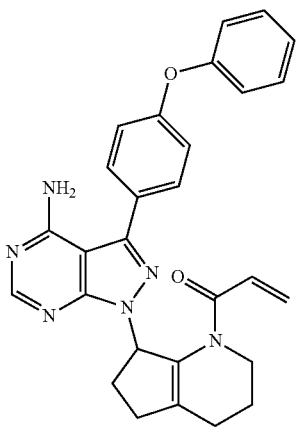 [SMILES: C=CC(=O)N1CCCC2=C1C(n1nc(-c3ccc(Oc4ccccc4)cc3)c3c(N)ncnc31)CC2] | 1-(7-(4-amino-3-(4-phenoxyphenyl)-1H-pyrazolo[3,4-d]pyrimidin-1-yl)-2,3,4,5,6,7-hexahydro-1H-cyclopenta[b]pyridin-1-yl)prop-2-en-1-one |
| 77 | 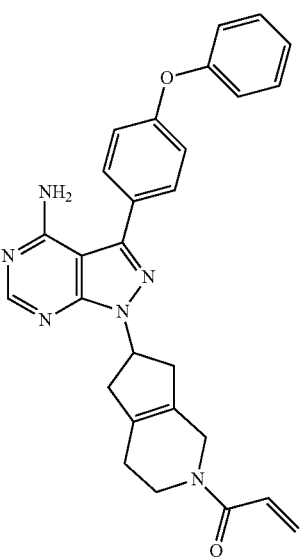 [SMILES: C=CC(=O)N1CCC2=C(CC(n3nc(-c4ccc(Oc5ccccc5)cc4)c4c(N)ncnc43)C2)C1] | 1-(6-(4-amino-3-(4-phenoxyphenyl)-1H-pyrazolo[3,4-d]pyrimidin-1-yl)-3,4,6,7-tetrahydro-1H-cyclopenta[c]pyridin-2(5H)-yl)prop-2-en-1-one |

TABLE 2-continued

| Compd | Structures | IUPAC Names |
|---|---|---|
| 78 | 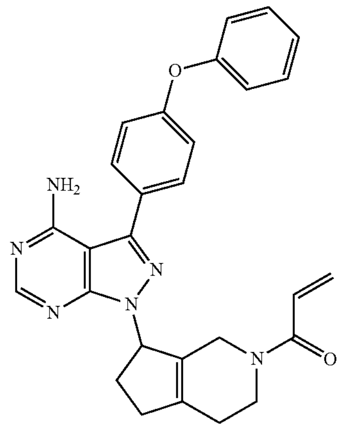 [SMILES: C=CC(=O)N1CCC2=C(C1)C(n1nc(-c3ccc(Oc4ccccc4)cc3)c3c(N)ncnc31)CC2] | 1-(7-(4-amino-3-(4-phenoxyphenyl)-1H-pyrazolo[3,4-d]pyrimidin-1-yl)-3,4,6,7-tetrahydro-1H-cyclopenta[c]pyridin-2(5H)-yl)prop-2-en-1-one |
| 79 | 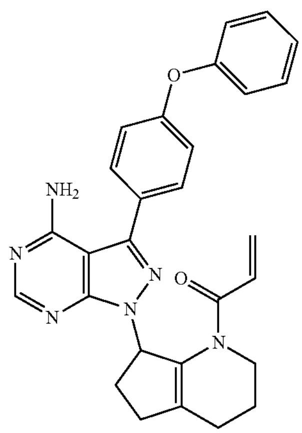 [SMILES: C=CC(=O)N1CCCC2=C1C(n1nc(-c3ccc(Oc4ccccc4)cc3)c3c(N)ncnc31)CC2] | 1-(7-(4-amino-3-(4-phenoxyphenyl)-1H-pyrazolo[3,4-d]pyrimidin-1-yl)-2,3,4,5,6,7-hexahydro-1H-cyclopenta[b]pyridin-1-yl)prop-2-en-1-one |
| 80 | 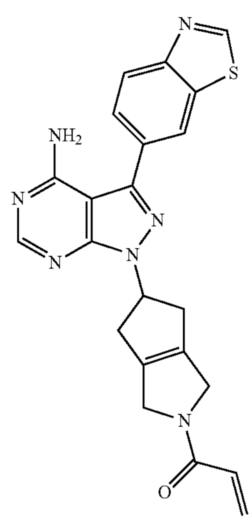 [SMILES: C=CC(=O)N1CC2=C(CC(n3nc(-c4ccc5ncsc5c4)c4c(N)ncnc43)C2)C1] | 1-(5-(4-amino-3-(benzo[d]thiazol-6-yl)-1H-pyrazolo[3,4-d]pyrimidin-1-yl)-5,6-dihydrocylcopenta[c]pyrrol-2(1H,3H,4H)-yl)prop-2-en-1-one |

TABLE 2-continued

| Compd | Structures | IUPAC Names |
|---|---|---|
| 81 | 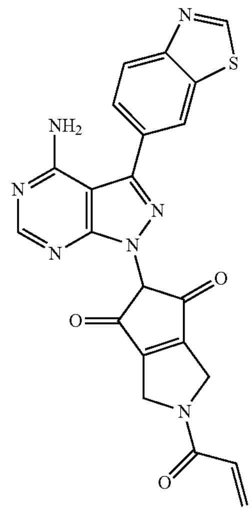 [SMILES: C=CC(=O)N1CC2=C(C1)C(=O)C(n1nc(-c3ccc4ncsc4c3)c3c(N)ncnc31)C2=O] | 2-acryloyl-5-(4-amino-3-(benzo[d]thiazol-6-yl)-1H-pyrazolo[3,4-d]pyrimidin-1-yl)-2,3-dihydrocyclopenta[c]pyrrole-4,6(1H,5H)-dione |
| 82 | 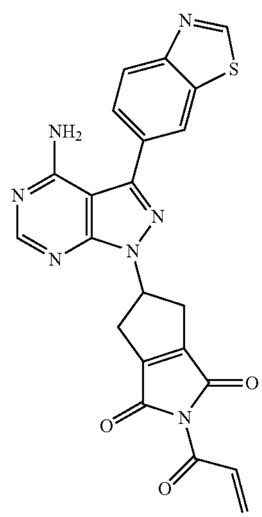 [SMILES: C=CC(=O)N1C(=O)C2=C(CC(n3nc(-c4ccc5ncsc5c4)c4c(N)ncnc43)C2)C1=O] | 2-acryloyl-5-(4-amino-3-(benzo[d]thiazol-6-yl)-1H-pyrazolo[3,4-d]pyrimidin-1-yl)-5,6-dihydrocyclopenta[c]pyrrole-1,3(2H,4H)-dione |
| 83 | 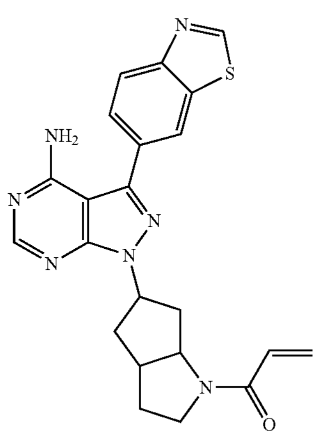 [SMILES: C=CC(=O)N1CCC2CC(n3nc(-c4ccc5ncsc5c4)c4c(N)ncnc43)CC21] | 1-(5-(4-amino-3-(benzo[d]thiazol-6-yl)-1H-pyrazolo[3,4-d]pyrimidin-1-yl)hexahydrocyclopenta[b]pyrrol-1(2H)-yl)prop-2-en-1-one |

TABLE 2-continued

| Compd | Structures | IUPAC Names |
|---|---|---|
| 84 | 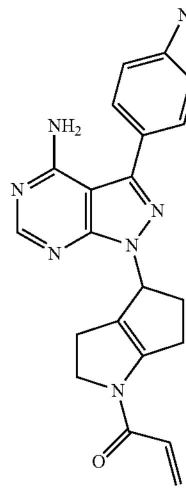 | 1-(4-(4-amino-3-(benzo[d]thiazol-6-yl)-1H-pyrazolo[3,4-d]pyrimidin-1-yl)-2,3,5,6-tetrahydrocyclopenta[b]pyrrol-1(4H)-yl)prop-2-en-1-one |
| 85 | 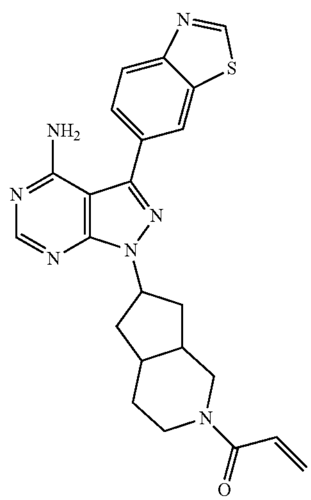 [SMILES: C=CC(=O)N1CCC2CC(n3nc(-c4ccc5ncsc5c4)c4c(N)ncnc43)CC2C1] | 1-(6-(4-amino-3-(benzo[d]thiazol-6-yl)-1H-pyrazolo[3,4-d]pyrimidin-1-yl)hexahydro-1H-cyclopenta[c]pyridin-2(3H)-yl)prop-2-en-1-one |
| 86 | 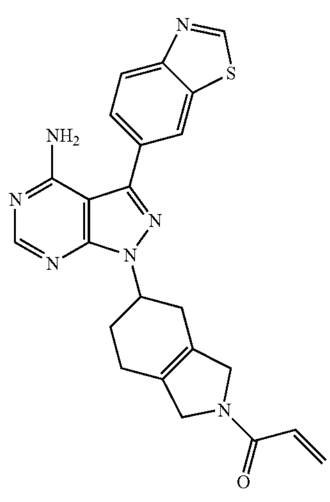 [SMILES: C=CC(=O)N1CC2=C(CC(n3nc(-c4ccc5ncsc5c4)c4c(N)ncnc43)CC2)C1] | 1-(5-(4-amino-3-(benzo[d]thiazol-6-yl)-1H-pyrazolo[3,4-d]pyrimidin-1-yl)-4,5,6,7-tetrahydro-1H-isoindol-2(3H)-yl)prop-2-en-1-one |

TABLE 2-continued
| Compd | Structures | IUPAC Names |
|---|---|---|
| 87 | 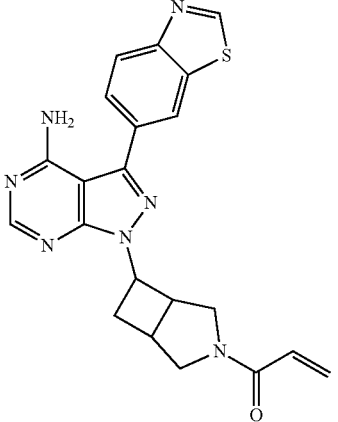 [SMILES: C=CC(=O)N1CC2CC(n3nc(-c4ccc5ncsc5c4)c4c(N)ncnc43)C2C1] | 1-(6-(4-amino-3-(benzo[d]thiazol-6-yl)-1H-pyrazolo[3,4-d]pyrimidin-1-yl)-3-azabicyclo[3.2.0]heptan-3-yl)prop-2-en-1-one |
| 88 | 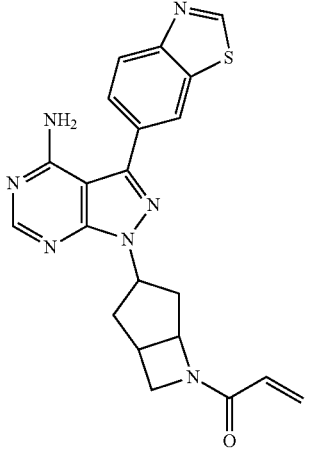 [SMILES: C=CC(=O)N1CC2CC(n3nc(-c4ccc5ncsc5c4)c4c(N)ncnc43)CC21] | 1-(3-(4-amino-3-(benzo[d]thiazol-6-yl)-1H-pyrazolo[3,4-d]pyrimidin-1-yl)-6-azabicyclo[3.2.0]heptan-6-yl)prop-2-en-1-one |
| 89 | 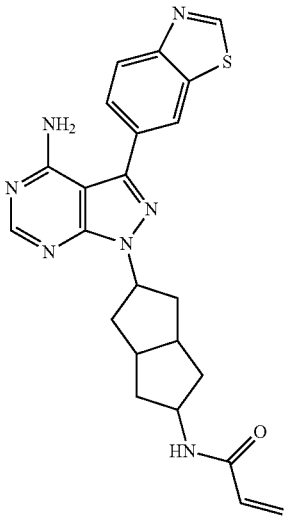 [SMILES: C=CC(=O)NC1CC2CC(n3nc(-c4ccc5ncsc5c4)c4c(N)ncnc43)CC2C1] | N-(5-(4-amino-3-(benzo[d]thiazol-6-yl)-1H-pyrazolo[3,4-d]pyrimidin-1-yl)octahydropentalen-2-yl)acrylamide |

TABLE 2-continued

| Compd | Structures | IUPAC Names |
|---|---|---|
| 90 | 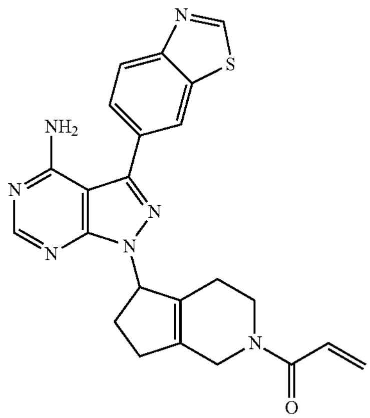 [SMILES: C=CC(=O)N1CCC2=C(CCC2n2nc(-c3ccc4ncsc4c3)c3c(N)ncnc32)C1] | 1-(5-(4-amino-3-(benzo[d]thiazol-6-yl)-1H-pyrazolo[3,4-d]pyrimidin-1-yl)-3,4,6,7-tetrahydro-1H-cyclopenta[c]pyridin-2(5H)-yl)prop-2-en-1-one |
| 91 | 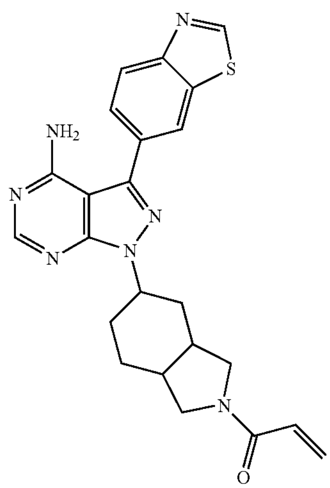 [SMILES: C=CC(=O)N1CC2CCC(n3nc(-c4ccc5ncsc5c4)c4c(N)ncnc43)CC2C1] | 1-(5-(4-amino-3-(benzo[d]thiazol-6-yl)-1H-pyrazolo[3,4-d]pyrimidin-1-yl)hexahydro-1H-isoindol-2(3H)-yl)prop-2-en-1-one |
| 92 | 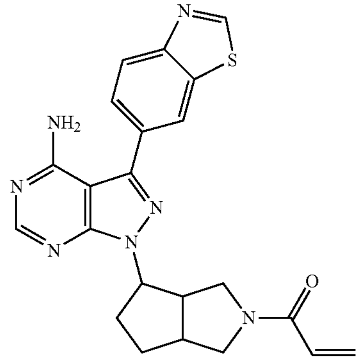 [SMILES: C=CC(=O)N1CC2CCC(n3nc(-c4ccc5ncsc5c4)c4c(N)ncnc43)C2C1] | 1-(4-(4-amino-3-(benzo[d]thiazol-6-yl)-1H-pyrazolo[3,4-d]pyrimidin-1-yl)hexahydrocyclopenta[c]pyrrol-2(1H)-yl)prop-2-en-1-one |

TABLE 2-continued
| Compd | Structures | IUPAC Names |
|---|---|---|
| 93 | 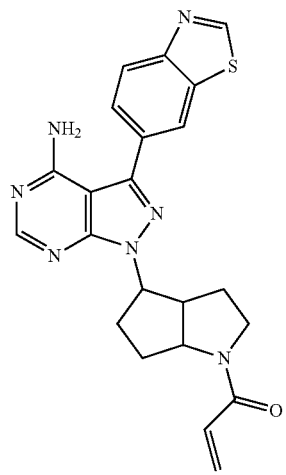 [SMILES: C=CC(=O)N1CCC2C1CCC2n1nc(-c2ccc3ncsc3c2)c2c(N)ncnc21] | 1-(4-(4-amino-3-(benzo[d]thiazol-6-yl)-1H-pyrazolo[3,4-d]pyrimidin-1-yl)hexahydrocyclopenta[b]pyrrol-1(2H)-yl)prop-2-en-1-one |
| 94 | 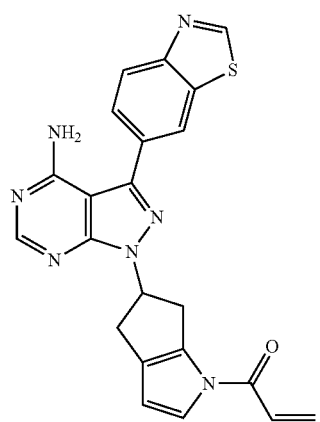 [SMILES: C=CC(=O)n1ccc2c1CC(n1nc(-c3ccc4ncsc4c3)c3c(N)ncnc31)C2] | 1-(5-(4-amino-3-(benzo[d]thiazol-6-yl)-1H-pyrazolo[3,4-d]pyrimidin-1-yl)-2,3,5,6-tetrahydrocyclopenta[b]pyrrol-1(4H)-yl)prop-2-en-1-one |
| 95 | 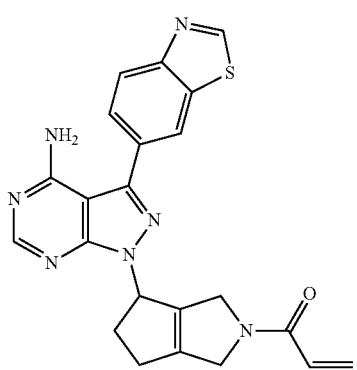 [SMILES: C=CC(=O)N1CC2=C(C1)C(n1nc(-c3ccc4ncsc4c3)c3c(N)ncnc31)CC2] | 1-(4-(4-amino-3-(benzo[d]thiazol-6-yl)-1H-pyrazolo[3,4-d]pyrimidin-1-yl)-5,6-dihydrocyclopenta[c]pyrrol-2(1H,3H,4H)-yl)prop-2-en-1-one |

TABLE 2-continued

| Compd | Structures | IUPAC Names |
|---|---|---|
| 96 | 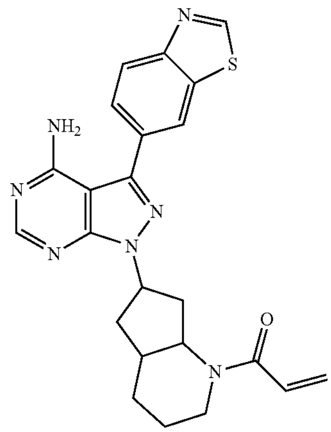 [SMILES: C=CC(=O)N1CCCC2CC(n3nc(-c4ccc5ncsc5c4)c4c(N)ncnc43)CC21] | 1-(6-(4-amino-3-(benzo[d]thiazol-6-yl)-1H-pyrazolo[3,4-d]pyrimidin-1-yl)octahydro-1H-cyclopenta[b]pyridin-1-yl)prop-2-en-1-one |
| 97 | 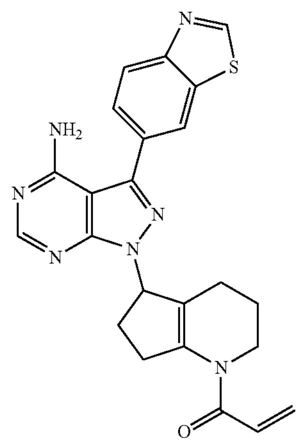 [SMILES: C=CC(=O)N1CCCC2=C1CCC2n1nc(-c2ccc3ncsc3c2)c2c(N)ncnc21] | 1-(5-(4-amino-3-(benzo[d]thiazol-6-yl)-1H-pyrazolo[3,4-d]pyrimidin-1-yl)-2,3,4,5,6,7-hexahydro-1H-cyclopenta[b]pyridin-1-yl)prop-2-en-1-one |
| 98 | 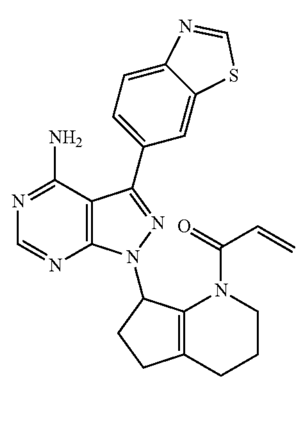 [SMILES: C=CC(=O)N1CCCC2=C1C(n1nc(-c3ccc4ncsc4c3)c3c(N)ncnc31)CC2] | 1-(7-(4-amino-3-(benzo[d]thiazol-6-yl)-1H-pyrazolo[3,4-d]pyrimidin-1-yl)-2,3,4,5,6,7-hexahydro-1H-cyclopenta[b]pyridin-1-yl)prop-2-en-1-one |

TABLE 2-continued
| Compd | Structures | IUPAC Names |
|---|---|---|
| 99 | 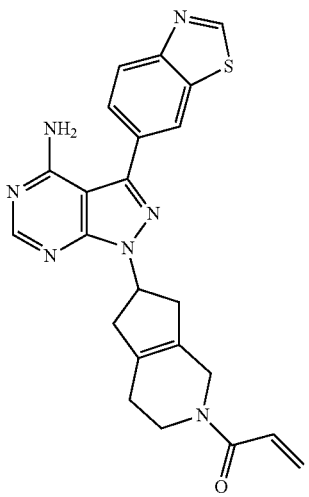 [SMILES: C=CC(=O)N1CCC2=C(CC(n3nc(-c4ccc5ncsc5c4)c4c(N)ncnc43)C2)C1] | 1-(6-(4-amino-3-(benzo[d]thiazol-6-yl)-1H-pyrazolo[3,4-d]pyrimidin-1-yl)-3,4,6,7-tetrahydro-1H-cyclopenta[c]pyridin-2(5H)-yl)prop-2-en-1-one |
| 100 | 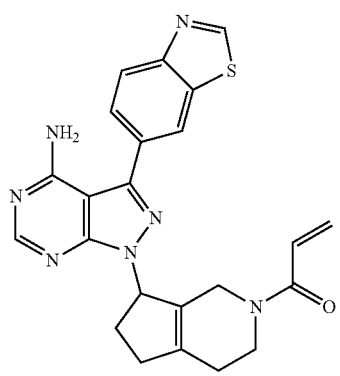 [SMILES: C=CC(=O)N1CCC2=C(C1)C(n1nc(-c3ccc4ncsc4c3)c3c(N)ncnc31)CC2] | 1-(7-(4-amino-3-(benzo[d]thiazol-6-yl)-1H-pyrazolo[3,4-d]pyrimidin-1-yl)-3,4,6,7-tetrahydro-1H-cylcopenta[c]pyridin-2(5H)-yl)prop-2-en-1-one |
| 101 | 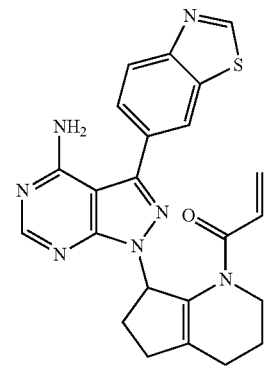 [SMILES: C=CC(=O)N1CCCC2=C1C(n1nc(-c3ccc4ncsc4c3)c3c(N)ncnc31)CC2] | 1-(7-(4-amino-3-(benzo[d]thiazol-6-yl)-1H-pyrazolo[3,4-d]pyrimidin-1-yl)-2,3,4,5,6,7-hexahydro-1H-cyclopenta[b]pyridin-1-yl)prop-2-en-1-one |

TABLE 2-continued

| Compd | Structures | IUPAC Names |
|---|---|---|
| 102 | 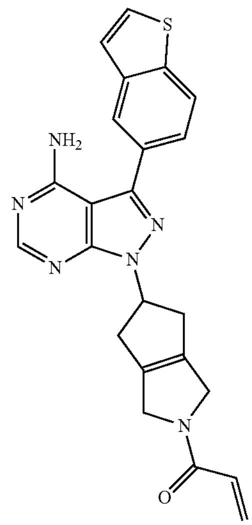 [SMILES: C=CC(=O)N1CC2=C(CC(n3nc(-c4ccc5sccc5c4)c4c(N)ncnc43)C2)C1] | 1-(5-(4-amino-3-(benzo[b]thiophen-5-yl)-1H-pyrazolo[3,4-d]pyrimidin-1-yl)-5,6-dihydrocyclopenta[c]pyrrol-2(1H,3H,4H)-yl)prop-2-en-1-one |
| 103 | 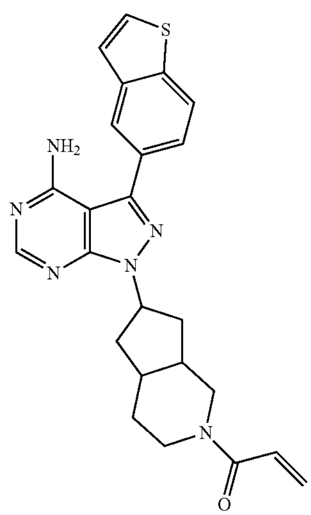 [SMILES: C=CC(=O)N1CCC2CC(n3nc(-c4ccc5sccc5c4)c4c(N)ncnc43)CC2C1] | 1-(6-(4-amino-3-(benzo[b]thiophen-5-yl)-1H-pyrazolo[3,4-d]pyrimidin-1-yl)hexahydro-1H-cyclopenta[c]pyridin-2(3H)-yl)prop-2-en-1-one |
| 104 | 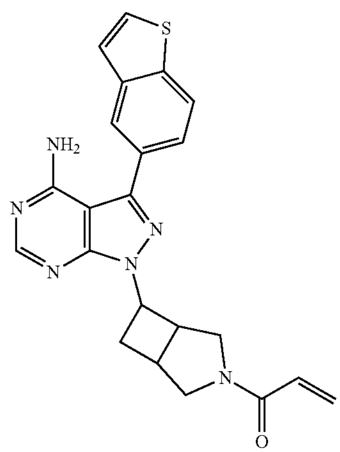 [SMILES: C=CC(=O)N1CC2CC(n3nc(-c4ccc5sccc5c4)c4c(N)ncnc43)C2C1] | 1-(6-(4-amino-3-(benzo[b]thiophen-5-yl)-1H-pyrazolo[3,4-d]pyrimidin-1-yl)-3-azabicyclo[3.2.0]heptan-3-yl)prop-2-en-1-one |

TABLE 2-continued

| Compd | Structures | IUPAC Names |
| --- | --- | --- |
| 105 | 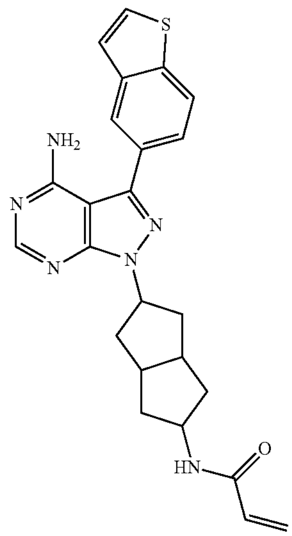 [SMILES: C=CC(=O)NC1CC2CC(n3nc(-c4ccc5sccc5c4)c4c(N)ncnc43)CC2C1] | N-(5-(4-amino-3-(benzo[b]thiophen-5-yl)-1H-pyrazolo[3,4-d]pyrimidin-1-yl)octahydropentalen-2-yl)acrylamide |
| 106 | 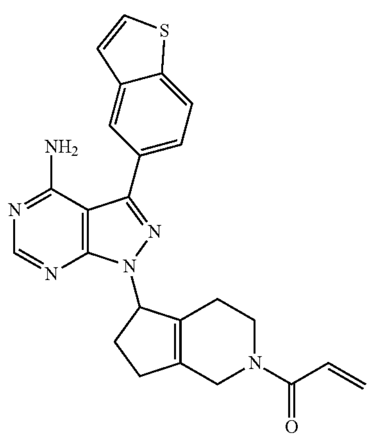 [SMILES: C=CC(=O)N1CCC2=C(CCC2n2nc(-c3ccc4sccc4c3)c3c(N)ncnc32)C1] | 1-(5-(4-amino-3-(benzo[b]thiophen-5-yl)-1H-pyrazolo[3,4-d]pyrimidin-1-yl)-3,4,6,7-tetrahydro-1H-cyclopenta[c]pyridin-2(5H)-yl)prop-2-en-1-one |
| 107 | 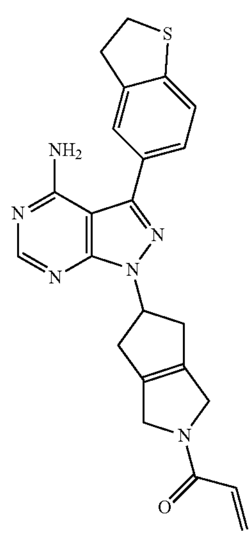 [SMILES: C=CC(=O)N1CC2=C(CC(n3nc(-c4ccc5c(c4)CCS5)c4c(N)ncnc43)C2)C1] | 1-(5-(4-amino-3-(2,3-dihydrobenzo[b]thiophen-5-yl)-1H-pyrazolo[3,4-d]pyrimidin-1-yl)-5,6-dihydrocyclopenta[c]pyrrol-2(1H,3H,4H)-yl)prop-2-en-1-one |

| Compd | Structures | IUPAC Names |
|---|---|---|
| 108 | 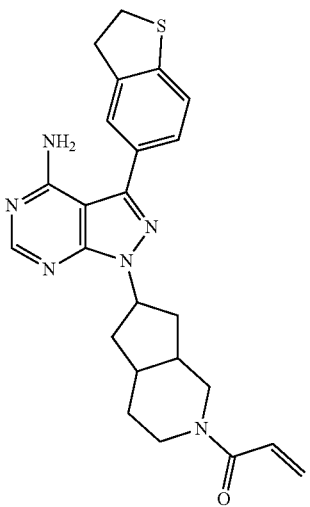 [SMILES: C=CC(=O)N1CCC2CC(n3nc(-c4ccc5c(c4)CCS5)c4c(N)ncnc43)CC2C1] | 1-(6-(4-amino-3-(2,3-dihydrobenzo[b]thiophen-5-yl)-1H-pyrazolo[3,4-d]pyrimidin-1-yl)hexahydro-1H-cyclopenta[c]pyridin-2(3H)-yl)prop-2-en-1-one |
| 109 | 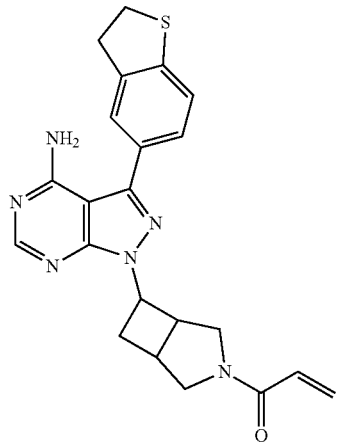 [SMILES: C=CC(=O)N1CC2CC(n3nc(-c4ccc5c(c4)CCS5)c4c(N)ncnc43)C2C1] | 1-(6-(4-amino-3-(2,3-dihydrobenzo[b]thiophen-5-yl)-1H-pyrazolo[3,4-d]pyrimidin-1-yl)-3-azabicyclo[3.2.0]heptan-3-yl)prop-2-en-1-one |
| 110 | 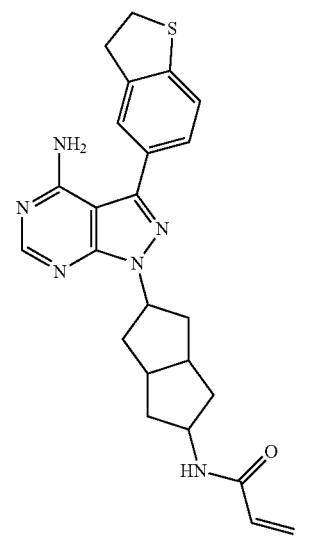 [SMILES: C=CC(=O)NC1CC2CC(n3nc(-c4ccc5c(c4)CCS5)c4c(N)ncnc43)CC2C1] | N-(5-(4-amino-3-(2,3-dihydrobenzo[b]thiophen-5-yl)-1H-pyrazolo[3,4-d]pyrimidin-1-yl)octahydropentalen-2-yl)acrylamide |

TABLE 2-continued

| Compd | Structures | IUPAC Names |
|---|---|---|
| 111 | 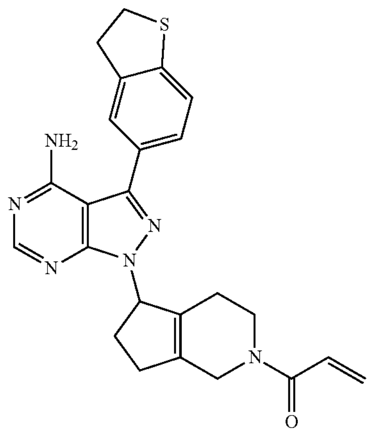 [SMILES: C=CC(=O)N1CCC2=C(CCC2n2nc(-c3ccc4c(c3)CCS4)c3c(N)ncnc32)C1] | 1-(5-(4-amino-3-(2,3-dihydrobenzo[b]thiophen-5-yl)-1H-pyrazolo[3,4-d]pyrimidin-1-yl)-3,4,6,7-tetrahydro-1H-cyclopenta[c]pyridin-2(5H)-yl)prop-2-en-1-one |
| 112 | 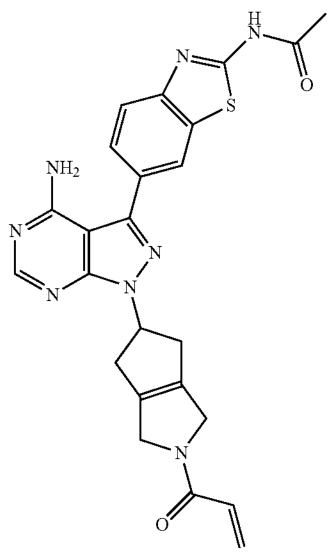 [SMILES: C=CC(=O)N1CC2=C(CC(n3nc(-c4ccc5nc(NC(C)=O)sc5c4)c4c(N)ncnc43)C2)C1] | N-(6-(1-(2-acryloyl-1,2,3,4,5,6-hexahydrocyclopenta[c]pyrrol-5-yl)-4-amino-1H-pyrazolo[3,4-d]pyrimidin-3-yl)benzo[d]thiazol-2-yl)acetamide |
| 113 | 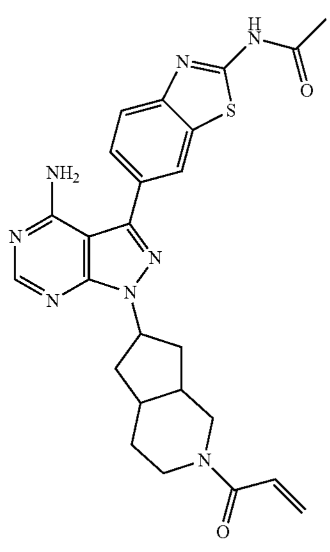 [SMILES: C=CC(=O)N1CCC2CC(n3nc(-c4ccc5nc(NC(C)=O)sc5c4)c4c(N)ncnc43)CC2C1] | N-(6-(1-(2-acryloyloctahydro-1H-cyclopenta[c]pyridin-6-yl)-4-amino-1H-pyrazolo[3,4-d]pyrimidin-3-yl)benzo[d]thiazol-2-yl)acetamide |

TABLE 2-continued
| Compd | Structures | IUPAC Names |
|---|---|---|
| 114 | 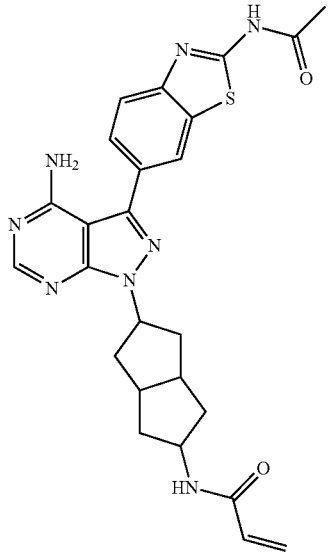 [SMILES: C=CC(=O)NC1CC2CC(n3nc(-c4ccc5nc(NC(C)=O)sc5c4)c4c(N)ncnc43)CC2C1] | N-(5-(3-(2-acetamidobenzo[d]thiazol-6-yl)-4-amino-1H-pyrazolo[3,4-d]pyrimidin-1-yl)octahydropentalen-2-yl)acrylamide |
| 115 | 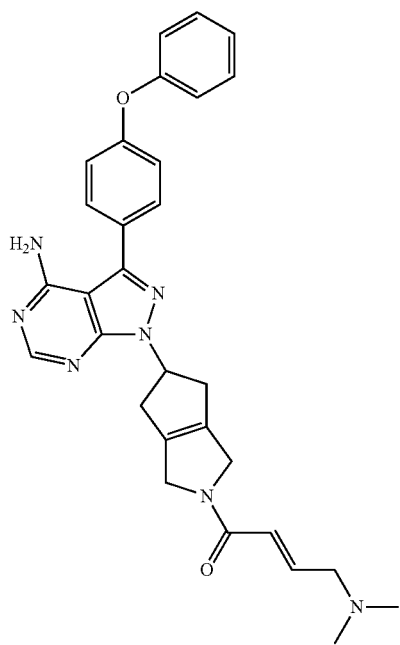 [SMILES: CN(C)C/C=C/C(=O)N1CC2=C(CC(n3nc(-c4ccc(Oc5ccccc5)cc4)c4c(N)ncnc43)C2)C1] | (E)-1-(5-(4-amino-3-(4-phenoxyphenyl)-1H-pyrazolo[3,4-d]pyrimidin-1-yl)-5,6-dihydrocylcopenta[c]pyrrol-2(1H,3H,4H)-yl)-4-(dimethylamino)but-2-en-1-one |

TABLE 2-continued

| Compd | Structures | IUPAC Names |
|---|---|---|
| 116 | 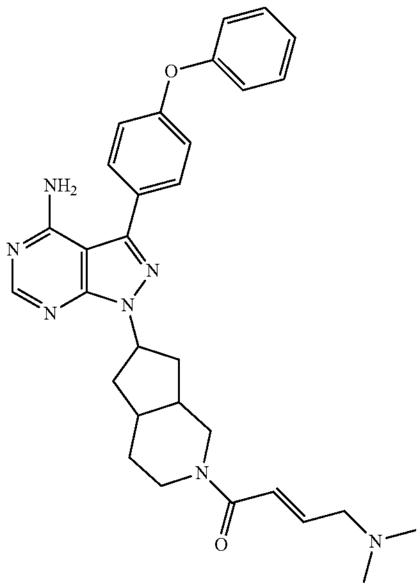 [SMILES: CN(C)C/C=C/C(=O)N1CCC2CC(n3nc(-c4ccc(Oc5ccccc5)cc4)c4c(N)ncnc43)CC2C1] | (E)-1-(6-(4-amino-3-(4-phenoxyphenyl)-1H-pyrazolo[3,4-d]pyrimidin-1-yl)hexahydro-1H-cyclopenta[c]pyridin-2(3H)-yl)-4-(dimethylamino)but-2-en-1-one |
| 117 | 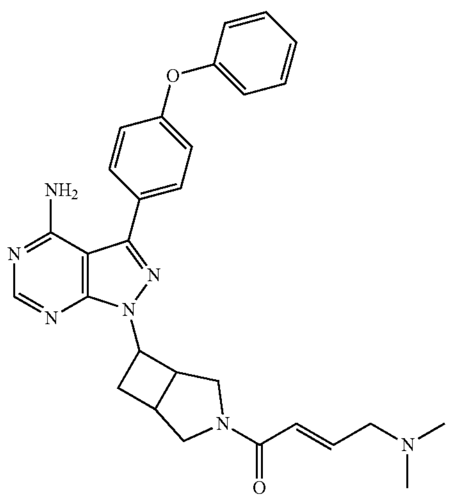 [SMILES: CN(C)C/C=C/C(=O)N1CC2CC(n3nc(-c4ccc(Oc5ccccc5)cc4)c4c(N)ncnc43)C2C1] | (E)-1-(6-(4-amino-3-(4-phenoxyphenyl)-1H-pyrazolo[3,4-d]pyrimidin-1-yl)-3-azabicyclo[3.2.0]heptan-3-yl)-4-(dimethylamino)but-2-en-1-one |
| 118 | 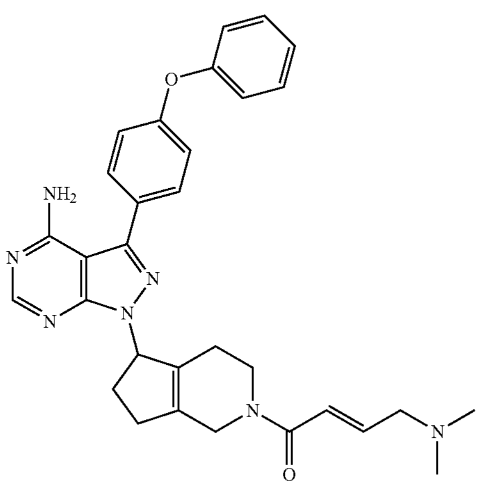 [SMILES: CN(C)C/C=C/C(=O)N1CCC2=C(CCC2n2nc(-c3ccc(Oc4ccccc4)cc3)c3c(N)ncnc32)C1] | (E)-1-(5-(4-amino-3-(4-phenoxyphenyl)-1H-pyrazolo[3,4-d]pyrimidin-1-yl)-3,4,6,7-tetrahydro-1H-cyclopenta[c]pyridin-2(5H)-yl)-4-(dimethylamino)but-2-en-1-one |

TABLE 2-continued

| Compd | Structures | IUPAC Names |
|---|---|---|
| 119 | 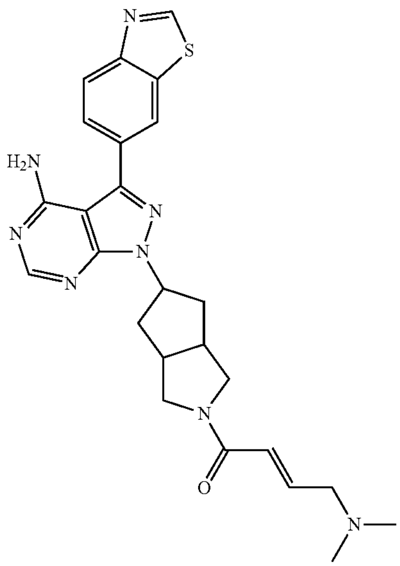 [SMILES: CN(C)C/C=C/C(=O)N1CC2CC(n3nc(-c4ccc5ncsc5c4)c4c(N)ncnc43)CC2C1] | (E)-1-(5-(4-amino-3-(benzo[d]thiazol-6-yl)-1H-pyrazolo[3,4-d]pyrimidin-1-yl)hexahydrocyclopenta[c]pyrrol-2(1H)-yl-4-(dimethylamino)but-2-en-1-one |
| 120 | 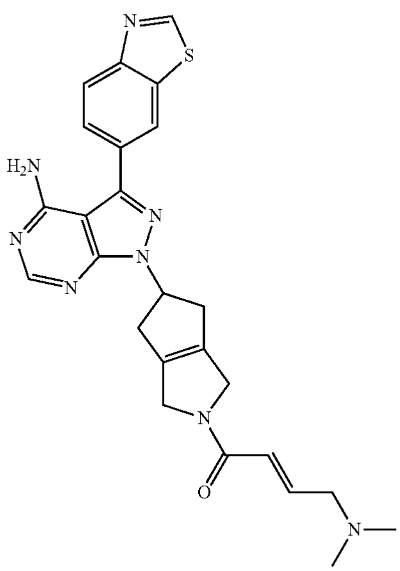 [SMILES: CN(C)C/C=C/C(=O)N1CC2=C(CC(n3nc(-c4ccc5ncsc5c4)c4c(N)ncnc43)C2)C1] | (E)-1-(5-(4-amino-3-(benzo[d]thiazol-6-yl)-1H-pyrazolo[3,4-d]pyrimidin-1-yl)-5,6-dihydrocyclopenta[c]pyrrol-2(1H,3H,4H)-yl)-4-(dimethylamino)but-2-en-1-one |
| 121 | 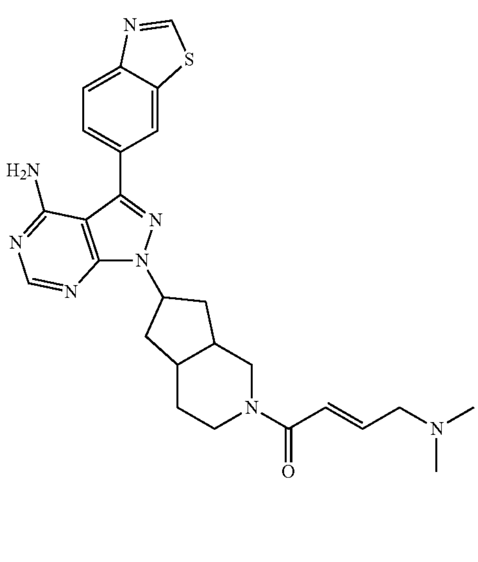 [SMILES: CN(C)C/C=C/C(=O)N1CCC2CC(n3nc(-c4ccc5ncsc5c4)c4c(N)ncnc43)CC2C1] | (E)-1-(6-(4-amino-3-(benzo[d]thiazol-6-yl)-1H-pyrazolo[3,4-d]pyrimidin-1-yl)hexahydro-1H-cyclopenta[c]pyridin-2(3H)-yl)-4-(dimethylamino)but-2-en-1-one |

TABLE 2-continued

| Compd | Structures | IUPAC Names |
|---|---|---|
| 122 | 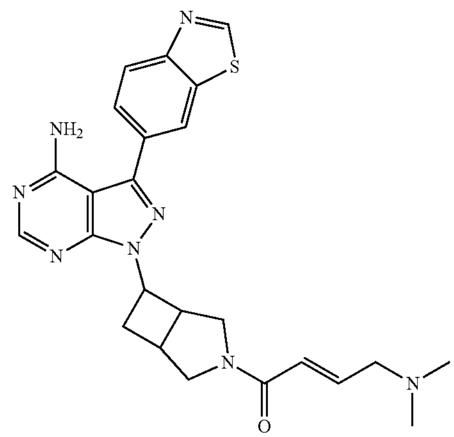 [SMILES: CN(C)C/C=C/C(=O)N1CC2CC(n3nc(-c4ccc5ncsc5c4)c4c(N)ncnc43)C2C1] | (E)-1-(6-(4-amino-3-(benzo[d]thiazol-6-yl)-1H-pyrazolo[3,4-d]pyrimidin-1-yl)-3-azabicyclo[3.2.0]heptan-3-yl)-4-(dimethylamino)but-2-en-1-one |
| 123 | 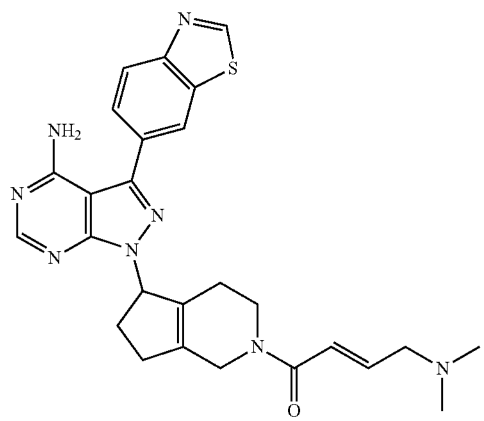 [SMILES: CN(C)C/C=C/C(=O)N1CCC2=C(CCC2n2nc(-c3ccc4ncsc4c3)c3c(N)ncnc32)C1] | (E)-1-(5-(4-amino-3-(benzo[d]thiazol-6-yl)-1H-pyrazolo[3,4-d]pyrimidin-1-yl)-3,4,6,7-tetrahydro-1H-cyclopenta[c]pyridin-2(5H)-yl)-4-(dimethylamino)but-2-en-1-one |
| 124 | 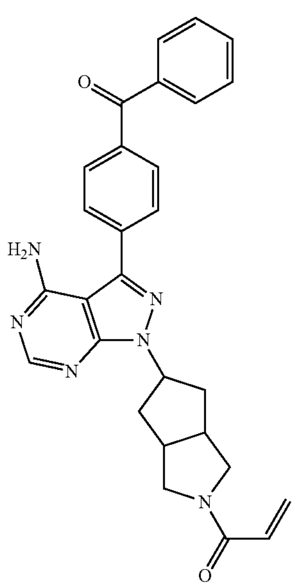 [SMILES: C=CC(=O)N1CC2CC(n3nc(-c4ccc(C(=O)c5ccccc5)cc4)c4c(N)ncnc43)CC2C1] | 1-(5-(4-amino-3-(4-benzoylphenyl)-1H-pyrazolo[3,4-d]pyrimidin-1-yl)hexahydrocyclopenta[c]pyrrol-2(1H)-yl)prop-2-en-1-one |

TABLE 2-continued

| Compd | Structures | IUPAC Names |
|---|---|---|
| 125 | 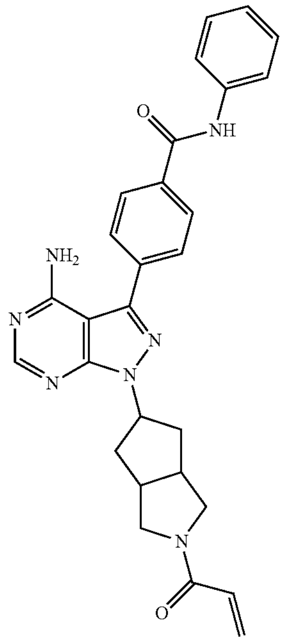 [SMILES: C=CC(=O)N1CC2CC(n3nc(-c4ccc(C(=O)Nc5ccccc5)cc4)c4c(N)ncnc43)CC2C1] | 4-(1-(2-acryloyloctahydrocyclopenta[c]pyrrol-5-yl)-4-amino-1H-pyraozlo[3,4-d]pyrimidin-3-yl)-N-phenylbenzamide |
| 126 | 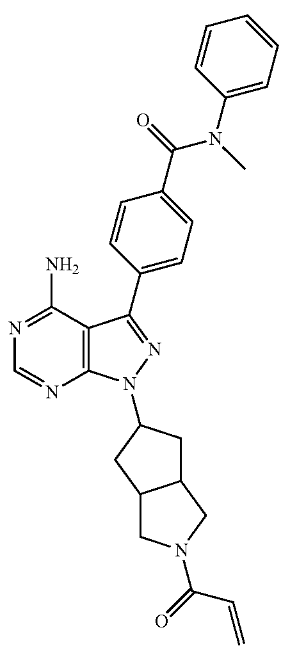 [SMILES: C=CC(=O)N1CC2CC(n3nc(-c4ccc(C(=O)N(C)c5ccccc5)cc4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-N-methyl-N-phenylbenzamide |

TABLE 2-continued

| Compd | Structures | IUPAC Names |
|---|---|---|
| 127 | 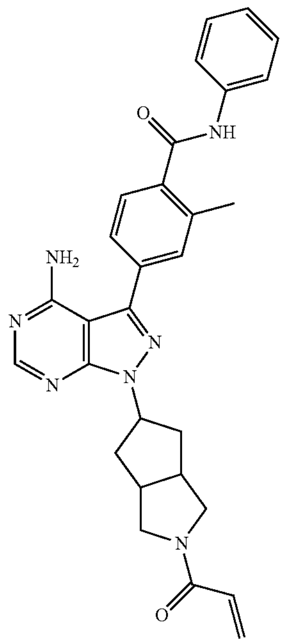 [SMILES: C=CC(=O)N1CC2CC(n3nc(-c4ccc(C(=O)Nc5ccccc5)c(C)c4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-2-methyl-N-phenylbenzamide |
| 128 | 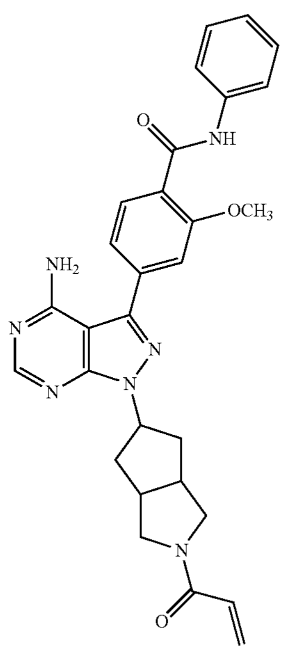 [SMILES: C=CC(=O)N1CC2CC(n3nc(-c4ccc(C(=O)Nc5ccccc5)c(OC)c4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-2-methoxy-N-phenylbenzamide |

TABLE 2-continued
| Compd | Structures | IUPAC Names |
|---|---|---|
| 129 | 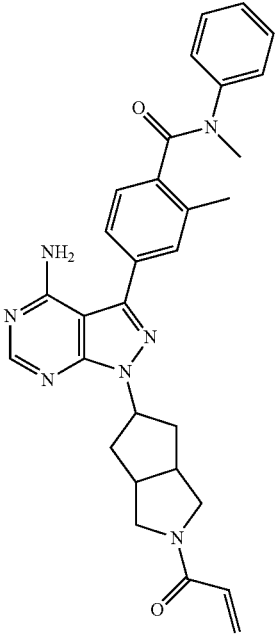 [SMILES: C=CC(=O)N1CC2CC(n3nc(-c4ccc(C(=O)N(C)c5ccccc5)c(C)c4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-N,2-dimethyl-N-phenylbenzamide |
| 130 | 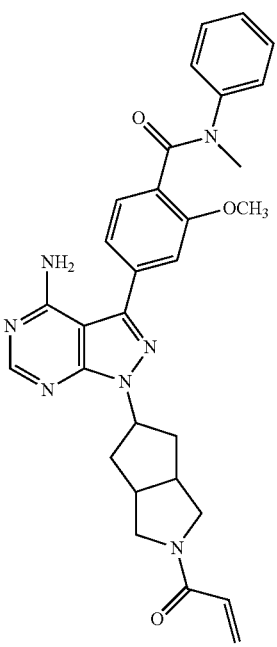 [SMILES: C=CC(=O)N1CC2CC(n3nc(-c4ccc(C(=O)N(C)c5ccccc5)c(OC)c4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-2-methoxy-N-methyl-N-phenylbenzamide |

TABLE 2-continued
| Compd | Structures | IUPAC Names |
|---|---|---|
| 131 | 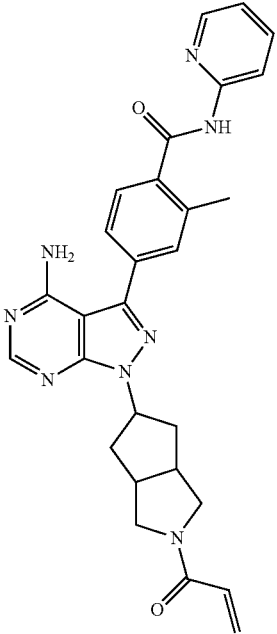 [SMILES: C=CC(=O)N1CC2CC(n3nc(-c4ccc(C(=O)Nc5ccccn5)c(C)c4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-2-methyl-N-(pyridin-2-yl)benzamide |
| 132 | 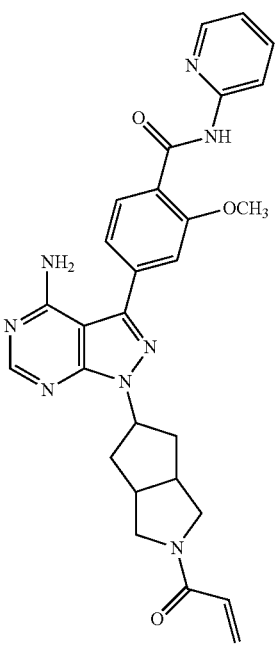 [SMILES: C=CC(=O)N1CC2CC(n3nc(-c4ccc(C(=O)Nc5ccccn5)c(OC)c4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-2-methoxy-N-(pyridin-2-yl)benzamide |

TABLE 2-continued
| Compd | Structures | IUPAC Names |
|---|---|---|
| 133 | 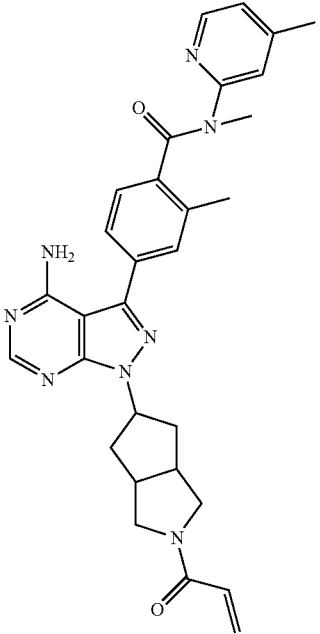 [SMILES: C=CC(=O)N1CC2CC(n3nc(-c4ccc(C(=O)N(C)c5cc(C)ccn5)c(C)c4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-2-methyl-N-(4-methylpyridin-2-yl)benzamide |
| 134 | 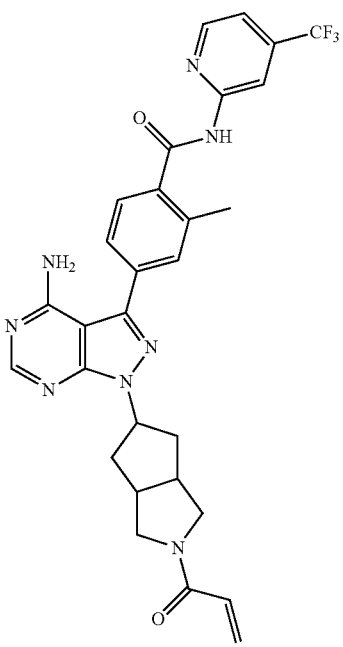 [SMILES: C=CC(=O)N1CC2CC(n3nc(-c4ccc(C(=O)Nc5cc(C(F)(F)F)ccn5)c(C)c4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-2-methyl-N-(4-(trifluoromethyl)pyridin-2-yl)benzamide |

TABLE 2-continued
| Compd | Structures | IUPAC Names |
|---|---|---|
| 135 | 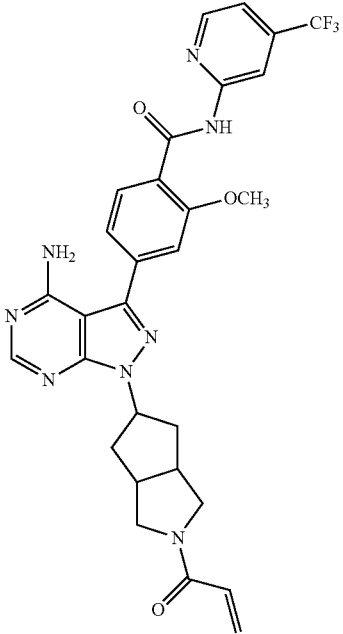 [SMILES: C=CC(=O)N1CC2CC(n3nc(-c4ccc(C(=O)Nc5cc(C(F)(F)F)ccn5)c(OC)c4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-2-methoxy-N-(4-(trifluoromethyl)pyridin-2-yl)benzamide |
| 136 | 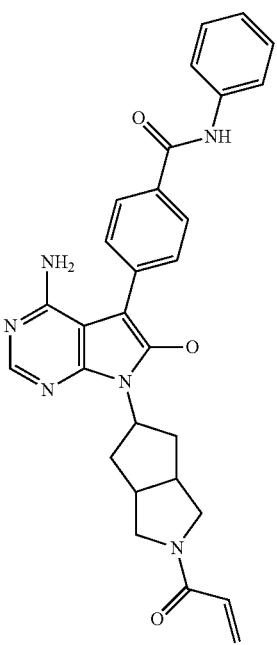 [SMILES: C=CC(=O)N1CC2CC(n3c(O)c(-c4ccc(C(=O)Nc5ccccc5)cc4)c4c(N)ncnc43)CC2C1] | 4-(7-(2-acryloyloctahydrocyclopenta[c]pyrrol-5-yl)-4-amino-6-chloro-7H-pyrrolo[2,3-d]pyrimidin-5-yl)-N-phenylbenzamide |

TABLE 2-continued
| Compd | Structures | IUPAC Names |
|---|---|---|
| 137 | 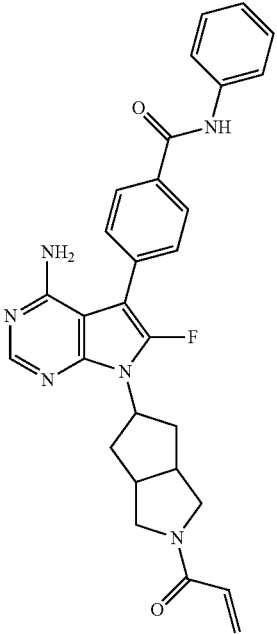 | 4-(7-(2-acryloyloctahydrocyclopenta[c]pyrrol-5-yl)-4-amino-6-fluoro-7H-pyrrolo[2,3-d]pyrimidin-5-yl)-N-phenylbenzamide |
| 138 | 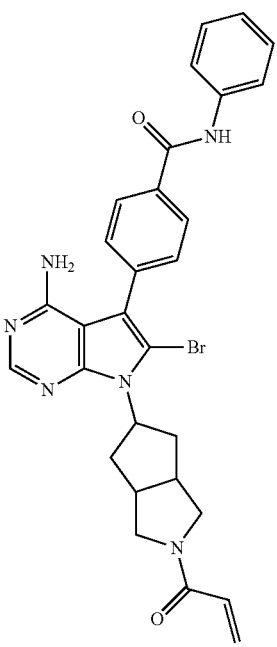 | 4-(7-(2-acryloyloctahydrocyclopenta[c]pyrrol-5-yl)-4-amino-6-bromo-7H-pyrrolo[2,3-d]pyrimidin-5-yl)-N-phenylbenzamide |

TABLE 2-continued
| Compd | Structures | IUPAC Names |
|---|---|---|
| 139 | 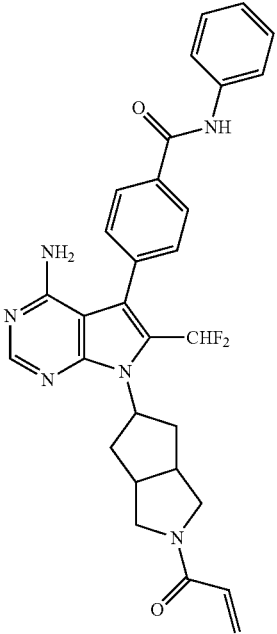 [SMILES: C=CC(=O)N1CC2CC(n3c(C(F)F)c(-c4ccc(C(=O)Nc5ccccc5)cc4)c4c(N)ncnc43)CC2C1] | 4-(7-(2-acryloyloctahydrocyclopenta[c]pyrrol-5-yl)-4-amino-6-(difluoromethyl)-7H-pyrrolo[2,3-d]pyrimidin-5-yl)-N-phenylbenzamide |
| 140 | 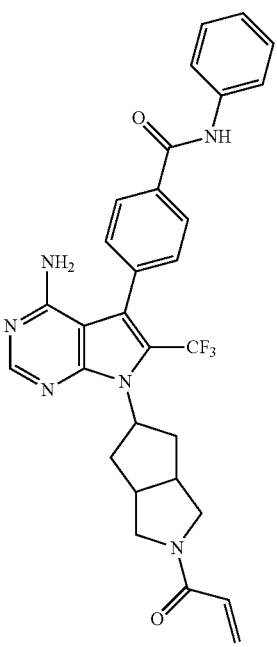 | 4-(7-(2-acryloyloctahydrocyclopenta[c]pyrrol-5-yl)-4-amino-6-(trifluoromethyl)-7H-pyrrolo[2,3-d]pyrimidin-5-yl)-N-phenylbenzamide |

TABLE 2-continued
| Compd | Structures | IUPAC Names |
|---|---|---|
| 141 | 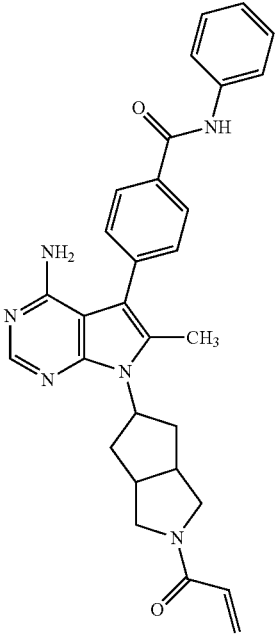 [SMILES: C=CC(=O)N1CC2CC(n3c(C)c(-c4ccc(C(=O)Nc5ccccc5)cc4)c4c(N)ncnc43)CC2C1] | 4-(7-(2-acryloyloctahydrocylcopenta[c]pyrrol-5-yl)-4-amino-6-methyl-7H-pyrrolo[2,3-d]pyrimidin-5-yl)-N-phenylbenzamide |
| 142 | 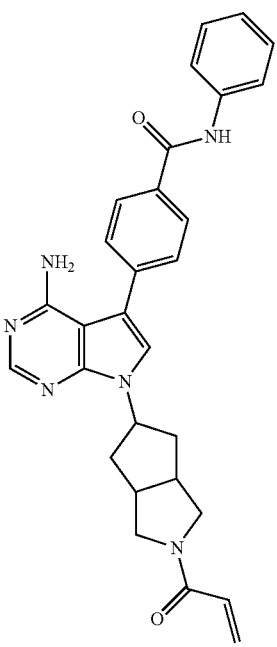 [SMILES: C=CC(=O)N1CC2CC(n3cc(-c4ccc(C(=O)Nc5ccccc5)cc4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-N-phenylbenzamide |

TABLE 2-continued

| Compd | Structures | IUPAC Names |
|---|---|---|
| 143 | 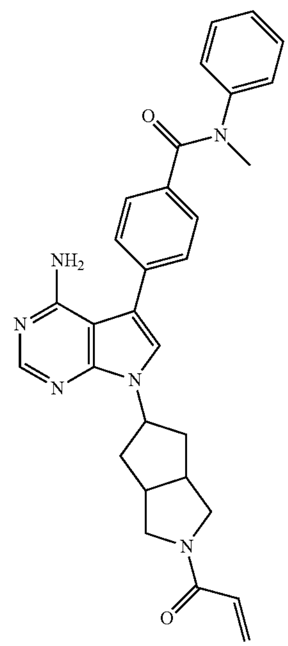 [SMILES: C=CC(=O)N1CC2CC(n3cc(-c4ccc(C(=O)N(C)c5ccccc5)cc4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-N-methyl-N-phenylbenzamide |
| 144 | 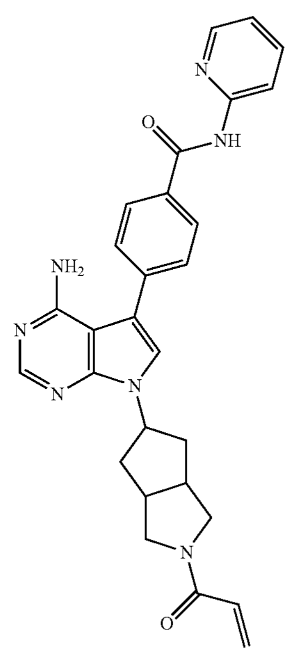 [SMILES: C=CC(=O)N1CC2CC(n3cc(-c4ccc(C(=O)Nc5ccccn5)cc4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-N-(pyridin-2-yl)benzamide |

| Compd | Structures | IUPAC Names |
|---|---|---|
| 145 | 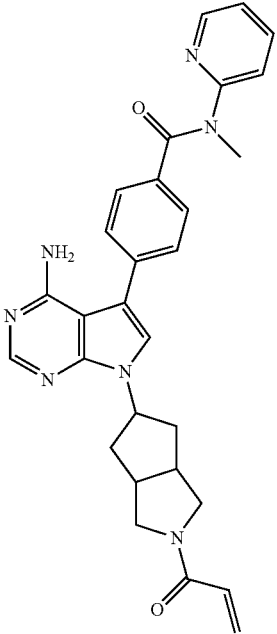 [SMILES: C=CC(=O)N1CC2CC(n3cc(-c4ccc(C(=O)N(C)c5ccccn5)cc4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-N-methyl-N-(pyridin-2-yl)benzamide |
| 146 | 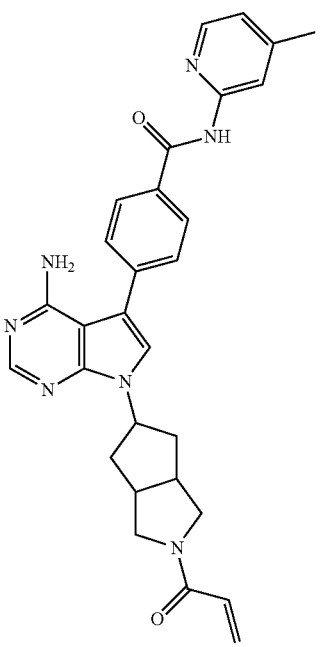 [SMILES: C=CC(=O)N1CC2CC(n3cc(-c4ccc(C(=O)Nc5cc(C)ccn5)cc4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-N-(4-methylpyridin-2-yl)benzamide |

TABLE 2-continued
| Compd | Structures | IUPAC Names |
|---|---|---|
| 147 | 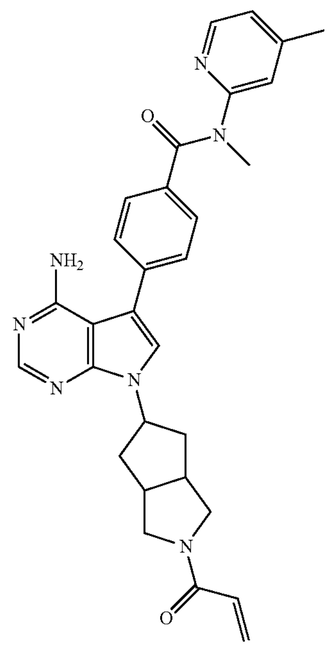 [SMILES: C=CC(=O)N1CC2CC(n3cc(-c4ccc(C(=O)N(C)c5cc(C)ccn5)cc4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-N-methyl-N-(4-methylpyridin-2-yl)benzamide |
| 148 | 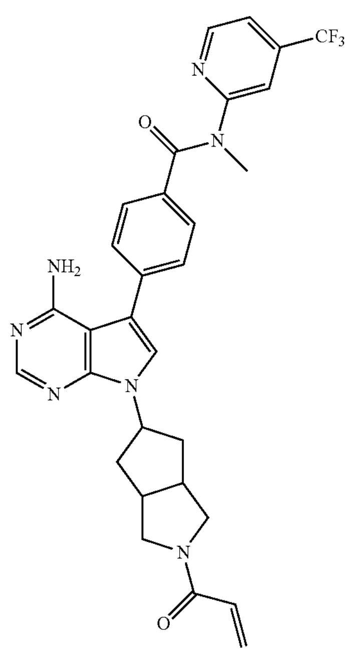 [SMILES: C=CC(=O)N1CC2CC(n3cc(-c4ccc(C(=O)N(C)c5cc(C(F)(F)F)ccn5)cc4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-N-methyl-N-(4-(trifluoromethyl)pyridin-2-yl)benzamide |

TABLE 2-continued
| Compd | Structures | IUPAC Names |
|---|---|---|
| 149 | 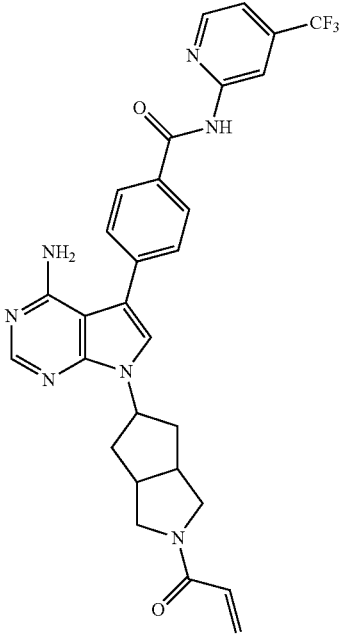 [SMILES: C=CC(=O)N1CC2CC(n3cc(-c4ccc(C(=O)Nc5cc(C(F)(F)F)ccn5)cc4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-N-(4-(trifluoromethyl)pyridin-2-yl)benzamide |
| 150 | 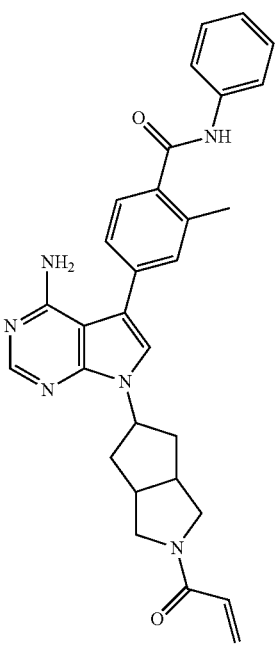 [SMILES: C=CC(=O)N1CC2CC(n3cc(-c4ccc(C(=O)Nc5ccccc5)c(C)c4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-2-methyl-N-phenylbenzamide |

TABLE 2-continued
| Compd | Structures | IUPAC Names |
|---|---|---|
| 151 | 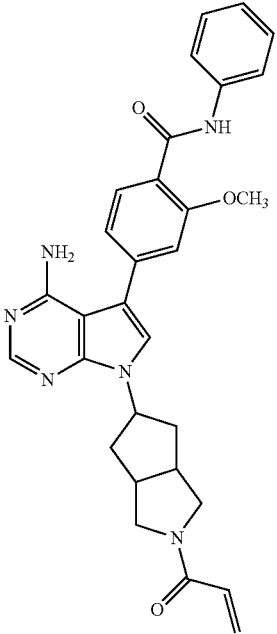 [SMILES: C=CC(=O)N1CC2CC(n3cc(-c4ccc(C(=O)Nc5ccccc5)c(OC)c4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-2-methoxy-N-phenylbenzamide |
| 152 | 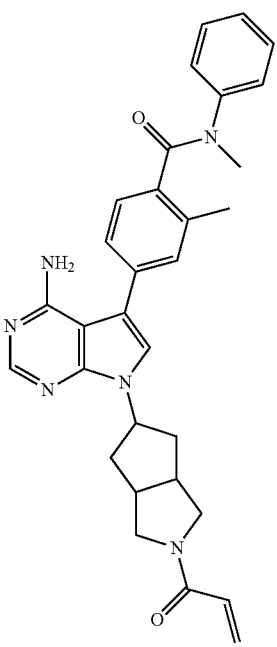 [SMILES: C=CC(=O)N1CC2CC(n3cc(-c4ccc(C(=O)N(C)c5ccccc5)c(C)c4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-N,2-dimethyl-N-phenylbenzamide |

TABLE 2-continued

| Compd | Structures | IUPAC Names |
|---|---|---|
| 153 | 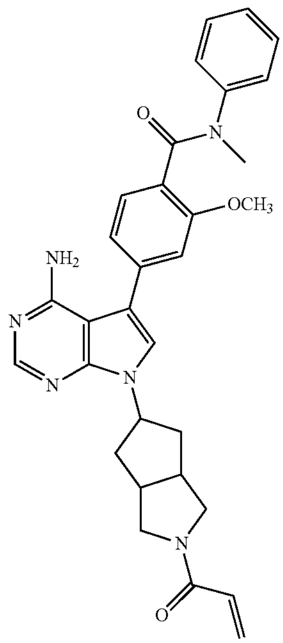 [SMILES: C=CC(=O)N1CC2CC(n3cc(-c4ccc(C(=O)N(C)c5ccccc5)c(OC)c4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-2-methoxy-N-methyl-N-phenylbenzamide |
| 154 | 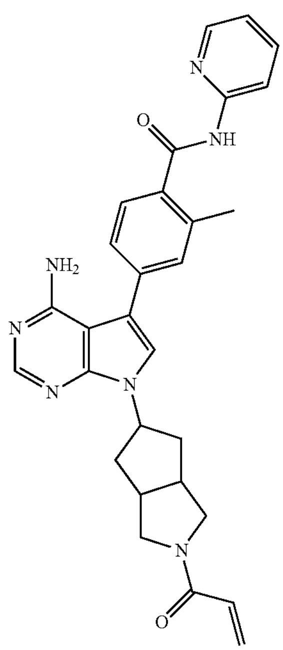 [SMILES: C=CC(=O)N1CC2CC(n3cc(-c4ccc(C(=O)Nc5ccccn5)c(C)c4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-2-methyl-N-(pyridin-2-yl)benzamide |

TABLE 2-continued
| Compd | Structures | IUPAC Names |
|---|---|---|
| 155 | 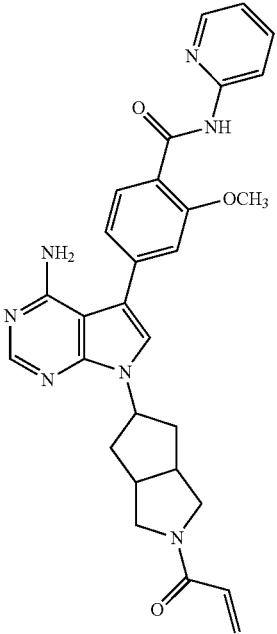 [SMILES: C=CC(=O)N1CC2CC(n3cc(-c4ccc(C(=O)Nc5ccccn5)c(OC)c4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-2-methoxy-N-(pyridin-2-yl)benzamide |
| 156 | 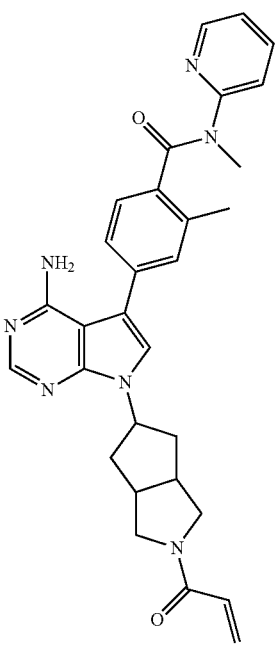 [SMILES: C=CC(=O)N1CC2CC(n3cc(-c4ccc(C(=O)N(C)c5ccccn5)c(C)c4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-N,2-dimethyl-N-(pyridin-2-yl)benzamide |

TABLE 2-continued
| Compd | Structures | IUPAC Names |
|---|---|---|
| 157 | 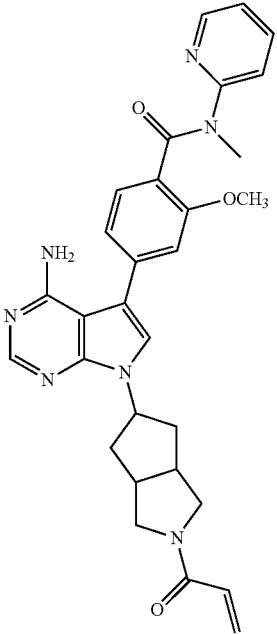 [SMILES: C=CC(=O)N1CC2CC(n3cc(-c4ccc(C(=O)N(C)c5ccccn5)c(OC)c4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-2-methoxy-N-methyl-N-(pyridin-2-yl)benzamide |
| 158 | 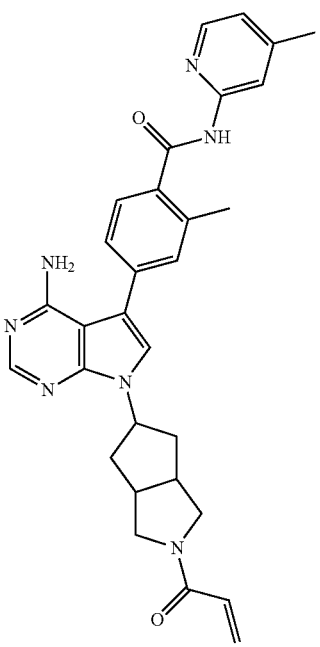 [SMILES: C=CC(=O)N1CC2CC(n3cc(-c4ccc(C(=O)Nc5cc(C)ccn5)c(C)c4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-2-methyl-N-(4-methylpyridin-2-yl)benzamide |

TABLE 2-continued
| Compd | Structures | IUPAC Names |
|---|---|---|
| 159 | 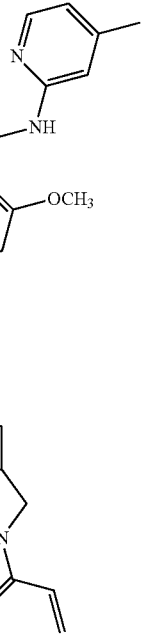 | 4-(7-(2-acryloyloctahydrocyclopenta[c]pyrrol-5-yl)-4-amino-7H-pyrrolo[2,3-d]pyrimidin-5-yl)-2-methoxy-N-(4-methylpyridin-2-yl)benzamide |
| 160 | 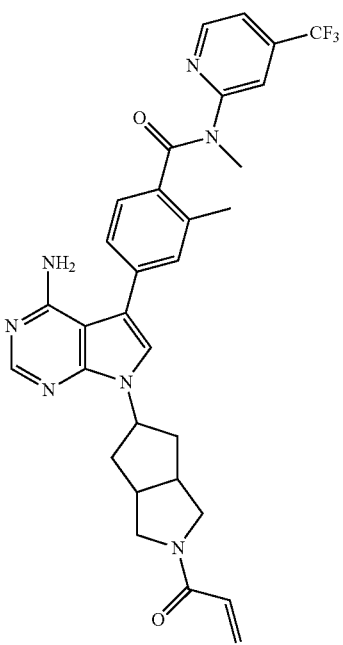 [SMILES: C=CC(=O)N1CC2CC(n3cc(-c4ccc(C(=O)N(C)c5cc(C(F)(F)F)ccn5)c(C)c4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-N,2-dimethyl-N-(4-(trifluoromethyl)pyridin-2-yl)benzamide |

TABLE 2-continued
| Compd | Structures | IUPAC Names |
|---|---|---|
| 161 | 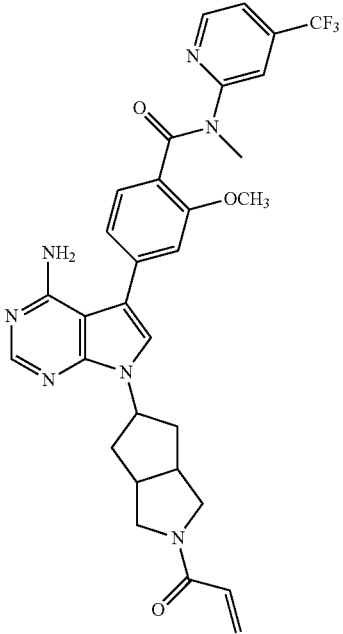 [SMILES: C=CC(=O)N1CC2CC(n3cc(-c4ccc(C(=O)N(C)c5cc(C(F)(F)F)ccn5)c(OC)c4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-2-methoxy-N-methyl-N-(4-(trifluoromethyl)pyridin-2-yl)benzamide |
| 162 | 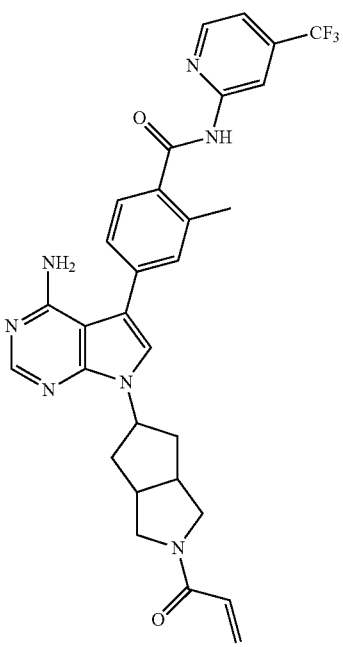 [SMILES: C=CC(=O)N1CC2CC(n3cc(-c4ccc(C(=O)Nc5cc(C(F)(F)F)ccn5)c(C)c4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-2-methyl-N-(4-(trifluoromethyl)pyridin-2-yl)benzamide |

TABLE 2-continued
| Compd | Structures | IUPAC Names |
|---|---|---|
| 163 | 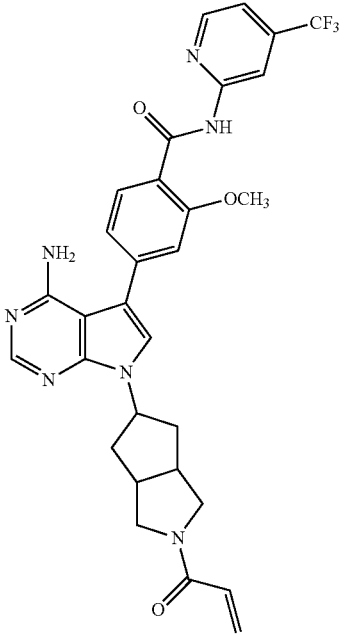 [SMILES: C=CC(=O)N1CC2CC(n3cc(-c4ccc(C(=O)Nc5cc(C(F)(F)F)ccn5)c(OC)c4)c4c(N)ncnc43)CC2C1] | 4-(7-(2-acryloyloctahydrocyclopenta[c]pyrrol-5-yl)-4-amino-7H-pyrrolo[2,3-d]pyrimidin-5-yl)-2-methoxy-N-(4-(trifluoromethyl)pyridin-2-yl)benzamide |
| 164 | 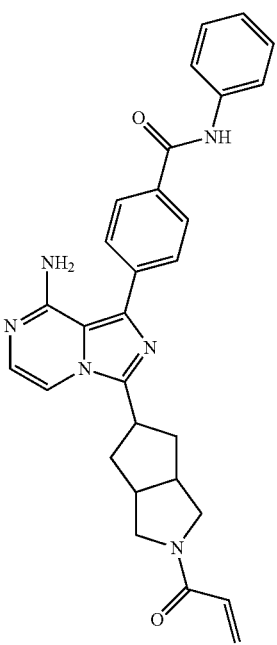 [SMILES: C=CC(=O)N1CC2CC(c3nc(-c4ccc(C(=O)Nc5ccccc5)cc4)c4c(N)nccn34)CC2C1] | 4-(3-(2-acryloyloctahydrocyclopenta[c]pyrrol-5-yl)-8-aminoimidazo[1,5-a]pyrazin-1-yl)-N-phenylbenzamide |

TABLE 2-continued

| Compd | Structures | IUPAC Names |
|---|---|---|
| 165 | 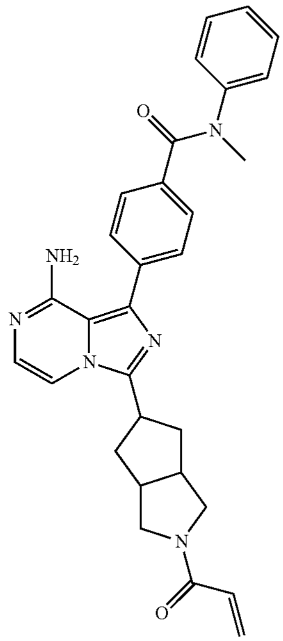 [SMILES: C=CC(=O)N1CC2CC(c3nc(-c4ccc(C(=O)N(C)c5ccccc5)cc4)c4c(N)nccn34)CC2C1] | 4-(3-(2-acryloyloctahydrocyclopenta[c]pyrrol-5-yl)-8-aminoimidazo[1,5-a]pyrazin-1-yl)-N-methyl-N-phenylbenzamide |
| 166 | 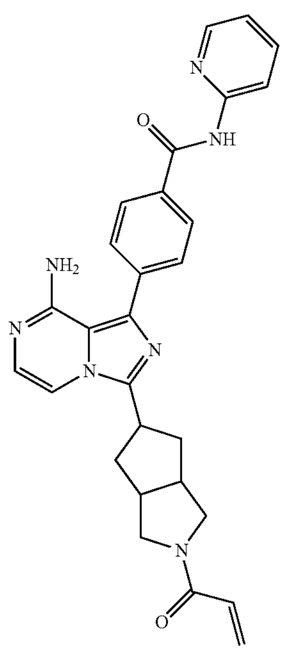 [SMILES: C=CC(=O)N1CC2CC(c3nc(-c4ccc(C(=O)Nc5ccccn5)cc4)c4c(N)nccn34)CC2C1] | 4-(3-(2-acryloyloctahydrocyclopenta[c]pyrrol-5-yl)-8-aminoimidazo[1,5-a]pyrazin-1-yl)-N-(pyridin-2-yl)benzamide |

TABLE 2-continued
| Compd | Structures | IUPAC Names |
|---|---|---|
| 167 | 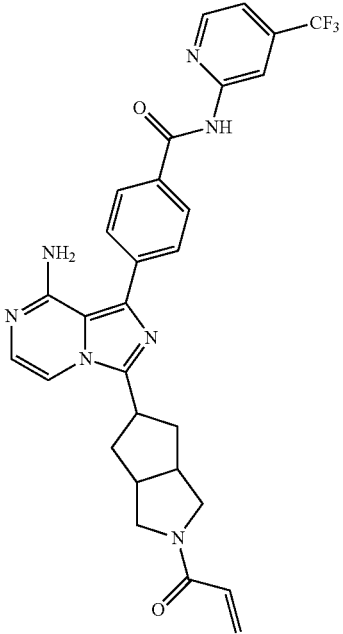 [SMILES: C=CC(=O)N1CC2CC(c3nc(-c4ccc(C(=O)Nc5cc(C(F)(F)F)ccn5)cc4)c4c(N)nccn34)CC2C1] | 4-(3-(2-acryloyloctahydrocyclopenta[c]pyrrol-5-yl)-8-aminoimidazo[1,5-a]pyrazin-1-yl)-N-(4-(trifluoromethyl)pyridin-2-yl)benzamide |
| 168 | 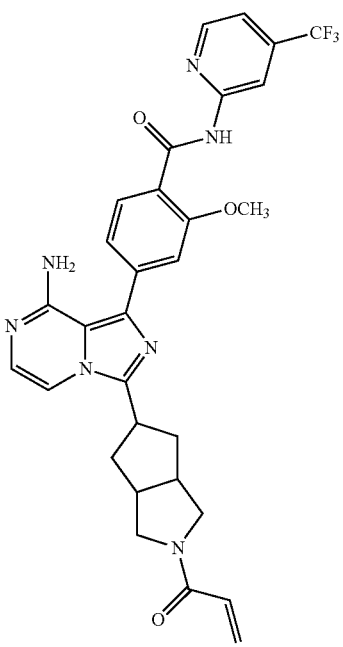 [SMILES: C=CC(=O)N1CC2CC(c3nc(-c4ccc(C(=O)Nc5cc(C(F)(F)F)ccn5)c(OC)c4)c4c(N)nccn34)CC2C1] | 4-(3-(2-acryloyloctahydrocyclopenta[c]pyrrol-5-yl)-8-aminoimidazo[1,5-a]pyrazin-1-yl)-2-methoxy-N-(4-(trifluoromethyl)pyridin-2-yl)benzamide |

TABLE 2-continued
| Compd | Structures | IUPAC Names |
|---|---|---|
| 169 | 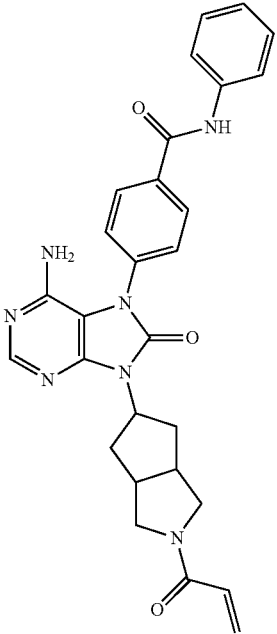 [SMILES: C=CC(=O)N1CC2CC(n3c(=O)n(-c4ccc(C(=O)Nc5ccccc5)cc4)c4c(N)ncnc43)CC2C1] | 4-(9-(2-acryloyloctahydrocyclopenta[c]pyrrol-5-yl)-6-amino-8-oxo-8,9-dihydro-7H-purin-7-yl)-N-phenylbenzamide |
| 170 | 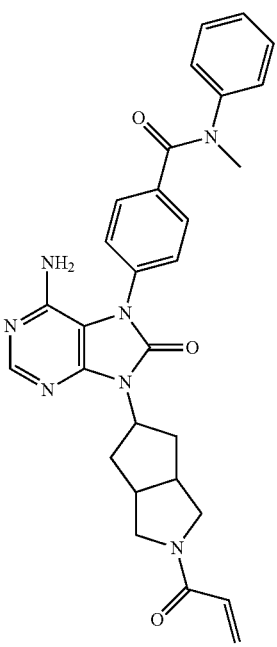 [SMILES: C=CC(=O)N1CC2CC(n3c(=O)n(-c4ccc(C(=O)N(C)c5ccccc5)cc4)c4c(N)ncnc43)CC2C1] | 4-(9-(2-acryloyloctahydrocyclopenta[c]pyrrol-5-yl)-6-amino-8-oxo-8,9-dihydro-7H-purin-7-yl)-N-methyl-N-phenylbenzamide |

TABLE 2-continued
| Compd | Structures | IUPAC Names |
|---|---|---|
| 171 | 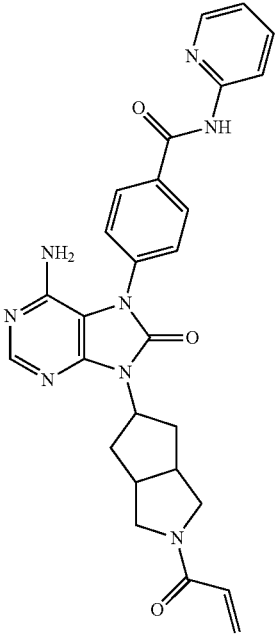 [SMILES: C=CC(=O)N1CC2CC(n3c(=O)n(-c4ccc(C(=O)Nc5ccccn5)cc4)c4c(N)ncnc43)CC2C1] | 4-(9-(2-acryloyloctahydrocyclopenta[c]pyrrol-5-yl)-6-amino-8-oxo-8,9-dihydro-7H-purin-7-yl)-N-(pyridin-2-yl)benzamide |
| 172 | 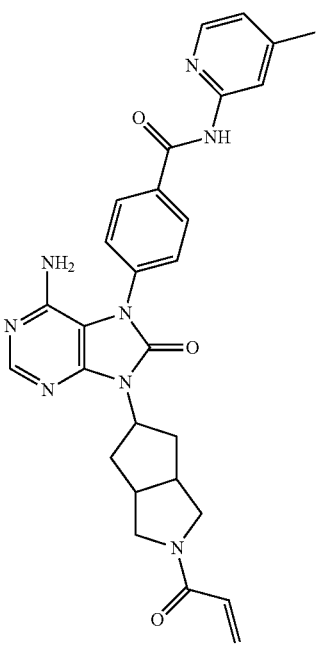 [SMILES: C=CC(=O)N1CC2CC(n3c(=O)n(-c4ccc(C(=O)Nc5cc(C)ccn5)cc4)c4c(N)ncnc43)CC2C1] | 4-(9-(2-acryloyloctahydrocyclopenta[c]pyrrol-5-yl)-6-amino-8-oxo-8,9-dihydro-7H-purin-7-yl)-N-(4-methylpyridin-2-yl)benzamide |

TABLE 2-continued
| Compd | Structures | IUPAC Names |
|---|---|---|
| 173 | 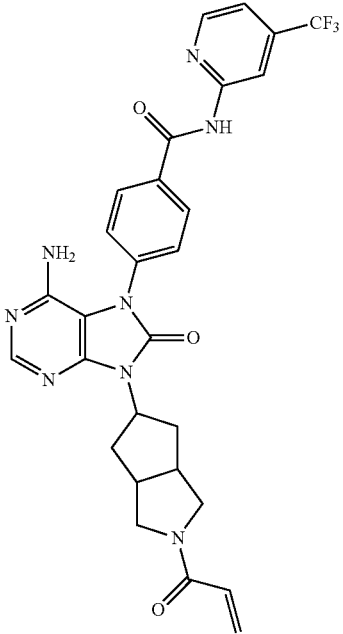 [SMILES: C=CC(=O)N1CC2CC(n3c(=O)n(-c4ccc(C(=O)Nc5cc(C(F)(F)F)ccn5)cc4)c4c(N)ncnc43)CC2C1] | 4-(9-(2-acryloyloctahydrocyclopenta[c]pyrrol-5-yl)-6-amino-8-oxo-8,9-dihydro-7H-purin-7-yl)-N-(4-(trifluoromethyl)pyridin-2-yl)benzamide |
| 174 | 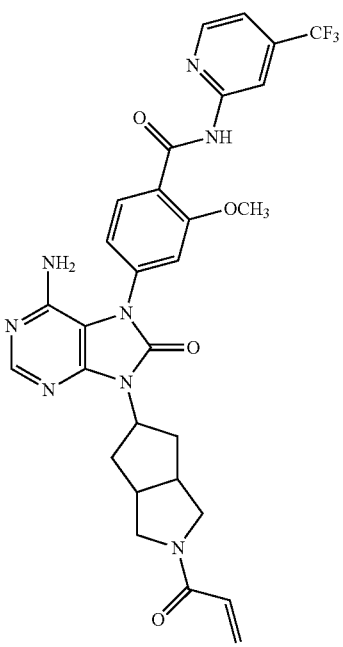 [SMILES: C=CC(=O)N1CC2CC(n3c(=O)n(-c4ccc(C(=O)Nc5cc(C(F)(F)F)ccn5)c(OC)c4)c4c(N)ncnc43)CC2C1] | 4-(9-(2-acryloyloctahydrocyclopenta[c]pyrrol-5-yl)-6-amino-8-oxo-8,9-dihydro-7H-purin-7-yl)-2-methoxy-N-(4-(trifluoromethyl)pyridin-2-yl)benzamide |

TABLE 2-continued
| Compd | Structures | IUPAC Names |
|---|---|---|
| 175 | 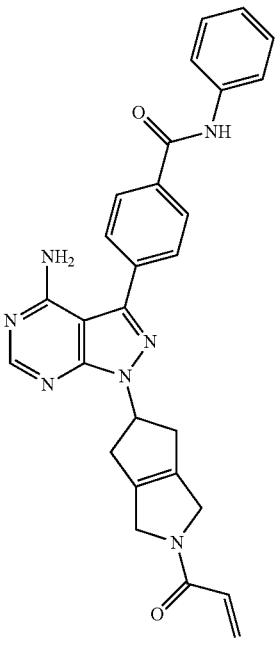 [SMILES: C=CC(=O)N1CC2=C(CC(n3nc(-c4ccc(C(=O)Nc5ccccc5)cc4)c4c(N)ncnc43)C2)C1] | 4-(1-(2-acryloyl-1,2,3,4,5,6-hexahydrocyclopenta[c]pyrrol-5-yl)-4-amino-1H-pyrazolo[3,4-d]pyrimidin-3-yl)-N-phenylbenzamide |
| 176 | 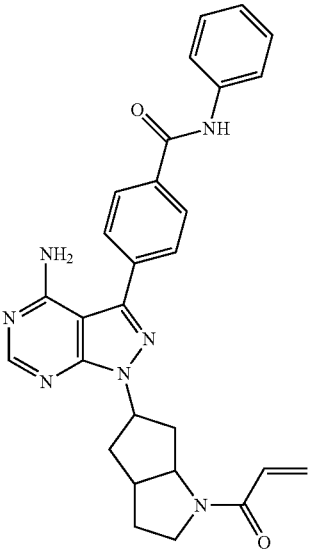 [SMILES: C=CC(=O)N1CCC2CC(n3nc(-c4ccc(C(=O)Nc5ccccc5)cc4)c4c(N)ncnc43)CC21] | 4-(1-(1-acryloyloctahydrocyclopenta[b]pyrrol-5-yl)-4-amino-1H-pyrazolo[3,4-d]pyrimidin-3-yl)-N-phenylbenzamide |

TABLE 2-continued
| Compd | Structures | IUPAC Names |
|---|---|---|
| 177 | 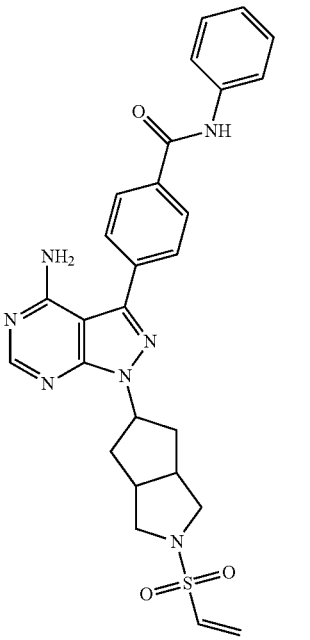 [SMILES: C=CS(=O)(=O)N1CC2CC(n3nc(-c4ccc(C(=O)Nc5ccccc5)cc4)c4c(N)ncnc43)CC2C1] | 4-(4-amino-1-(2-(vinylsulfonyl)octahydrocyclopenta[c]pyrrol-5-yl)-1H-pyrazolo[3,4-d]pyrimidin-3-yl)-N-phenylbenzamide |
| 178 | 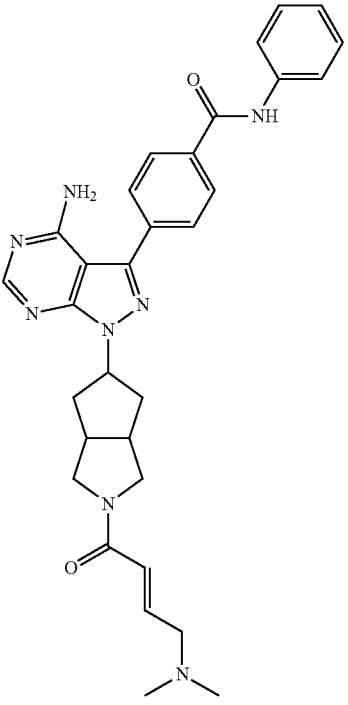 [SMILES: CN(C)C/C=C/C(=O)N1CC2CC(n3nc(-c4ccc(C(=O)Nc5ccccc5)cc4)c4c(N)ncnc43)CC2C1] | (E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-phenylbenzamide |

TABLE 2-continued
| Compd | Structures | IUPAC Names |
|---|---|---|
| 179 | 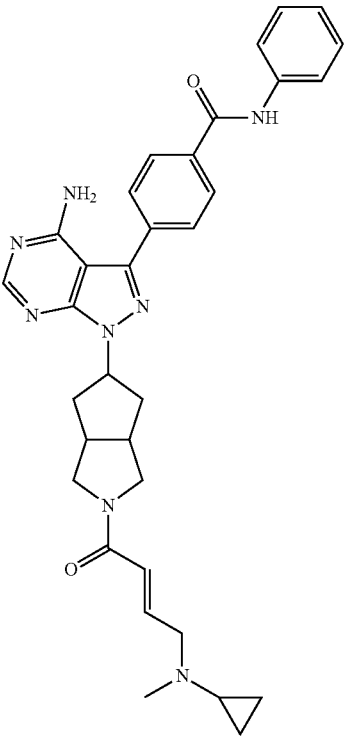 [SMILES: CN(C/C=C/C(=O)N1CC2CC(n3nc(-c4ccc(C(=O)Nc5ccccc5)cc4)c4c(N)ncnc43)CC2C1)C1CC1] | (E)-4-(4-amino-1-(2-(4-(cyclopropyl(methyl)amino)but-2-enoyl)octahydrocyclopenta[c]pyrrol-5-yl)-1H-pyrazolo[3,4-d]pyrimidin-3-yl)-N-phenylbenzamide |
| 180 | 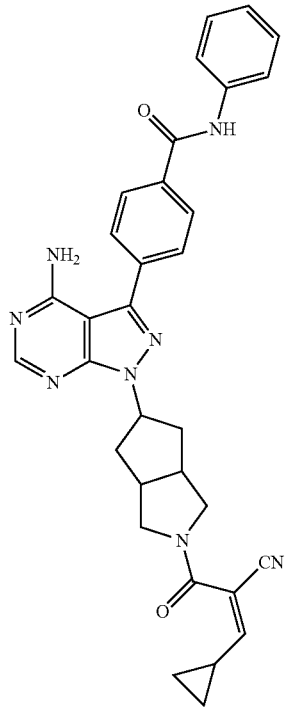 [SMILES: N#C/C(=C/C1CC1)C(=O)N1CC2CC(n3nc(-c4ccc(C(=O)Nc5ccccc5)cc4)c4c(N)ncnc43)CC2C1] | (Z)-4-(4-amino-1-(2-(2-cyano-3-cyclopropylacryloyl)octahydrocyclopenta[c]pyrrol-5-yl)-1H-pyrazolo[3,4-d]pyrimidin-3-yl)-N-phenylbenzamide |

TABLE 2-continued

| Compd | Structures | IUPAC Names |
|---|---|---|
| 181 | 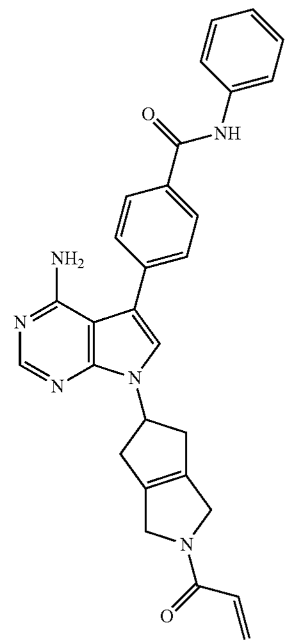 [SMILES: C=CC(=O)N1CC2=C(CC(n3cc(-c4ccc(C(=O)Nc5ccccc5)cc4)c4c(N)ncnc43)C2)C1] | 4-(7-(2-acryloyl-1,2,3,4,5,6-hexahydrocyclopenta[c]pyrrol-5-yl)-4-amino-7H-pyrrolo[2,3-d]pyrimidin-5-yl)-N-phenylbenzamide |
| 182 | 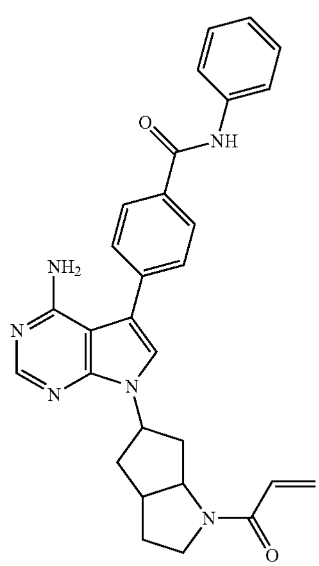 [SMILES: C=CC(=O)N1CCC2CC(n3cc(-c4ccc(C(=O)Nc5ccccc5)cc4)c4c(N)ncnc43)CC21] | 4-(7-(1-acryloyloctahydrocyclopenta[b]pyrrol-5-yl)-4-amino-7H-pyrrolo[2,3-d]pyrimidin-5-yl)-N-phenylbenzamide |

TABLE 2-continued

| Compd | Structures | IUPAC Names |
|---|---|---|
| 183 | 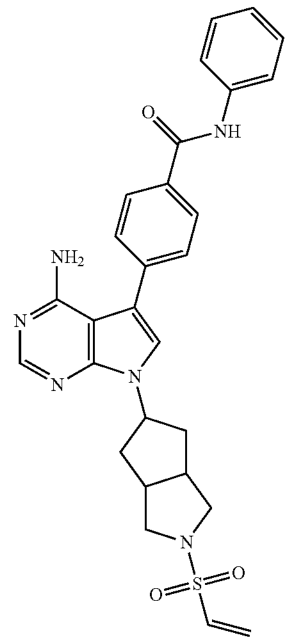 [SMILES: C=CS(=O)(=O)N1CC2CC(n3cc(-c4ccc(C(=O)Nc5ccccc5)cc4)c4c(N)ncnc43)CC2C1] | 4-(4-amino-7-(2-(vinylsulfonyl)octahydrocyclopenta[c]pyrrol-5-yl)-7H-pyrrolo[2,3-d]pyrimidin-5-yl)-N-phenylbenzamide |
| 184 | 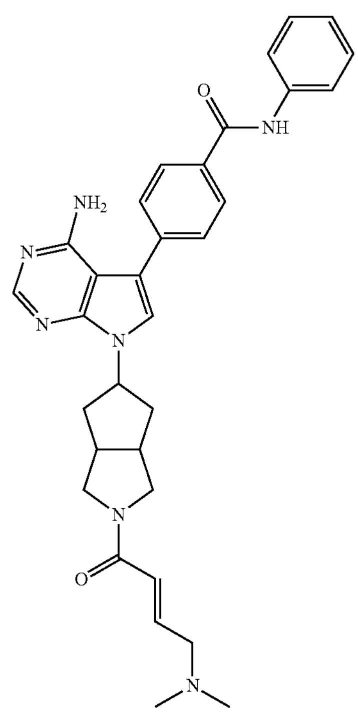 [SMILES: CN(C)C/C=C/C(=O)N1CC2CC(n3cc(-c4ccc(C(=O)Nc5ccccc5)cc4)c4c(N)ncnc43)CC2C1] | (E)-4-(4-amino-7-(2-(4-(dimethylamino)but-2-enoyl)octahydrocyclopenta[c]pyrrol-5-yl)-7H-pyrrolo[2,3-d]pyrimidin-5-yl)-N-phenylbenzamide |

TABLE 2-continued
| Compd | Structures | IUPAC Names |
|---|---|---|
| 185 | 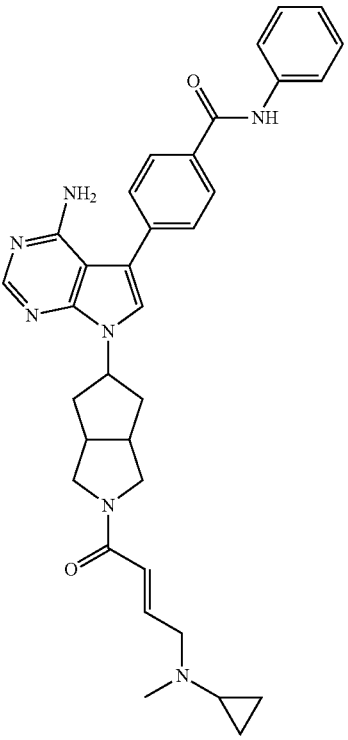 | (E)-4-(4-amino-7-(2-(4-(cyclopropyl(methyl)amino)but-2-enoyl)octahydrocyclopenta[c]pyrrol-5-yl)-7H-pyrrolo[2,3-d]pyrimidin-5-yl)-N-phenylbenzamide |
| 186 | 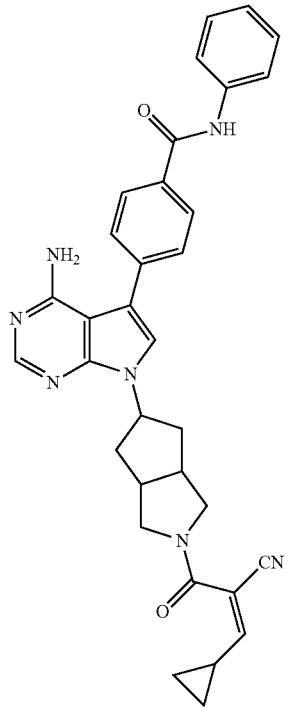 [SMILES: N#C/C(=C/C1CC1)C(=O)N1CC2CC(n3cc(-c4ccc(C(=O)Nc5ccccc5)cc4)c4c(N)ncnc43)CC2C1] | (Z)-4-(4-amino-7-(2-(2-cyano-3-cyclopropylacryloyl)octahydrocyclopenta[c]pyrrol-5-yl)-7H-pyrrolo[2,3-d]pyrimidin-5-yl)-N-phenylbenzamide |

TABLE 2-continued
| Compd | Structures | IUPAC Names |
|---|---|---|
| 187 | 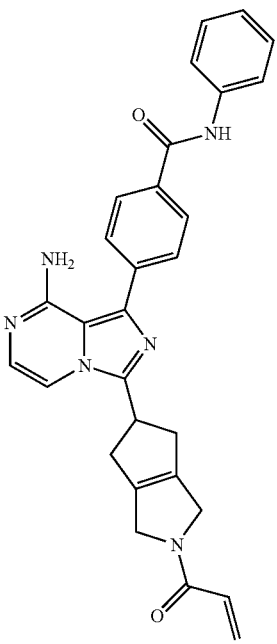 [SMILES: C=CC(=O)N1CC2=C(CC(c3nc(-c4ccc(C(=O)Nc5ccccc5)cc4)c4c(N)nccn34)C2)C1] | 4-(3-(2-acryloyl-1,2,3,4,5,6-hexahydrocyclopenta[c]pyrrol-5-yl)-8-aminoimidazo[1,5-a]pyrazin-1-yl)-N-phenylbenzamide |
| 188 | 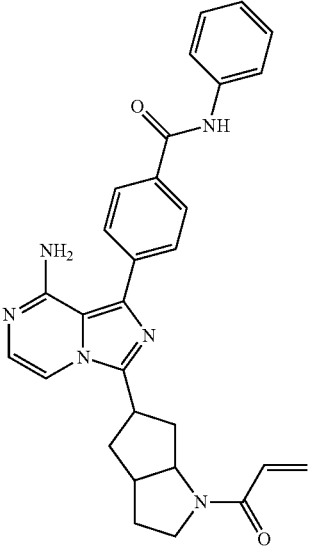 [SMILES: C=CC(=O)N1CCC2CC(c3nc(-c4ccc(C(=O)Nc5ccccc5)cc4)c4c(N)nccn34)CC21] | 4-(3-(1-acryloyloctahydrocyclopenta[b]pyrrol-5-yl)-8-aminoimidazo[1,5-a]pyrazin-1-yl)-N-phenylbenzamide |

TABLE 2-continued
| Compd | Structures | IUPAC Names |
|---|---|---|
| 189 | 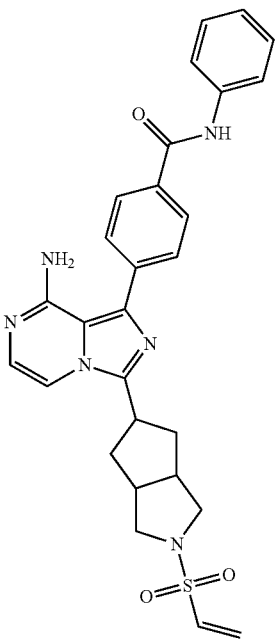 [SMILES: C=CS(=O)(=O)N1CC2CC(c3nc(-c4ccc(C(=O)Nc5ccccc5)cc4)c4c(N)nccn34)CC2C1] | 4-(8-amino-3-(2-(vinylsulfonyl)octahydrocyclopenta[c]pyrrol-5-yl)imidazo[1,5-a]pyrazin-1-yl)-N-phenylbenzamide |
| 190 | 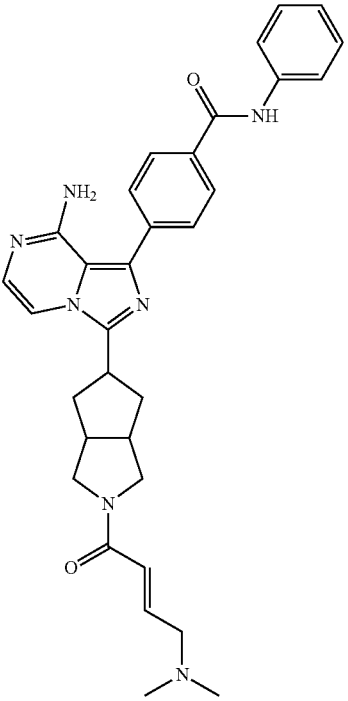 [SMILES: CN(C)C/C=C/C(=O)N1CC2CC(c3nc(-c4ccc(C(=O)Nc5ccccc5)cc4)c4c(N)nccn34)CC2C1] | (E)-4-(8-amino-3-(2-(4-(dimethylamino)but-2-enoyl)octahydrocyclopenta[c]pyrrol-5-yl)imidazo[1,5-a]pyrazin-1-yl)-N-phenylbenzamide |

TABLE 2-continued
| Compd | Structures | IUPAC Names |
|---|---|---|
| 191 | 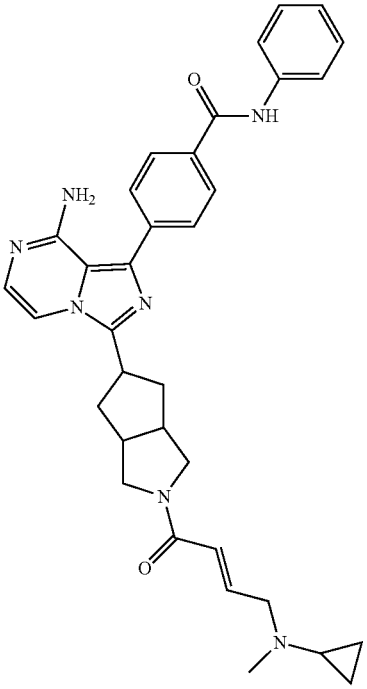 [SMILES: CN(C/C=C/C(=O)N1CC2CC(c3nc(-c4ccc(C(=O)Nc5ccccc5)cc4)c4c(N)nccn34)CC2C1)C1CC1] | (E)-4-(8-amino-3-(2-(4-(cyclopropyl(methyl)amino)but-2-enoyl)octahydrocyclopenta[c]pyrrol-5-yl)imidazo[1,5-a]pyrazin-1-yl)-N-phenylbenzamide |
| 192 | 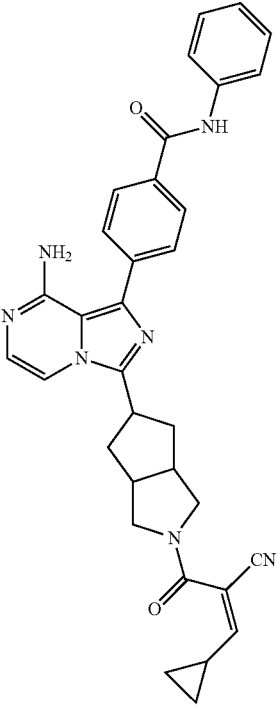 [SMILES: N#C/C(=C/C1CC1)C(=O)N1CC2CC(c3nc(-c4ccc(C(=O)Nc5ccccc5)cc4)c4c(N)nccn34)CC2C1] | (Z)-4-(8-amino-3-(2-(2-ayno-3-cyclopropylacryloyl)octahydrocyclopenta[c]pyrrol-5-yl)imidazo[1,5-a]pyrazin-1-yl)-N-phenylbenzamide |

TABLE 2-continued
| Compd | Structures | IUPAC Names |
|---|---|---|
| 193 | 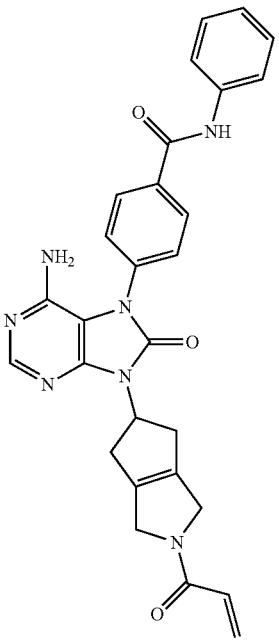 [SMILES: C=CC(=O)N1CC2=C(CC(n3c(=O)n(-c4ccc(C(=O)Nc5ccccc5)cc4)c4c(N)ncnc43)C2)C1] | 4-(9-(2-acryloyl-1,2,3,4,5,6-hexahydrocyclopenta[c]pyrrol-5-yl)-6-amino-8-oxo-8,9-dihydro-7H-purin-7-yl)-N-phenylbenzamide |
| 194 | 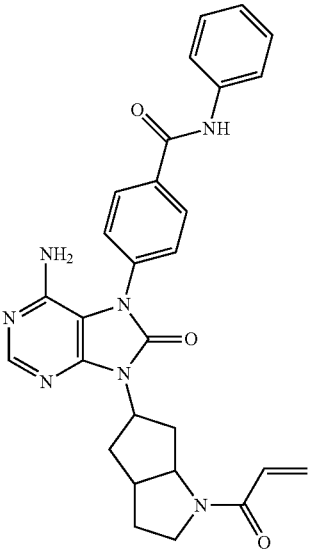 [SMILES: C=CC(=O)N1CCC2CC(n3c(=O)n(-c4ccc(C(=O)Nc5ccccc5)cc4)c4c(N)ncnc43)CC21] | 4-(9-(1-acryloyloctahydrocyclopenta[b]pyrrol-5-yl)-6-amino-8-oxo-8,9-dihydro-7H-purin-7-yl)-N-phenylbenzamide |

TABLE 2-continued
| Compd | Structures | IUPAC Names |
|---|---|---|
| 195 | 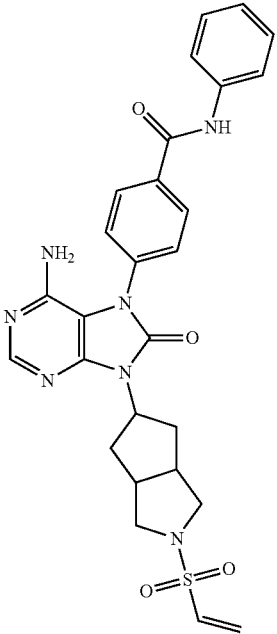 [SMILES: C=CS(=O)(=O)N1CC2CC(n3c(=O)n(-c4ccc(C(=O)Nc5ccccc5)cc4)c4c(N)ncnc43)CC2C1] | 4-(6-amino-8-oxo-9-(2-(vinylsulfonyl)octahydrocyclopenta[c]pyrrol-5-yl)-8,9-dihydro-7H-purin-7-yl)-N-phenylbenzamide |
| 196 | 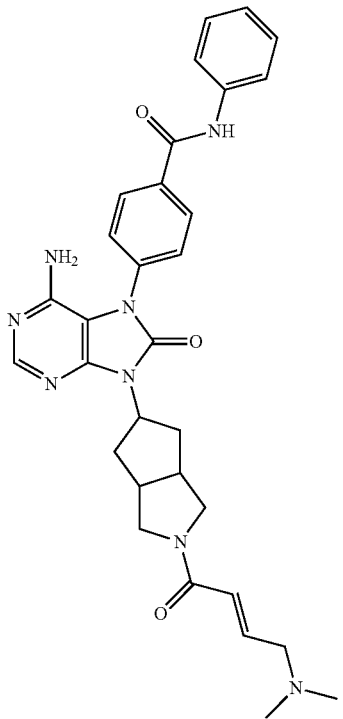 [SMILES: CN(C)C/C=C/C(=O)N1CC2CC(n3c(=O)n(-c4ccc(C(=O)Nc5ccccc5)cc4)c4c(N)ncnc43)CC2C1] | (E)-4-(6-amino-9-(2-(4-(dimethylamino)but-2-enoyl)octahydrocyclopenta[c]pyrrol-5-yl)-8-oxo-8,9-dihydro-7H-purin-7-yl)-N-phenylbenzamide |

TABLE 2-continued
| Compd | Structures | IUPAC Names |
|---|---|---|
| 197 | 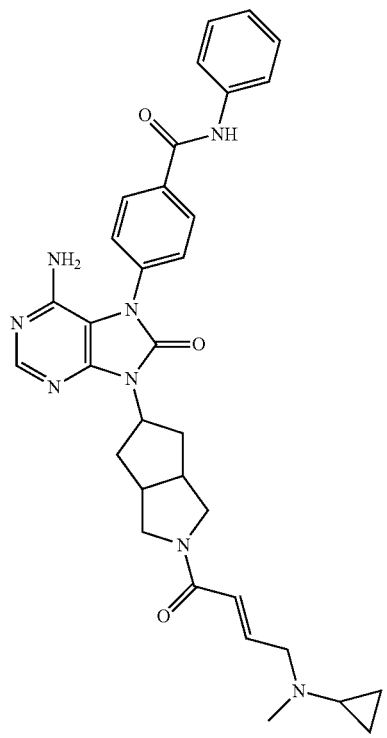 [SMILES: CN(C/C=C/C(=O)N1CC2CC(n3c(=O)n(-c4ccc(C(=O)Nc5ccccc5)cc4)c4c(N)ncnc43)CC2C1)C1CC1] | (E)-4-(6-amino-9-(2-(4-(cyclopropyl(methyl)amino)but-2-enoyl)octahydrocyclopenta[c]pyrrol-5-yl)-8-oxo-8,9-dihydro-7H-purin-7-yl)-N-phenylbenzamide |
| 198 | 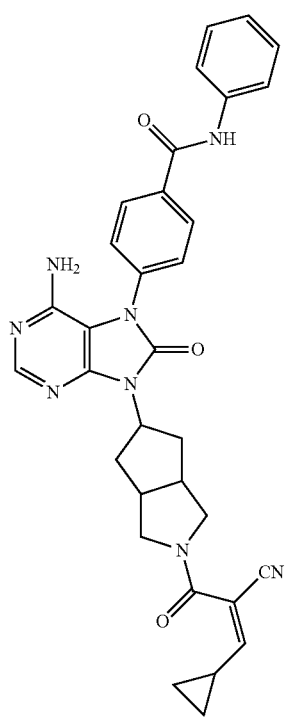 [SMILES: N#C/C(=C/C1CC1)C(=O)N1CC2CC(n3c(=O)n(-c4ccc(C(=O)Nc5ccccc5)cc4)c4c(N)ncnc43)CC2C1] | (Z)-4-(6-amino-9-(2-(2-cyano-3-cyclopropylacryloyl)octahydrocyclopenta[c]pyrrol-5-yl)-8-oxo-8,9-dihydro-7H-purin-7-yl)-N-phenylbenzamide |

TABLE 2-continued
| Compd | Structures | IUPAC Names |
|---|---|---|
| 199 | 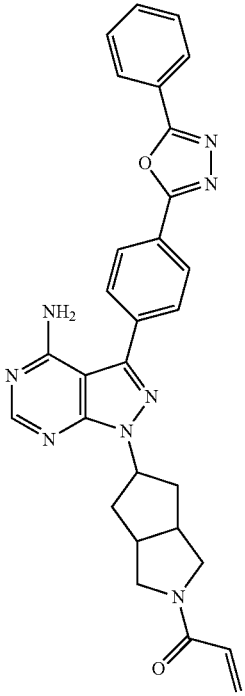 [SMILES: C=CC(=O)N1CC2CC(n3nc(-c4ccc(-c5nnc(-c6ccccc6)o5)cc4)c4c(N)ncnc43)CC2C1] | 1-(5-(4-amino-3-(4-(5-phenyl-1,3,4-oxadiazol-2-yl)phenyl)-1H-pyrazolo[3,4-d]pyrimidin-1-yl)hexahydrocyclopenta[c]pyrrol-2(1H)-yl)prop-2-en-1-one |
| 200 | 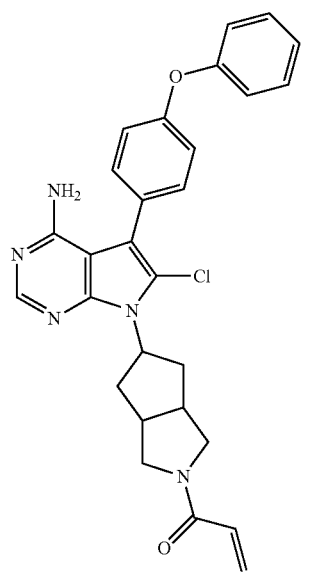 [SMILES: C=CC(=O)N1CC2CC(n3c(Cl)c(-c4ccc(Oc5ccccc5)cc4)c4c(N)ncnc43)CC2C1] | 1-(5-(4-amino-6-chloro-5-(4-phenoxyphenyl)-7H-pyrrolo[2,3-d]pyrimidin-7-yl)hexahydrocyclopenta[c]pyrrol-2(1H)-yl)prop-2-en-1-one |

US 9,840,509 B2
247                                                                                               248
TABLE 2-continued
| Compd | Structures | IUPAC Names |
|---|---|---|
| 201 | 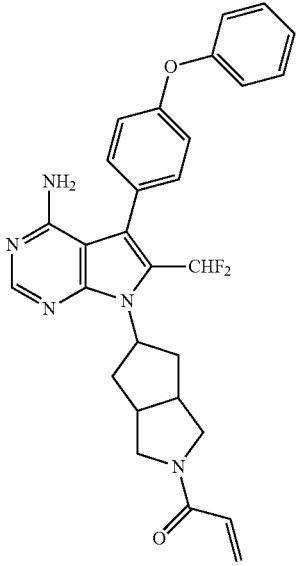 [SMILES: C=CC(=O)N1CC2CC(n3c(C(F)F)c(-c4ccc(Oc5ccccc5)cc4)c4c(N)ncnc43)CC2C1] | 1-(5-(4-amino-6-(difluoromethyl)-5-(4-phenoxyphenyl)-7H-pyrrolo[2,3-d]pyrimidin-7-yl)hexahydrocyclopenta[c]pyrrol-2(1H)-yl)prop-2-en-1-one |
| 202 | 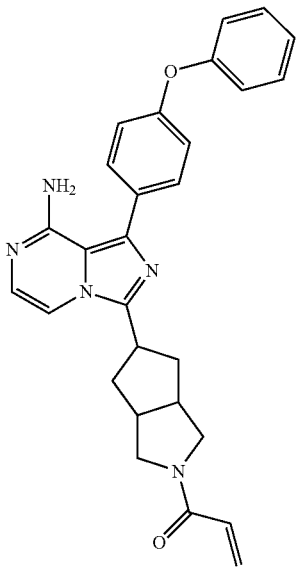 [SMILES: C=CC(=O)N1CC2CC(c3nc(-c4ccc(Oc5ccccc5)cc4)c4c(N)nccn34)CC2C1] | 1-(5-(8-amino-1-(4-phenoxyphenyl)imidazo[1,5-a]pyrazin-3-yl)hexahydrocyclopenta[c]pyrrol-2(1H)-yl)prop-2-en-1-one |

TABLE 2-continued
| Compd | Structures | IUPAC Names |
|---|---|---|
| 203 | 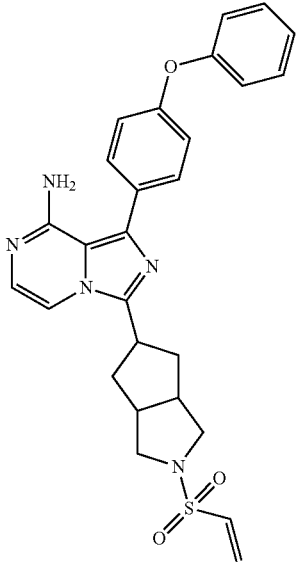 [SMILES: C=CS(=O)(=O)N1CC2CC(c3nc(-c4ccc(Oc5ccccc5)cc4)c4c(N)nccn34)CC2C1] | 1-(4-phenoxyphenyl)-3-(2-(vinylsulfonyl)octahydrocyclopenta[c]pyrrol-5-yl)imidazo[1,5-a]pyrazin-8-amine |
| 204 | 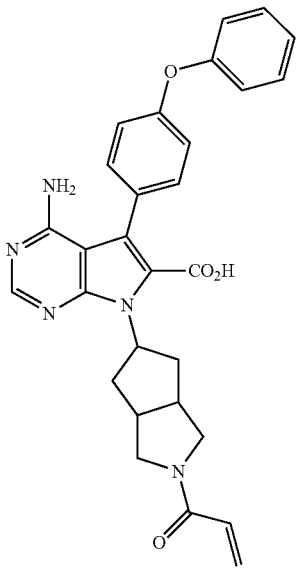 [SMILES: C=CC(=O)N1CC2CC(n3c(C(=O)O)c(-c4ccc(Oc5ccccc5)cc4)c4c(N)ncnc43)CC2C1] | 7-(2-acryloyloctahydrocyclopenta[c]pyrrol-5-yl)-4-amino-5-(4-phenoxyphenyl)-7H-pyrrolo[2,3-d]pyrimidine-6-carboxylic acid |

TABLE 2-continued
| Compd | Structures | IUPAC Names |
|---|---|---|
| 205 | 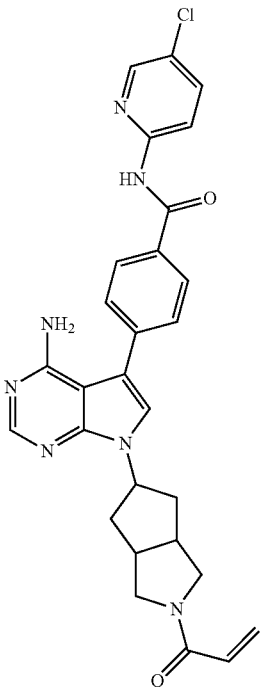 [SMILES: C=CC(=O)N1CC2CC(n3cc(-c4ccc(C(=O)Nc5ccc(Cl)cn5)cc4)c4c(N)ncnc43)CC2C1] | 4-(1-(2-acryloyloctahydrocyclopenta[c]pyrrol-5-yl)-4-amino-1H-pyrazolo[3,4-d]pyrimidin-3-yl)-N-(5-chloropyridin-2-yl)benzamide |
| 206 | 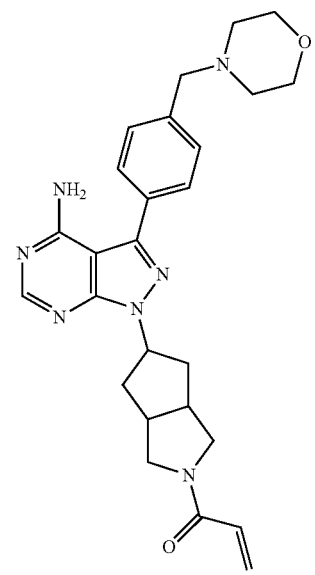 | 1-(5-(4-aminio-3-(4-(morpholinomethyl)phenyl)-1H-pyrazolo[3,4-d]pyrimidin-1-yl)hexahydrocyclopenta[c]pyrrol-2(1H)-yl)prop-2-en-1-one |

TABLE 2-continued
| Compd | Structures | IUPAC Names |
|---|---|---|
| 207 | 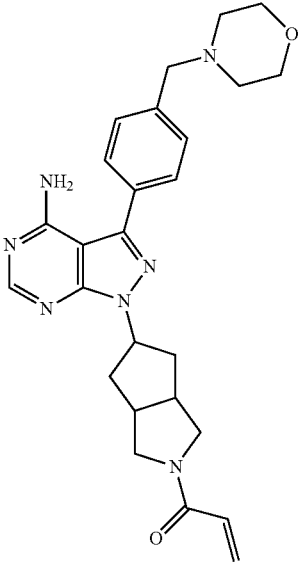 [SMILES: C=CC(=O)N1CC2CC(n3nc(-c4ccc(CN5CCOCC5)cc4)c4c(N)ncnc43)CC2C1] | 1-(5-(4-amino-3-(4-(piperidin-1-ylmethyl)phenyl)-1H-pyrazolo[3,4-d]pyrimidin-1-yl)hexahydrocyclopenta[c]pyrrol-2(1H)-yl)prop-2-en-1-one |
| 208 | 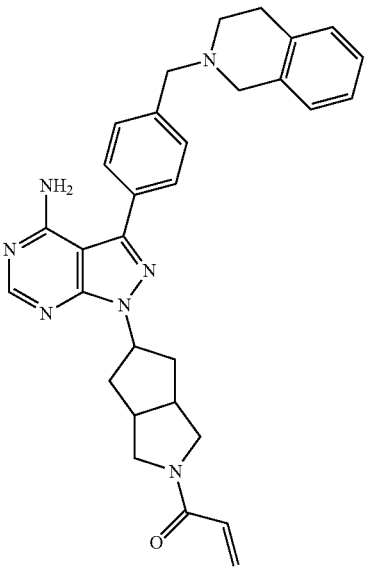 [SMILES: C=CC(=O)N1CC2CC(n3nc(-c4ccc(CN5CCc6ccccc6C5)cc4)c4c(N)ncnc43)CC2C1] | 1-(5-(4-amino-3-(4-((3,4-dihydroisoquinolin-2(1H)-yl)methyl)phenyl)-1H-pyrazolo[3,4-d]pyrimdiin-1-yl)hexahydrocyclopenta[c]pyrrol-2(1H)-yl)prop-2-en-1-one |

TABLE 2-continued
| Compd | Structures | IUPAC Names |
|---|---|---|
| 209 | 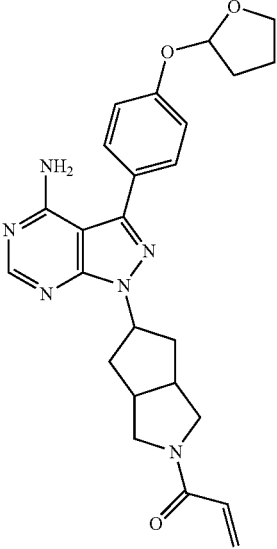 [SMILES: C=CC(=O)N1CC2CC(n3nc(-c4ccc(OC5CCCO5)cc4)c4c(N)ncnc43)CC2C1] | 1-(5-(4-amino-3-(4-((tetrahydrofuran-2-yl)oxy)phenyl)-1H-pyrazolo[3,4-d]pyrimidin-1-yl)hexahydrocyclopenta[c]pyrrol-2(1H)-yl)prop-2-en-1-one |
| 210 | 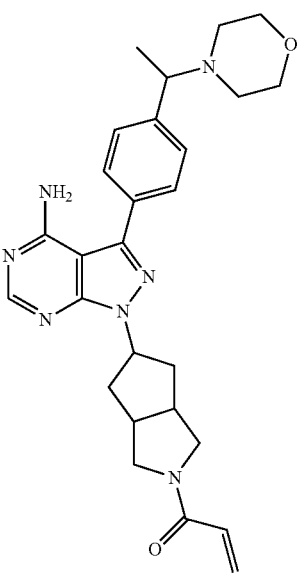 [SMILES: C=CC(=O)N1CC2CC(n3nc(-c4ccc(C(C)N5CCOCC5)cc4)c4c(N)ncnc43)CC2C1] | 1-(5-(4-amino-3-(4-(1-morpholinoethyl)phenyl)-1H-pyrazolo[3,4-d]pyrimidin-1-yl)hexahydrocyclopenta[c]pyrrol-2(1H)-yl)prop-2-en-1-one |

TABLE 2-continued
| Compd | Structures | IUPAC Names |
|---|---|---|
| 211 | 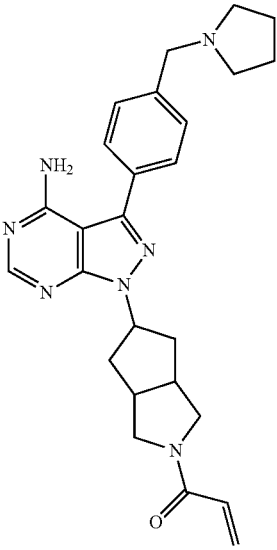 [SMILES: C=CC(=O)N1CC2CC(n3nc(-c4ccc(CN5CCCC5)cc4)c4c(N)ncnc43)CC2C1] | 1-(5-(4-amino-3-(4-(pyrrolidin-1-ylmethyl)phenyl)-1H-pyrazolo[3,4-d]pyrimidin-1-yl)hexahydrocyclopenta[c]pyrrol-2(1H)-yl)prop-2-en-1-one |
| 212 | 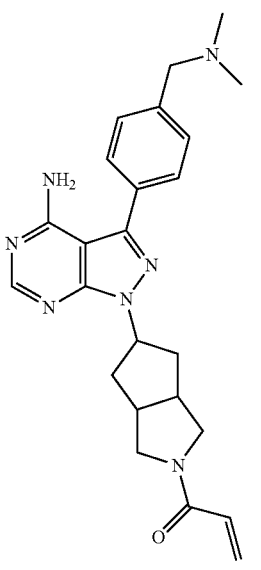 [SMILES: C=CC(=O)N1CC2CC(n3nc(-c4ccc(CN(C)C)cc4)c4c(N)ncnc43)CC2C1] | 1-(5-(4-amino-3-(4-((dimethylamino)methyl)phenyl)-1H-pyrazolo[3,4-d]pyrimidin-1-yl)hexahydrocyclopenta[c]pyrrol-2(1H)-yl)prop-2-en-1-one |

TABLE 2-continued
| Compd | Structures | IUPAC Names |
|---|---|---|
| 213 | 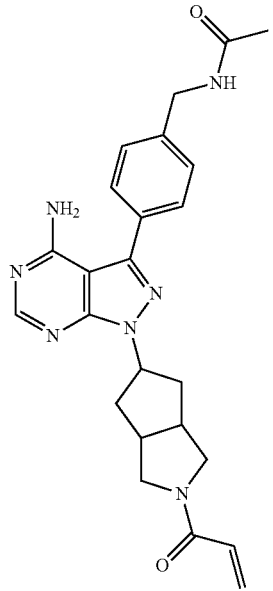 [SMILES: C=CC(=O)N1CC2CC(n3nc(-c4ccc(CNC(C)=O)cc4)c4c(N)ncnc43)CC2C1] | N-(4-(1-(2-acryloyloctahydrocyclopenta[c]pyrrol-5-yl)-4-amino-1H-pyrazolo[3,4-d]pyrimidin-3-yl)benzyl)acetamide |
| 214 | 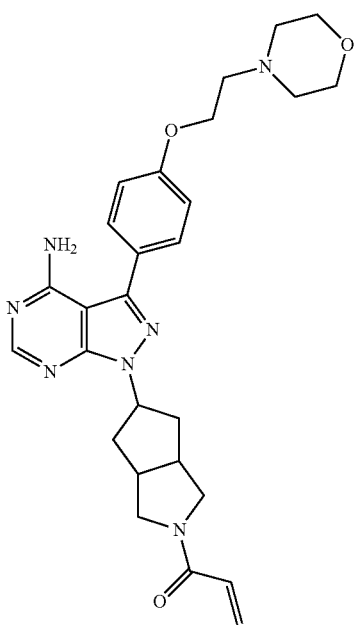 [SMILES: C=CC(=O)N1CC2CC(n3nc(-c4ccc(OCCN5CCOCC5)cc4)c4c(N)ncnc43)CC2C1] | 1-(5-(4-amino-3-(4-(2-morpholinoethoxy)phenyl)-1H-pyrazolo[3,4-d]pyrimidin-1-yl)hexahydrocyclopenta[c]pyrrol-2(1H)-yl)prop-2-en-1-one |

TABLE 2-continued
| Compd | Structures | IUPAC Names |
|---|---|---|
| 215 | 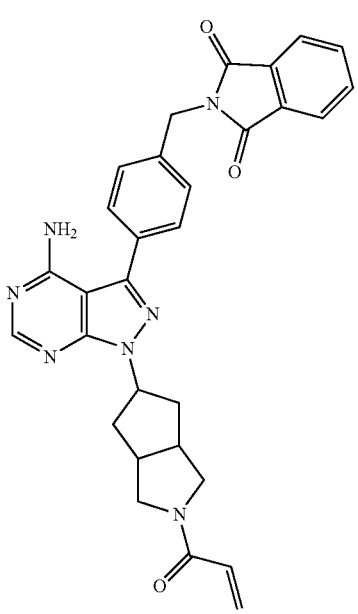 [SMILES: C=CC(=O)N1CC2CC(n3nc(-c4ccc(CN5C(=O)c6ccccc6C5=O)cc4)c4c(N)ncnc43)CC2C1] | 2-(4-(1-(2-acryloyloctahydrocyclopenta[c]pyrrol-5-yl)-4-amino-1H-pyrazolo[3,4-d]pyrimidin-3-yl)benzyl)isoindoline-1,3-dione |
| 216 | 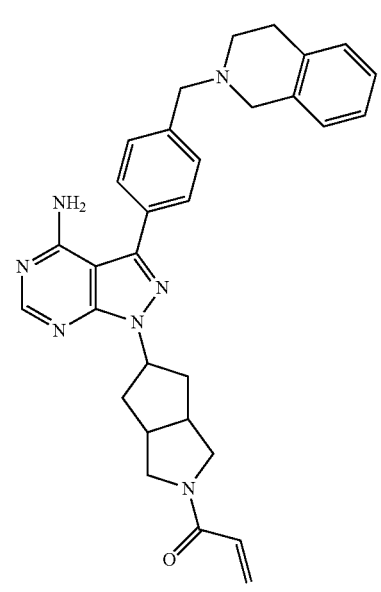 [SMILES: C=CC(=O)N1CC2CC(n3nc(-c4ccc(CN5CCc6ccccc6C5)cc4)c4c(N)ncnc43)CC2C1] | 1-(5-(4-amino-3-(4-((3,4-dihydroisoquinolin-2(1H)-yl)methyl)phenyl)-1H-pyrazolo[3,4-d]pyrimidin-1-yl)hexahydrocyclopenta[c]pyrrol-2(1H)-yl)prop-2-en-1-one |

TABLE 2-continued
| Compd | Structures | IUPAC Names |
|---|---|---|
| 217 | 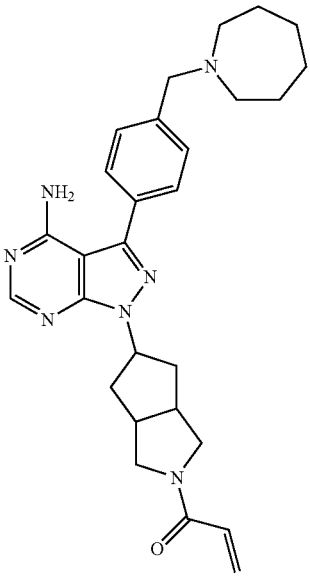 [SMILES: C=CC(=O)N1CC2CC(n3nc(-c4ccc(CN5CCCCCC5)cc4)c4c(N)ncnc43)CC2C1] | 1-(5-(4-amino-3-(4-(azepan-1-ylmethyl)phenyl)-1H-pyrazolo[3,4-d]pyrimidin-1-yl)hexahydrocyclopenta[c]pyrrol-2(1H)-yl)prop-2-en-1-one |
| 218 | 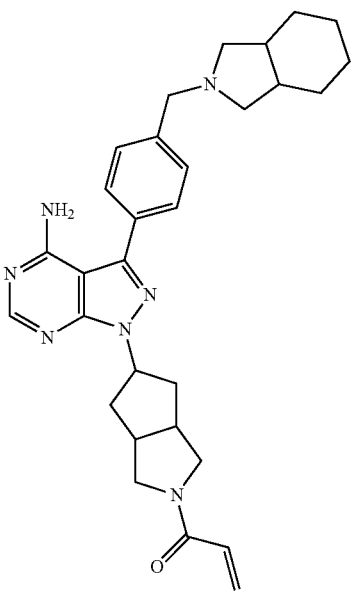 [SMILES: C=CC(=O)N1CC2CC(n3nc(-c4ccc(CN5CC6CCCCC6C5)cc4)c4c(N)ncnc43)CC2C1] | 1-(5-(4-amino-3-(4-((hexahydro-1H-isoindol-2(3H)-yl)methyl)phenyl)-1H-pyrazolo[3,4-d]pyrimidin-1-yl)hexahydrocyclopenta[c]pyrrol-2(1H)-yl)prop-2-en-1-one |

TABLE 2-continued
| Compd | Structures | IUPAC Names |
|---|---|---|
| 219 | 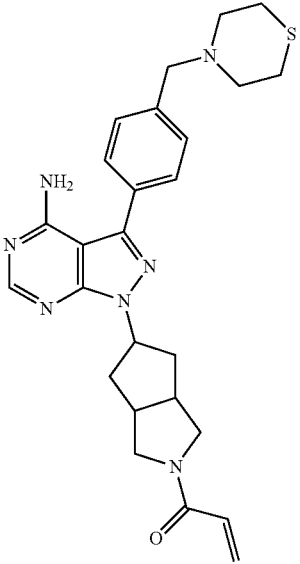 [SMILES: C=CC(=O)N1CC2CC(n3nc(-c4ccc(CN5CCSCC5)cc4)c4c(N)ncnc43)CC2C1] | 1-(5-(4-amino-3-(4-(thiomorpholinomethyl)phenyl)-1H-pyrazolo[3,4-d]pyrimidin-1-yl)hexahydrocyclopenta[c]pyrrol-2(1H)-yl)prop-2-en-1-one |
| 220 | 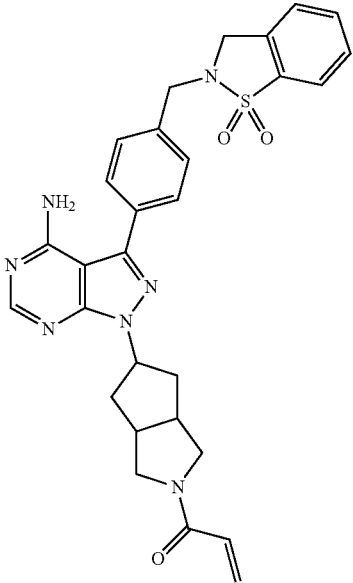 [SMILES: C=CC(=O)N1CC2CC(n3nc(-c4ccc(CN5Cc6ccccc6S5(=O)=O)cc4)c4c(N)ncnc43)CC2C1] | 1-(5-(4-amino-3-(4-((1,1-dioxidobenzo[d]isothiazol-2(3H)-yl)methyl)phenyl)-1H-pyrazolo[3,4-d]pyrimidin-1-yl)hexahydrocyclopenta[c]pyrrol-2(1H)-yl)prop-2-en-1-one |

TABLE 2-continued
| Compd | Structures | IUPAC Names |
|---|---|---|
| 221 | 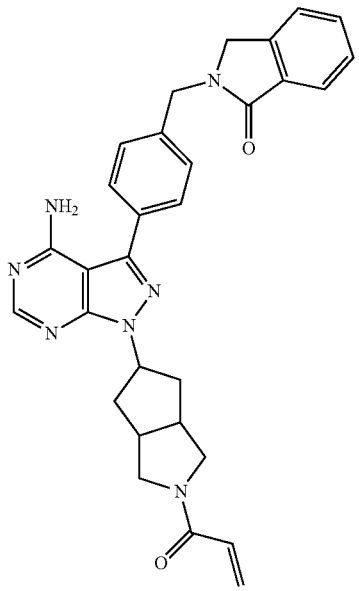 [SMILES: C=CC(=O)N1CC2CC(n3nc(-c4ccc(CN5Cc6ccccc6C5=O)cc4)c4c(N)ncnc43)CC2C1] | 2-(4-(1-(2-acryloyloctahydrocyclopenta[c]pyrrol-5-yl)-4-amino-1H-pyrazolo[3,4-d]pyrimidin-3-yl)benzyl)isoindolin-1-one |
| 222 | 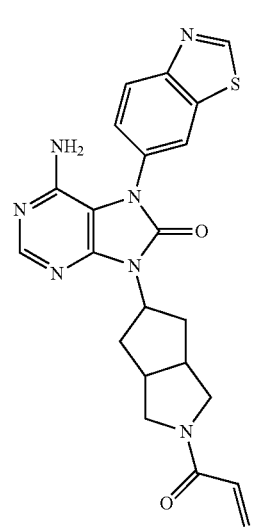 [SMILES: C=CC(=O)N1CC2CC(n3c(=O)n(-c4ccc5ncsc5c4)c4c(N)ncnc43)CC2C1] | 9-(2-acryloyloctahydrocyclopenta[c]pyrrol-5-yl)-6-amino-7-(benzo[d]thiazol-6-yl)-7H-purin-8(9H)-one |

TABLE 2-continued
| Compd | Structures | IUPAC Names |
|---|---|---|
| 223 | 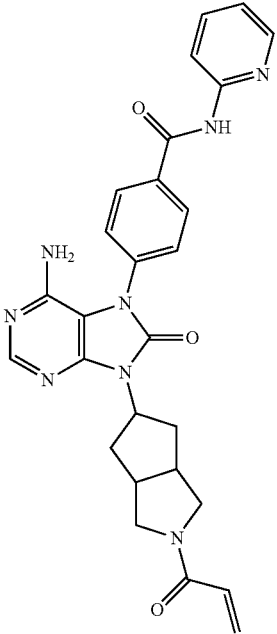 [SMILES: C=CC(=O)N1CC2CC(n3c(=O)n(-c4ccc(C(=O)Nc5ccccn5)cc4)c4c(N)ncnc43)CC2C1] | 4-(9-(2-acryloyloctahydrocyclopenta[c]pyrrol-5-yl)-6-amino-8-oxo-8,9-dihydro-7H-purin-7-yl)-N-methyl-N-(4-methylpyridin-2-yl)benzamide |
| 224 | 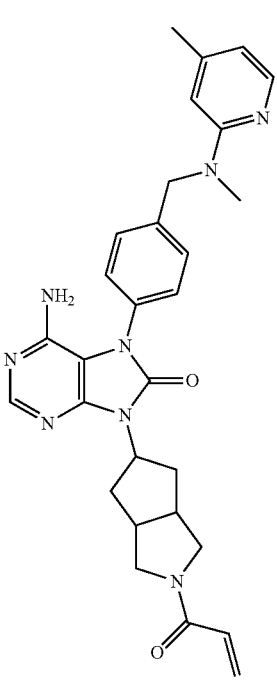 [SMILES: C=CC(=O)N1CC2CC(n3c(=O)n(-c4ccc(CN(C)c5cc(C)ccn5)cc4)c4c(N)ncnc43)CC2C1] | 9-(2-acryloyloctahydrocyclopenta[c]pyrrol-5-yl)-6-amino-7-(4-((methyl(4-methylpyridin-2-yl)amino)methyl)phenyl)-7H-purin-8(9H)-one |

TABLE 2-continued

| Compd | Structures | IUPAC Names |
|---|---|---|
| 225 | 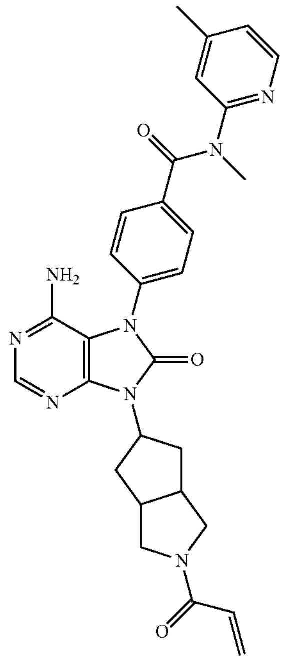 [SMILES: C=CC(=O)N1CC2CC(n3c(=O)n(-c4ccc(C(=O)N(C)c5cc(C)ccn5)cc4)c4c(N)ncnc43)CC2C1] | 4-(9-(2-acryloyloctahydrocyclopenta[c]pyrrol-5-yl)-6-amino-8-oxo-8,9-dihydro-7H-purin-7-yl)-N-(pyridin-2-yl)benzamide |
| 226 | 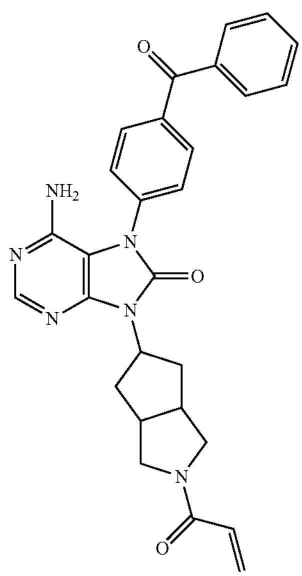 [SMILES: C=CC(=O)N1CC2CC(n3c(=O)n(-c4ccc(C(=O)c5ccccc5)cc4)c4c(N)ncnc43)CC2C1] | 9-(2-acryloyloctahydrocyclopenta[c]pyrrol-5-yl)-6-amino-7-(4-benzoylphenyl)-7H-purin-8(9H)-one |

Testing of Compounds of the Invention
Biological Studies:
In vitro BTK Inhibitory Activity Assay:

In vitro BTK inhibitory activity of test compounds were screened using BTK kinase assay on ADP Glo platform (Li, H., Totoritis, R. D., Lor, L. A., Schwartz, B., Caprioli, P., Jurewicz, A. J and Zhang, G., Assay Drug Dev. Technol., 2009, 7(6), 598-605). Briefly, fixed amount of recombinant purified human BTK (3 ng/reaction from SignalChem, USA) were incubated with increasing concentration of test compounds, in 1× kinase reaction buffer (40 mM Tris-Cl, pH7.5, 20 mM $MgCl_2$, 2 mM $MnCl_2$, 0.1 mg/ml BSA and 50 µM DTT). Enzymatic reaction was initiated by adding a substrate cocktail containing 50 M of ATP (final concentration) and 5 g of polyGln4Tyr1 (Signal Chem) in total 25 µl of reaction, in round bottom white 96 well plate. The reaction mixture was incubated at room temperature for 2 hr. After 2 hr of incubation, 10 µl of the reaction mix was mixed with 10 t of ADP Glo reagent, in another round bottom white 96 well plate and incubated at room temperature for 40 min. This was followed by addition of kinase detection reagent (20 µl per reaction) and incubation at room temperature for 30 min. Finally, plate was read for luminescence at an integration time of 500 millisecond per well. Data were plotted taking Enzyme with no inhibitor set as the 100% kinase activity and for dose response curve, % Kinase activity was plotted against conc on Log scale and $IC_{50}$ was determined by non linear curve fitting method using Graph- Pad Prism software 6. The in vitro BTK inhibitory activity (IC$_{50}$) for representative compounds are listed in

TABLE 3

Table 3: Invitro (IC$_{50}$) BTK inhibitory & CYP inhibition data of representative compounds

| compd No. | In-vitro BTK inhibitory activity: IC$_{50}$ (nM) | CYP inhibition @ 10 $\mu$M concn | | | | | |
|---|---|---|---|---|---|---|---|
| | | 1A2 | 2C8 | 2C9 | 2C19 | 2D6 | 3A4 |
| 1 | 1.3 | A | A | A | A | A | A |
| 2 | 1.1 | A | A | A | A | A | A |
| 3 | 8 | A | A | B | A | A | A |
| 4 | 2 | A | A | A | A | A | A |
| 5 | 8 | A | A | A | A | A | B |
| 6 | 1.7 | A | A | A | A | A | A |
| 7 | 6 | A | A | B | A | A | B |
| 8 | 4 | A | A | A | B | A | A |
| 9 | 28 | A | B | B | A | A | B |
| 10 | 25 | A | B | A | A | B | B |
| 11 | 13 | A | A | A | A | A | A |
| 12 | 37 | A | B | B | A | A | B |
| 13 | 1.8 | A | A | A | B | A | A |
| 14 | 1.4 | A | A | A | A | A | A |
| 15 | 18 | A | A | A | A | A | B |
| 16 | 1.7 | A | A | A | A | A | A |
| 17 | 5 | A | A | A | A | A | B |
| 18 | 218 | A | B | B | A | A | B |
| 19 | 4 | A | A | A | A | A | A |
| 20 | 223 | A | B | B | A | A | B |
| 21 | 50 | B | A | A | A | A | A |
| 22 | 40 | A | A | A | A | B | A |
| 23 | 48 | A | B | B | A | A | B |
| 24 | 2.5 | A | A | A | A | A | A |
| 25 | 5 | A | A | A | A | A | A |
| 26 | 1.1 | A | A | A | A | A | A |
| 27 | 1.6 | A | A | A | A | A | A |
| 28 | 16 | A | A | B | A | A | B |
| 29 | 1.2 | A | A | A | A | A | A |
| 30 | 6 | A | A | A | A | A | A |
| 31 | 0.6 | A | A | A | A | A | A |
| 32 | 4 | A | A | A | A | A | B |
| 33 | 1.5 | A | A | A | A | A | A |
| 34 | 359 | B | A | A | B | A | B |
| 35 | 1.2 | A | A | A | A | A | A |
| 36 | 1.1 | A | A | A | A | A | A |
| 37 | 1 | A | A | A | A | A | A |
| 38 | 17 | A | A | A | A | B | A |
| 39 | 1.4 | A | A | A | A | A | A |
| 40 | 6 | B | A | B | A | A | A |
| 41 | 3.5 | A | A | A | A | A | B |
| 42 | 0.1 | A | A | A | A | A | A |
| 43 | 2 | A | A | A | A | A | A |
| 44 | 1.4 | A | A | A | A | A | A |
| 45 | 10 | B | A | A | A | A | A |
| 46 | 1 | A | A | A | A | A | A |
| 47 | 3 | A | A | A | A | A | A |
| 48 | 50 | B | A | A | A | A | B |
| 49 | 2.5 | A | A | A | A | A | A |
| 50 | 19 | A | A | A | A | B | B |
| 51 | 100 | A | B | B | A | A | B |
| 52 | 162 | B | A | A | B | A | B |
| 53 | 10 | A | A | A | A | A | B |
| 54 | 0.1 | A | A | A | A | A | A |
| 55 | 80 | A | B | B | B | A | B |
| 56 | 50 | B | B | B | A | B | B |
| 57 | 100 | A | B | B | A | A | B |

A: <50% CYP inhibition @ 10 $\mu$M concentrations;
B: >50% CYP inhibition @ 10 $\mu$M concentrations CYP Inhibition Studies:
CYP inhibition studies were performed with test compounds, at two concentrations (2 M and 10 μM), using human liver microsomes (Yao, M., Zhu, M., Sinz, M. W., Zhang, H., Humphreys, W. F., Rodrigues, A. D and Dai, R., Journal of Pharmaceutical and Biomedical Analysis, 2007, 44, 211-223; Walsky, R. L and Obach, R. S., Drug Metab. Dispos., 2004, 32, 647-660). Human liver microsomes were mixed with 100 mM phosphate buffer (pH 7.4) and probe substrate and warmed to 370 in microcentrifuge tubes. Aliquots of this mixture (499 μL) were transferred to each pre-labeled microcentrifuge tubes, followed by addition of the 1 μL of inhibitors (test compound/CYP-specific positive control inhibitor) or control solvent (DMSO). Aliquots of this mixture (90 μL) were transferred to each pre-labeled microcentrifuge tubes in duplicate. Final solvent concentrations were 0.2% (v/v) or less. Incubations were commenced with the addition of 10 μL NADPH stock (assay concentration, 1 mM) to a final incubation volume of 100 μL and incubated in shaking water bath (at 37° C. and 100 rpm), for the period defined in Tables 1. Incubations were terminated by addition of 400 μL of termination solvent (CH$_3$CN) containing internal standard. The terminated samples were vortex-mixed, centrifuged at 10000 rpm for 5 min and supernatant transferred into HPLC vials for LC-MS/MS analysis to monitor metabolites produced by marker CYP reactions. CYP inhibitory activity (% inhibition) of test compounds is listed in Table 3.

In Vivo Efficacy Studies:
Demonstration of in vivo efficacy of test compounds in rats mice, oral routes of administration.

Animals
All the animal experiments were carried out in female rats and mice, bred in-house. Animals were housed in groups of 6 animals per cage, for a week, in order to habituate them to vivarium conditions (25±4° C., 60-65% relative humidity, 12: 12 h light: dark cycle, with lights on at 7.30 am). All the animal experiments were carried out according to the internationally valid guidelines following approval by the 'Zydus Research Center animal ethical committee'.

SCW Arthritis
Female Sprague dawley (SD) rats were primed with an intra-articular injection of 20 μl of peptidoglycan polysaccharide (PGPS), at 0.5 mg/ml of rhamnose in the right ankle. At 2 weeks the paw swelling were measured using a plethysmometer and rats assigned to groups based on initial paw swelling. On day 14 after model initiation, rats were dosed orally (po) with the test compounds. Following the dose administration, 1 h later, the rats received a booster dose of 0.5 ml of PGPS (0.5 mg/ml of rhamnose) via i.v. injection using their tail vein. Compounds were dosed for the following two more days and their paw volumes were measured for 3 more days. The efficacy of the compound was determined as percentage inhibition of paw swelling verses the control (untreated) group. Representative data of some of the test compounds are listed in Table-4.

Diffused Large B Cell Lymphoma Xenografts Using TMD-8 Cell Line
Female SCID mice were inoculated sc with 10×10$^6$ TMD-8 cells in 0.1 mL of PBS to the right flank. Animals were observed twice weekly for occurrence of tumor. Once the tumors became palpable (around 100 mm$^3$) around 14 days after injection, treatment was initiated via oral route. Tumor volume was determined every alternate day using digital calipers and the tumor volume was calculated using the formula: [length/2]×[width$^2$]. Body weights of the animals were also recorded 3 times a week as a measure of treatment related side effect. Treatment was continued for two more weeks and inhibition of tumor volume compared to vehicle control was considered as efficacy endpoint. Representative data of some of the test compounds are listed in Table-4.

Protocol for Collagen Induced Arthritis (CIA) Study in Mice

CIA is a frequently used animal model of human RA (Courtenay, J. S., Dallman, M. J., Dayan, A. D., Martin, A. and Mosedale, B., Nature, 1980, 283, 666-668; Bevaart, L., Vervoordeldonk, M. J., Tak, P. P., Methods Mol. Biol., 2010, 602, 181-192). Following 7 days acclimation, mice were randomly assigned to groups according body weight. Mice were immunized subcutaneously in the tail using bovine type II collagen mix in complete Freund's adjuvant (CFA). Twenty-one days after the first immunization, mice were given booster dose of collagen in incomplete Freund's adjuvant (IFA). Mice were monitored every other day after the booster dose for the development of arthritis. Mice were recruited for the study once clinical signs were visible. Eight animals were assigned each of three groups [vehicle, positive control and test compounds] and treatment was continued for four weeks and percentage inhibition in clinical score is recorded as per graded score. Body weights of the animals were also recorded 3 times a week as a measure of treatment related side effect, paw thickness measured twice a week and blood serum are collected at termination for cytokines profile. Representative data of some of the test compounds are listed in Table-4.

TABLE 4

Invivo efficacy data of representative compounds

| Compounds (Dose: 10 mpk, po) | % inhibition of paw inflammation, Day-16, in SCW Arthritis Model | % Inhibition in tumor volume, Day-16, in TMD-8 Xenografts Model | % inhibition of clinical score, Day-28, in CIA Arthritis Model |
|---|---|---|---|
| 25 | 69.6 ± 12.7 | 50.2 ± 10.1 | 90.1 ± 6.3 |
| 32 | 75.3 ± 6.2 | 56.1 ± 8.2 | 100 ± 3.9 |
| 42 | 51.3 ± 9.7 | 62.2 ± 8.8 | 100 ± 4.2 |
| 46 | 81.8 ± 11.2 | 54.3 ± 9.1 | 88 ± 7.1 |
| 54 | 89.2 ± 10.3 | 92.1 ± 13.1 | 98 ± 4.5 |

Date represent Mean ± SD, n = 8 animals in each group

The novel compounds of the present invention can be formulated into suitable pharmaceutically acceptable compositions by combining with suitable excipients by techniques and processes and concentrations as are well known. The compounds of formula (I) or pharmaceutical compositions containing them are useful as a medicament for the inhibition of BTK activity and suitable for humans and other warm blooded animals, and may be administered either by oral, topical or parenteral administration.

Thus, a pharmaceutical composition comprising the compounds of the present invention may comprise a suitable binder, suitable bulking agent &/or diluent and any other suitable agents as may be necessary. Optionally, the pharmaceutical composition may be suitably coated with suitable coating agents.

The compounds of the present invention (I) are BTK inhibitors and are useful in the treatment of disease states mediated by BTK enzyme, preferably cancer, arthritis and related disorders.

In one of the embodiments the present invention of formula (I) in combination with one or more suitable pharmaceutically active agents selected from following therapeutic agents in any combination. Immunosuppressants (e.g., Methotrexate, mercaptopurine, cyclophosphamide), glucocorticoids, non-steroidal anti-inflammatory drugs, Cox-2 specific inhibitors, TNF-Ⓡ binding proteins (eg., Infliximab, etanercept), interferon-13, interferon-Ⓡ, interleukin-2, antihistamines, beta-agonist, anticolinergics, anticancer agents or their suitable pharmaceutically acceptable salts. Further examples of anticancer agents for use in combination with BTK inhibitors include chemotherapy or a targeted therapy, alkylating agents, platinum compounds, DNA altering agents, Topoisomerase inhibitors, microtubule modifiers, antimetabolites, anticancer antibiotics, hormones, Aromatase inhibitors, antibodies, cytokines, vaccines, drug conjugates, inhibitors of mitogen-activated protein kinase signaling (ex: BAY 43-9006), Syk inhibitors, mTOR inhibitors, antibodies (Rituxan), other anticancer agents that can be employed in combination include, Vinblastin, Bleomycin, Cisplatin, Acivicin, Azacitidine, Decitabine, Doxorubicin, Enloplatin, Flurouracil, Methotrexate, Vinblastin, Vincristine and BCR/ABL antagonist The quantity of active component, that is, the compounds of Formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

We claim:

1. Compound having the structure of general formula (I)

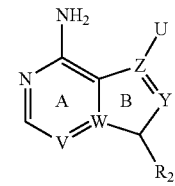

and their pharmaceutically acceptable salts, enantiomers and their diastereomers, Bicyclic ring A-B is selected from the group consisting of:

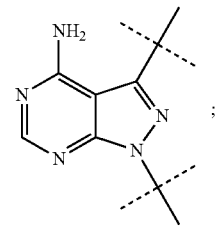

Wherein $R_2$ is selected from the following ring system:

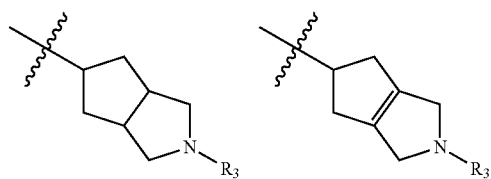

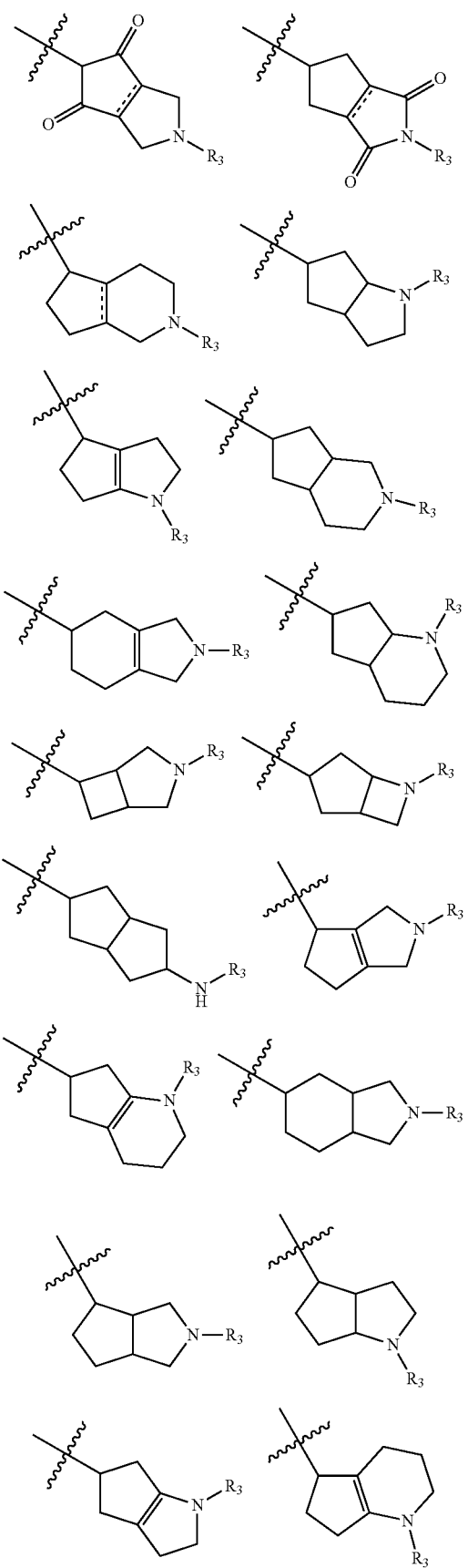

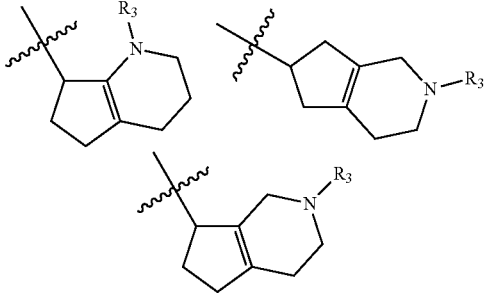

R₃ at each occurrence is independently selected from C(O)NH(C₁₋₇)alkyl, C(O)—CH=CH₂, C(O)—CH≡C—R₁₁, C(O)—CH=CH—R₄, C(O)—C(CN)=CH₂, C(O)—C(CN)=CH—R₄, SO₂—NH(C₁₋₇)alkyl, SO₂—CH=CH₂, SO₂—CH=CH—R₄ groups; wherein, R₁₁ is independently selected from hydrogen and alkyl group;

R₄ at each occurrence is selected from —(CH₂)n-NR₅R₆; wherein, n=0-7 and each of R₅ and R₆ are independently selected from hydrogen, haloalkyl, C₁₋₇ alkyl, C₂₋₇ alkenyl, C₂₋₇ alkynyl, aryl, cycloalkyl, carbocycle, heterocycloalkyl, cycloalkyl(C₁₋₇)alkyl, heterocycloalkyl(C₁₋₇)alkyl;

'U' is selected from unsubstituted or substituted groups selected from heteroaryl, heterocycle, heterocycloalkyl, aryloxyaryl, aryloxyalkyl, aryloxyheteroaryl, heteroaryloxyaryl, heteroaryloxyalkyl, heteroaryloxyheteroaryl, Ph-CO—N(R₇R₈), Ph-N(R₉)—CO—R₁₀, wherein, R₇, R₈ and R₁₀ are independently selected from hydrogen, halogen, alkyl, haloalkyl, alkoxy, aryl, cycloalkyl, heteroaryl, heterocycloalkyl and wherein each of the alkyl, haloalkyl, alkoxy, aryl, cycloalkyl, heteroaryl, heterocycloalkyl groups are when substituted are further substituted with halogen, alkyl, alkoxy, haloalkoxy groups; R₉ are independently selected from hydrogen, C₁₋₇ alkyl, C₂₋₇ alkenyl, C₂₋₇ alkynyl.

2. A compound as claimed in claim 1 selected from the group comprising of:
1-(5-(4-amino-3-(4-phenoxyphenyl)-1H-pyrazolo[3,4-d]pyrimidin-1-yl)hexahydrocyclopenta[c]pyrrol-2(1H)-yl)prop-2-en-1-one;
1-(5-(4-amino-3-(benzo[d]thiazol-6-yl)-1H-pyrazolo[3,4-d]pyrimidin-1-yl)hexahydrocyclopenta[c]pyrrol-2(1H)-yl)prop-2-en-1-one;
1-(5-(4-amino-3-(2-methylbenzo[d]thiazol-6-yl)-1H-pyrazolo[3,4-d]pyrimidin-1-yl)hexahydrocyclopenta[c]pyrrol-2(1H)-yl)prop-2-en-1-one;
1-(5-(4-amino-3-(benzo[b]thiophen-5-yl)-1H-pyrazolo[3,4-d]pyrimidin-1-yl)hexahydrocyclopenta[c]pyrrol-2(1H)-yl)prop-2-en-1-one;
1-(5-(4-amino-3-(2,3-dihydrobenzo[b]thiophen-5-yl)-1H-pyrazolo[3,4-d]pyrimidin-1-yl)hexahydrocyclopenta[c]pyrrol-2(1H)-yl)prop-2-en-1-one;
1-(5-(4-amino-3-(dibenzo[b,d]furan-3-yl)-1H-pyrazolo[3,4-d]pyrimidin-1-yl)hexahydrocyclopenta[c]pyrrol-2(1H)-yl)prop-2-en-1-one;
N-(6-(1-(2-acryloyloctahydrocyclopenta[c]pyrrol-5-yl)-4-amino-1H-pyrazolo[3,4-d]pyrimidin-3-yl)benzo[d]thiazol-2-yl)acetamide;
1-(5-(4-amino-3-(2-methoxybenzo[d]thiazol-6-yl)-1H-pyrazolo[3,4-d]pyrimidin-1-yl)hexahydrocyclopenta[c]pyrrol-2(1H)-yl)prop-2-en-1-one;

1-(5-(4-amino-3-(4-phenoxyphenyl)-1H-pyrazolo[3,4-d]pyrimidin-1-yl)hexahydrocyclopenta[c]pyrrol-2(1H)-yl)prop-2-yn-1-one;

1-(5-(4-amino-3-(3-methoxy-4-phenoxyphenyl)-1H-pyrazolo[3,4-d]pyrimidin-1-yl)hexahydrocyclopenta[c]pyrrol-2(1H)-yl)prop-2-en-1-one;

4-(1-(2-acryloyloctahydrocyclopenta[c]pyrrol-5-yl)-4-amino-1H-pyrazolo[3,4-d]pyrimidin-3-yl)-N-(pyridin-2-yl)benzamide;

1-(5-(4-amino-3-(2-phenylbenzo[d]thiazol-6-yl)-1H-pyrazolo[3,4-d]pyrimidin-1-yl)hexahydrocyclopenta[c]pyrrol-2(1H)-yl)prop-2-en-1-one;

1-(5-(4-amino-3-(benzo[d][1,3]dioxol-5-yl)-1H-pyrazolo[3,4-d]pyrimidin-1-yl)hexahydrocyclopenta[c]pyrrol-2(1H)-yl)prop-2-en-1-one;

1-(5-(4-amino-3-(4-(5-methyl-1,3,4-oxadiazol-2-yl)phenyl)-1H-pyrazolo[3,4-d]pyrimidin-1-yl)hexahydrocyclopenta[c]pyrrol-2(1H)-yl)prop-2-en-1-one;

1-(5-(4-amino-3-(benzo[d]oxazol-6-yl)-1H-pyrazolo[3,4-d]pyrimidin-1-yl)hexahydrocyclopenta[c]pyrrol-2(1H)-yl)prop-2-en-1-one;

3-(4-phenoxyphenyl)-1-(2-(vinylsulfonyl)octahydrocyclopenta[c]pyrrol-5-yl)-1H-pyrazolo[3,4-d]pyrimidin-4-amine;

1-(5-(4-amino-3-(2-phenylbenzo[d]oxazol-6-yl)-1H-pyrazolo[3,4-d]pyrimidin-1-yl)hexahydrocyclopenta[c]pyrrol-2(1H)-yl)prop-2-en-1-one;

1-(5-(4-amino-3-(2-phenoxybenzo[d]thiazol-6-yl)-1H-pyrazolo[3,4-d]pyrimidin-1-yl)hexahydrocyclopenta[c]pyrrol-2(1H)-yl)prop-2-en-1-one;

1-(5-(4-amino-3-(4-(1-methyl-1H-pyrazol-4-yl)phenyl)-1H-pyrazolo[3,4-d]pyrimidin-1-yl)hexahydrocyclopenta[c]pyrrol-2(1H)-yl)prop-2-en-1-one;

1-(5-(4-amino-3-(benzo[d]oxazol-5-yl)-1H-pyrazolo[3,4-d]pyrimidin-1-yl)hexahydrocyclopenta[c]pyrrol-2(1H)-yl)prop-2-en-1-one;

1-(5-(4-amino-3-(2-phenylbenzo[d]oxazol-5-yl)-1H-pyrazolo[3,4-d]pyrimidin-1-yl)hexahydrocyclopenta[c]pyrrol-2(1H)-yl)prop-2-en-1-one;

(E)-1-(5-(4-amino-3-(4-phenoxyphenyl)-1H-pyrazolo[3,4-d]pyrimidin-1-yl)hexahydrocyclopenta[c]pyrrol-2(1H)-yl)-4-(dimethylamino)but-2-en-1-one;

1-(5-(4-amino-3-(4-(5-(pyridin-2-yl)-1,3,4-oxadiazol-2-yl)phenyl)-1H-pyrazolo[3,4-d]pyrimidin-1-yl)hexahydrocyclopenta[c]pyrrol-2(1H)-yl)prop-2-en-1-one;

(E)-2-(5-(4-amino-3-(4-phenoxyphenyl)-1H-pyrazolo[3,4-d]pyrimidin-1-yl)octahydrocyclopenta[c]pyrrole-2-carbonyl)-3-cyclopropylacrylonitrile;

4-(1-(2-acryloyloctahydrocyclopenta[c]pyrrol-5-yl)-4-amino-1H-pyrazolo[3,4-d]pyrimidin-3-yl)-2-methoxy-N-(4-methylpyridin-2-yl)benzamide;

4-(1-(2-acryloyloctahydrocyclopenta[c]pyrrol-5-yl)-4-amino-1H-pyrazolo[3,4-d]pyrimidin-3-yl)-N-(4-methylpyridin-2-yl)benzamide;

N-(4-(1-(2-acryloyloctahydrocyclopenta[c]pyrrol-5-yl)-4-amino-1H-pyrazolo[3,4-d]pyrimidin-3-yl)phenyl)picolinamide;

4-(1-(2-acryloyloctahydrocyclopenta[c]pyrrol-5-yl)-4-amino-1H-pyrazolo[3,4-d]pyrimidin-3-yl)-N-(benzo[d]thiazol-2-yl)benzamide;

N-(4-(1-(2-acryloyloctahydrocyclopenta[c]pyrrol-5-yl)-4-amino-1H-pyrazolo[3,4-d]pyrimidin-3-yl)phenyl)pyrazine-2-carboxamide;

1-(5-(4-amino-3-(2,2-difluorobenzo[d][1,3]dioxol-5-yl)-1H-pyrazolo[3,4-d]pyrimidin-1-yl)hexahydrocyclopenta[c]pyrrol-2(1H)-yl)prop-2-en-1-one;

4-(1-(2-acryloyloctahydrocyclopenta[c]pyrrol-5-yl)-4-amino-1H-pyrazolo[3,4-d]pyrimidin-3-yl)-N-(pyrazin-2-yl)benzamide;

N-(4-(1-(2-acryloyloctahydrocyclopenta[c]pyrrol-5-yl)-4-amino-1H-pyrazolo[3,4-d]pyrimidin-3-yl)phenyl)benzamide;

1-(5-(4-amino-3-(4-(5-(pyridin-2-yl)-1,3,4-thiadiazol-2-yl)phenyl)-1H-pyrazolo[3,4-d]pyrimidin-1-yl)hexahydrocyclopenta[c]pyrrol-2(1H)-yl)prop-2-en-1-one;

4-(1-(2-acryloyloctahydrocyclopenta[c]pyrrol-5-yl)-4-amino-1H-pyrazolo[3,4-d]pyrimidin-3-yl)-N-(4-(trifluoromethyl)pyridin-2-yl)benzamide;

Z)-methyl 4-(1-(2-acryloyloctahydrocyclopenta[c]pyrrol-5-yl)-4-amino-1H-pyrazolo[3,4-d]pyrimidin-3-yl)-N-(4-methylpyridin-2-yl)benzimidate;

6-(1-(2-acryloyloctahydrocyclopenta[c]pyrrol-5-yl)-4-amino-1H-pyrazolo[3,4-d]pyrimidin-3-yl)-N-(4-methylpyridin-2-yl)nicotinamide;

1-(5-(4-amino-3-(4-(pyridin-2-yloxy)phenyl)-1H-pyrazolo[3,4-d]pyrimidin-1-yl)hexahydrocyclopenta[c]pyrrol-2(1H)-yl)prop-2-en-1-one;

(E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-(pyridin-2-yl)benzamide;

(E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-(4-methylpyridin-2-yl)benzamide;

1-(5-(4-amino-3-(4-(5-(pyrazin-2-yl)-1,3,4-thiadiazol-2-yl)phenyl)-1H-pyrazolo[3,4-d]pyrimidin-1-yl)hexahydrocyclopenta[c]pyrrol-2(1H)-yl)prop-2-en-1-one;

(E)-1-(5-(4-amino-3-(4-(pyridin-2-yloxy)phenyl)-1H-pyrazolo[3,4-d]pyrimidin-1-yl)hexahydrocyclopenta[c]pyrrol-2(1H)-yl)-4-(dimethylamino)but-2-en-1-one;

(E)-1-(5-(4-amino-3-(4-phenoxyphenyl)-1H-pyrazolo[3,4-d]pyrimidin-1-yl)hexahydrocyclopenta[c]pyrrol-2(1H)-yl)-4-(dimethylamino)but-2-en-1-one;

(E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-(pyrazin-2-yl)benzamide;

(Z)-methyl 4-(4-amino-1-(2-((E)-4-(dimethylamino)but-2-enoyl)octahydrocyclopenta[c]pyrrol-5-yl)-1H-pyrazolo[3,4-d]pyrimidin-3-yl)-N-(4-methylpyridin-2-yl)benzimidate;

(E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-(4-(trifluoromethyl)pyridin-2-yl)benzamide;

1-(5-(4-amino-3-(4-(pyridin-3-yloxy)phenyl)-1H-pyrazolo[3,4-d]pyrimidin-1-yl)hexahydrocyclopenta[c]pyrrol-2(1H)-yl)prop-2-en-1-one;

(E)-1-(5-(4-amino-3-(4-(pyridin-3-yloxy)phenyl)-1H-pyrazolo[3,4-d]pyrimidin-1-yl)hexahydrocyclopenta[c]pyrrol-2(1H)-yl)-4-(dimethylamino)but-2-en-1-one;

4-(1-(2-acryloyloctahydrocyclopenta[c]pyrrol-5-yl)-4-amino-1H-pyrazolo[3,4-d]pyrimidin-3-yl)-N-methyl-N-(4-methylpyridin-2-yl)benzamide;

(E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-methyl-N-(4-methylpyridin-2-yl)benzamide;

(E)-1-(5-(4-amino-3-(4-(5-(pyrazin-2-yl)-1,3,4-thiadiazol-2-yl)phenyl)-1H-pyrazolo[3,4-d]pyrimidin-1-yl)hexahydrocyclopenta[c]pyrrol-2(1H)-yl)-4-(dimethylamino)but-2-en-1-one; or (E)-1-(5-(4-amino-3-(4-(5-(pyridin-2-yl)-1,3,4-oxadiazol-2-yl)phenyl)-1H-pyrazolo[3,4-d]pyrimidin-1-yl)hexahydrocyclopenta[c]pyrrol-2(1H)-yl)-4-(dimethylamino)but-2-en-1-one.

3. A compound as claimed in claim 1 selected from the group comprising of:

1-(5-(4-amino-3-(4-phenoxyphenyl)-1H-pyrazolo[3,4-d]pyrimidin-1-yl)hexahydrocyclopenta[c]pyrrol-2(1H)-yl)prop-2-en-1-one;

1-(5-(4-amino-3-(benzo[d]thiazol-6-yl)-1H-pyrazolo[3,4-d]pyrimidin-1-yl)hexahydrocyclopenta[c]pyrrol-2(1H)-yl)prop-2-en-1-one;

1-(5-(5-((4-amino-3-(4-phenoxyphenyl)-1H-pyrazolo[3,4-d]pyrimidin-1-yl)methyl)pyridin-2-yl)hexahydropyrrolo[3,4-c]pyrrol-2(1H)-yl)prop-2-en-1-one;

1-(5-(2-(4-amino-3-(4-phenoxyphenyl)-1H-pyrazolo[3,4-d]pyrimidin-1-yl)ethyl)hexahydropyrrolo[3,4-c]pyrrol-2(1H)-yl)prop-2-en-1-one;

1-(5-(4-amino-3-(2-methylbenzo[d]thiazol-6-yl)-1H-pyrazolo[3,4-d]pyrimidin-1-yl)hexahydrocyclopenta[c]pyrrol-2(1H)-yl)prop-2-en-1-one;

1-(5-(4-amino-3-(benzo[b]thiophen-5-yl)-1H-pyrazolo[3,4-d]pyrimidin-1-yl)hexahydrocyclopenta[c]pyrrol-2(1H)-yl)prop-2-en-1-one;

1-(5-(4-amino-3-(2,3-dihydrobenzo[b]thiophen-5-yl)-1H-pyrazolo[3,4-d]pyrimidin-1-yl)hexahydrocyclopenta[c]pyrrol-2(1H)-yl)prop-2-en-1-one;

1-(5-(4-amino-3-(dibenzo[b,d]furan-3-yl)-1H-pyrazolo[3,4-d]pyrimidin-1-yl)hexahydrocyclopenta[c]pyrrol-2(1H)-yl)prop-2-en-1-one;

N-(6-(1-(2-acryloyloctahydrocyclopenta[c]pyrrol-5-yl)-4-amino-1H-pyrazolo[3,4-d]pyrimidin-3-yl)benzo[d]thiazol-2-yl)acetamide;

1-(5-(4-amino-3-(2-methoxybenzo[d]thiazol-6-yl)-1H-pyrazolo[3,4-d]pyrimidin-1-yl)hexahydrocyclopenta[c]pyrrol-2(1H)-yl)prop-2-en-1-one;

1-(5-(4-amino-3-(4-phenoxyphenyl)-1H-pyrazolo[3,4-d]pyrimidin-1-yl)hexahydrocyclopenta[c]pyrrol-2(1H)-yl)prop-2-yn-1-one;

1-(5-(4-amino-3-(3-methoxy-4-phenoxyphenyl)-1H-pyrazolo[3,4-d]pyrimidin-1-yl)hexahydrocyclopenta[c]pyrrol-2(1H)-yl)prop-2-en-1-one;

4-(1-(2-acryloyloctahydrocyclopenta[c]pyrrol-5-yl)-4-amino-1H-pyrazolo[3,4-d]pyrimidin-3-yl)-N-(pyridin-2-yl)benzamide;

1-(5-(4-amino-3-(2-phenylbenzo[d]thiazol-6-yl)-1H-pyrazolo[3,4-d]pyrimidin-1-yl)hexahydrocyclopenta[c]pyrrol-2(1H)-yl)prop-2-en-1-one;

1-(5-(4-amino-3-(benzo[d][1,3]dioxol-5-yl)-1H-pyrazolo[3,4-d]pyrimidin-1-yl)hexahydrocyclopenta[c]pyrrol-2(1H)-yl)prop-2-en-1-one;

1-(5-(4-amino-3-(4-(5-methyl-1,3,4-oxadiazol-2-yl)phenyl)-1H-pyrazolo[3,4-d]pyrimidin-1-yl)hexahydrocyclopenta[c]pyrrol-2(1H)-yl)prop-2-en-1-one;

1-(5-(4-amino-3-(benzo[d]oxazol-6-yl)-1H-pyrazolo[3,4-d]pyrimidin-1-yl)hexahydrocyclopenta[c]pyrrol-2(1H)-yl)prop-2-en-1-one;

3-(4-phenoxyphenyl)-1-(2-(vinylsulfonyl)octahydrocyclopenta[c]pyrrol-5-yl)-1H-pyrazolo[3,4-d]pyrimidin-4-amine;

1-(5-(4-amino-3-(2-phenylbenzo[d]oxazol-6-yl)-1H-pyrazolo[3,4-d]pyrimidin-1-yl)hexahydrocyclopenta[c]pyrrol-2(1H)-yl)prop-2-en-1-one;

1-(5-(4-amino-3-(2-phenoxybenzo[d]thiazol-6-yl)-1H-pyrazolo[3,4-d]pyrimidin-1-yl)hexahydrocyclopenta[c]pyrrol-2(1H)-yl)prop-2-en-1-one;

1-(5-(4-amino-3-(4-(1-methyl-1H-pyrazol-4-yl)phenyl)-1H-pyrazolo[3,4-d]pyrimidin-1-yl)hexahydrocyclopenta[c]pyrrol-2(1H)-yl)prop-2-en-1-one;

1-(5-(4-amino-3-(benzo[d]oxazol-5-yl)-1H-pyrazolo[3,4-d]pyrimidin-1-yl)hexahydrocyclopenta[c]pyrrol-2(1H)-yl)prop-2-en-1-one;

1-(5-(4-amino-3-(2-phenylbenzo[d]oxazol-5-yl)-1H-pyrazolo[3,4-d]pyrimidin-1-yl)hexahydrocyclopenta[c]pyrrol-2(1H)-yl)prop-2-en-1-one;

(E)-1-(5-(4-amino-3-(4-phenoxyphenyl)-1H-pyrazolo[3,4-d]pyrimidin-1-yl)hexahydrocyclopenta[c]pyrrol-2(1H)-yl)-4-(dimethylamino)but-2-en-1-one;

1-(5-(4-amino-3-(4-(5-(pyridin-2-yl)-1,3,4-oxadiazol-2-yl)phenyl)-1H-pyrazolo[3,4-d]pyrimidin-1-yl)hexahydrocyclopenta[c]pyrrol-2(1H)-yl)prop-2-en-1-one;

(E)-2-(5-(4-amino-3-(4-phenoxyphenyl)-1H-pyrazolo[3,4-d]pyrimidin-1-yl)octahydrocyclopenta[c]pyrrole-2-carbonyl)-3-cyclopropylacrylonitrile;

4-(1-(2-acryloyloctahydrocyclopenta[c]pyrrol-5-yl)-4-amino-1H-pyrazolo[3,4-d]pyrimidin-3-yl)-2-methoxy-N-(4-methylpyridin-2-yl)benzamide;

4-(1-(2-acryloyloctahydrocyclopenta[c]pyrrol-5-yl)-4-amino-1H-pyrazolo[3,4-d]pyrimidin-3-yl)-N-(4-methylpyridin-2-yl)benzamide;

N-(4-(1-(2-acryloyloctahydrocyclopenta[c]pyrrol-5-yl)-4-amino-1H-pyrazolo[3,4-d]pyrimidin-3-yl)phenyl)picolinamide;

4-(1-(2-acryloyloctahydrocyclopenta[c]pyrrol-5-yl)-4-amino-1H-pyrazolo[3,4-d]pyrimidin-3-yl)-N-(benzo[d]thiazol-2-yl)benzamide;

N-(4-(1-(2-acryloyloctahydrocyclopenta[c]pyrrol-5-yl)-4-amino-1H-pyrazolo[3,4-d]pyrimidin-3-yl)phenyl)pyrazine-2-carboxamide;

1-(5-(4-amino-3-(2,2-difluorobenzo[d][1,3]dioxol-5-yl)-1H-pyrazolo[3,4-d]pyrimidin-1-yl)hexahydrocyclopenta[c]pyrrol-2(1H)-yl)prop-2-en-1-one;

4-(1-(2-acryloyloctahydrocyclopenta[c]pyrrol-5-yl)-4-amino-1H-pyrazolo[3,4-d]pyrimidin-3-yl)-N-(pyrazin-2-yl)benzamide;

N-(4-(1-(2-acryloyloctahydrocyclopenta[c]pyrrol-5-yl)-4-amino-1H-pyrazolo[3,4-d]pyrimidin-3-yl)phenyl)benzamide;

1-(5-(4-amino-3-(4-(5-(pyridin-2-yl)-1,3,4-thiadiazol-2-yl)phenyl)-1H-pyrazolo[3,4-d]pyrimidin-1-yl)hexahydrocyclopenta[c]pyrrol-2(1H)-yl)prop-2-en-1-one;

4-(1-(2-acryloyloctahydrocyclopenta[c]pyrrol-5-yl)-4-amino-1H-pyrazolo[3,4-d]pyrimidin-3-yl)-N-(4-(trifluoromethyl)pyridin-2-yl)benzamide;

Z)-methyl 4-(1-(2-acryloyloctahydrocyclopenta[c]pyrrol-5-yl)-4-amino-1H-pyrazolo[3,4-d]pyrimidin-3-yl)-N-(4-methylpyridin-2-yl)benzimidate;

6-(1-(2-acryloyloctahydrocyclopenta[c]pyrrol-5-yl)-4-amino-1H-pyrazolo[3,4-d]pyrimidin-3-yl)-N-(4-methylpyridin-2-yl)nicotinamide;

1-(5-(4-amino-3-(4-(pyridin-2-yloxy)phenyl)-1H-pyrazolo[3,4-d]pyrimidin-1-yl)hexahydrocyclopenta[c]pyrrol-2(1H)-yl)prop-2-en-1-one;

(E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-(pyridin-2-yl)benzamide;

(E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-(4-methylpyridin-2-yl)benzamide;

1-(5-(4-amino-3-(4-(5-(pyrazin-2-yl)-1,3,4-thiadiazol-2-yl)phenyl)-1H-pyrazolo[3,4-d]pyrimidin-1-yl)hexahydrocyclopenta[c]pyrrol-2(1H)-yl)prop-2-en-1-one;

(E)-1-(5-(4-amino-3-(4-(pyridin-2-yloxy)phenyl)-1H-pyrazolo[3,4-d]pyrimidin-1-yl)hexahydrocyclopenta[c]pyrrol-2(1H)-yl)-4-(dimethylamino)but-2-en-1-one;

(E)-1-(5-(4-amino-3-(4-phenoxyphenyl)-1H-pyrazolo[3,4-d]pyrimidin-1-yl)hexahydrocyclopenta[c]pyrrol-2(1H)-yl)-4-(dimethylamino)but-2-en-1-one;

(E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-(pyrazin-2-yl)benzamide;

(Z)-methyl 4-(4-amino-1-(2-((E)-4-(dimethylamino)but-2-enoyl)octahydrocyclopenta[c]pyrrol-5-yl)-1H-pyrazolo[3,4-d]pyrimidin-3-yl)-N-(4-methylpyridin-2-yl)benzimidate;

(E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-(4-(trifluoromethyl)pyridin-2-yl)benzamide;

1-(5-(4-amino-3-(4-(pyridin-3-yloxy)phenyl)-1H-pyrazolo[3,4-d]pyrimidin-1-yl)hexahydrocyclopenta[c]pyrrol-2(1H)-yl)prop-2-en-1-one;

(E)-1-(5-(4-amino-3-(4-(pyridin-3-yloxy)phenyl)-1H-pyrazolo[3,4-d]pyrimidin-1-yl)hexahydrocyclopenta[c]pyrrol-2(1H)-yl)-4-(dimethylamino)but-2-en-1-one;

4-(1-(2-acryloyloctahydrocyclopenta[c]pyrrol-5-yl)-4-amino-1H-pyrazolo[3,4-d]pyrimidin-3-yl)-N-methyl-N-(4-methylpyridin-2-yl)benzamide;

(E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-methyl-N-(4-methylpyridin-2-yl)benzamide;

(E)-1-(5-(4-amino-3-(4-(5-(pyrazin-2-yl)-1,3,4-thiadiazol-2-yl)phenyl)-1H-pyrazolo[3,4-d]pyrimidin-1-yl)hexahydrocyclopenta[c]pyrrol-2(1H)-yl)-4-(dimethylamino)but-2-en-1-one;

(E)-1-(5-(4-amino-3-(4-(5-(pyridin-2-yl)-1,3,4-oxadiazol-2-yl)phenyl)-1H-pyrazolo[3,4-d]pyrimidin-1-yl)hexahydrocyclopenta[c]pyrrol-2(1H)-yl)-4-(dimethylamino)but-2-en-1-one;

1-(5-(4-amino-3-(4-phenoxyphenyl)-1H-pyrazolo[3,4-d]pyrimidin-1-yl)-5,6-dihydrocyclopenta[c]pyrrol-2(1H,3H,4H)-yl)prop-2-en-1-one;

2-acryloyl-5-(4-amino-3-(4-phenoxyphenyl)-1H-pyrazolo[3,4-d]pyrimidin-1-yl)-2,3-dihydrocyclopenta[c]pyrrole-4,6(1H,5H)-dione;

2-acryloyl-5-(4-amino-3-(4-phenoxyphenyl)-1H-pyrazolo[3,4-d]pyrimidin-1-yl)-5,6-dihydrocyclopenta[c]pyrrole-1,3 (2H,4H)-dione;

1-(5-(4-amino-3-(4-phenoxyphenyl)-1H-pyrazolo[3,4-d]pyrimidin-1-yl)hexahydrocyclopenta[b]pyrrol-1(2H)-yl)prop-2-en-1-one;

1-(4-(4-amino-3-(4-phenoxyphenyl)-1H-pyrazolo[3,4-d]pyrimidin-1-yl)-2,3,5,6-tetrahydrocyclopenta[b]pyrrol-1(4H)-yl)prop-2-en-1-one;

1-(6-(4-amino-3-(4-phenoxyphenyl)-1H-pyrazolo[3,4-d]pyrimidin-1-yl)hexahydro-1H-cyclopenta[c]pyridin-2(3H)-yl)prop-2-en-1-one;

1-(5-(4-amino-3-(4-phenoxyphenyl)-1H-pyrazolo[3,4-d]pyrimidin-1l-yl)-4, 5,6,7-tetrahydro-1H-isoindol-2(3H)-yl)prop-2-en-1-one;

1-(6-(4-amino-3-(4-phenoxyphenyl)-1H-pyrazolo[3,4-d]pyrimidin-1-yl)-3-azabicyclo[3.2.0]heptan-3-yl)prop-2-en-1-one;

1-(3-(4-amino-3-(4-phenoxyphenyl)-1H-pyrazolo[3,4-d]pyrimidin-1-yl)-6-azabicyclo[3.2.0]heptan-6-yl)prop-2-en-1-one;

N-(5-(4-amino-3-(4-phenoxyphenyl)-1H-pyrazolo[3,4-d]pyrimidin-1-yl)octahydropentalen-2-yl)acrylamide;

1-(5-(4-amino-3-(4-phenoxyphenyl)-1H-pyrazolo[3,4-d]pyrimidin-1l-yl)-3,4,6,7-tetrahydro-1H-cyclopenta[c]pyridin-2(5H)-yl)prop-2-en-1-one;

1-(5-(4-amino-3-(4-phenoxyphenyl)-1H-pyrazolo[3,4-d]pyrimidin-1-yl)hexahydro-1H-isoindol-2(3H)-yl)prop-2-en-1-one;

1-(4-(4-amino-3-(4-phenoxyphenyl)-1H-pyrazolo[3,4-d]pyrimidin-1-yl)hexahydrocyclopenta[c]pyrrol-2(1H)-yl)prop-2-en-1-one;

1-(4-(4-amino-3-(4-phenoxyphenyl)-1H-pyrazolo[3,4-d]pyrimidin-1-yl)hexahydrocyclopenta[b]pyrrol-1(2H)-yl)prop-2-en-1-one;

1-(5-(4-amino-3-(4-phenoxyphenyl)-1H-pyrazolo[3,4-d]pyrimidin-1-yl)-2,3,5,6-tetrahydrocyclopenta[b]pyrrol-1(4H)-yl)prop-2-en-1-one;

1-(4-(4-amino-3-(4-phenoxyphenyl)-1H-pyrazolo[3,4-d]pyrimidin-1l-yl)-5,6-dihydrocyclopenta[c]pyrrol-2(1H,3H,4H)-yl)prop-2-en-1-one;

1-(6-(4-amino-3-(4-phenoxyphenyl)-1H-pyrazolo[3,4-d]pyrimidin-1-yl)octahydro-1H-cyclopenta[b]pyridin-1-yl)prop-2-en-1-one;

1-(5-(4-amino-3-(4-phenoxyphenyl)-1H-pyrazolo[3,4-d]pyrimidin-1-yl)-2,3,4,5,6,7-hexahydro-1H-cyclopenta[b]pyridin-1-yl)prop-2-en-1-one;

1-(7-(4-amino-3-(4-phenoxyphenyl)-1H-pyrazolo[3,4-d]pyrimidin-1-yl)-2,3,4,5,6,7-hexahydro-1H-cyclopenta[b]pyridin-1-yl)prop-2-en-1-one;

1-(6-(4-amino-3-(4-phenoxyphenyl)-1H-pyrazolo[3,4-d]pyrimidin-1l-yl)-3,4,6,7-tetrahydro-1H-cyclopenta[c]pyridin-2(5H)-yl)prop-2-en-1-one;

1-(7-(4-amino-3-(4-phenoxyphenyl)-1H-pyrazolo[3,4-d]pyrimidin-1l-yl)-3,4,6,7-tetrahydro-1H-cyclopenta[c]pyridin-2(5H)-yl)prop-2-en-1-one;

1-(7-(4-amino-3-(4-phenoxyphenyl)-1H-pyrazolo[3,4-d]pyrimidin-1-yl)-2,3,4,5,6,7-hexahydro-1H-cyclopenta[b]pyridin-1-yl)prop-2-en-1-one;

1-(5-(4-amino-3-(benzo[d]thiazol-6-yl)-1H-pyrazolo[3,4-d]pyrimidin-1-yl)-5,6-dihydrocyclopenta[c]pyrrol-2(1H,3H,4H)-yl)prop-2-en-1-one;

2-acryloyl-5-(4-amino-3-(benzo[d]thiazol-6-yl)-1H-pyrazolo[3,4-d]pyrimidin-1-yl)-2,3-dihydrocyclopenta[c]pyrrole-4,6(1H,5H)-dione;

2-acryloyl-5-(4-amino-3-(benzo[d]thiazol-6-yl)-1H-pyrazolo[3,4-d]pyrimidin-1-yl)-5,6-dihydrocyclopenta[c]pyrrole-1,3 (2H,4H)-dione;

1-(5-(4-amino-3-(benzo[d]thiazol-6-yl)-1H-pyrazolo[3,4-d]pyrimidin-1-yl)hexahydrocyclopenta[b]pyrrol-1(2H)-yl)prop-2-en-1-one;

1-(4-(4-amino-3-(benzo[d]thiazol-6-yl)-1H-pyrazolo[3,4-d]pyrimidin-1-yl)-2,3,5,6-tetrahydrocyclopenta[b]pyrrol-1(4H)-yl)prop-2-en-1-one;

1-(6-(4-amino-3-(benzo[d]thiazol-6-yl)-1H-pyrazolo[3,4-d]pyrimidin-1-yl)hexahydro-1H-cyclopenta[c]pyridin-2(3H)-yl)prop-2-en-1-one;

1-(5-(4-amino-3-(benzo[d]thiazol-6-yl)-1H-pyrazolo[3,4-d]pyrimidin-1-yl)-4, 5,6,7-tetrahydro-1H-isoindol-2(3H)-yl)prop-2-en-1-one;

1-(6-(4-amino-3-(benzo[d]thiazol-6-yl)-1H-pyrazolo[3,4-d]pyrimidin-1-yl)-3-azabicyclo[3.2.0]heptan-3-yl)prop-2-en-1-one;

1-(3-(4-amino-3-(benzo[d]thiazol-6-yl)-1H-pyrazolo[3,4-d]pyrimidin-1-yl)-6-azabicyclo[3.2.0]heptan-6-yl)prop-2-en-1-one;

N-(5-(4-amino-3-(benzo[d]thiazol-6-yl)-1H-pyrazolo[3,4-d]pyrimidin-1-yl)octahydropentalen-2-yl)acrylamide;

1-(5-(4-amino-3-(benzo[d]thiazol-6-yl)-1H-pyrazolo[3,4-d]pyrimidin-1-yl)-3,4,6,7-tetrahydro-1H-cyclopenta[c]pyridin-2(5H)-yl)prop-2-en-1-one;

1-(5-(4-amino-3-(benzo[d]thiazol-6-yl)-1H-pyrazolo[3,4-d]pyrimidin-1-yl)hexahydro-1H-isoindol-2(3H)-yl)prop-2-en-1-one;

1-(4-(4-amino-3-(benzo[d]thiazol-6-yl)-1H-pyrazolo[3,4-d]pyrimidin-1-yl)hexahydrocyclopenta[c]pyrrol-2(1H)-yl)prop-2-en-1-one;

1-(4-(4-amino-3-(benzo[d]thiazol-6-yl)-1H-pyrazolo[3,4-d]pyrimidin-1-yl)hexahydrocyclopenta[b]pyrrol-1(2H)-yl)prop-2-en-1-one;

1-(5-(4-amino-3-(benzo[d]thiazol-6-yl)-1H-pyrazolo[3,4-d]pyrimidin-1-yl)-2,3,5,6-tetrahydrocyclopenta[b]pyrrol-1(4H)-yl)prop-2-en-1-one;

1-(4-(4-amino-3-(benzo[d]thiazol-6-yl)-1H-pyrazolo[3,4-d]pyrimidin-1-yl)-5,6-dihydrocyclopenta[c]pyrrol-2(1H,3H,4H)-yl)prop-2-en-1-one;

1-(6-(4-amino-3-(benzo[d]thiazol-6-yl)-1H-pyrazolo[3,4-d]pyrimidin-1-yl)octahydro-1H-cyclopenta[b]pyridin-1-yl)prop-2-en-1-one;

1-(5-(4-amino-3-(benzo[d]thiazol-6-yl)-1H-pyrazolo[3,4-d]pyrimidin-1-yl)-2,3,4,5,6,7-hexahydro-1H-cyclopenta[b]pyridin-1-yl)prop-2-en-1-one;

1-(7-(4-amino-3-(benzo[d]thiazol-6-yl)-1H-pyrazolo[3,4-d]pyrimidin-1-yl)-2,3,4,5,6,7-hexahydro-1H-cyclopenta[b]pyridin-1-yl)prop-2-en-1-one;

1-(6-(4-amino-3-(benzo[d]thiazol-6-yl)-1H-pyrazolo[3,4-d]pyrimidin-1-yl)-3,4,6,7-tetrahydro-1H-cyclopenta[c]pyridin-2(5H)-yl)prop-2-en-1-one;

1-(7-(4-amino-3-(benzo[d]thiazol-6-yl)-1H-pyrazolo[3,4-d]pyrimidin-1-yl)-3,4,6,7-tetrahydro-1H-cyclopenta[c]pyridin-2(5H)-yl)prop-2-en-1-one;

1-(7-(4-amino-3-(benzo[d]thiazol-6-yl)-1H-pyrazolo[3,4-d]pyrimidin-1-yl)-2,3,4,5,6,7-hexahydro-1H-cyclopenta[b]pyridin-1-yl)prop-2-en-1-one;

1-(5-(4-amino-3-(benzo[b]thiophen-5-yl)-1H-pyrazolo[3,4-d]pyrimidin-1-yl)-5,6-dihydrocyclopenta[c]pyrrol-2(1H,3H,4H)-yl)prop-2-en-1-one;

1-(6-(4-amino-3-(benzo[b]thiophen-5-yl)-1H-pyrazolo[3,4-d]pyrimidin-1-yl)hexahydro-1H-cyclopenta[c]pyridin-2(3H)-yl)prop-2-en-1-one;

1-(6-(4-amino-3-(benzo[b]thiophen-5-yl)-1H-pyrazolo[3,4-d]pyrimidin-1-yl)-3-azabicyclo[3.2.0]heptan-3-yl)prop-2-en-1-one;

N-(5-(4-amino-3-(benzo[b]thiophen-5-yl)-1H-pyrazolo[3,4-d]pyrimidin-1-yl)octahydropentalen-2-yl)acrylamide;

1-(5-(4-amino-3-(benzo[b]thiophen-5-yl)-1H-pyrazolo[3,4-d]pyrimidin-1-yl)-3,4,6,7-tetrahydro-1H-cyclopenta[c]pyridin-2(5H)-yl)prop-2-en-1-one;

1-(5-(4-amino-3-(2,3-dihydrobenzo[b]thiophen-5-yl)-1H-pyrazolo[3,4-d]pyrimidin-1-yl)-5,6-dihydrocyclopenta[c]pyrrol-2(1H,3H,4H)-yl)prop-2-en-1-one;

1-(6-(4-amino-3-(2,3-dihydrobenzo[b]thiophen-5-yl)-1H-pyrazolo[3,4-d]pyrimidin-1-yl)hexahydro-1H-cyclopenta[c]pyridin-2(3H)-yl)prop-2-en-1-one 1-(6-(4-amino-3-(2,3-dihydrobenzo[b]thiophen-5-yl)-1H-pyrazolo[3,4-d]pyrimidin-1-yl)-3-azabicyclo[3.2.0]heptan-3-yl)prop-2-en-1-one;

N-(5-(4-amino-3-(2,3-dihydrobenzo[b]thiophen-5-yl)-1H-pyrazolo[3,4-d]pyrimidin-1-yl)octahydropentalen-2-yl)acrylamide;

1-(5-(4-amino-3-(2,3-dihydrobenzo[b]thiophen-5-yl)-1H-pyrazolo[3,4-d]pyrimidin-1-yl)-3,4,6,7-tetrahydro-1H-cyclopenta[c]pyridin-2(5H)-yl)prop-2-en-1-one;

N-(6-(1-(2-acryloyl-1,2,3,4,5,6-hexahydrocyclopenta[c]pyrrol-5-yl)-4-amino-1H-pyrazolo[3,4-d]pyrimidin-3-yl)benzo[d]thiazol-2-yl)acetamide;

N-(6-(1-(2-acryloyloctahydro-1H-cyclopenta[c]pyridin-6-yl)-4-amino-1H-pyrazolo[3,4-d]pyrimidin-3-yl)benzo[d]thiazol-2-yl)acetamide;

N-(5-(3-(2-acetamidobenzo[d]thiazol-6-yl)-4-amino-1H-pyrazolo[3,4-d]pyrimidin-1-yl)octahydropentalen-2-yl)acrylamide;

(E)-1-(5-(4-amino-3-(4-phenoxyphenyl)-1H-pyrazolo[3,4-d]pyrimidin-1-yl)-5,6-dihydrocyclopenta[c]pyrrol-2(1H,3H,4H)-yl)-4-(dimethylamino)but-2-en-1-one;

(E)-1-(6-(4-amino-3-(4-phenoxyphenyl)-1H-pyrazolo[3,4-d]pyrimidin-1-yl)hexahydro-1H-cyclopenta[c]pyridin-2(3H)-yl)-4-(dimethylamino)but-2-en-1-one;

(E)-1-(6-(4-amino-3-(4-phenoxyphenyl)-1H-pyrazolo[3,4-d]pyrimidin-1-yl)-3-azabicyclo[3.2.0]heptan-3-yl)-4-(dimethylamino)but-2-en-1-one;

(E)-1-(5-(4-amino-3-(4-phenoxyphenyl)-1H-pyrazolo[3,4-d]pyrimidin-1-yl)-3,4,6,7-tetrahydro-1H-cyclopenta[c]pyridin-2(5H)-yl)-4-(dimethylamino)but-2-en-1-one;

(E)-1-(5-(4-amino-3-(benzo[d]thiazol-6-yl)-1H-pyrazolo[3,4-d]pyrimidin-1-yl)hexahydrocyclopenta[c]pyrrol-2(1H)-yl)-4-(dimethylamino)but-2-en-1-one;

(E)-1-(5-(4-amino-3-(benzo[d]thiazol-6-yl)-1H-pyrazolo[3,4-d]pyrimidin-1-yl)-5,6-dihydrocyclopenta[c]pyrrol-2(1H,3H,4H)-yl)-4-(dimethylamino)but-2-en-1-one;

(E)-1-(6-(4-amino-3-(benzo[d]thiazol-6-yl)-1H-pyrazolo[3,4-d]pyrimidin-1-yl)hexahydro-1H-cyclopenta[c]pyridin-2(3H)-yl)-4-(dimethylamino)but-2-en-1-one;

(E)-1-(6-(4-amino-3-(benzo[d]thiazol-6-yl)-1H-pyrazolo[3,4-d]pyrimidin-1-yl)-3-azabicyclo[3.2.0]heptan-3-yl)-4-(dimethylamino)but-2-en-1-one;

(E)-1-(5-(4-amino-3-(benzo[d]thiazol-6-yl)-1H-pyrazolo[3,4-d]pyrimidin-1-yl)-3,4,6,7-tetrahydro-1H-cyclopenta[c]pyridin-2(5H)-yl)-4-(dimethylamino)but-2-en-1-one;

1-(5-(4-amino-3-(4-benzoylphenyl)-1H-pyrazolo[3,4-d]pyrimidin-1-yl)hexahydrocyclopenta[c]pyrrol-2(1H)-yl)prop-2-en-1-one;

4-(1-(2-acryloyloctahydrocyclopenta[c]pyrrol-5-yl)-4-amino-1H-pyrazolo[3,4-d]pyrimidin-3-yl)-N-phenylbenzamide;

4-(1-(2-acryloyloctahydrocyclopenta[c]pyrrol-5-yl)-4-amino-1H-pyrazolo[3,4-d]pyrimidin-3-yl)-N-methyl-N-phenylbenzamide;

4-(1-(2-acryloyloctahydrocyclopenta[c]pyrrol-5-yl)-4-amino-1H-pyrazolo[3,4-d]pyrimidin-3-yl)-2-methyl-N-phenylbenzamide 4-(1-(2-acryloyloctahydrocyclopenta[c]pyrrol-5-yl)-4-amino-1H-pyrazolo[3,4-d]pyrimidin-3-yl)-2-methoxy-N-phenylbenzamide;

4-(1-(2-acryloyloctahydrocyclopenta[c]pyrrol-5-yl)-4-amino-1H-pyrazolo[3,4-d]pyrimidin-3-yl)-N,2-dimethyl-N-phenylbenzamide;

4-(1-(2-acryloyloctahydrocyclopenta[c]pyrrol-5-yl)-4-amino-1H-pyrazolo[3,4-d]pyrimidin-3-yl)-2-methoxy-N-methyl-N-phenylbenzamide;

4-(1-(2-acryloyloctahydrocyclopenta[c]pyrrol-5-yl)-4-amino-1H-pyrazolo[3,4-d]pyrimidin-3-yl)-2-methyl-N-(pyridin-2-yl)benzamide;

4-(1-(2-acryloyloctahydrocyclopenta[c]pyrrol-5-yl)-4-amino-1H-pyrazolo[3,4-d]pyrimidin-3-yl)-2-methoxy-N-(pyridin-2-yl)benzamide;

4-(1-(2-acryloyloctahydrocyclopenta[c]pyrrol-5-yl)-4-amino-1H-pyrazolo[3,4-d]pyrimidin-3-yl)-2-methyl-N-(4-methylpyridin-2-yl)benzamide;

4-(1-(2-acryloyloctahydrocyclopenta[c]pyrrol-5-yl)-4-amino-1H-pyrazolo[3,4-d]pyrimidin-3-yl)-2-methyl-N-(4-(trifluoromethyl)pyridin-2-yl)benzamide;

4-(1-(2-acryloyloctahydrocyclopenta[c]pyrrol-5-yl)-4-amino-1H-pyrazolo[3,4-d]pyrimidin-3-yl)-2-methoxy-N-(4-(trifluoromethyl)pyridin-2-yl)benzamide;

4-(1-(2-acryloyl-1,2,3,4,5,6-hexahydrocyclopenta[c]pyrrol-5-yl)-4-amino-1H-pyrazolo[3,4-d]pyrimidin-3-yl)-N-phenylbenzamide;

4-(1-(1-acryloyloctahydrocyclopenta[b]pyrrol-5-yl)-4-amino-1H-pyrazolo[3,4-d]pyrimidin-3-yl)-N-phenylbenzamide;

4-(4-amino-1-(2-(vinylsulfonyl)octahydrocyclopenta[c]pyrrol-5-yl)-1H-pyrazolo[3,4-d]pyrimidin-3-yl)-N-phenylbenzamide;

(E)-4-(4-amino-1-(2-(4-(dimethylamino)but-2-enoyl)octahydrocyclopenta[c]pyrrol-5-yl)-1H-pyrazolo[3,4-d]pyrimidin-3-yl)-N-phenylbenzamide;

(E)-4-(4-amino-1-(2-(4-(cyclopropyl(methyl)amino)but-2-enoyl)octahydrocyclopenta[c]pyrrol-5-yl)-1H-pyrazolo[3,4-d]pyrimidin-3-yl)-N-phenylbenzamide;

(Z)-4-(4-amino-1-(2-(2-cyano-3-cyclopropylacryloyl)octahydrocyclopenta[c]pyrrol-5-yl)-1H-pyrazolo[3,4-d]pyrimidin-3-yl)-N-phenylbenzamide;

1-(5-(4-amino-3-(4-(5-phenyl-1,3,4-oxadiazol-2-yl)phenyl)-1H-pyrazolo[3,4-d]pyrimidin-1-yl)hexahydrocyclopenta[c]pyrrol-2(1H)-yl)prop-2-en-1-one;

4-(1-(2-acryloyloctahydrocyclopenta[c]pyrrol-5-yl)-4-amino-1H-pyrazolo[3,4-d]pyrimidin-3-yl)-N-(5-chloropyridin-2-yl)benzamide;

1-(5-(4-amino-3-(4-(morpholinomethyl)phenyl)-1H-pyrazolo[3,4-d]pyrimidin-1-yl)hexahydrocyclopenta[c]pyrrol-2(1H)-yl)prop-2-en-1-one;

1-(5-(4-amino-3-(4-(piperidin-1-ylmethyl)phenyl)-1H-pyrazolo[3,4-d]pyrimidin-1-yl)hexahydrocyclopenta[c]pyrrol-2(1H)-yl)prop-2-en-1-one;

1-(5-(4-amino-3-(4-((3,4-dihydroisoquinolin-2(1H)-yl)methyl)phenyl)-1H-pyrazolo[3,4-d]pyrimidin-1-yl)hexahydrocyclopenta[c]pyrrol-2(1H)-yl)prop-2-en-1-one;

1-(5-(4-amino-3-(4-((tetrahydrofuran-2-yl)oxy)phenyl)-1H-pyrazolo[3,4-d]pyrimidin-1-yl)hexahydrocyclopenta[c]pyrrol-2(1H)-yl)prop-2-en-1-one;

1-(5-(4-amino-3-(4-(1-morpholinoethyl)phenyl)-1H-pyrazolo[3,4-d]pyrimidin-1-yl)hexahydrocyclopenta[c]pyrrol-2(1H)-yl)prop-2-en-1-one;

1-(5-(4-amino-3-(4-(pyrrolidin-1-ylmethyl)phenyl)-1H-pyrazolo[3,4-d]pyrimidin-1-yl)hexahydrocyclopenta[c]pyrrol-2(1H)-yl)prop-2-en-1-one;

1-(5-(4-amino-3-(4-((dimethylamino)methyl)phenyl)-1H-pyrazolo[3,4-d]pyrimidin-1-yl)hexahydrocyclopenta[c]pyrrol-2(1H)-yl)prop-2-en-1-one;

N-(4-(1-(2-acryloyloctahydrocyclopenta[c]pyrrol-5-yl)-4-amino-1H-pyrazolo[3,4-d]pyrimidin-3-yl)benzyl)acetamide;

1-(5-(4-amino-3-(4-(2-morpholinoethoxy)phenyl)-1H-pyrazolo[3,4-d]pyrimidin-1-yl)hexahydrocyclopenta[c]pyrrol-2(1H)-yl)prop-2-en-1-one;

2-(4-(1-(2-acryloyloctahydrocyclopenta[c]pyrrol-5-yl)-4-amino-1H-pyrazolo[3,4-d]pyrimidin-3-yl)benzyl)isoindoline-1,3-dione;

1-(5-(4-amino-3-(4-((3,4-dihydroisoquinolin-2(1H)-yl)methyl)phenyl)-1H-pyrazolo[3,4-d]pyrimidin-1-yl)hexahydrocyclopenta[c]pyrrol-2(1H)-yl)prop-2-en-1-one;

1-(5-(4-amino-3-(4-(azepan-1-ylmethyl)phenyl)-1H-pyrazolo[3,4-d]pyrimidin-1-yl)hexahydrocyclopenta[c]pyrrol-2(1H)-yl)prop-2-en-1-one;

1-(5-(4-amino-3-(4-((hexahydro-1H-isoindol-2(3H)-yl)methyl)phenyl)-1H-pyrazolo[3,4-d]pyrimidin-1-yl)hexahydrocyclopenta[c]pyrrol-2(1H)-yl)prop-2-en-1-one;

1-(5-(4-amino-3-(4-(thiomorpholinomethyl)phenyl)-1H-pyrazolo[3,4-d]pyrimidin-1-yl)hexahydrocyclopenta[c]pyrrol-2(1H)-yl)prop-2-en-1-one;

1-(5-(4-amino-3-(4-((1,1-dioxidobenzo[d]isothiazol-2(3H)-yl)methyl)phenyl)-1H-pyrazolo[3,4-d]pyrimidin-1-yl)hexahydrocyclopenta[c]pyrrol-2(1H)-yl)prop-2-en-1-one; or 2-(4-(1-(2-acryloyloctahydrocyclopenta[c]pyrrol-5-yl)-4-amino-1H-pyrazolo[3,4-d]pyrimidin-3-yl)benzyl)isoindolin-1-one.

4. A pharmaceutical composition comprising a therapeutically effective amount of a compound of Formula (I) as claimed in claim 1 and optionally one or more pharmaceutically acceptable carriers, diluents or excipients.

5. A method of treating autoimmune and/or allergic disorders selected from rheumatoid arthritis, systemic lupus erythromatosis, scleroderma, asthma, allergic rhinitis, allergic eczema, B-cell lymphoma, multiple sclerosis, juvenile rheumatoid arthritis, juvenile idiopathic arthritis, inflammatory bowel disease, graft versus host disease, psoriatic arthritis, ankylosing spondylitis and uveritis, B cell lymphoma, multiple sclerosis, diffuse large B-cell lymphoma, follicular lymphoma or chronic lymphocytic leukemia and B-cell prolymphocytic leukemia, the method comprising:
   administering to a patient in need the compound of Formula (I) of claim 1, and a suitable pharmaceutically acceptable agent selected from anti-cancer and anti-inflammatory agents or their pharmaceutically acceptable salts for the treatment of the autoimmune and/or allergic disorders.

6. A method of treating autoimmune and/or allergic disorders selected from rheumatoid arthritis, systemic lupus erythromatosis, scleroderma, asthma, allergic rhinitis, allergic eczema, B-cell lymphoma, multiple sclerosis, juvenile rheumatoid arthritis, juvenile idiopathic arthritis, inflammatory bowel disease, graft versus host disease, psoriatic arthritis, ankylosing spondylitis and uveritis, B cell lymphoma, multiple sclerosis, diffuse large B-cell lymphoma, follicular lymphoma or chronic lymphocytic leukemia and B-cell prolymphocytic leukemia, the method comprising:
   administering to a patient in need the pharmaceutical composition of claim 4, and a suitable pharmaceutically acceptable agent selected from anti-cancer and anti-inflammatory agents or their pharmaceutically acceptable salts for the treatment of autoimmune and/or allergic disorders.

* * * * *